US012522612B2

(12) United States Patent
Chan et al.

(10) Patent No.: US 12,522,612 B2
(45) Date of Patent: Jan. 13, 2026

(54) PDE4 INHIBITORS, PHARMACEUTICAL COMPOSITIONS, AND THERAPEUTIC APPLICATIONS

(71) Applicant: BioTheryX, Inc., San Diego, CA (US)

(72) Inventors: Kyle W.H. Chan, San Diego, CA (US); Paul E. Erdman, San Diego, CA (US); Leah M. Fung, San Diego, CA (US); David Aaron Hecht, Chula Vista, CA (US); Frank Mercurio, Rancho Santa Fe, CA (US); Robert W. Sullivan, Vista, CA (US)

(73) Assignee: BioTheryX Inc., San Diego, CA (US)

( * ) Notice: Subject to any disclaimer, the term of this patent is extended or adjusted under 35 U.S.C. 154(b) by 863 days.

(21) Appl. No.: 17/757,105

(22) PCT Filed: Dec. 14, 2020

(86) PCT No.: PCT/US2020/064740
§ 371 (c)(1),
(2) Date: Jun. 9, 2022

(87) PCT Pub. No.: WO2021/119571
PCT Pub. Date: Jun. 17, 2021

(65) Prior Publication Data

US 2023/0071529 A1 Mar. 9, 2023

Related U.S. Application Data

(60) Provisional application No. 62/947,421, filed on Dec. 12, 2019.

(51) Int. Cl.

| | |
|---|---|
| ***C07D 495/04*** | (2006.01) |
| ***C07D 401/14*** | (2006.01) |
| ***C07D 405/14*** | (2006.01) |
| ***C07D 417/14*** | (2006.01) |
| ***C07F 5/02*** | (2006.01) |

(52) U.S. Cl.
CPC ......... *C07D 495/04* (2013.01); *C07D 401/14* (2013.01); *C07D 405/14* (2013.01); *C07D 417/14* (2013.01); *C07F 5/027* (2013.01)

(58) Field of Classification Search
CPC .. C07D 495/04; C07D 401/14; C07D 405/14; C07D 417/14; C07F 5/027
See application file for complete search history.

(56) References Cited

U.S. PATENT DOCUMENTS

| | | | | |
|---|---|---|---|---|
| 10,570,147 | B2 * | 2/2020 | Sullivan | A61P 29/00 |
| 11,236,105 | B2 | 2/2022 | Sullivan et al. | |
| 2018/0354967 | A1 | 12/2018 | Sullivan et al. | |
| 2024/0124418 | A1 * | 4/2024 | Chan | A61P 29/00 |

FOREIGN PATENT DOCUMENTS

| | | | |
|---|---|---|---|
| WO | 2017176958 | A1 | 10/2017 |
| WO | 2020242960 | A1 | 12/2020 |
| WO | 2024168096 | A2 | 8/2024 |

OTHER PUBLICATIONS

Li, et al.; Frontiers in Pharmacology, v9, Article 1048, pp. 1-21; 2018 (Year: 2018).*
Ohoka, The Journal of Biological Chemistry, v292, pp. 4556-4570; 2017 (Year: 2017).*
Paiva, S.-L. and Crews, C. M.; Current Opinion in Chemical Biology, v50, pp. 111-119; 2019 (Year: 2019).*
Berge et al., "Pharmaceutical salts," J. Pharm. Sci. 1977, 66, 1-19.
Steinebach et al., "A MedChem toolbox for cereblon-directed PROTACs," MedChemComm 2019, 10, 1037-41.

* cited by examiner

*Primary Examiner* — Jeffrey S Lundgren
*Assistant Examiner* — W. Justin Youngblood
(74) *Attorney, Agent, or Firm* — Lin Yu; Juniv LLP

(57) ABSTRACT

Provided herein are phosphodiesterase 4 (PDE4) inhibitors, e.g., a compound of Formula (I) or (II), and pharmaceutical compositions thereof. Also provided herein are methods of their use for treating, preventing, or ameliorating one or more symptoms of a disease, disorder, or condition associated with PDE4 malfunction.

(I)

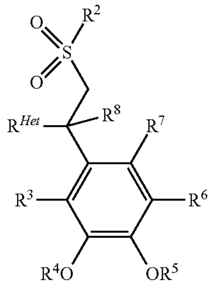

(II)

$R^W—L^2—X—L^1—R^1$

37 Claims, No Drawings

PDE4 INHIBITORS, PHARMACEUTICAL COMPOSITIONS, AND THERAPEUTIC APPLICATIONS

CROSS REFERENCE TO RELATED APPLICATION

This application is a National Stage of International Application No. PCT/US2020/064740, filed Dec. 14, 2020: which claims the benefit of U.S. Provisional Application No. 62/947,421, filed Dec. 12, 2019; the disclosure of each of which is incorporated herein by reference in its entirety.

FIELD

Provided herein are phosphodiesterase 4 (PDE4) inhibitors and pharmaceutical compositions thereof. Also provided herein are methods of their use for treating, preventing, or ameliorating one or more symptoms of a disease, disorder, or condition mediated by a PDE4.

BACKGROUND

Aberrant protein function or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, interleukin-4 (IL-4), interleukin-10 (IL-10), and interleukin-13 (IL-13) are potent activators of B lymphocytes, and also act as anti-inflammatory agents. They are anti-inflammatory cytokines by virtue of their ability to suppress genes for pro-inflammatory cytokines, such as interleukin-1 (IL-1), a tumor necrosis factor (TNF), and chemokines.

Unregulated activities of these mediators can lead to the development of serious inflammatory conditions. For example, autoimmune diseases arise when immune system cells (lymphocytes and macrophages) become sensitized against the "self." Lymphocytes as well as macrophages are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

For example, a phosphodiesterase 4 (PDE4) is involved in the cytokine production of inflammatory cells, angiogenesis, and the functional properties of other cell types such as keratinocytes, in part, through degradation of cyclic adenosine monophosphate (cAMP). cAMP is an important second messenger that regulates inflammatory responses. Accordingly, inhibitors of PDE4 may block the synthesis of several pro-inflammatory cytokines and chemokines, such as tumor necrosis factor alpha (TNF-α), interleukin-23 (IL-23), chemokine ligand 9 (CXCL9, also known as monokine induced by interferon gamma (MIG)), and chemokine ligand 10 (CXCL10, also known as interferon gamma-induced protein 10 (IP-10)) in multiple cell types, and may interfere with the production of leukotriene B4, inducible nitric oxide synthase, and matrix metalloproteinases. This interference reduces certain inflammatory processes, such as dendritic cell infiltration, epidermal skin thickening, and joint destruction, for example, in psoriasis and other inflammatory and/or autoimmune diseases such as arthritis, ankylosing spondylitis, osteoarthritis, rheumatoid arthritis, Behcet's disease, inflammatory bowel diseases (e.g., Crohn's disease and ulcerative colitis), psoriasis, atopic dermatitis, and contact dermatitis.

Psoriasis is an autoimmune skin disease caused by pro-inflammatory cytokines, interferon gamma (IFN-γ) and TNF-α. The psoriatic immune response involves monocytes, dendritic cells, neutrophils and T cells, which all contribute to aberrant keratinocyte proliferation. PDE4 inhibition may reduce production of multiple mediators, including TNF-α, IFN-γ, CXCL9, CXCL10, interleukin-2 (IL-2), interleukin-12 (IL-12), interleukin-23 (IL-23), macrophage inflammatory protein-1-alpha (MIP-1α), monocyte chemoattractant protein-1 (MCP1), and granulocyte macrophage-colony stimulating factor (GM-CSF) from PBMCs. Thus, there is a continued need for small molecule PDE4 inhibitors as an effective therapy for treating an inflammatory disease.

SUMMARY

Provided herein is a compound of Formula (I):

(I)

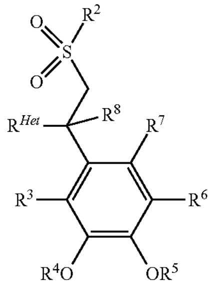

or a pharmaceutically acceptable salt thereof, wherein:

$R^{Het}$ is

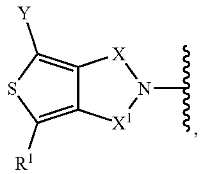

,

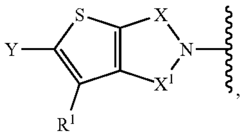

, or

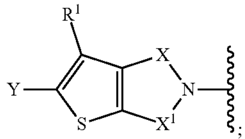

;

each of X and $X^1$ is independently $CH_2$, C═O, SO, $SO_2$, or $CH_2C(═O)$;

each Y is independently H, deuterium, halogen, or optionally substituted $C_1$-$C_6$ alkyl;

each $R^1$ is independently deuterium, hydroxyl, halogen, nitro, cyano, $—NR^9R^{10}$, $—NR^9C(═O)R^{11}$, $—NR^9SO_2R^{11}$, $—N(C(═O)R^9)(C(═O)R^{11})$, optionally substituted $C_1$-$C_6$ alkyl, optionally substituted $C_1$-$C_6$ alkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

$R^2$ is hydroxyl, —$NR^9R^{10}$, optionally substituted $C_1$-$C_6$ alkyl, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^3$, $R^6$, and $R^7$ is independently H, deuterium, halogen, optionally substituted $C_1$-$C_6$ alkyl, $C_1$-$C_6$ haloalkyl, optionally substituted $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^4$ and $R^5$ is independently optionally substituted $C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

$R^8$ is H or deuterium;

each of $R^9$ and $R^{10}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl; and $R^{11}$ is optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

provided that at least one of $R^2$, $R^4$, and $R^5$ is optionally substituted $C_3$-$C_7$ cycloalkyl.

Also provided herein is a compound of Formula (II):

$$R^W\text{-}L^2\text{-}X\text{-}L^1\text{-}R^1 \quad \text{(II)}$$

or a pharmaceutically acceptable salt thereof, wherein:

$R^1$ is

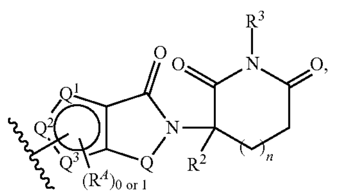

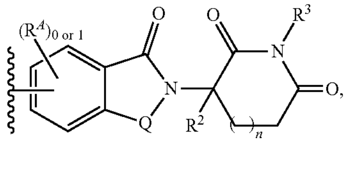

-continued

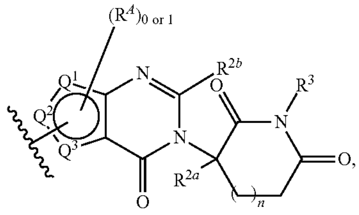

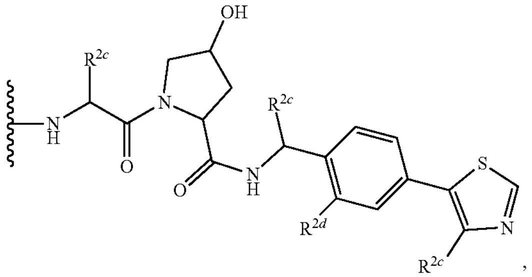

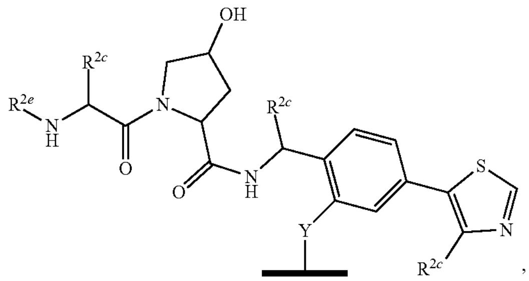

, or

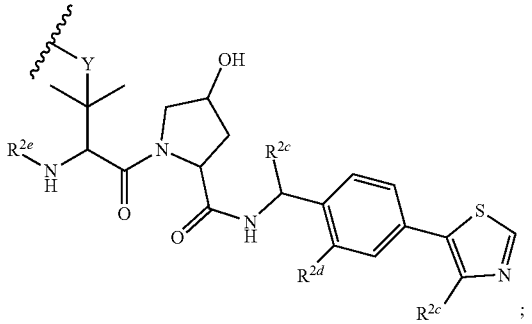

;

$R^w$ is

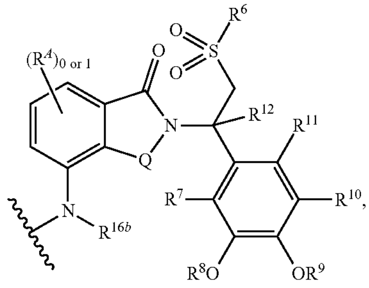

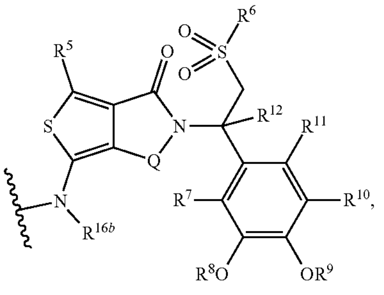

-continued
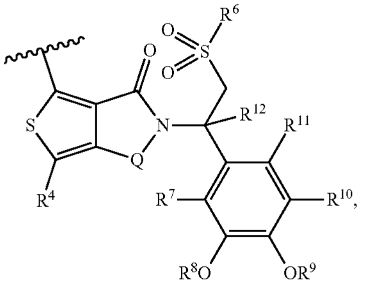
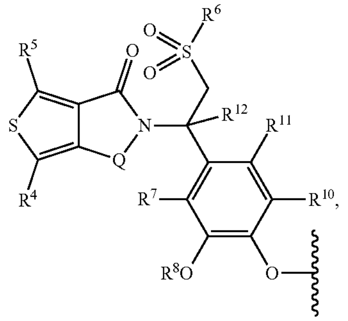
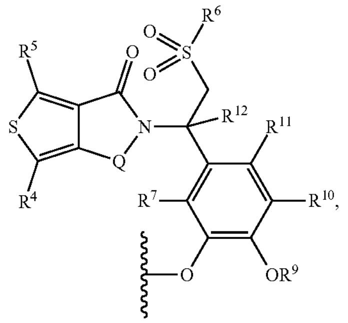
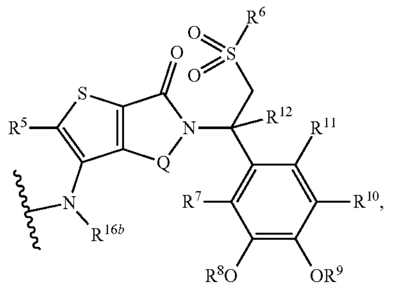
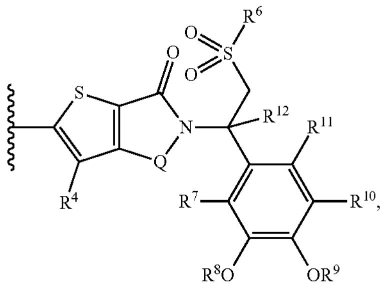
-continued
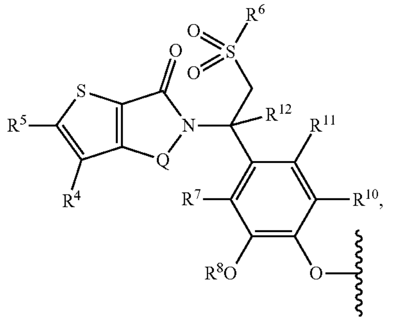
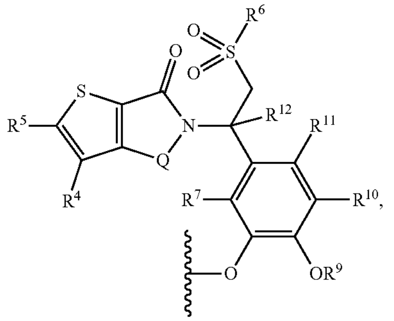
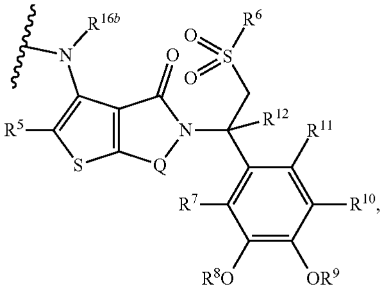
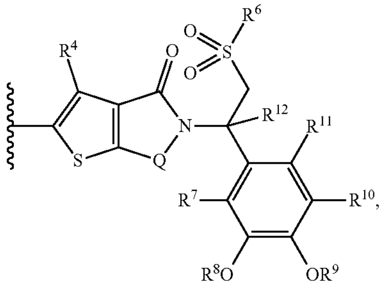
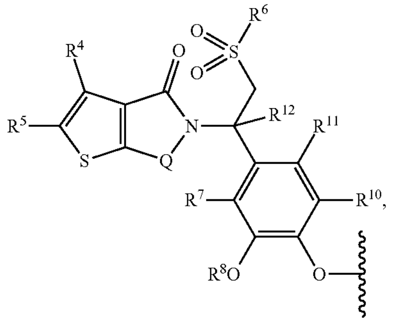

-continued

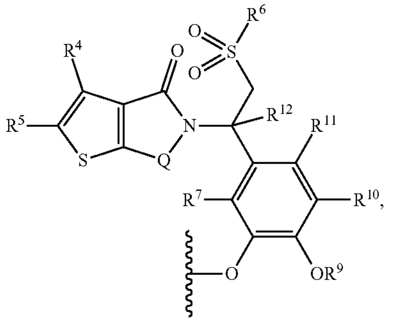

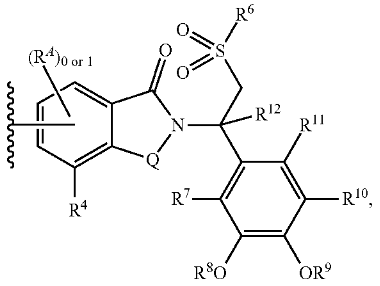

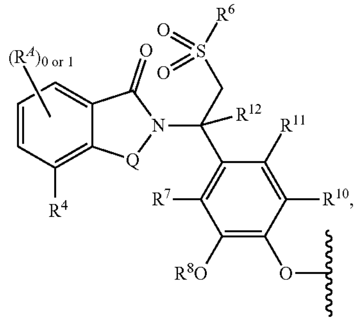

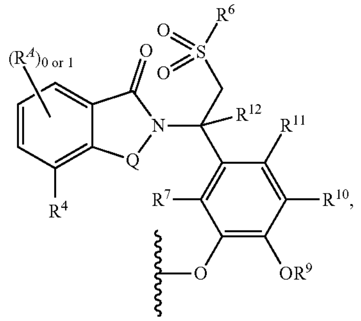

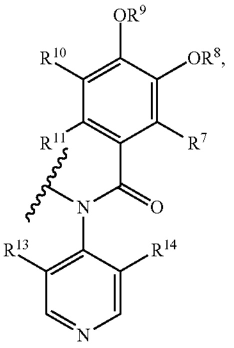

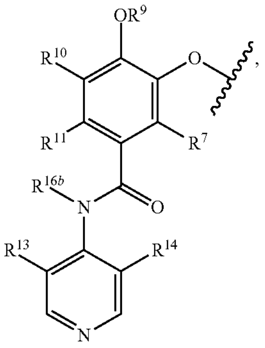

-continued

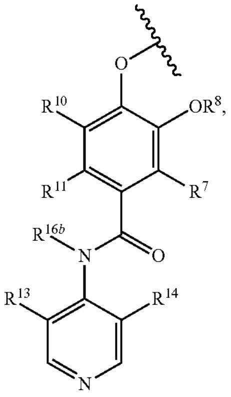

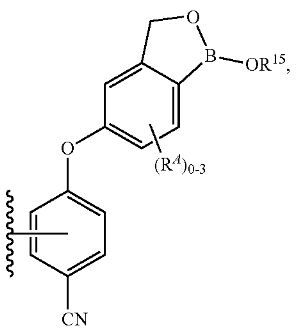

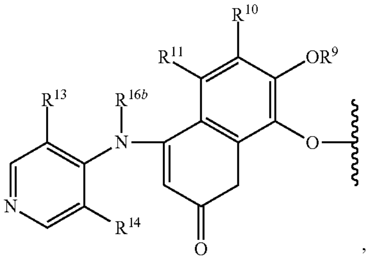

,

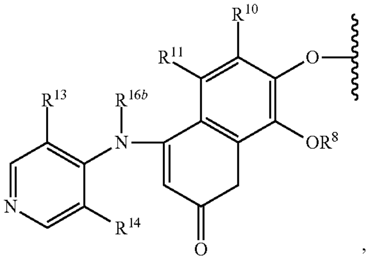

, or

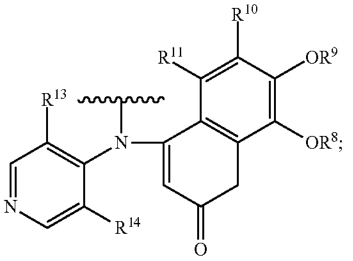

X is $C_1$-$C_{15}$ alkylene, heteroalkylene, $C_2$-$C_{10}$ alkenylene, $C_2$-$C_{10}$ alkynylene, phenylene, five to six membered heteroarylene, five to six membered heterocyclylene, or $C_3$-$C_8$ cycloalkylene, wherein each of phenylene, five to six membered heteroarylene, five to six membered heterocyclylene, or $C_3$-$C_8$ cycloalkylene is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure selected from the group consisting of phenylene, five to six membered heteroarylene, five to six membered heterocyclylene, or $C_3$-$C_8$ cycloalkylene, and wherein each ring structure is optionally substituted with one or more $R^{18}$;

each Y is independently $CH_2$, O, S, or NH;

$L^1$ is a bond,

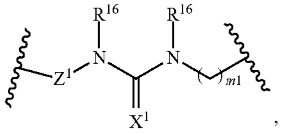

,

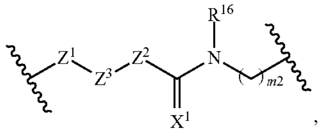

,

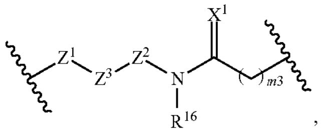

,

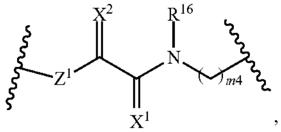

,

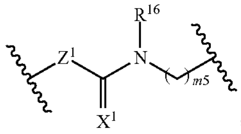

,

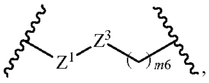

,

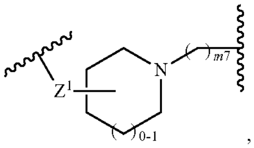

,

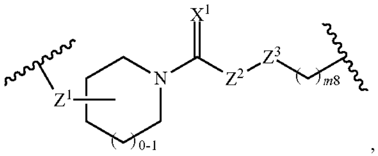

,

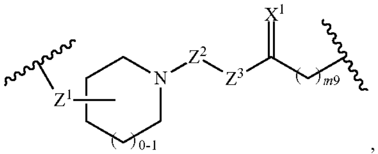

,

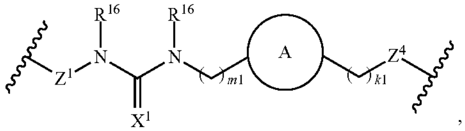

,

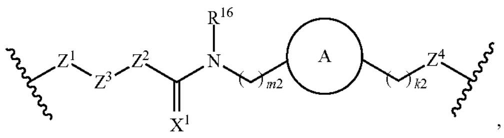

,

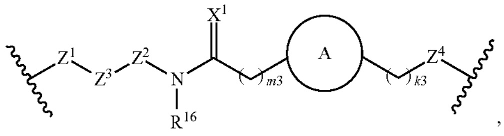

,

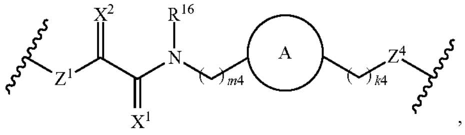

,

-continued

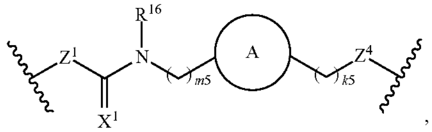

,

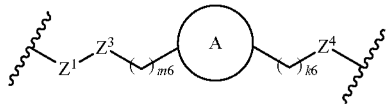

,

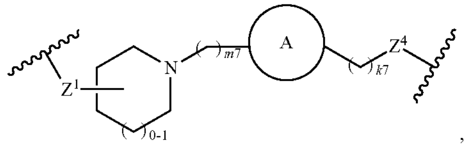

,

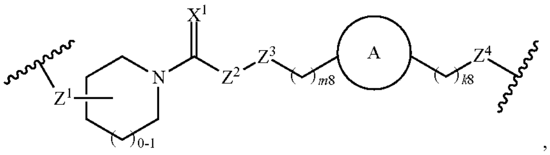

, or

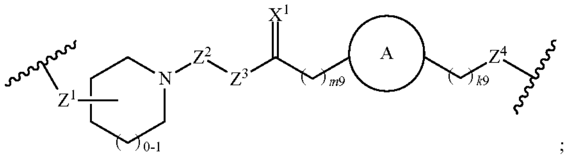

;

$L^2$ is a bond, —O—, —S—, —$NR^{16a}$—, —$(CH_2)_{1-3}$—, —C(═O)—, or —$(CH_2)_{0-3}C(═O)NR^{16a}$—;

each Q is independently $CH_2$ or C(═O);

each of $Q^1$, $Q^2$, and $Q^3$ is independently S or CH, provided that one of $Q^1$, $Q^2$, and $Q^3$ is S;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C═O)$NR^{17a}R^{17b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^2$, $R^{2a}$ and $R^{2b}$ is independently H, deuterium, halogen, or $C_1$-$C_6$ alkyl;

each $R^{2c}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$ haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein —O—$C_3$-$C_8$ cycloalkyl is optionally substituted with $C_1$-$C_6$ alkyl, halogen, or $C_1$-$C_6$ haloalkyl;

each $R^{2e}$ is independently —C(═O)—$C_1$-$C_6$ alkyl or —C(═O)—$C_3$-$C_8$ cycloalkyl, each optionally substituted with one or more substituents, each of which is independently selected from the group consisting of cyano, halogen, hydroxyl, amino, and $C_1$-$C_6$ haloalkyl;

each $R^3$ is independently H, deuterium, $C_1$-$C_6$ alkyl,

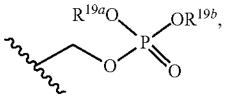 or 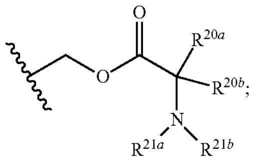

each $R^4$ is independently $—NR^{4A}R^{4B}$, $—NR^{4A}C(=O)R^{4C}$, $—NR^{4A}SO_2R^{4C}$, or $—N(C(=O)R^{4A})(C(=O)R^{4C})$.

each of $R^{4A}$ and $R^{4B}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl;

each $R^{4C}$ is independently $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^5$ is independently H, deuterium, halogen, or optionally substituted $C_1$-$C_6$ alkyl;

each $R^6$ is independently hydroxyl, $—NR^{4A}R^{4B}$, $C_1$-$C_6$ alkyl, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^7$, $R^{10}$, and $R^{11}$ is independently H, deuterium, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^8$ and $R^9$ is independently optionally substituted $C_1$-$C_6$ alkyl, $C_1$-$C_6$ haloalkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^{12}$ is independently H or deuterium;

each of $R^{13}$ and $R^{14}$ is independently halogen, hydroxyl, cyano, nitro, optionally substituted $C_1$-$C_6$ alkyl, $C_1$-$C_6$ haloalkyl, $C_1$-$C_6$ alkoxy, $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{15}$, $R^{16}$, $R^{16a}$, and $R^{16b}$ is independently H or $C_1$-$C_6$ alkyl;

each $R^{17a}$ and $R^{17b}$ is independently H or $C_1$-$C_6$ alkyl, or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of $X^1$ and $X^2$ is independently O or S;

each $Z^1$ is independently a bond, $—(CR^aR^b)_{q1}—$, —C(=O)—, —CH=CH—, or —C≡C—;

each $Z^2$ is independently $—(CR^cR^d)_{q2}—$;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each Ring A is independently phenylene, five to six membered heteroarylene, five to six membered heterocyclylene, or $C_3$-$C_8$ cycloalkylene, each optionally substituted with one or more $R^{18}$;

each of m1, m2, m3, m4, m5, m6, m7, m8, m9, k1, k2, k3, k4, k5, k6, k7, k8, and k9 is independently an integer of 0, 1, 2, 3, 4, or 5;

each n is independently an integer of 0, 1, or 2; and each q1 and q2 is independently an integer of 1, 2, or 3.

Additionally, provided herein is a pharmaceutical composition comprising a compound of Formula (I) or (II), or a pharmaceutically acceptable salt thereof, and a pharmaceutically acceptable excipient.

Furthermore, provided herein is a method of treating, preventing, or ameliorating one or more symptoms of a disease, disorder, or condition associated with a PDE4 in a subject, comprising administering to the subject in need thereof a therapeutically effective amount of a compound of Formula (I) or (II), or a pharmaceutically acceptable salt thereof.

Provided herein is a method of treating, preventing, or ameliorating one or more symptoms of an inflammatory disease in a subject, comprising administering to the subject in need thereof a therapeutically effective amount of a compound of Formula (I) or (II), or a pharmaceutically acceptable salt thereof.

Provided herein is a method of treating, preventing, or ameliorating one or more symptoms of psoriasis, psoriatic arthritis, or atopic dermatitis in a subject, comprising administering to the subject in need thereof a therapeutically effective amount of a compound of Formula (I) or (II), or a pharmaceutically acceptable salt thereof.

Provided herein is a method of inhibiting the activity of a phosphodiesterase 4 (PDE4), comprising contacting the PDE4 with an effective amount of a compound of Formula (I) or (II), or a pharmaceutically acceptable salt thereof.

DETAILED DESCRIPTION

Unless defined otherwise, all technical and scientific terms used herein have the same meanings as are commonly understood by one of ordinary skill in the art. In the event that there are a plurality of definitions for a term herein, those in this section prevail unless stated otherwise. As used in the specification and the appended claims, the singular forms "a," "an," and "the" include plural referents unless the context clearly dictates otherwise. Unless otherwise indicated, conventional methods of mass spectroscopy, NMR, HPLC, protein chemistry, biochemistry, recombinant DNA techniques, and pharmacology are employed. The use of "or" or "and" means "and/or" unless stated otherwise. Furthermore, use of the term "including" as well as other forms, such as "include," "includes," and "included," is not limiting.

Unless otherwise defined, all terms (including technical and scientific terms) are to be given their ordinary and customary meaning to a person of ordinary skill in the art and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, any "R" group(s) represent substituents that can be attached to the indicated atom. An R group may be substituted or unsubstituted. If two "R" groups are described as being "taken together," the R groups and the atoms they are attached to can form cycloalkyl, aryl, heteroaryl, or heterocyclyl. For example, without limitation, if $R^a$ and $R^b$, and the atom to which they are attached, are indicated to be "taken together" or "joined together," it means that they are covalently bonded to one another to form a ring.

Whenever a group is described as being "optionally substituted," that group may be unsubstituted or substituted with one or more of the substituents specified. Likewise, when a group is described as being "substituted," the substituent may be selected from one or more of the substituents specified. If no substituents are specified, it is meant that the "optionally substituted" or "substituted" group may be substituted with one or more groups, each of which is individually and independently alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (e.g., $C_3$-$C_8$ cycloalkyl, $C_3$-$C_8$ cycloalkenyl, or $C_3$-$C_8$ cycloalkynyl, each further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); aryl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (further optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, or —O($C_1$-$C_6$ alkoxy)$C_1$-$C_6$ alkyl); (5-10 membered heteroaryl)$C_1$-$C_6$ alkyl (further optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, or iodo); cyano; hydroxyl; protected hydroxyl; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy, such as —$OCF_3$); ($C_1$-$C_6$ alkoxy)$C_1$-$C_6$ alkyl; —O($C_1$-$C_6$ alkoxy) $C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino; mono-substituted amino (e.g., NH($C_1$-$C_6$ alkyl); di-substituted amino (e.g., N($C_1$-$C_6$ alkyl)$_2$); oxo (=O); or thioxo (=S).

As used herein, the term "$C_a$ to $C_b$," in which "a" and "b" are each an integer, refers to, for example, the number of carbon atoms in an alkyl, alkenyl, or alkynyl group, or the number of ring atoms of a cycloalkyl, aryl, heteroaryl, or heterocyclyl group. That is, the alkyl, the ring of the cycloalkyl, or the ring of the aryl, contains from "a" to "b," inclusive, carbon atoms. Likewise, the ring of the heteroaryl or the ring of the heterocyclyl contains from "a" to "b," inclusive, total ring atoms. Thus, for example, a "$C_1$ to $C_4$ alkyl" group refers to all alkyl groups having from 1 to 4 carbons, e.g., —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, and —C($CH_3$)$_3$; a $C_3$ to $C_4$ cycloalkyl group refers to all cycloalkyl groups having from 3 to 4 carbon atoms, e.g., cyclopropyl and cyclobutyl. Similarly, a "4 to 6 membered heterocyclyl" group refers to all heterocyclyl groups with 4 to 6 total ring atoms, e.g., azetidinyl, oxetanyl, oxazolinyl, pyrrolidinyl, piperidinyl, piperazinyl, and morpholinyl. If no "a" and "b" are designated with regard to an alkyl, cycloalkyl, aryl, heteroaryl, or heterocyclyl group, the broadest range described in these definitions is to be assumed. As used herein, the term "$C_1$-$C_6$" includes $C_1$, $C_2$, $C_3$, $C_4$, $C_5$, and $C_6$, and a range defined by any of the two numbers. For example, $C_1$-$C_6$ alkyl includes $C_1$, $C_2$, $C_3$, $C_4$, $C_5$, and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7, and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group can have 1 to 20 carbon atoms (whenever it appears herein, a numerical range such as "1 to 20" refers to each integer in the given range; e.g., "1 to 20 carbon atoms" means that the alkyl group can consist of 1 carbon atom, 2 carbon atoms, 3 carbon atoms, etc., up to and including 20 carbon atoms, although the present definition also covers the occurrence of the term "alkyl" where no numerical range is designated). The alkyl group can be a medium size alkyl having 1 to 10 carbon atoms. The alkyl group can be a lower alkyl having 1 to 6 carbon atoms. By way of example only, "$C_1$-$C_4$ alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Exemplary alkyl groups include, but are not limited to, methyl, ethyl, n-propyl, isopropyl, butyl, isobutyl, tertiary butyl, pentyl (straight chain or branched), and hexyl (straight chain or branched). The alkyl group can be substituted or unsubstituted.

As used herein, "alkenyl" refers to a straight or branched hydrocarbon chain containing one or more double bonds. The alkenyl group can have 2 to 20 carbon atoms. By way of example only, "$C_2$-$C_6$ alkenyl" indicates that there are two to six carbon atoms in the alkenyl chain, e.g., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Exemplary alkenyl groups include, but are not limited to, ethenyl, propenyl, butenyl, pentenyl, and hexenyl. The alkenyl group can be substituted or unsubstituted.

As used herein, "alkynyl" refers to a straight or branched hydrocarbon chain containing one or more triple bonds. The alkynyl group can have 2 to 20 carbon atoms. By way of example only, "$C_2$-$C_6$ alkynyl" indicates that there are two to six carbon atoms in the alkynyl chain, e.g., the alkynyl chain is selected from the group consisting of ethynyl, propyn-1-yl, propyn-2-yl, butyn-1-yl, butyn-3-yl, butyn-4-yl, and 2-butynyl. Exemplary alkynyl groups include, but are not limited to, ethynyl, propynyl, butynyl, pentynyl, and hexynyl. The alkynyl group can be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged, or spiro fashion. As used herein, the term "fused" refers to two rings that have two atoms and one bond in common. As used herein, the term "bridged" refers to a cycloalkyl that contains a linkage of one or more atoms connecting non-adjacent atoms. As used herein, the term "spiro" refers to two rings that have one atom in common and the two rings are not linked by a bridge. A cycloalkyl group can contain 3 to 10 atoms in the ring(s), 3 to 8 atoms in the ring(s), or 3 to 6 atoms in the ring(s). A cycloalkyl group can be unsubstituted or substituted. Examples of monocyclic cycloalkyl groups include, but are not limited to, cyclopropyl, cyclobutyl, cyclopentyl, cyclohexyl, cycloheptyl, and cyclooctyl. Examples of bicyclic fused cycloalkyl groups include, but are not limited to, decahydronaphthalenyl, dodecahydro-1H-phenalenyl, and tetradecahydroanthracenyl. Examples of bicyclic bridged cycloalkyl groups include, but are not limited to, bicyclo[1.1.1]pentyl, adamantanyl, and norbornenyl. Examples of bicyclic spiro cycloalkyl groups include, but are not limited to, spiro[3.3]heptanyl and spiro[4.5]decanyl.

As used herein, "carbocyclyl" refers to a non-aromatic mono- or multi-cyclic hydrocarbon ring system. When composed of two or more rings, the rings may be joined together in a fused, bridged, or spiro fashion. A carbocyclyl group can contain 3 to 30 atoms in the ring(s), 3 to 20 atoms in the ring(s), 3 to 10 atoms in the ring(s), 3 to 8 atoms in the ring(s), or 3 to 6 atoms in the ring(s). A carbocyclyl group can be unsubstituted or substituted. Examples of carbocyclyl groups include, but are not limited to, cycloalkyl groups, and the non-aromatic portions of 1,2,3,4-tetrahydronaphthyl, 2,3-dihydro-1H-indenyl, 5,6,7,8-tetrahydroquinolinyl, and 6,7-dihydro-5H-cyclopenta[b]pyridinyl.

As used herein, "aryl" refers to a carbocyclic (all carbon) monocyclic or multicyclic aromatic ring system (including fused ring systems where two carbocyclic rings share a chemical bond). For example, the aryl group can be a $C_6$ aryl group or a $C_{10}$ aryl group. Examples of aryl groups include, but are not limited to, phenyl and naphthyl. An aryl group can be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2, or 3 heteroatoms), that is, an element other than carbon, including, but not limited to, nitrogen, oxygen, and sulfur. For example, the heteroaryl group can contain 5 to 10 atoms in the ring(s), 6 to 10 atoms in the ring(s), or 5 to 6 atoms in the ring(s); such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems, where two rings, such as at least one aryl ring and at least one heteroaryl ring, or at least two heteroaryl rings, share at least one chemical bond. Examples of heteroaryl rings include, but are not limited to, furanyl, furazanyl, thiophenyl, benzothiophenyl, phthalazinyl, pyrrolyl, oxazolyl, benzoxazolyl, 1,2,3-oxadiazolyl, 1,2,4-oxadiazolyl, thiazolyl, 1,2,3-thiadiazolyl, 1,2,4-thiadiazolyl, benzothiazolyl, imidazolyl, benzimidazolyl, indolyl, indazolyl, pyrazolyl, benzopyrazolyl, isoxazolyl, benzoisoxazolyl, isothiazolyl, triazolyl, benzotriazolyl, thiadiazolyl, tetrazolyl, pyridinyl, pyridazinyl, pyrimidinyl, pyrazinyl, purinyl, pteridinyl, quinolinyl, isoquinolinyl, quinazolinyl, quinoxalinyl, cinnolinyl, and triazinyl. A heteroaryl group can be substituted or unsubstituted.

As used herein, "heterocyclyl" refers to a three-, four-, five-, six-, seven-, eight-, nine-, or ten-membered monocyclic, bicyclic, or tricyclic ring system, wherein carbon atoms together with from 1 to 5 heteroatoms constitute the ring system. A heterocyclyl group may optionally contain one or more unsaturated bonds situated in such a way, however, that a fully delocalized pi-electron system does not occur throughout all the rings (i.e., heterocyclyl groups are not aromatic). The heteroatom(s) is an element other than carbon, including, but not limited to, oxygen, sulfur, and nitrogen. A heterocyclyl group can further contain one or more carbonyl functionalities so as to make the definition to include oxo-systems such as lactams, lactones, and cyclic carbamates. When composed of two or more rings, the rings can be joined together in a fused, bridged, or spiro fashion. As used herein, the term "fused" refers to two rings that have two atoms and one bond in common. As used herein, the term "bridged heterocyclyl" refers to a heterocyclyl that contains a linkage of one or more atoms connecting non-adjacent atoms. As used herein, the term "spiro" refers to two rings that have one atom in common and the two rings are not linked by a bridge. A heterocyclyl group can contain 3 to 10 atoms in the ring(s), 3 to 8 atoms in the ring(s), 3 to 6 atoms in the ring(s), or 5 to 6 atoms in the ring(s); for example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group can be quaternized. A heterocyclyl group can be linked to the rest of a molecule via a carbon atom in the heterocyclyl group (C-linked) or via a heteroatom in the heterocyclyl group, such as a nitrogen atom (N-linked). Heterocyclyl groups can be unsubstituted or substituted. Examples of heterocyclyl groups include, but are not limited to, aziridinyl, oxiranyl, thiiranyl, azetidinyl, oxetanyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, barbituryl, thiobarbituryl, dioxopiperazinyl, hydantoinyl, dihydrouracyl, trioxanyl, hexahydro-1,3,5-triazinyl, imidazolinyl, imidazolidinyl, isoxazolinyl, isoxazolidinyl, oxazolinyl, oxazolidinyl, oxazolidinonyl, thiazolinyl, thiazolidinyl, morpholinyl, oxiranyl, N-oxypiperidinyl, piperidinyl, piperazinyl, pyrrolidinyl, azepanyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, thiamorpholinyl, benzimidazolidinonyl, tetrahydroquinolinyl, and 3,4-methylenedioxyphenyl. Examples of spiro heterocyclyl groups include, but are not limited to, 2-azaspiro[3.3]heptanyl, 2-oxaspiro[3.3]heptanyl, 2-oxa-6-azaspiro[3.3]heptanyl, 2,6-diazaspiro[3.3]heptanyl, 2-oxaspiro[3.4]octanyl, and 2-azaspiro[3.4]octanyl.

As used herein, "alkylene" refers to a branched or straight chain fully saturated di-radical hydrocarbon group, which is attached to the rest of a molecule via two points of attachment. By way of example only, "$C_1$-$C_{10}$ alkylene" indicates that there are one to ten carbon atoms in the alkylene chain. Non-limiting examples include ethylene ($—CH_2CH_2—$), propylene ($—CH_2CH_2CH_2—$), butylene ($—CH_2CH_2CH_2CH_2—$), and pentylene ($—CH_2CH_2CH_2CH_2CH_2—$).

As used herein, "alkenylene" refers to a straight or branched chain di-radical hydrocarbon group containing at least one carbon-carbon double bond, which is attached to the rest of a molecule via two points of attachment. By way of example only, "$C_2$-$C_{10}$ alkenylene" indicates that there are two to ten carbon atoms in the alkenylene chain.

As used herein, "alkynylene" refers to a straight or branched chain di-radical hydrocarbon group containing at least one carbon-carbon triple bond, which is attached to the rest of a molecule via two points of attachment. By way of example only, "$C_2$-$C_{10}$ alkynylene" indicates that there are two to ten carbon atoms in the alkynylene chain.

As used herein, "heteroalkylene" refers to an alkylene group as defined herein that contains one or more heteroatoms in the carbon backbone (i.e., an alkylene group in which one or more carbon atoms is replaced with a heteroatom, for example, a nitrogen atom, oxygen atom, or sulfur atom). Heteroalkylene groups include, but are not limited to, ether, thioether, amino-alkylene, and alkylene-amino-alkylene moieties.

As used herein, "aralkyl" and "(aryl)alkyl" refer to an aryl group as defined herein, connected, as a substituent, via an alkylene group as defined herein. The alkylene and aryl groups of an aralkyl can each be independently substituted or unsubstituted. Examples include, but are not limited to, benzyl, 2-phenylalkyl, 3-phenylalkyl, and naphthylalkyl.

As used herein, "heteroaralkyl" and "(heteroaryl)alkyl" refer to a heteroaryl group as defined herein, connected, as a substituent, via an alkylene group as defined herein. The alkylene and heteroaryl groups of heteroaralkyl can each be independently substituted or unsubstituted. Examples include, but are not limited to 2-thienylalkyl, 3-thienylalkyl, furylalkyl, thienylalkyl, pyrrolylalkyl, pyridylalkyl, isoxazolylalkyl, and imidazolylalkyl.

As used herein, "(heterocyclyl)alkyl" refer to a heterocyclic or heterocyclyl group as defined herein, connected, as a substituent, via an alkylene group as defined herein. The alkylene and heterocyclyl groups of (heterocyclyl)alkyl can each be independently substituted or unsubstituted. Examples include, but are not limited to, (tetrahydro-2H-pyran-4-yl)methyl, (piperidin-4-yl)ethyl, (piperidin-4-yl) propyl, (tetrahydro-2H-thiopyran-4-yl)methyl, and (1,3-thiazinan-4-yl)methyl.

As used herein, "cycloalkylalkyl" and "(cycloalkyl)alkyl" refer to a cycloalkyl group as defined herein, connected, as a substituent, via an alkylene group. The alkylene and cycloalkyl groups of (cycloalkyl)alkyl can each be independently substituted or unsubstituted. Examples include, but are not limited to, cyclopropylmethyl, cyclobutylmethyl, cyclopentylethyl, and cyclohexylpropyl.

As used herein, "alkoxy" refers to the formula —OR, wherein R is an alkyl group as defined herein. Examples include, but are not limited to, methoxy, ethoxy, n-propoxy, 1-methylethoxy (isopropoxy), n-butoxy, isobutoxy, sec-butoxy, and tert-butoxy. An alkoxy can be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Examples include, but are not limited to, chloromethyl, fluoromethyl, difluoromethyl, trifluoromethyl, 1-chloro-2-fluoromethyl, and 2-fluoroisobutyl. A haloalkyl can be substituted or unsubstituted.

As used herein, "haloalkoxy" refers to an alkoxy group in which one or more of the hydrogen atoms are replaced by a halogen (e.g., mono-haloalkoxy, di-haloalkoxy, and tri-haloalkoxy). Examples include, but are not limited to, chloromethoxy, fluoromethoxy, difluoromethoxy, trifluoromethoxy, 1-chloro-2-fluoromethoxy, and 2-fluoroisobutoxy. A haloalkoxy can be substituted or unsubstituted.

As used herein, "amino" refer to an $—NH_2$ group. The term "mono-substituted amino group" as used herein refers to an amino ($—NH_2$) group, where one of the hydrogen atom is replaced by a substituent. The term "di-substituted amino group" as used herein refers to an amino ($—NH_2$) group, where each of the two hydrogen atoms is independently replaced by a substituent. The term "optionally substituted amino" as used herein refer to an $—NR_AR_B$ group, where $R_A$ and $R_B$ are each independently hydrogen, alkyl, cycloalkyl, aryl, heteroaryl, heterocyclyl, aralkyl, or heterocyclyl(alkyl), each as defined herein.

As used herein, "alkylamino" or "(alkyl)amino" refers to a $—NR_AR_B$ group, where $R_A$ is hydrogen or alkyl and $R_B$ is alkyl. Examples of alkylamino groups include, but are not limited to, methylamino (—NHMe), ethylamino (—NHEt), dimethylamino ($—N(Me)_2$), methylethylamino (—N(Me)(Et)), and isopropylamino (—NHiPr).

As used herein, "aminoalkyl" or "(amino)alkyl" refers to an alkyl group in which one or more of the hydrogen atoms are replaced by an amino group or "$—NR_AR_B$" group as defined herein. Examples of aminoalkyl groups include, but are not limited to, —$(CH_2)_{1-4}NH_2$, —$(CH_2)_{1-4}$—$NHCH_3$, —$(CH_2)_{1-4}$—$NHC_2H_5$, —$(CH_2)_{1-4}$—$N(CH_3)_2$, —$(CH_2)_{1-4}$—$N(C_2H_5)_2$, —$(CH_2)_{1-4}$—NH—$CH(CH_3)_2$, —$(CH_2)_{1-4}N(CH_3)C_2H_5$, and —$CH(NH_2)CH_3$.

The term "halogen atom" or "halogen" as used herein refers to fluorine, chlorine, bromine, or iodine.

As used herein, "alkoxyalkyl" or "(alkoxy)alkyl" refers to an alkoxy group connected via an alkylene group, such as $C_2$-$C_8$ alkoxyalkyl or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to —OR and —SR, respectively, wherein R is an aryl as defined herein, e.g., phenyl. An aryloxy and arylthio can each be independently substituted or unsubstituted.

A "sulfenyl" group refers to an "—SR" group in which R is hydrogen, alkyl, alkenyl, alkynyl, carbocyclyl, aryl, heteroaryl, heterocyclyl, aralkyl, or heterocyclyl(alkyl), each as defined herein. A sulfenyl can be substituted or unsubstituted.

A "sulfinyl" group refers to an "—S(═O)R" group in which R is hydrogen, alkyl, alkenyl, alkynyl, carbocyclyl, aryl, heteroaryl, heterocyclyl, aralkyl, or heterocyclyl(alkyl), each as defined herein. A sulfinyl can be substituted or unsubstituted.

A "sulfonyl" group refers to an "—$SO_2R$" group in which R is hydrogen, alkyl, alkenyl, alkynyl, carbocyclyl, aryl, heteroaryl, heterocyclyl, aralkyl, or heterocyclyl(alkyl), each as defined herein. A sulfonyl can be substituted or unsubstituted.

An "O-carboxy" group refers to an "—OC(═O)R" group in which R is hydrogen, alkyl, alkenyl, alkynyl, carbocyclyl, aryl, heteroaryl, heterocyclyl, aralkyl, or heterocyclyl(alkyl), each as defined herein. An O-carboxy can be substituted or unsubstituted.

The terms "ester" and "C-carboxy" refer to a "—C(═O)OR" group in which R is hydrogen, alkyl, alkenyl, alkynyl, carbocyclyl, aryl, heteroaryl, heterocyclyl, aralkyl, or heterocyclyl(alkyl), each as defined herein. An ester or C-carboxy can be substituted or unsubstituted.

A "trihalomethanesulfonyl" group refers to an "—$O_2SCX'_3$" group, wherein X' is a halogen.

A "trihalomethanesulfonamido" group refers to an "—N(R)$S(O)_2CX'_3$" group, wherein X' is a halogen and R is hydrogen, alkyl, alkenyl, alkynyl, carbocyclyl, aryl, heteroaryl, heterocyclyl, aralkyl, or heterocyclyl(alkyl), each as defined herein.

A "mercapto" group refers to an "—SH" group.

An "S-sulfonamido" group refers to an "—$SO_2N(R_AR_B)$" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An S-sulfonamido can be substituted or unsubstituted.

An "N-sulfonamido" group refers to an "—$N(R_A)SO_2R$" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-sulfonamido can be substituted or unsubstituted.

An "O-carbamyl" group refers to an "—OC(═O)N($R_AR_B$)" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An O-carbamyl can be substituted or unsubstituted.

An "N-carbamyl" group refers to an "—N($R_A$)C(═O)OR" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-carbamyl can be substituted or unsubstituted.

An "O-thiocarbamyl" group refers to an "—OC(═S)N($R_AR_B$)" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. An O-thiocarbamyl can be substituted or unsubstituted.

An "N-thiocarbamyl" group refers to an "—N($R_A$)C(═S)OR" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-thiocarbamyl can be substituted or unsubstituted.

A "C-amido" group refers to a "—C(═O)N($R_AR_B$)" group in which $R_A$ and $R_B$ can each be independently hydrogen, alkyl, alkenyl, alkynyl, carbocyclyl, aryl, heteroaryl, heterocyclyl, aralkyl, or heterocyclyl(alkyl), each as defined herein. A C-amido can be substituted or unsubstituted.

An "N-amido" group refers to an "—N($R_A$)C(═O)R" group in which R and $R_A$ can each be independently hydrogen, alkyl, alkenyl, alkynyl, carbocyclyl, aryl, heteroaryl, heterocyclyl, aralkyl, or heterocyclyl(alkyl), each as defined herein. An N-amido can be substituted or unsubstituted.

Where the number of substituents is not specified (e.g., haloalkyl), there can be one or more substituents present. For example, "haloalkyl" can include one or more of the same or different halogens.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

It is understood that, in any compound described herein having one or more chiral centers, if an absolute stereochemistry is not expressly indicated, then each center may independently be of R-configuration or S-configuration or a mixture thereof. Thus, the compounds provided herein can be enantiomerically pure or enantiomerically enriched, or can be stereoisomeric mixtures, and include all diastereomeric and enantiomeric forms. In addition, it is understood that, in any compound described herein having one or more double bond(s) generating geometrical isomers that can be defined as E or Z, each double bond can independently be E or Z or a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of a molecule), it is to be understood that the substituent can be attached in any directional configuration unless otherwise indicated. For example, unless a particular orientation is specified, the formula -AE- represents both -AE- and -EA-. In addition, if a group or substituent is depicted as

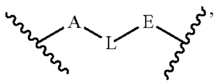

and when L is defined as a bond or absent; such group or substituent is equivalent to

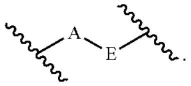

In addition, when a group is depicted as a di-radical, such as X or ring A in Formula (II), one of ordinary skill in the art understands that the definition of such a group should also be di-radical. For example, when X is defined as phenyl, 5 to 6 membered heteroaryl, 5 to 6 membered heterocyclyl, or $C_3$-$C_8$ cycloalkyl, one skilled in the art understands that X is a phenylene, 5 to 6 membered heteroarylene, 5 to 6 membered heterocyclylene, or $C_3$-$C_8$ cycloalkylene.

It is to be understood that, where a compound disclosed herein has an unfilled valency, the valency is to be filled with hydrogen or deuterium.

It is understood that the compounds described herein can be labeled isotopically or by another other means, including, but not limited to, the use of chromophores or fluorescent moieties, bioluminescent labels, or chemiluminescent labels. Substitution with isotopes such as deuterium can afford certain therapeutic advantages from greater metabolic stability, such as, for example, increased in vivo half-life or reduced dosage requirements. Each chemical element as represented in a compound structure may include any isotope of said element. For example, in a compound structure, a hydrogen atom may be explicitly disclosed or understood to be present in the compound. At any position of the compound that a hydrogen atom may be present, the hydrogen atom can be any isotope of hydrogen, including, but not limited to, hydrogen-1 (protium), hydrogen-2 (deuterium), and hydrogen-3 (tritium). Thus, a reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of the compounds provided herein, as well as metabolites and active metabolites of these compounds having the same type of activity. A conformer is a structure that is a conformational isomer. Conformational isomerism is the phenomenon of a molecule with the same structural formula but different conformations (conformers) of atoms about a rotating bond. In certain embodiments, the compounds described herein exist in solvated forms with pharmaceutically acceptable solvents such as water or ethanol. In certain embodiments, the compounds provided herein exist in unsolvated form. Solvates contain either stoichiometric or non-stoichiometric amounts of a solvent and may be formed during the process of crystallization with pharmaceutically acceptable solvents such as water or ethanol. Hydrates are formed when the solvent is water, or alcoholates are formed when the solvent is alcohol. In addition, the compounds provided herein can exist in unsolvated as well as solvated forms. Other forms in which the compounds provided herein can be provided include amorphous forms, milled forms, and nano-particulate forms.

Likewise, it is understood that a compound described herein include the compound in any of the forms described herein (e.g., pharmaceutically acceptable salts, crystalline forms, amorphous form, solvated forms, enantiomeric forms, and tautomeric forms).

As used herein, the abbreviations for any protective groups, amino acids, and other compounds are, unless indicated otherwise, in accord with their common usage, recognized abbreviations, or the IUPAC-IUB Commission on Biochemical Nomenclature (See, *Eur. J. Biochem.* 1992, 204, 1-3).

The term "protecting group" as used herein refer to any atom or group of atoms that is added to a molecule in order to prevent existing groups in the molecule from undergoing unwanted chemical reactions. Examples of protecting group moieties are described in Greene and Wuts, *Protective Groups in Organic Synthesis,* 3rd. Ed. John Wiley & Sons, 1999; and in McOmie, *Protective Groups in Organic Chemistry*, Plenum Press, 1973; each of which is hereby incorporated by reference for the limited purpose of disclosing suitable protecting groups. The protecting group moiety may be chosen in such a way that they are stable to certain reaction conditions and readily removed at a convenient stage using methodology known in the art.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and a biological molecule (e.g., a protein, enzyme, RNA, or DNA), cell, or tissue such that a physiological and/or chemical effect takes place as a result of such contact. Contacting can take place in vitro, ex vivo, or in vivo. In one embodiment, a therapeutic agent is contacted with a biological molecule in vitro to determine the effect of the therapeutic agent on the biological molecule. In another embodiment, a therapeutic agent is contacted with a cell in cell culture (in vitro) to determine the effect of the therapeutic agent on the cell. In yet another embodiment, the contacting of a therapeutic agent with a biological molecule, cell, or tissue includes the administration of a therapeutic agent to a subject having the biological molecule, cell, or tissue to be contacted.

The term “therapeutically effective amount” or “effective amount” is meant to include the amount of a compound that, when administered, is sufficient to prevent development of, or alleviate to some extent, one or more of the symptoms of the disorder, disease, or condition being treated. The term “therapeutically effective amount” or “effective amount” also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term “$IC_{50}$” or “$EC_{50}$” refers to an amount, concentration, or dosage of a compound that is required for 50% inhibition of a maximal response in an assay that measures such a response.

The term “pharmaceutically acceptable carrier,” “pharmaceutically acceptable excipient,” “physiologically acceptable carrier,” or “physiologically acceptable excipient” refers to a pharmaceutically acceptable material, composition, or vehicle, such as a liquid or solid filler, diluent, solvent, or encapsulating material. In one embodiment, each component is “pharmaceutically acceptable” in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, and commensurate with a reasonable benefit/risk ratio. See, e.g., *Remington: The Science and Practice of Pharmacy,* 22nd ed.; Allen Ed.; Pharmaceutical Press: London, 2012; *Handbook of Pharmaceutical Excipients,* 8th ed.; Sheskey et al., Eds.; Pharmaceutical Press: London, 2017; *Handbook of Pharmaceutical Additives,* 3rd ed.; Ash and Ash Eds.; Synapse Information Resources: 2007; *Pharmaceutical Preformulation and Formulation,* 2nd ed.; Gibson Ed.; Drugs and the Pharmaceutical Sciences 199; Informa Healthcare: New York, NY., 2009.

The term “about” or “approximately” means an acceptable error for a particular value as determined by one of ordinary skill in the art, which depends in part on how the value is measured or determined. In certain embodiments, the term “about” or “approximately” means within 1, 2, or 3 standard deviations. In certain embodiments, the term “about” or “approximately” means within 25%, 20%, 15%, 10%, 9%, 8%, 7%, 6%, 5%, 4%, 3%, 2%, 1%, 0.5%, or 0.05% of a given value or range.

Compounds of Formula (I)

In one embodiment, provided herein is a compound of Formula (I):

(I)

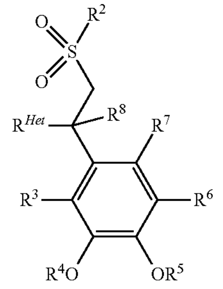

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{Het}$ is

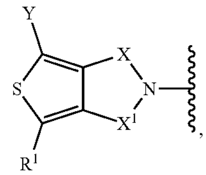

,

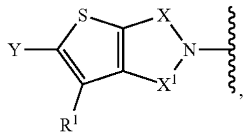

, or

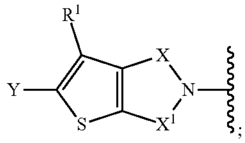

;

each of X and $X^1$ is independently $CH_2$, C(=O), SO, $SO_2$, or $CH_2C(=O)$;

each Y is independently H, deuterium, halogen, or optionally substituted $C_1$-$C_6$ alkyl;

each $R^1$ is independently deuterium, hydroxyl, halogen, nitro, cyano, —$NR^9R^{10}$, —$NR^9C(=O)R^{11}$, —$NR^9SO_2R^{11}$, —$N(C(=O)R^9)(C(=O)R^{11})$, optionally substituted $C_1$-$C_6$ alkyl, optionally substituted $C_1$-$C_6$ alkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

$R^2$ is hydroxyl, —$NR^9R^{10}$, optionally substituted $C_1$-$C_6$ alkyl, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^3$, $R^6$, and $R^7$ is independently H, deuterium, halogen, optionally substituted $C_1$-$C_6$ alkyl, $C_1$-$C_6$ haloalkyl, optionally substituted $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^4$ and $R^5$ is independently optionally substituted $C_1$-$C_6$ alkyl, optionally substituted $C_3$-$C_7$ cycloalkyl, optionally substituted ($C_3$-$C_7$ cycloalkyl) $C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

$R^8$ is H or deuterium;

each of $R^9$ and $R^{10}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl; and $R^{11}$ is optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

provided that at least one of $R^2$, $R^4$, and $R^5$ is optionally substituted $C_3$-$C_7$ cycloalkyl.

In certain embodiments, in Formula (I), $R^{Het}$ is

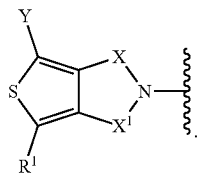

In certain embodiments, both X and $X^1$ are C═O. In certain embodiments, X is C═O and $X^1$ is $CH_2$. In certain embodiments, Y is H.

In certain embodiments, in Formula (I), $R^1$ is —$NR^9R^{10}$, —$NR^9C$(═O)$R^{11}$, —$NR^9SO_2R^{11}$ or —N(C(═O)$R^9$)(C(═O)$R^{11}$), wherein each $R^9$, $R^{10}$, and $R^{11}$ is as defined herein. In certain embodiments, $R^1$ is —$NR^9C$(═O)$R^{11}$, wherein $R^9$ is H or $C_1$-$C_6$ alkyl; and $R^{11}$ is as defined herein. In certain embodiments, $R^1$ is —NHC(═O)$R^{11}$, wherein $R^{11}$ is as defined herein. In certain embodiments, $R^{11}$ is $C_1$-$C_6$ alkyl, $C_1$-$C_6$ haloalkyl, ($C_1$-$C_6$ alkoxy)$C_1$-$C_6$ alkyl, $C_3$-$C_7$ cycloalkyl, or ($C_3$-$C_7$ cycloalkyl)$C_1$-$C_6$ alkyl. In certain embodiments, $R^{11}$ is methyl, ethyl, isopropyl, t-butyl, —$CH(C_2H_5)_2$, trifluoromethyl, —$CH(CF_3)CH_3$, —$CH_2OCH_3$, cyclopropyl, or —$CH_2$-cyclopropyl.

In certain embodiments, in Formula (I), each of $R^3$, $R^6$, and $R^7$ is independently H, halogen, $C_1$-$C_6$ alkyl, or $C_1$-$C_6$ haloalkyl. In certain embodiments, each of $R^3$, $R^6$, and $R^7$ is H. In certain embodiments, at least one of $R^3$, $R^6$, and $R^7$ is halogen (e.g., fluoro or chloro) or $C_1$-$C_6$ alkyl (e.g., methyl, ethyl, isopropyl, or t-butyl).

In certain embodiments, in Formula (I), $R^2$ is optionally substituted $C_3$-$C_7$ cycloalkyl. In certain embodiments, $R^2$ is $C_3$-$C_7$ cycloalkyl optionally substituted with one or more substituents, each of which is independently halogen, $C_1$-$C_6$ haloalkyl, or $C_1$-$C_6$ alkyl. In certain embodiments, $R^2$ is cyclopropyl optionally substituted with fluoro. In certain such embodiments, each of $R^4$ and $R^5$ is independently $C_1$-$C_6$ alkyl, for example, in one embodiment, $R^4$ is ethyl and $R^5$ is methyl.

In certain embodiments, Formula (I), $R^2$ is $C_1$-$C_6$ alkyl, for example, in one embodiment, methyl, ethyl, isopropyl, or t-butyl. In certain such embodiments, one of $R^4$ and $R^5$ is optionally substituted $C_3$-$C_7$ cycloalkyl and the other one of $R^4$ and $R^5$ is $C_1$-$C_6$ alkyl or $C_1$-$C_6$ haloalkyl. In certain embodiments, one of $R^4$ and $R^5$ is cyclopropyl and the other one of $R^4$ and $R^5$ is methyl. In certain embodiments, $R^4$ is $C_3$-$C_7$ cycloalkyl and $R^5$ is $C_1$-$C_6$ alkyl. In certain embodiments, $R^4$ is cyclopropyl and $R^5$ is methyl.

In one embodiment, provided here is a compound of Formula (I-A):

(I-A)

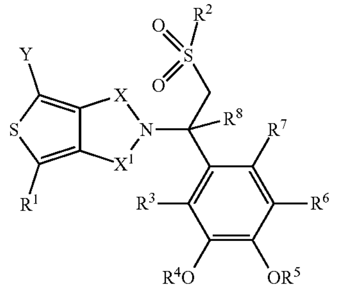

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^8$, X, $X^1$, and Y are each as defined herein.

In another embodiment, provided here is a compound of Formula (I-B):

(I-B)

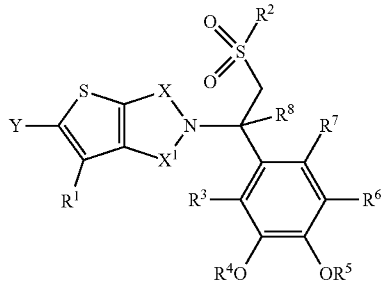

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^8$, X, $X^1$, and Y are each as defined herein.

In yet another embodiment, provided here is a compound of Formula (I-C):

(I-C)

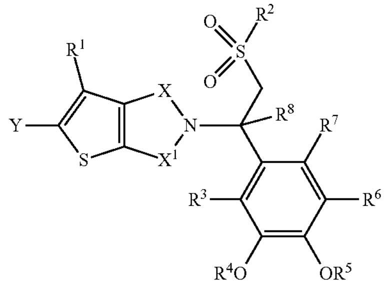

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^2$, $R^3$, $R^4$, $R^5$, $R^6$, $R^7$, $R^8$, X, $X^1$, and Y are each as defined herein.

In certain embodiments, in Formula (I), (I-A), (I-B), or (I-C), $R^1$ is —$NR^9R^{10}$ or —$NR^9C(=O)R^{11}$, wherein $R^9$, $R^{10}$, and $R^{11}$ are each as defined herein. In certain embodiments, in Formula (I), (I-A), (I-B), or (I-C), $R^1$ is —$NH_2$ or —$NHC(=O)R^{11}$, wherein $R^{11}$ is optionally substituted $C_1$-$C_6$ alkyl or optionally substituted $C_3$-$C_7$ cycloalkyl. In certain embodiments, in Formula (I), (I-A), (I-B), or (I-C), $R^1$ is —$NH_2$ or —$NHC(=O)R^{11}$, wherein $R^{11}$ is methyl, trifluoromethyl, methoxymethyl, or cyclopropyl. In certain embodiments, in Formula (I), (I-A), (I-B), or (I-C), $R^1$ is amino, acetamido, trifluoroacetamido, methoxyacetamido, or cyclopropamido.

In certain embodiments, in Formula (I), (I-A), (I-B), or (I-C), $R^2$ is optionally substituted $C_1$-$C_6$ alkyl or optionally substituted $C_3$-$C_7$ cycloalkyl. In certain embodiments, in Formula (I), (I-A), (I-B), or (I-C), $R^2$ is methyl or cyclopropyl.

In certain embodiments, in Formula (I), (I-A), (I-B), or (I-C), $R^3$ is H or deuterium. In certain embodiments, in Formula (I), (I-A), (I-B), or (I-C), $R^6$ is H or deuterium. In certain embodiments, in Formula (I), (I-A), (I-B), or (I-C), $R^7$ is H or deuterium. In certain embodiments, in Formula (I), (I-A), (I-B), or (I-C), $R^8$ is H or deuterium.

In certain embodiments, in Formula (I), (I-A), (I-B), or (I-C), $R^4$ is optionally substituted $C_1$-$C_6$ alkyl or optionally substituted $C_3$-$C_7$ cycloalkyl. In certain embodiments, in Formula (I), (I-A), (I-B), or (I-C), $R^4$ is methyl, ethyl, or cyclopropyl.

In certain embodiments, in Formula (I), (I-A), (I-B), or (I-C), $R^5$ is optionally substituted $C_1$-$C_6$ alkyl or optionally substituted $C_3$-$C_7$ cycloalkyl. In certain embodiments, in Formula (I), (I-A), (I-B), or (I-C), $R^5$ is methyl, ethyl, or cyclopropyl.

In certain embodiments, in Formula (I), (I-A), (I-B), or (I-C), X is C(=O). In certain embodiments, in Formula (I), (I-A), (I-B), or (I-C), $X^1$ is $CH_2$ or C(=O). In certain embodiments, Y is H or deuterium.

In certain embodiments, in Formula (I), (I-A), (I-B), or (I-C), $R^1$ is amino or —$NHC(=O)R^{11}$, wherein $R^{11}$ is optionally substituted $C_1$-$C_6$ alkyl or optionally substituted $C_3$-$C_7$ cycloalkyl; $R^2$ is optionally substituted $C_1$-$C_6$ alkyl or optionally substituted $C_3$-$C_7$ cycloalkyl; $R^3$, $R^6$, $R^7$, and $R^8$ are each independently H or deuterium; $R^4$ and $R^5$ is each independently optionally substituted $C_1$-$C_6$ alkyl or optionally substituted $C_3$-$C_7$ cycloalkyl; X is C(=O); $X^1$ is $CH_2$ or C(=O); and Y is H or deuterium.

In certain embodiments, in Formula (I), (I-A), (I-B), or (I-C), $R^1$ is amino, acetamido, trifluoroacetamido, methoxyacetamido, or cyclopropamido; $R^2$ is methyl or cyclopropyl; $R^3$, $R^6$, $R^7$, and $R^8$ are each independently H or deuterium; $R^4$ and $R^5$ is each independently methyl, ethyl, or cyclopropyl; X is C(=O); $X^1$ is $CH_2$ or C(=O); and Y is H or deuterium.

In one embodiment, provided herein is:

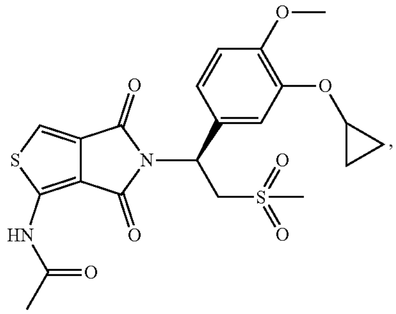
,

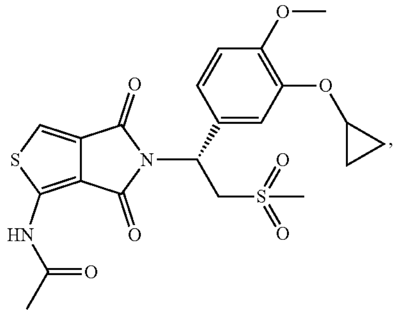
,

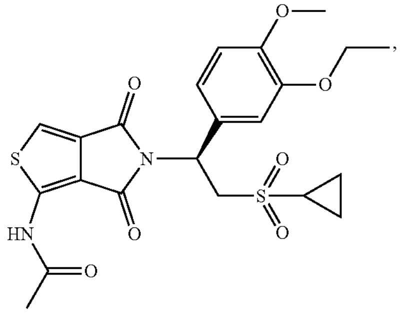
,

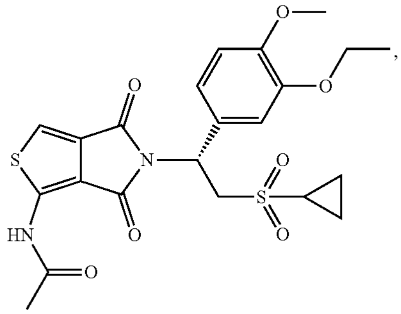
,

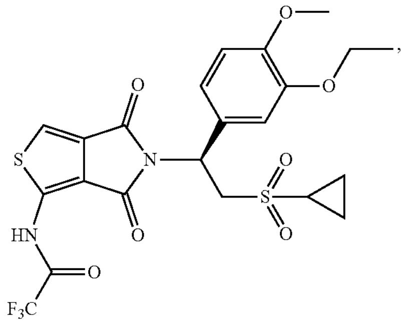
,

-continued

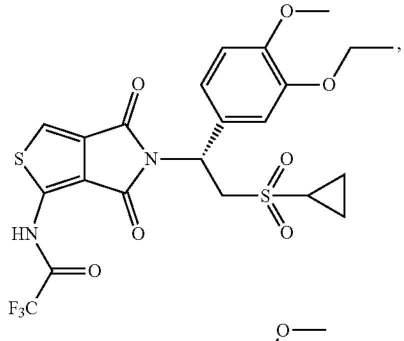

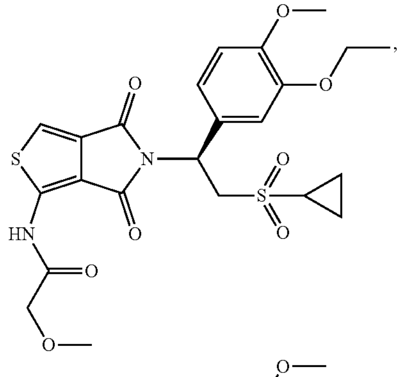

or

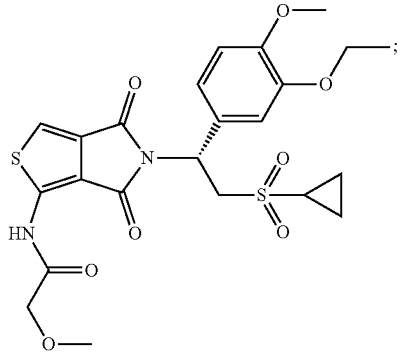

or a pharmaceutically acceptable salt thereof.

In another embodiment, provided herein is:

(S)-1-amino-5-(1-(3-ethoxy-4-methoxyphenyl)-2-(methylsulfonyl)ethyl)-4H-thieno[3,4-c]pyrrole-4,6(5H)-dione, (S)-1-amino-5-(1-(3-cyclopropoxy-4-methoxyphenyl)-2-(methylsulfonyl)ethyl)-4H-thieno[3,4-c]pyrrole-4,6(5H)-dione, (R)-1-amino-5-(1-(3-cyclopropoxy-4-methoxyphenyl)-2-(methylsulfonyl)ethyl)-4H-thieno[3,4-c]pyrrole-4,6(5H)-dione, (S)-1-amino-5-(1-(3-cyclopropoxy-4-methoxyphenyl)-2-(methylsulfonyl)ethyl)-4H-thieno[3,4-c]pyrrole-4,6(5H)-dione, (R)-1-amino-5-(1-(3-cyclopropoxy-4-methoxyphenyl)-2-(methylsulfonyl)ethyl)-4H-thieno[3,4-c]pyrrole-4,6(5H)-dione, or (S)-3-amino-5-(1-(3-ethoxy-4-methoxyphenyl)-2-(methylsulfonyl)ethyl)-4H-thieno[2,3-c]pyrrol-6(5H)-one;

or a pharmaceutically acceptable salt thereof.

In yet another embodiment, provided herein is:

(S)—N-(5-(1-(3-ethoxy-4-methoxyphenyl)-2-(methylsulfonyl)ethyl)-4-oxo-5,6-dihydro-4H-thieno[3,4-c]pyrrol-1-yl)-2,2,2-trifluoroacetamide A1, (S)—N-(5-(1-(3-ethoxy-4-methoxyphenyl)-2-(methylsulfonyl)ethyl)-6-oxo-5,6-dihydro-4H-thieno[2,3-c]pyrrol-3-yl)-2-methoxyacetamide A2, (S)—N-(5-(1-(3-ethoxy-4-methoxyphenyl)-2-(methylsulfonyl)ethyl)-6-oxo-5,6-dihydro-4H-thieno[2,3-c]pyrrol-3-yl)cyclopropanecarboxamide A3, (S)—N-(5-(1-(3-cyclopropoxy-4-methoxyphenyl)-2-(methylsulfonyl)ethyl)-4,6-dioxo-5,6-dihydro-4H-thieno[3,4-c]pyrrol-1-yl)acetamide A4, (R)—N-(5-(1-(3-cyclopropoxy-4-methoxyphenyl)-2-(methylsulfonyl)ethyl)-4,6-dioxo-5,6-dihydro-4H-thieno[3,4-c]pyrrol-1-yl)acetamide A5, (S)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)acetamide A6, (S)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)-2,2,2-trifluoroacetamide A7, (R)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)-2,2,2-trifluoroacetamide A8, (R)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)-2-methoxyacetamide A9, (R)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)acetamide A10, or (S)—N-(5-(2-(cyclopropylsulfonyl)-1-(3-ethoxy-4-methoxyphenyl)ethyl)-4,6-dioxo-5,6-dihydro-4H-thieno[3,4-c]pyrrol-1-yl)-2-methoxyacetamide A11;

or a pharmaceutically acceptable salt thereof.

Compounds of Formula (II)

In one embodiment, provided herein is a compound of Formula (II):

$$R^W\text{-}L^2\text{-}X\text{-}L^1\text{-}R^1 \qquad \text{(II)}$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is

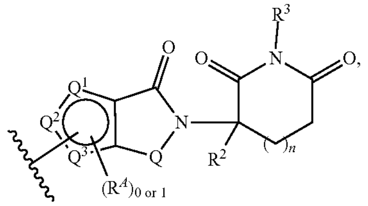

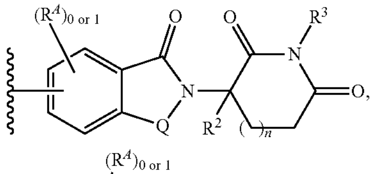

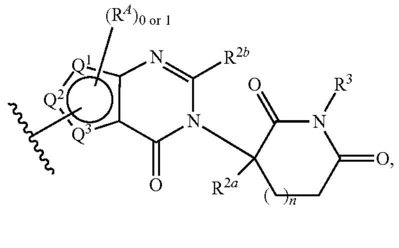

-continued
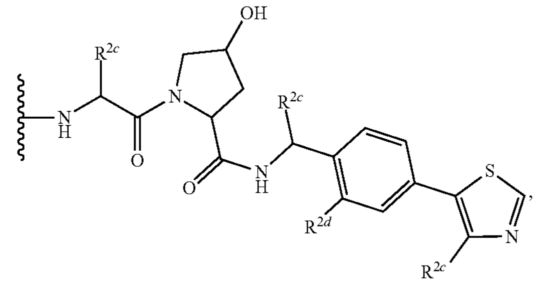
,
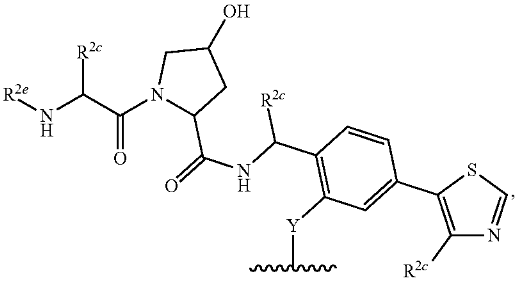
, or
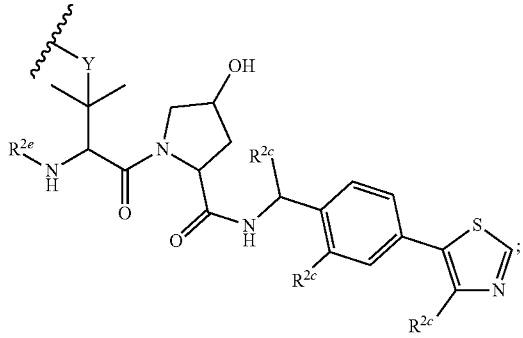
;
$R^W$ is
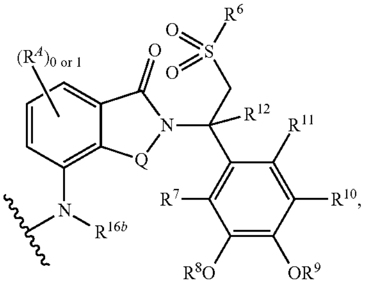
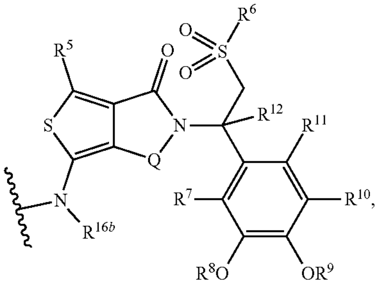
-continued
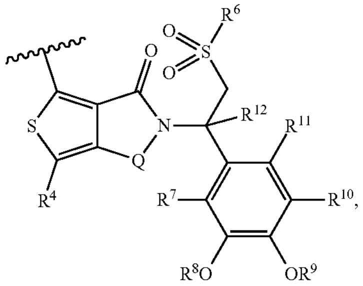
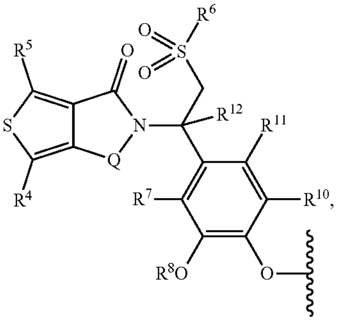
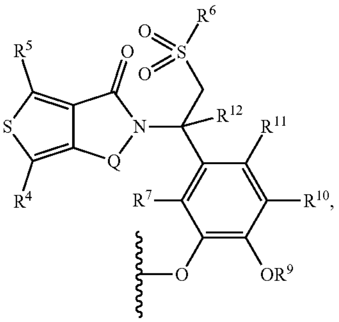
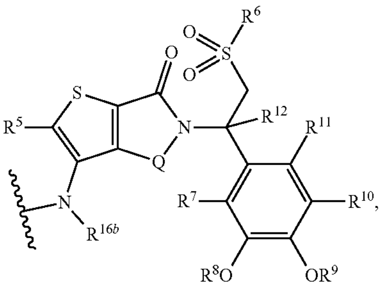
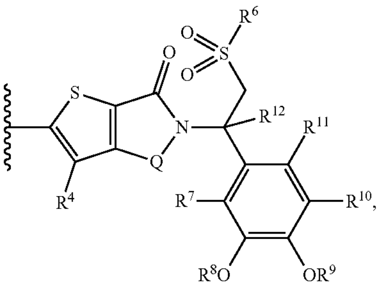

-continued
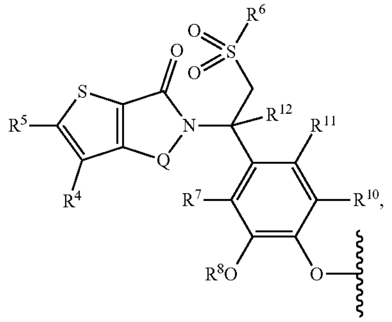
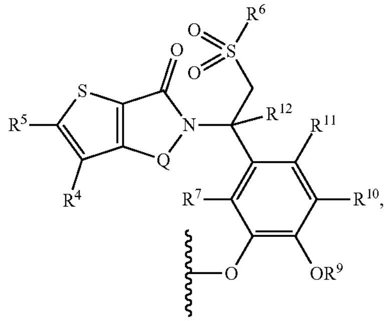
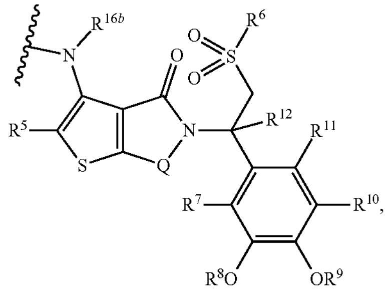
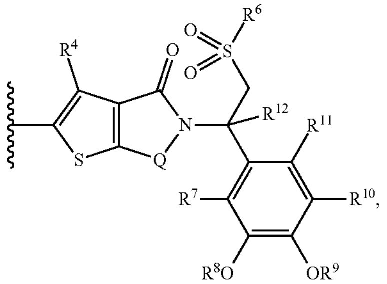
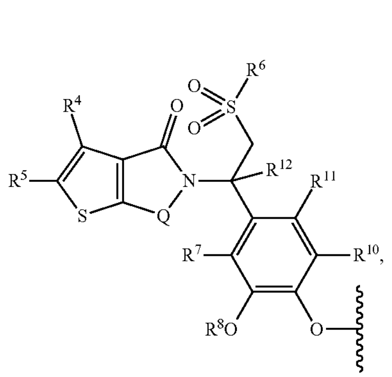
-continued
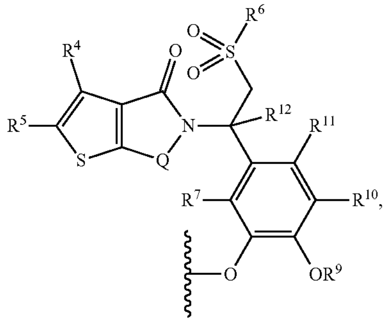
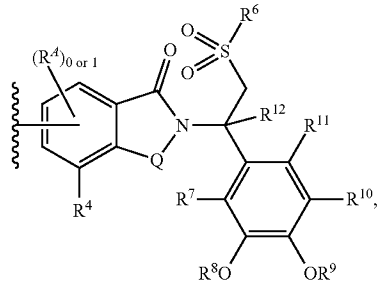
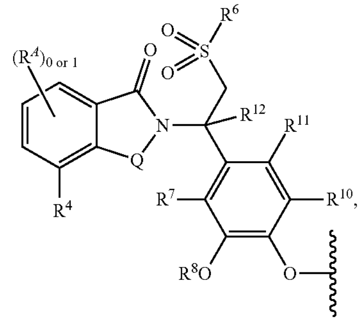
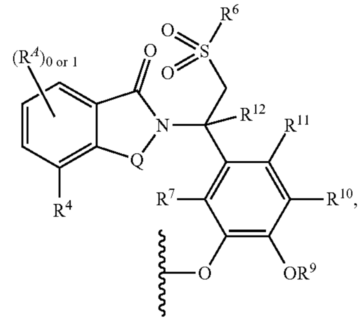
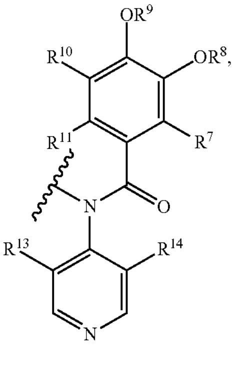
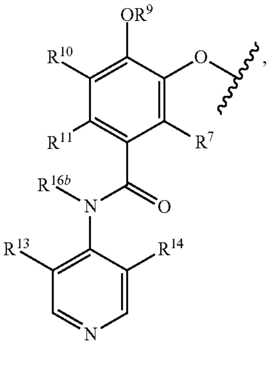

-continued

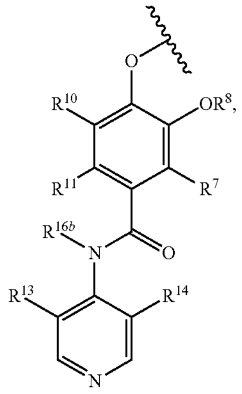

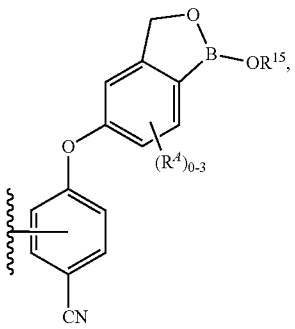

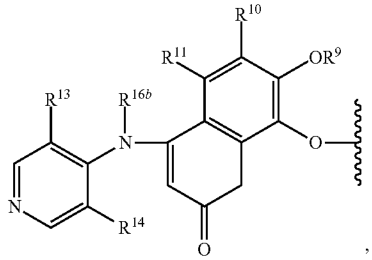

,

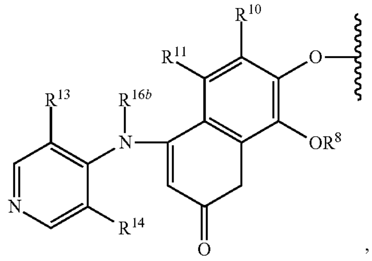

, or

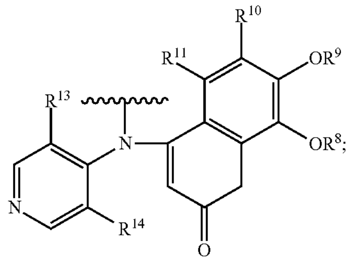

X is $C_1$-$C_{15}$ alkylene, heteroalkylene, $C_2$-$C_{10}$ alkenylene, $C_2$-$C_{10}$ alkynylene, phenylene, five to six membered heteroarylene, three to six membered heterocyclylene, or $C_3$-$C_8$ cycloalkylene, wherein each of phenylene, five to six membered heteroarylene, three to six membered heterocyclylene, or $C_3$-$C_8$ cycloalkylene is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure selected from the group consisting of phenylene, five to six membered heteroarylene, three to six membered heterocyclylene, or $C_3$-$C_8$ cycloalkylene, and wherein each ring structure is optionally substituted with one or more $R^{18}$;

each Y is independently $CH_2$, O, S, or NH;

$L^1$ is a bond,

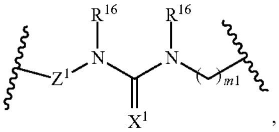

,

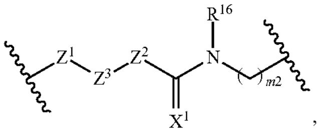

,

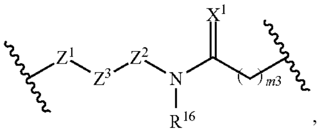

,

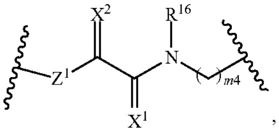

,

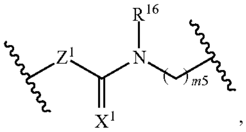

,

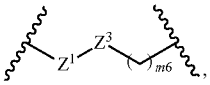

,

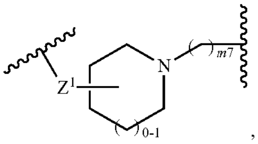

,

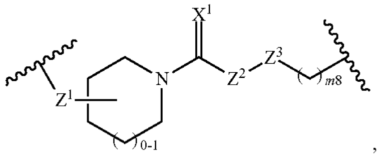

,

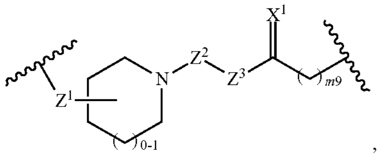

,

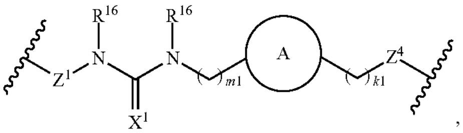

,

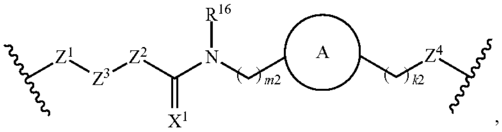

,

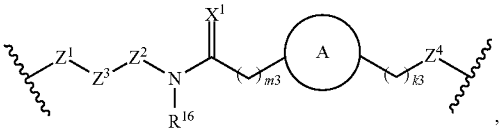

,

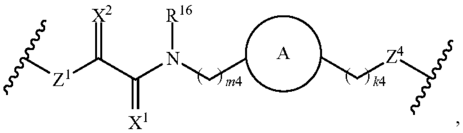

,

-continued

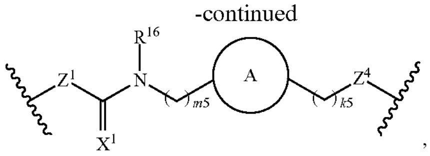

,

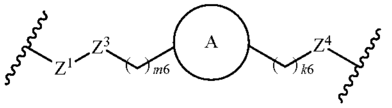

,

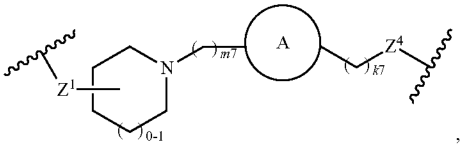

,

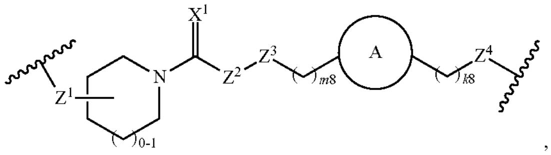

, or

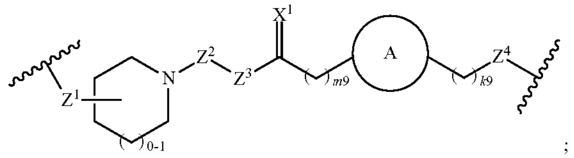

;

$L^2$ is a bond, —O—, —S—, —$NR^{16a}$—, —$(CH_2)_{1-3}$—, —C(═O)—, or —$(CH_2)_{0-3}C(═O)NR^{16a}$— each Q is independently $CH_2$ or C(═O);

each of $Q^1$, $Q^2$, and $Q^3$ is independently S or CH, provided that one of $Q^1$, $Q^2$, and $Q^3$ is S;

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C═O)$NR^{17a}R^{17b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^2$, $R^{2a}$ and $R^{2b}$ is independently H, deuterium, halogen, or $C_1$-$C_6$ alkyl;

each $R^{2c}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$ haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein —O—$C_3$-$C_8$ cycloalkyl is optionally substituted with $C_1$-$C_6$ alkyl, halogen, or $C_1$-$C_6$ haloalkyl;

each $R^{2e}$ is independently —C(═O)—$C_1$-$C_6$ alkyl or —C(═O)—$C_3$-$C_8$ cycloalkyl, each optionally substituted with one or more substituents, each of which is independently selected from the group consisting of cyano, halogen, hydroxyl, amino, and $C_1$-$C_6$ haloalkyl;

each $R^3$ is independently H, deuterium, $C_1$-$C_6$ alkyl,

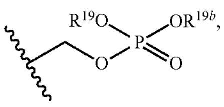

or

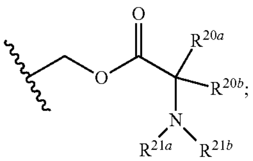

each $R^4$ is independently —$NR^{4A}R^{4B}$, —$NR^{4A}C(═O)R^{4C}$, —$NR^{4A}SO_2R^{4C}$, or —$N(C(═O)R^{4A})(C(═O)R^{4C})$.

each of $R^{4A}$ and $R^{4B}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl;

each $R^{4C}$ is independently $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^5$ is independently H, deuterium, halogen, or optionally substituted $C_1$-$C_6$ alkyl;

each $R^6$ is independently hydroxyl, —$NR^{4A}R^{4B}$, $C_1$-$C_6$ alkyl, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^7$, $R^{10}$, and $R^{11}$ is independently H, deuterium, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^8$ and $R^9$ is independently optionally substituted $C_1$-$C_6$ alkyl, $C_1$-$C_6$ haloalkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^{12}$ is independently H or deuterium;

each of $R^{13}$ and $R^{14}$ is independently halogen, hydroxyl, cyano, nitro, optionally substituted $C_1$-$C_6$ alkyl, $C_1$-$C_6$ haloalkyl, $C_1$-$C_6$ alkoxy, $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{15}$, $R^{16}$, $R^{16a}$ and $R^{16b}$ is independently H or $C_1$-$C_6$ alkyl;

each $R^{17a}$ and $R^{17b}$ is independently H or $C_1$-$C_6$ alkyl, or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of $X^1$ and $X^2$ is independently O or S;

each $Z^1$ is independently a bond, —$(CR^aR^b)_{q1}$—, —C(═O)—, —CH═CH—, or —C≡C—;

each $Z^2$ is independently —$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each Ring A is independently phenylene, five to six membered heteroarylene, three to six membered heterocyclylene, or $C_3$-$C_8$ cycloalkylene, each optionally substituted with one or more $R^{18}$.

each of m1, m2, m3, m4, m5, m6, m7, m8, m9, k1, k2, k3, k4, k5, k6, k7, k8, and k9 is independently an integer of 0, 1, 2, 3, 4, or 5;

each n is independently an integer of 0, 1, or 2; and each q1 and q2 is independently an integer of 1, 2, or 3.

In certain embodiments, in Formula (II), n is an integer of 1. In certain embodiments, in Formula (II), n is an integer of 0 or 2.

In certain embodiments, in Formula (II), $R^1$ is

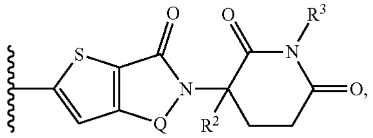

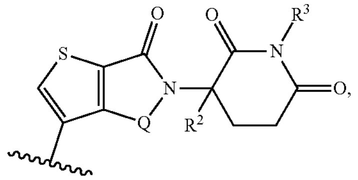

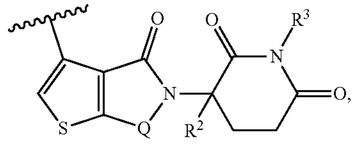

-continued

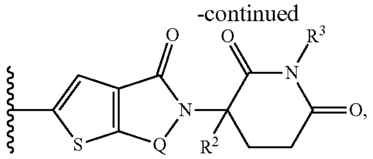

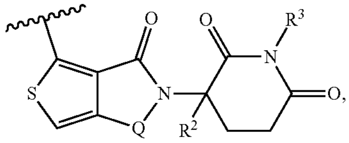

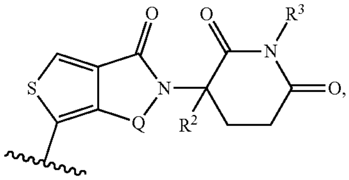

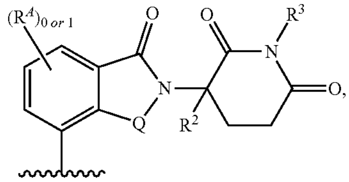

or

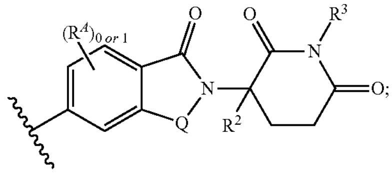

wherein $R^2$, $R^3$, $R^4$, and Q are each as defined herein. In certain embodiments, in Formula (II), $R^1$ is

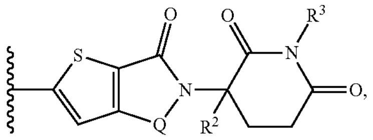

wherein $R^2$, $R^3$, and Q are each as defined herein. In certain embodiments, in Formula (II), $R^1$ is

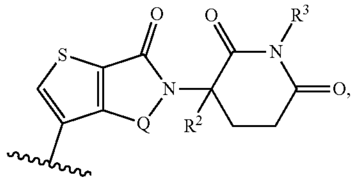

wherein $R^2$, $R^3$, and Q are each as defined herein. In certain embodiments, in Formula (II), $R^1$ is

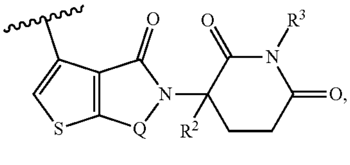

wherein $R^2$, $R^3$, and Q are each as defined herein. In certain embodiments, in Formula (II), $R^1$ is

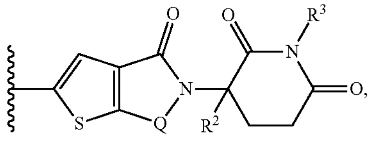

wherein $R^2$, $R^3$, and Q are each as defined herein. In certain embodiments, in Formula (II), $R^1$ is

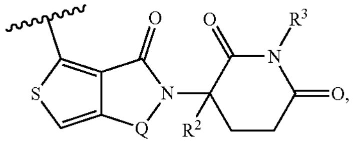

wherein $R^2$, $R^3$, and Q are each as defined herein. In certain embodiments, in Formula (II), $R^1$

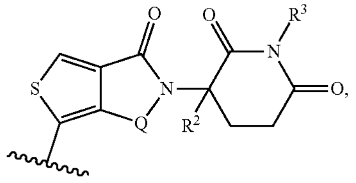

wherein $R^2$, $R^3$, and Q are each as defined herein. In certain embodiments, in Formula (II), $R^1$ is

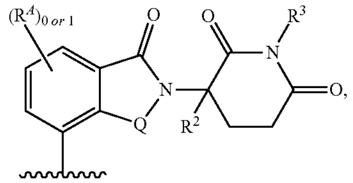

wherein $R^2$, $R^3$, $R^A$, and Q are each as defined herein. In certain embodiments, in Formula (II), $R^1$ is

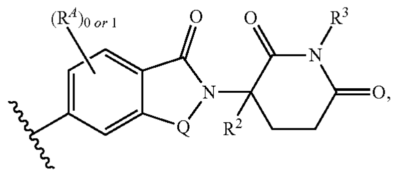

wherein $R^2$, $R^3$, $R^A$, and Q are each as defined herein.

In certain embodiments, in Formula (II), $R^1$ is unsubstituted. In certain embodiments, in Formula (II), $R^1$ is substituted with one $R^A$. In certain such embodiments, $R^A$ is halogen (e.g., F) or optionally substituted $C_1$-$C_6$ alkyl. In certain embodiments, in Formula (II), $R^1$ is

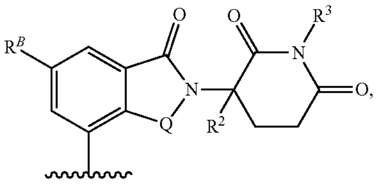

wherein $R^B$ is H or $R^A$; and $R^2$, $R^3$, $R^A$, and Q are each as defined herein.

In certain embodiments, in Formula (II), $R^1$ is

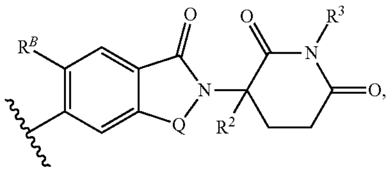

wherein $R^2$, $R^3$, $R^B$, are as defined herein. In certain embodiments, $R^B$ is H, halogen, or optionally substituted $C_1$-$C_6$ alkyl. In certain embodiments, $R^B$ is fluoro.

In certain embodiments, in Formula (II), $R^2$ is H. In certain embodiments, in Formula (II), $R^3$ is H.

In certain embodiments, in Formula (II), $R^1$ is

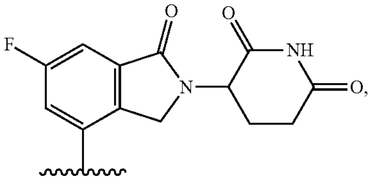

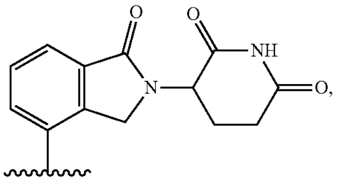

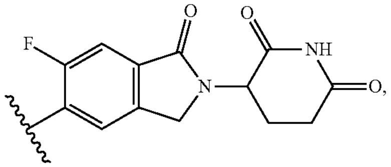

or

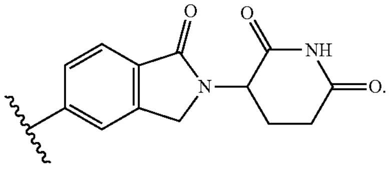

In certain embodiments, in Formula (II), $R^1$ is
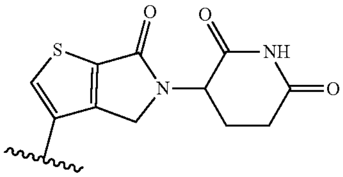
or
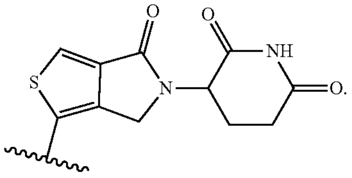
In certain embodiments, in Formula (II), $R^1$ is
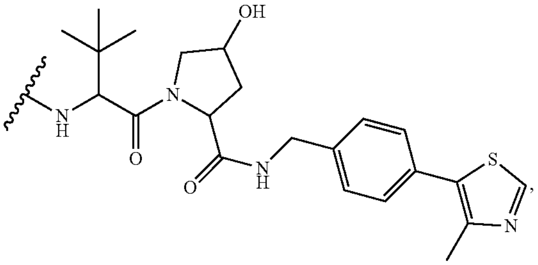
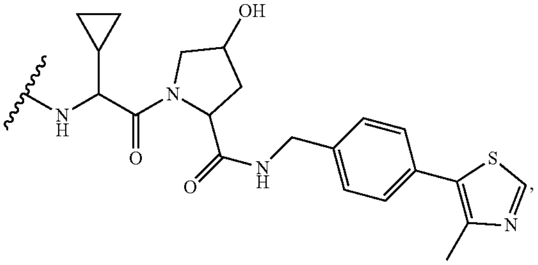
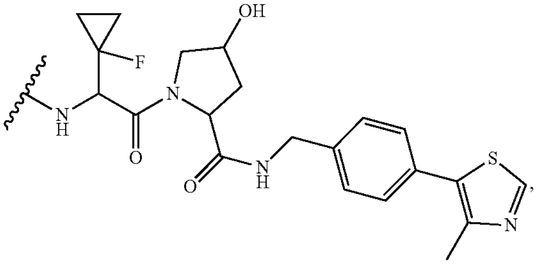
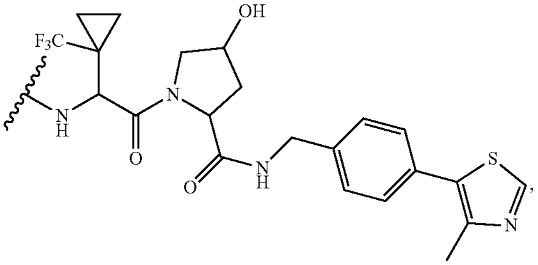
-continued
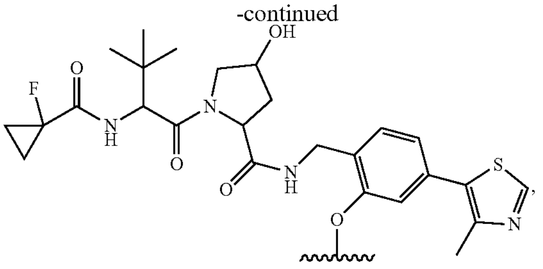
or
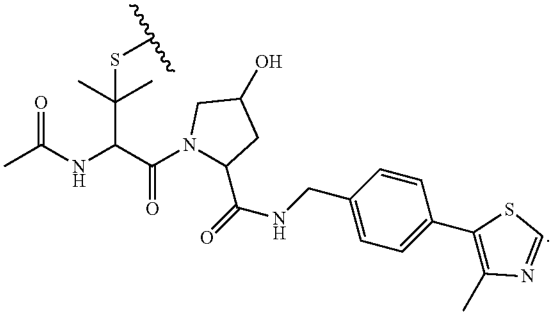
In certain embodiments, in Formula (II), $R^1$ is
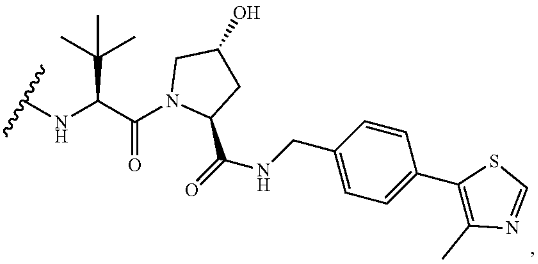
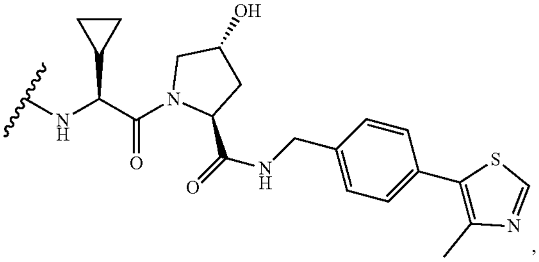
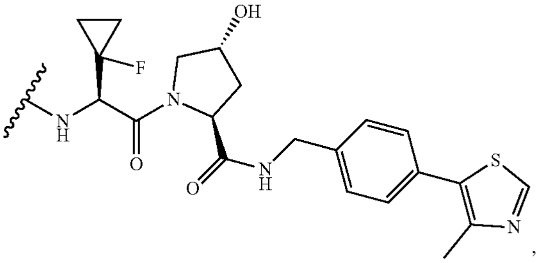
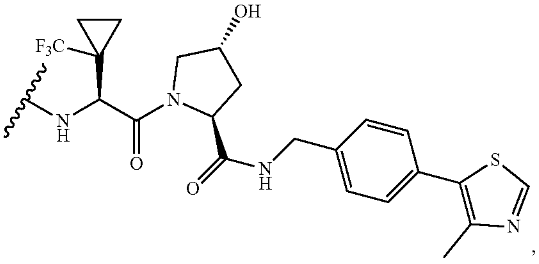

-continued
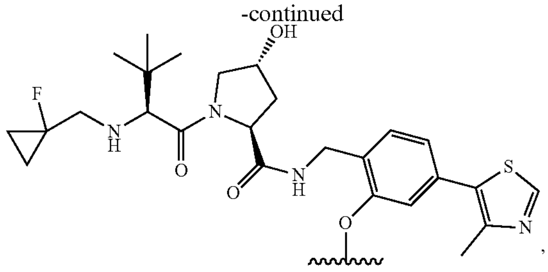
, or
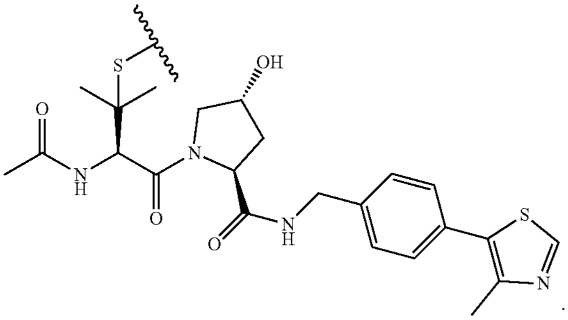
.
In certain embodiments, in Formula (II), $R^1$ is
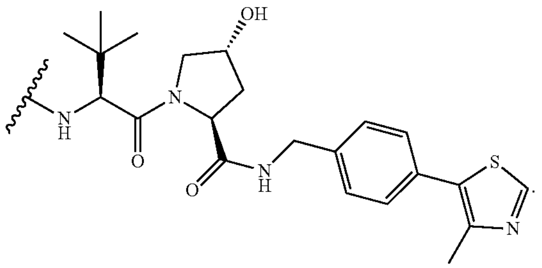 [SMILES: *N[C@H](C(=O)N1C[C@H](O)C[C@H]1C(=O)NCc1ccc(-c2scnc2C)cc1)C(C)(C)C]
In certain embodiments, in Formula (II), $L^1$ is a bond,
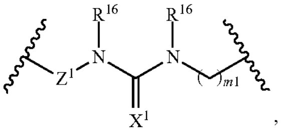
,
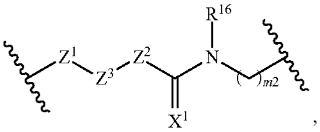
,
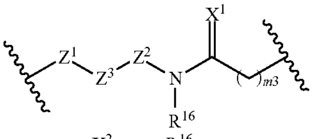
,
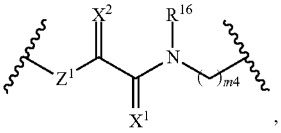
,
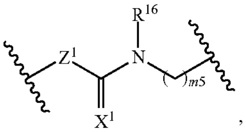
,
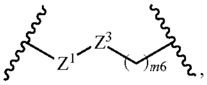
,
-continued
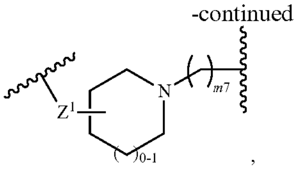
,
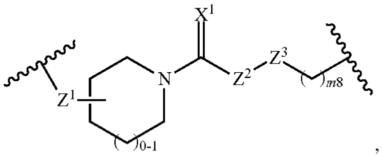
,
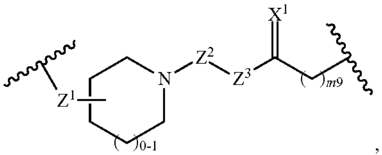
,
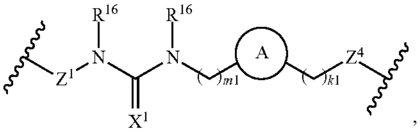
,
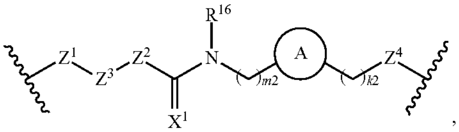
,
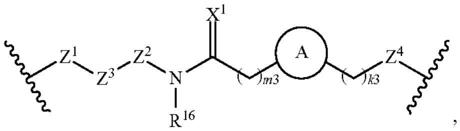
,
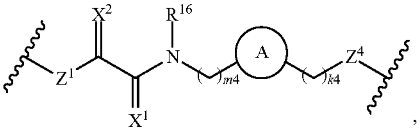
,
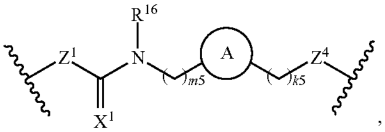
,
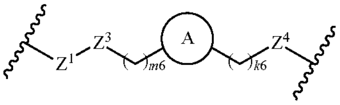
,
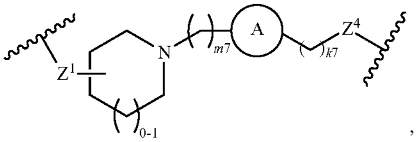
,
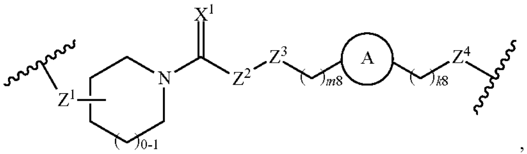
, or
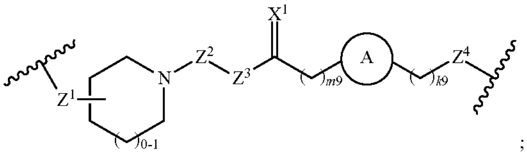
;

wherein $R^1$ is attached to $Z^1$; and ring A, $R^{16}$, $X^1$, $X^2$, $Z^1$, $Z^2$, $Z^3$, $Z^4$, k1, k2, k3, k4, k5, k6, k7, k8, k9, m1, m2, m3, m4, m5, m6, m7, m8, and m9 are each as defined herein.

In certain embodiments, in Formula (II), $L^1$ is

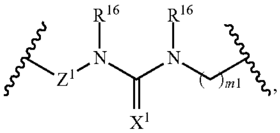

wherein $R^{16}$, $X^1$, $Z^1$, and m1 are each as defined herein; in one embodiment, each $R^{16}$ is H; $X^1$ is O; $Z^1$ is a bond or $—(CH_2)_{1-3}—$; and m1 is an integer of 0 or 1. In one embodiment, in Formula (II), $L^1$ is

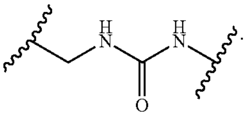 [SMILES: *CNC(=O)N*]

In certain embodiments, in Formula (II), $L^1$

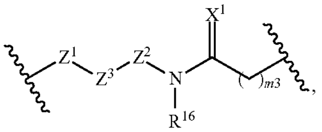

wherein $R^{16}$, $X^1$, $Z^1$, $Z^2$, $Z^3$, and m3 are each as defined herein; in one embodiment, $Z^3$ is O or $NR^{16}$; in another embodiment, each $R^{16}$ is H; $X^1$ is O; $Z^2$ is $—(CH_2)_{1-2}—$; $Z^1$ is a bond or $—(CH_2)_{1-3}—$; and m3 is an integer of 0 or 1. In certain embodiments, in Formula (II), $L^1$

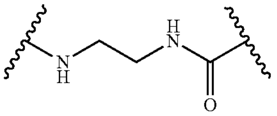

or

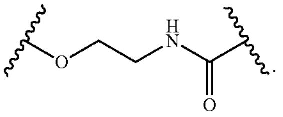

In certain embodiments, in Formula (II), $L^1$ is

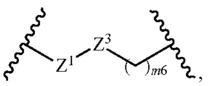

wherein $Z^1$, $Z^3$, and m6 are each as defined herein; in one embodiment, $Z^3$ is O or $NR^{16}$; in another embodiment, $R^{16}$ is H; $Z^1$ is a bond or $—(CH_2)_{1-3}—$; and m6 is an integer of 0 or 1; in yet another embodiment, $Z^1$ is —C(O)—; $Z^3$ is a bond; and m6 is an integer of 0 or 1. In certain embodiments, in Formula (I), $L^1$ is

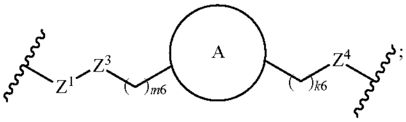

wherein ring A, $Z^1$, $Z^3$, $Z^4$, k6, and m6 are each as defined herein; in one embodiment, $Z^3$ is O or $NR^{16}$; in another embodiment, ring A is phenylene optionally substituted with $R^{18}$; $Z^1$ is a bond or $—(CH_2)_{1-3}—$; $Z^4$ is —O— or $—NR^{16}—$; each $R^{16}$ is H; and k6 and m6 are each independently an integer of 0 or 1. In certain embodiments, in Formula (II), $L^1$ is

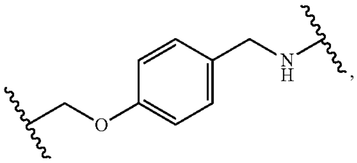

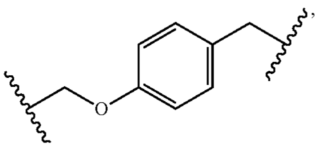

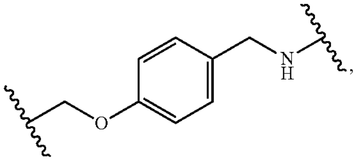

or

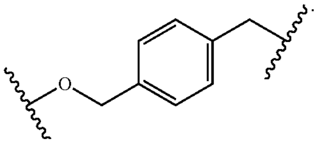

In certain embodiments, in Formula (II), $L^1$ is

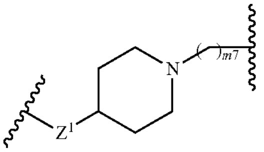

or

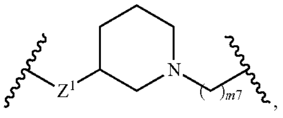

wherein each $Z^1$ and m7 is as defined herein; in one embodiment, each $Z^1$ is independently a bond or $—(CH_2)_{1-3}—$; and each m7 is independently an integer of 0 or 1. In one embodiment, $L^1$ is

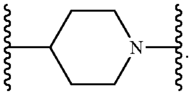 [SMILES: *C1CCN(*)CC1]

In certain embodiments, in Formula (II), $L^1$ is

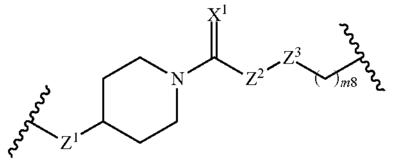

or

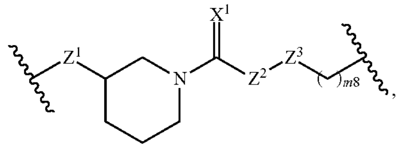

, wherein each $Z^3$ is independently $NR^{16}$; and $R^{16}$, $X^1$, $Z^1$, $Z^2$, $Z^3$, and m8 are each as defined herein; in one embodiment, $Z^1$ is —C≡C—; in another embodiment, $X^1$ is O; $Z^2$ is —$CH_2$—; $R^{16}$ is H; and each m8 is independently an integer of 0 or 1. In certain embodiments, in Formula (II), $L^1$ is

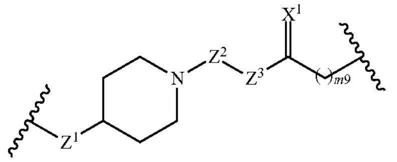

or

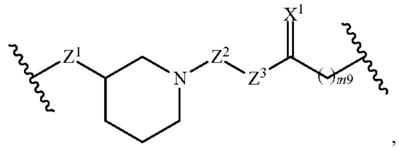

, wherein each $X^1$, $Z^1$, $Z^2$, $Z^3$, and m9 is as defined herein; in one embodiment, $Z^1$ is a bond; $X^1$ is O; and each m9 is independently an integer of 0 or 1. In one embodiment, in Formula (II), $L^1$ is

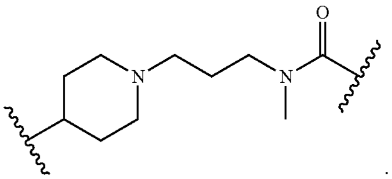 [SMILES: *C(=O)N(C)CCCN1CCC(*)CC1]

.

In certain embodiments, in Formula (II), $L^1$ is

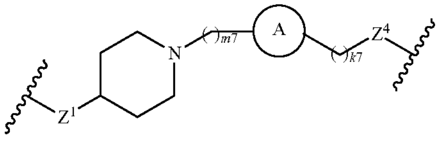

or

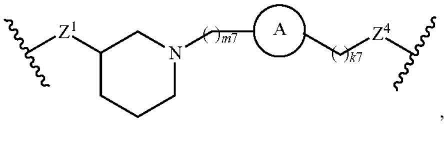

, wherein each $Z^4$ is independently O or $NR^{16}$; and ring A, $R^{16}$, $Z^1$, k7, and m7 are each as defined herein; in one embodiment, each ring A is independently phenylene, 6 membered heterocyclylene, or $C_6$-$C_8$ cycloalkylene; each $R^{16}$ is independently H or methyl; $Z^1$ is a bond; each k7 is independently an integer of 0 or 1; and each m7 is independently an integer of 0, 1, or 2. In certain embodiments, in Formula (II), $L^1$ is

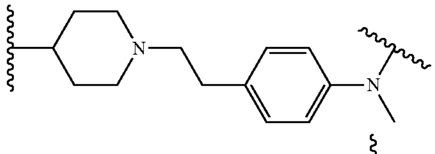

,

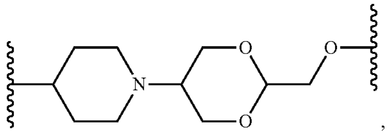

, or

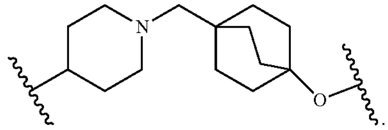

.

In any embodiments of $L^1$ that contains ring A, ring A can be a phenylene; five or six membered heteroarylene containing one, two, or three heteroatoms, each independently selected from the group consisting of N, O, and S; five or six membered heterocyclylene containing one or two heteroatoms, each independently selected from the group consisting of N, O, and S; or $C_3$-$C_8$ cycloalkylene (in one embodiment, cyclopropyl, cyclobutyl, cyclopentyl, cyclohexyl, cycloheptyl, bicyclo[2.2.1]heptanyl, or bicyclo[2.2.2]octanyl). In certain embodiments, ring A is optionally substituted with one or more $R^{18}$.

In one embodiment, in Formula (II), $L^1$ is —$NH(CH_2)_2NHC(=O)$—, —$O(CH_2)_2NHC(=O)$—, —NH—, —$CH_2NHC(O)NH$—,

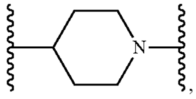

,

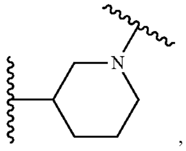

,

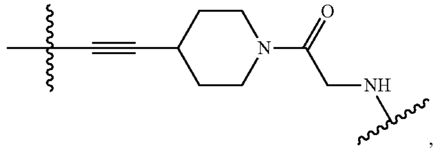

,

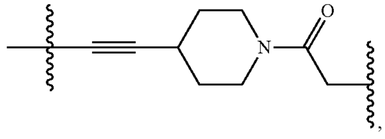

, or

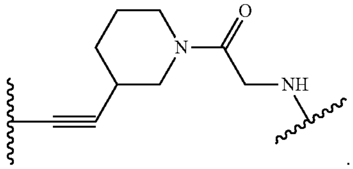

.

In another embodiment, in Formula (II), $L^1$ is *—$NH(CH_2)_2NHC(=O)$—, *—$O(CH_2)_2NHC(O)$—,

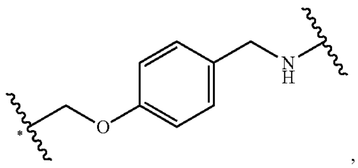
,
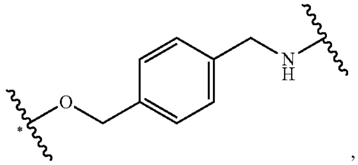
,
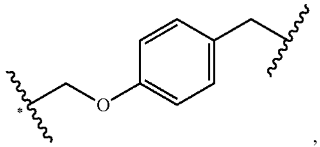
,
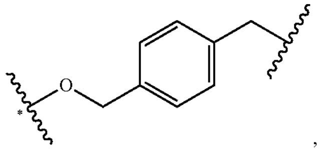
,
*—$CH_2NHC(O)NH$—,
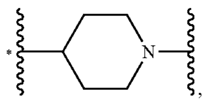
,
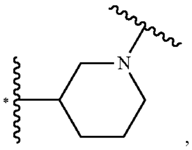
,
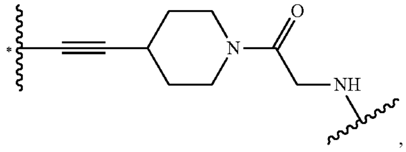
,
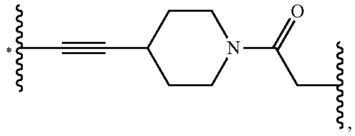
,
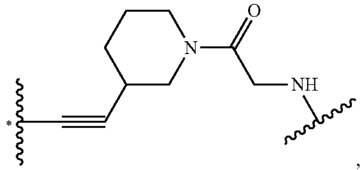
,
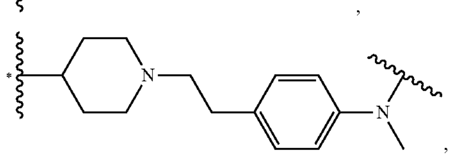
,
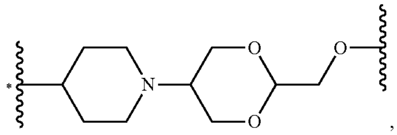
, or
-continued
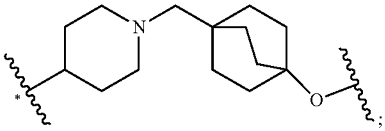
;
where * indicates the point of connection to $R^1$.
In certain embodiments, in Formula (II), $R^1$-$L^1$ is
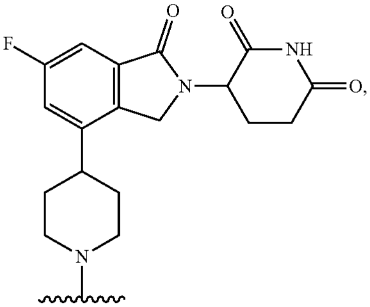
,
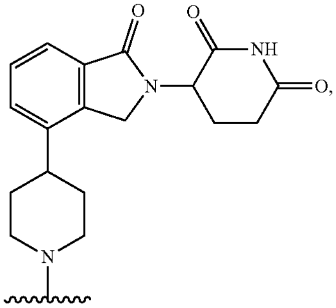
,
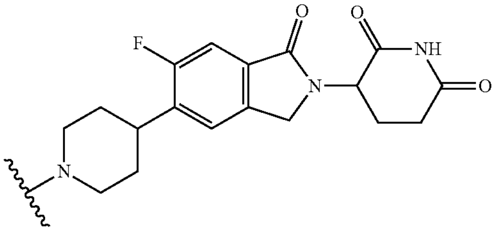
or
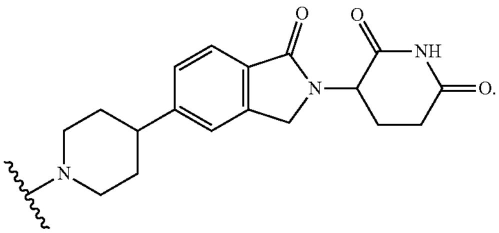
.
In certain embodiments, provided herein is a compound of Formula (Ia), (Ib), (IIc), or (IId):

(IIa)

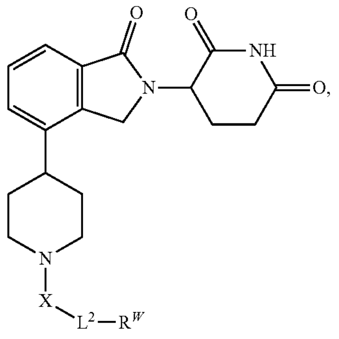

(IIb)

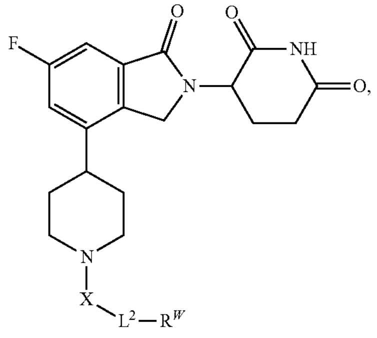

(IIc)

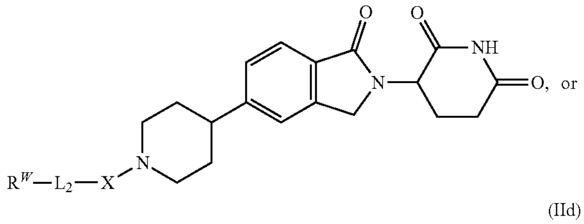

or (IId)

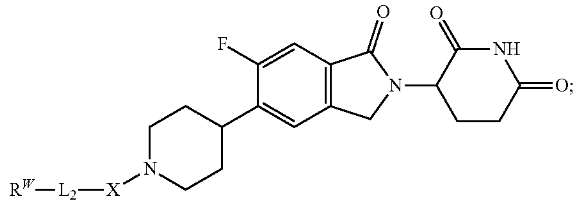

wherein $R^W$, $L^2$, and X are each as defined herein.

In certain embodiments, in Formula (II), (IIa), (IIb), (IIc), or (IId), $L^2$ is a bond. In certain embodiments, in Formula (II), (IIa), (IIb), (IIc), or (IId), $L^2$ is —O—. In certain embodiments, in Formula (II), (IIa), (IIb), (IIc), or (IId), $L^2$ is —$NR^{16a}$—, wherein $R^{16a}$ is as defined herein. In certain embodiments, in Formula (II), (IIa), (IIb), (IIc), or (IId), $L^2$ is —$(CH_2)_{1-2}$—. In certain embodiments, in Formula (II), (IIa), (IIb), (IIc), or (IId), $L^2$ is —C(═O)—. In certain embodiments, in Formula (II), (IIa), (IIb), (IIc), or (IId), $L^2$ is —$CH_2C$(═O)$NR^{16a}$—, wherein $R^{16a}$ is as defined herein. In certain embodiments, $R^{16a}$ is H. In certain embodiments, $R^{16a}$ is methyl. In certain embodiments, in Formula (II), (IIa), (IIb), (IIc), or (IId), $L^2$ is —$CH_2C$(═O)NH—*, where * indicates the point of connection to X. In certain embodiments, in Formula (II), (IIa), (IIb), (IIc), or (IId), $L^1$ and $L^2$ cannot both be a bond.

In certain embodiments, in Formula (II), (IIa), (IIb), (IIc), or (IId), X is alkylene. In certain embodiments, in Formula (II), (IIa), (IIb), (IIc), or (IId), X is $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkylene. In certain embodiments, in Formula (II), (IIa), (IIb), (IIc), or (IId), X is $C_1$-$C_8$ alkylene. In certain embodiments, in Formula (II), (IIa), (IIb), (IIc), or (IId), X is methylene, ethylene, propylene, butylene, pentylene, hexylene, heptylene, or octylene. In certain embodiments, in Formula (II), (IIa), (IIb), (IIc), or (IId), X is straight-chained alkylene. In certain embodiments, in Formula (II), (IIa), (IIb), (IIc), or (IId), X is straight-chained $C_1$-$C_8$ alkylene. In certain embodiments, in Formula (II), (IIa), (IIb), (IIc), or (IId), X is unsubstituted. In certain embodiments, in Formula (II), (IIa), (IIb), (IIc), or (IId), X is unsubstituted $C_7$ alkylene. In certain embodiments, in Formula (II), (IIa), (IIb), (IIc), or (IId), X is —$(CH_2)_5$—, —$(CH_2)_6$—, —$(CH_2)_7$—, or —$(CH_2)_8$—.

In certain embodiments, in Formula (II), (IIa), (IIb), (IIc), or (IId), X is heteroalkylene. In certain embodiments, in Formula (II), (IIa), (IIb), (IIc), or (IId), X is $C_1$-$C_{15}$ alkylene, wherein one or more methylene units are replaced by a heteroatom. In certain embodiments, the heteroatom in the heteroalkylene is oxygen (O), nitrogen (N), or sulfur (S). In certain embodiments, in Formula (II), (IIa), (IIb), (IIc), or (IId), X is a heteroalkylene containing carbon, hydrogen, and oxygen atoms, wherein at least one methylene unit is replaced by oxygen. In certain embodiments, in Formula (II), (IIa), (IIb), (IIc), or (IId), X is —$(CH_2CH_2O)_{1-5}$— or —$(CH_2CH_2O)_{1-5}CH_2CH_2$—. In certain embodiments, in Formula (II), (IIa), (IIb), (IIc), or (IId), X is heteroalkylene containing carbon, hydrogen, and nitrogen atoms, wherein at least one methylene unit is replaced by $NR^{16c}$, wherein $R^{16}$, is as defined herein. In certain embodiments, in Formula (II), (IIa), (IIb), (IIc), or (IId), X is —$(CH_2)_{1-5}$—$NR^{16c}$—$(CH_2)_{1-5}$—, wherein $R^{16}$, is H or $C_1$-$C_6$ alkyl, in one embodiment, methyl. In certain embodiments, in Formula (II), (IIa), (IIb), (IIc), or (IId), X is unsubstituted heteroalkylene containing carbon, hydrogen, and oxygen and/or nitrogen atoms. In certain embodiments, in Formula (II), (IIa), (IIb), (IIc), or (IId), X is straight-chained heteroalkylene. In certain embodiments, in Formula (II), (IIa), (IIb), (IIc), or (IId), X is —$CH_2CH_2O$—, —$(CH_2CH_2O)_2$—, —$(CH_2CH_2O)_3$—, —$CH_2CH_2OCH_2CH_2$—, —$(CH_2CH_2O)_2CH_2CH_2$—, —$(CH_2CH_2O)_3CH_2CH_2$—, —$(CH_2CH_2O)_4CH_2CH_2$—, —$CH_2NR^{16c}CH_2$—, —$CH_2CH_2NR^{16c}CH_2CH_2$—, —$(CH_2)_2OCH_2(CH_2)_3$—, or —$(CH_2)_3NR^{16c}(CH_2)_3$—, wherein each $R^{16c}$ is as defined herein. In certain embodiments, $R^{16c}$ is H or methyl. In certain embodiments, in Formula (II), (IIa), (IIb), (IIc), or (IId), X is phenylene; five or six membered heteroarylene containing one, two, or three heteroatoms, each independently selected from the group consisting of N, O, and S; five or six membered heterocyclylene containing one or two heteroatoms, each independently selected from the group consisting of N, O, and S; or $C_3$-$C_8$ cycloalkylene (in one embodiment, cyclopropyl, cyclobutylene, cyclopentylene, cyclohexylene, or cycloheptylene); each of which is optionally substituted with one or more $R^{18}$, wherein each $R^{18}$ is as defined herein. In certain embodiments, in Formula (II), (IIa), (IIb), (IIc), or (IId), X is $C_1$-$C_8$ alkylene or heteroalkylene, wherein at least one methylene unit is replaced by a ring structure selected from 5 or 6 membered heteroarylene containing one, two or three heteroatoms, each independently selected from the group consisting of N, O, and S; five or six membered heterocyclylene containing one or two heteroatoms, each independently selected from the group consisting of N, O, and S; and $C_3$-$C_8$ cycloalkylene (in one embodiment, cyclopropylene, cyclobutylene, cyclopentylene, cyclohexylene, or cycloheptylene); each of which is optionally substituted with one or more $R^{18}$, wherein each $R^{18}$ is as defined herein.

In certain embodiments, Formula (II), (IIa), (IIb), (IIc), or (IId), $R^W$ is

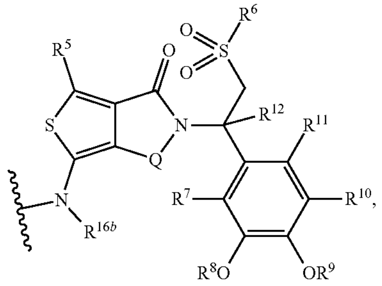

wherein $R^5$, $R^6$, $R^7$, $R^8$, $R^9$, $R^{10}$, $R^{11}$, $R^{12}$, $R^{16b}$, and Q are each as defined herein. In certain such embodiments, each of $R^5$, $R^7$, $R^{10}$, $R^{11}$, and $R^{12}$ is H. In certain such embodiments, $R^6$ is $C_1$-$C_6$ alkyl (e.g., methyl) or $C_3$-$C_7$ cycloalkyl (e.g., cyclopropyl). In certain such embodiments, each $R^8$ and $R^9$ is independently $C_1$-$C_6$ alkyl or $C_1$-$C_6$haloalkyl; for example, $R^8$ is ethyl and $R^9$ is methyl. In certain embodiments, $R^W$ is

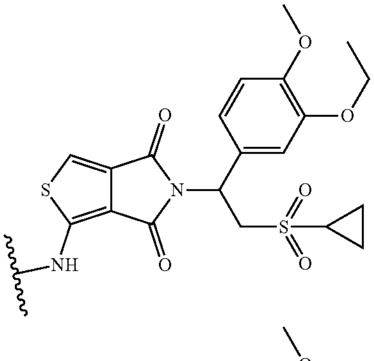

,

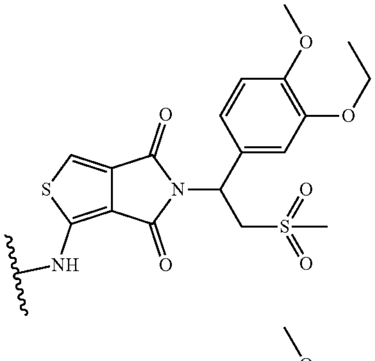

,

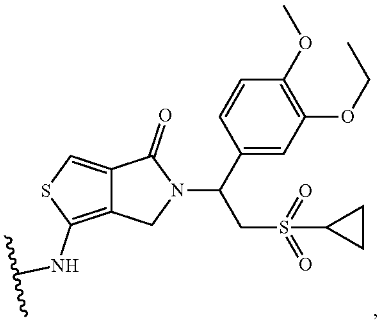

,

-continued

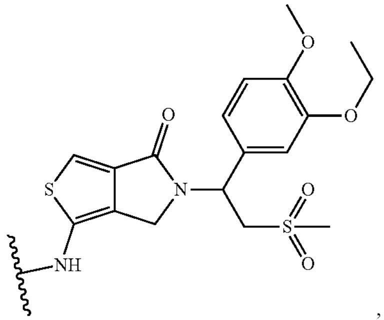

,

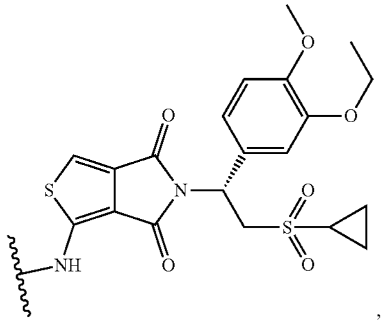

,

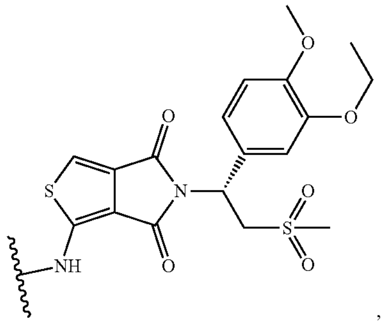

,

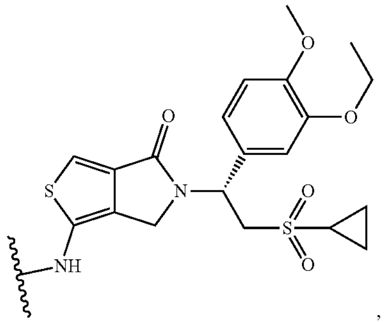

, or

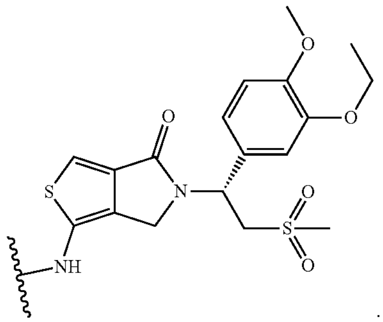

.

In certain embodiments, in Formula (II), (IIa), (IIb), (IIc), or (IId), $R^W$ is

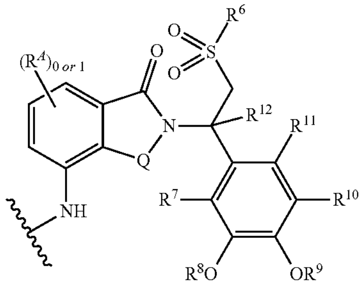

or

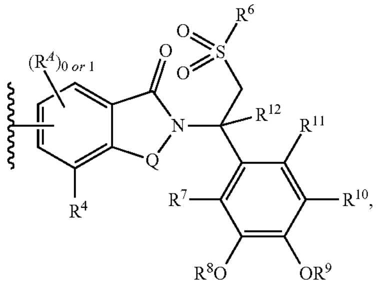

wherein each $R^4$, $R^6$, $R^7$, $R^8$, $R^9$, $R^{10}$, $R^{11}$, $R^{12}$, $R^{16b}$, $R^A$, and Q is as defined herein. In certain such embodiments, $R^A$ is absent, halogen, or $C_1$-$C_6$ alkyl; and each of $R^7$, $R^{10}$, $R^{11}$, and $R^{12}$ is H. In certain such embodiments, $R^4$ is —$NR^{4A}C(=O)R^{4C}$; $R^{4A}$ is H; and $R^{4C}$ is $C_1$-$C_6$ alkyl, $C_1$-$C_6$ haloalkyl, ($C_1$-$C_6$ alkoxy)$C_1$-$C_6$ alkyl or $C_3$-$C_7$ cycloalkyl. In certain such embodiments, $R^{4C}$ is methyl, ethyl, isopropyl, t-butyl, —$CH(C_2H_5)_2$, trifluoromethyl, —$CH(CF_3)CH_3$, —$CH_2OCH_3$, or cyclopropyl. In certain such embodiment, $R^{4C}$ is methyl. In certain such embodiments, each $R^6$, $R^8$ and $R^9$ is independently $C_1$-$C_6$alkyl, $C_1$-$C_6$ haloalkyl, or $C_3$-$C_7$ cycloalkyl. In certain embodiments, $R^W$ is

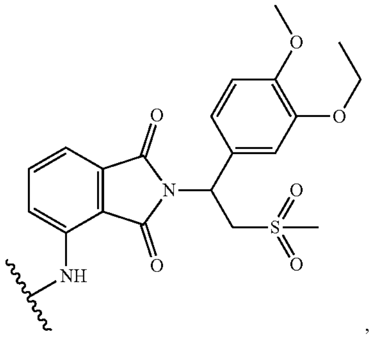

,

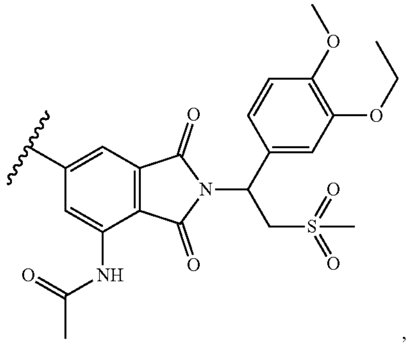

,

-continued

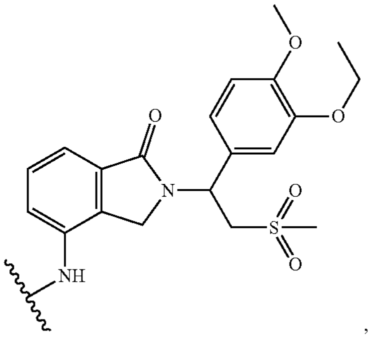

,

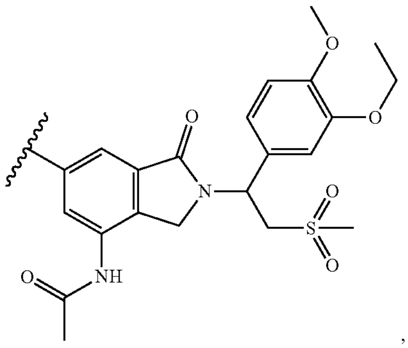

,

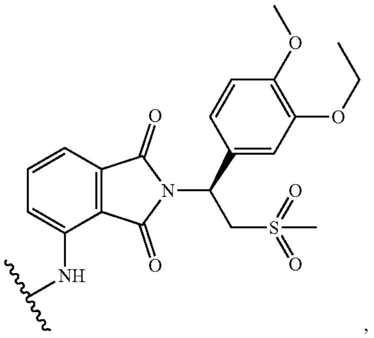

,

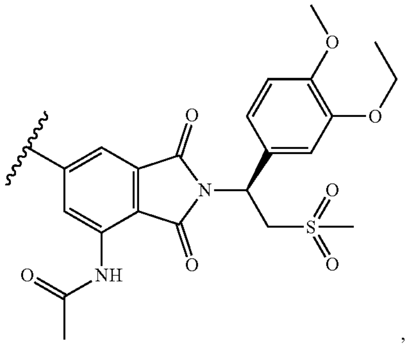

,

-continued

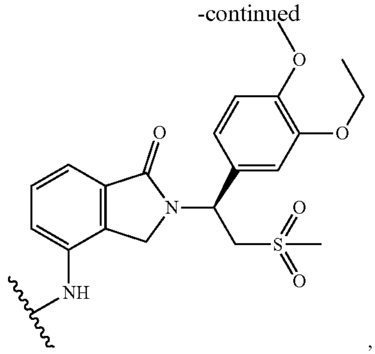

, or

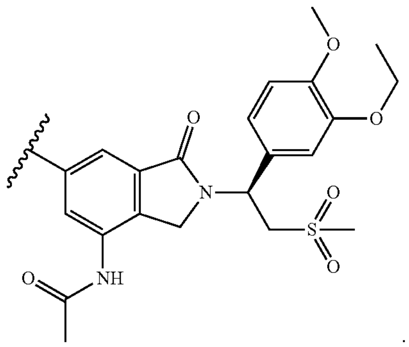

.

(IV)

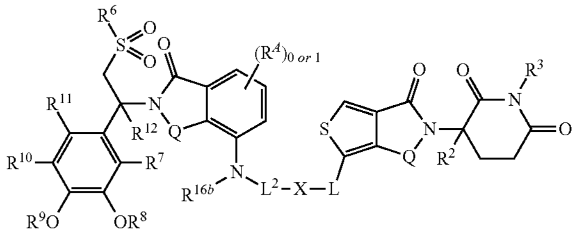

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^6$, $R^7$, $R^8$, $R^9$, $R^{10}$, $R^{11}$, $R^{12}$, $R^{16b}$, $R^A$, $L^1$, $L^2$, Q, and X are each as defined herein.

In yet another embodiment, provided herein is a compound of Formula (V):

(V)

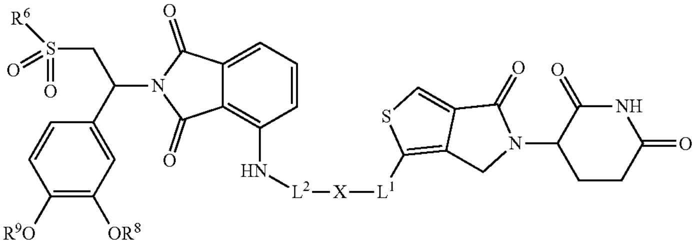

In one embodiment, provided herein is a compound of Formula (III):

(III)

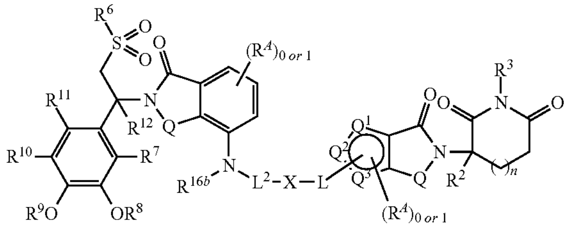

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^6$, $R^7$, $R^8$, $R^9$, $R^{10}$, $R^{11}$, $R^{12}$, $R^{16b}$, $R^A$, $L^1$, $L^2$, Q, $Q^1$, $Q^2$, $Q^3$, X, and n are each as defined herein.

In another embodiment, provided herein is a compound of Formula (IV):

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^1$, $L^2$, and X are each as defined herein.

In yet another embodiment, provided herein is a compound of Formula (VI):

(VI)

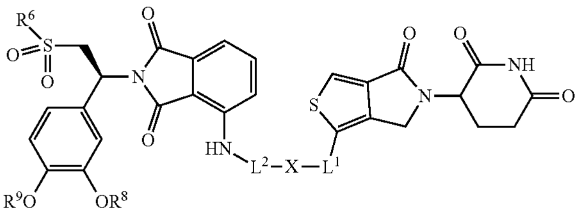

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^1$, $L^2$, and X are each as defined herein.

In yet another embodiment, provided herein is a compound of Formula (VII):

(VII)

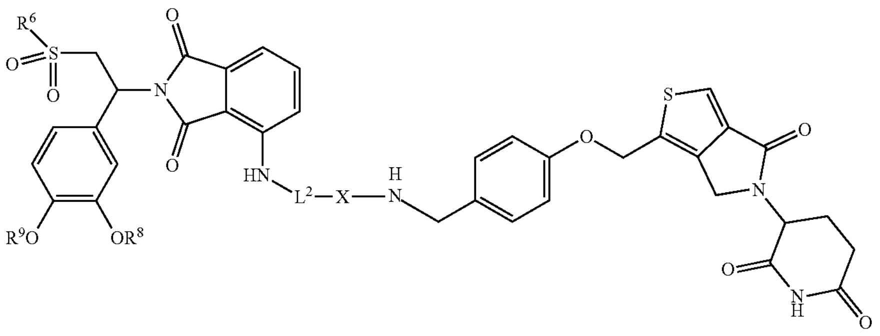

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^2$, and X are each as defined herein.

In still another embodiment, provided herein is a compound of Formula (VIII):

(VIII)

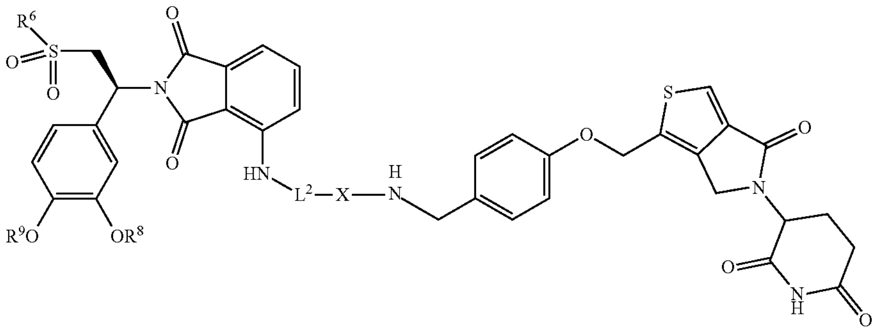

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^2$, and X are each as defined herein.

In one embodiment, provided herein is a compound of Formula (IX):

(IX)

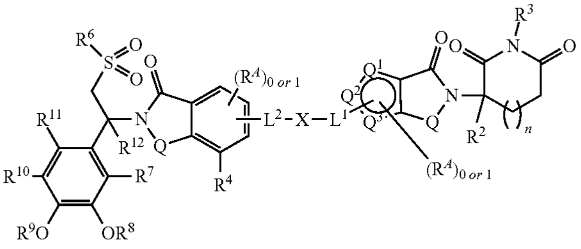

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $R^A$, $L^1$, $L^2$, Q, $Q^1$, $Q^2$, $Q^3$, X, and n are each as defined herein.

In another embodiment, provided herein is a compound of Formula (X):

(X)

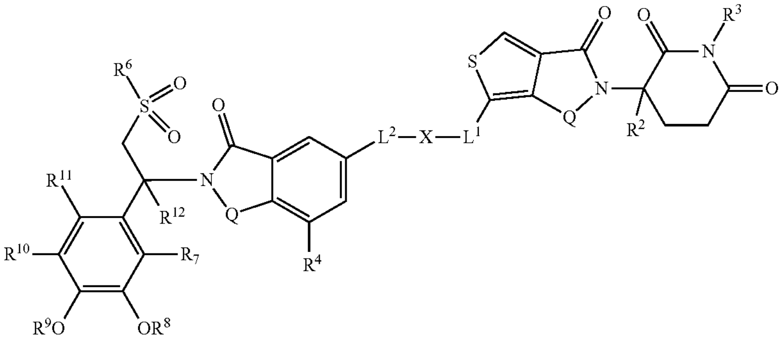

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $L^1$, $L^2$, Q, and X are each as defined herein.

In yet another embodiment, provided herein is a compound of Formula (XI):

(XI)

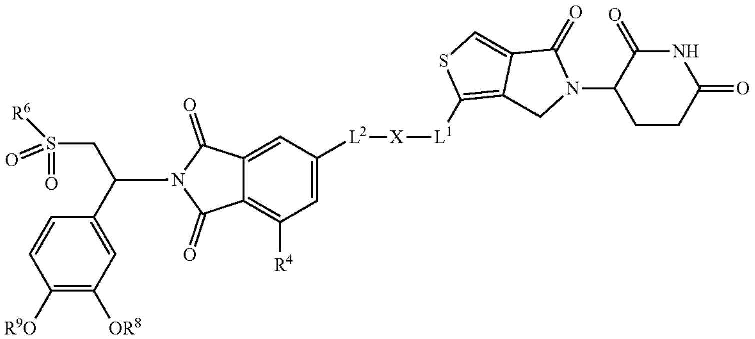

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^1$, $L^2$, and X are each as defined herein.

In yet another embodiment, provided herein is a compound of Formula (XII):

(XII)

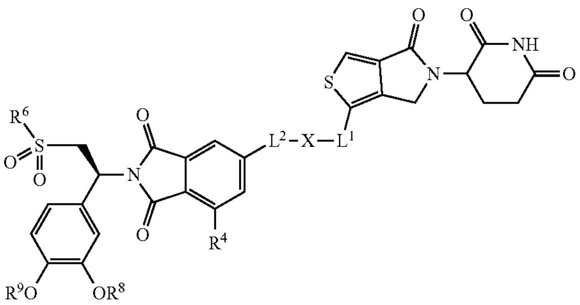

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^1$, $L^2$, and X are each as defined herein.

In yet another embodiment, provided herein is a compound of Formula (XIII):

(XIII)

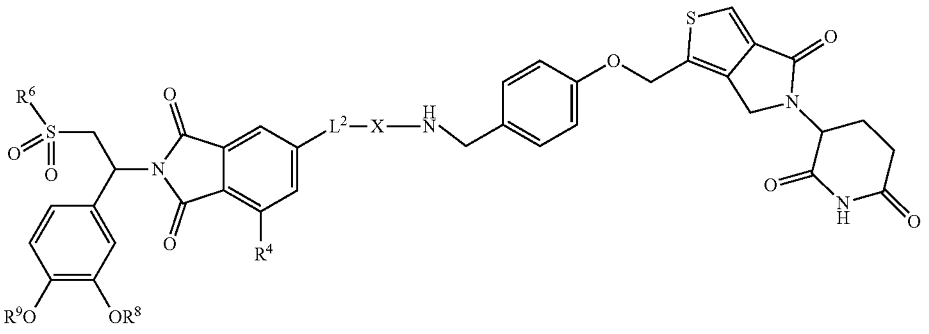

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^2$, and X are each as defined herein.

In still another embodiment, provided herein is a compound of Formula (XIV):

(XIV)

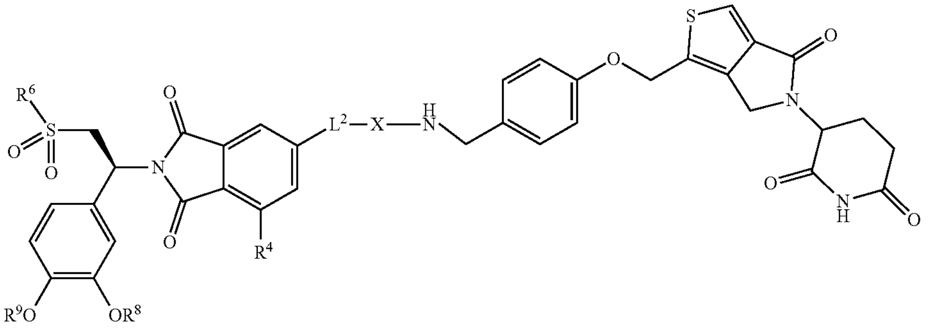

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^2$, and X are each as defined herein.

In one embodiment, provided herein is a compound of Formula (XV):

(XV)

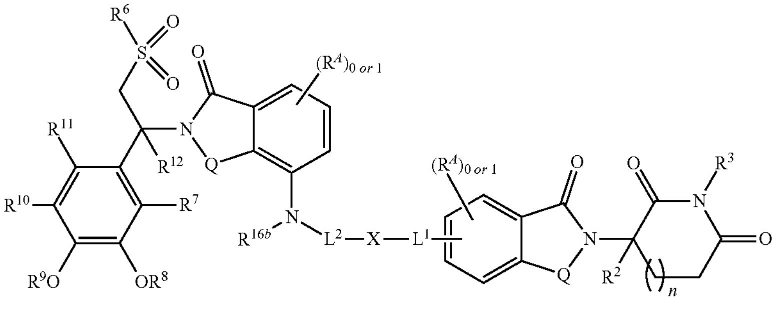

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^6$, $R^7$, $R^8$, $R^9$, $R^{10}$, $R^{11}$, $R^{12}$, $R^{16b}$, $R^A$, $L^1$, $L^2$, Q, X, and n are each as defined herein.

In one embodiment, provided herein is a compound of Formula (XVI):

(XVI)

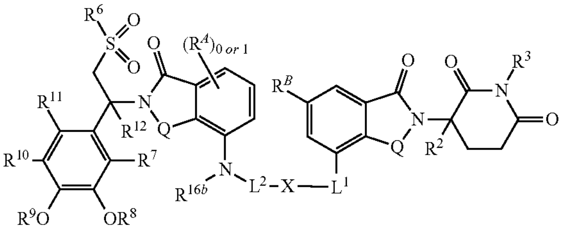

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^6$, $R^7$, $R^8$, $R^9$, $R^{10}$, $R^{11}$, $R^{12}$, $R^{16b}$, $R^A$, $R^B$, $L^1$, $L^2$, Q, and X are each as defined herein.

In another embodiment, provided herein is a compound of Formula (XVII):

(XVII)

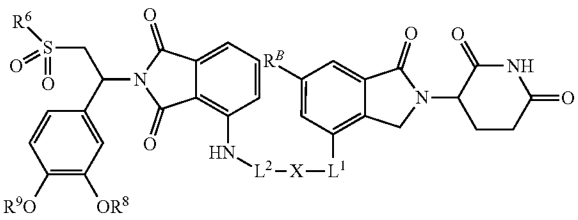

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^1$, $L^2$, and X are each as defined herein.

In yet another embodiment, provided herein is a compound of Formula (XVIII):

(XVIII)

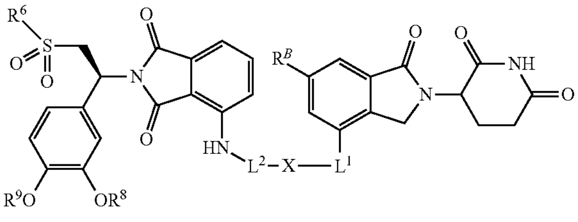

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^1$, $L^2$, and X are each as defined herein.

In yet another embodiment, provided herein is a compound of Formula (XIX):

(XIX)

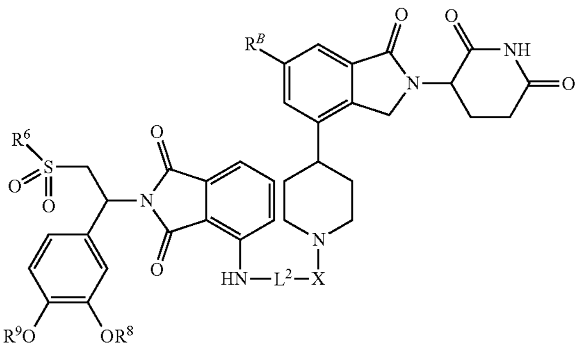

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^2$, and X are each as defined herein.

In still another embodiment, provided herein is a compound of Formula (XX):

(XX)

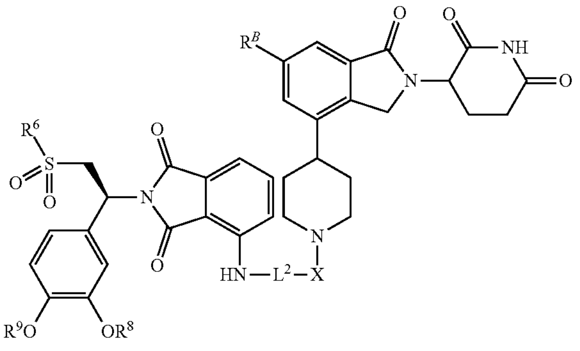

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^2$, and X are each as defined herein.

In one embodiment, provided herein is a compound of Formula (XXI):

(XXI)

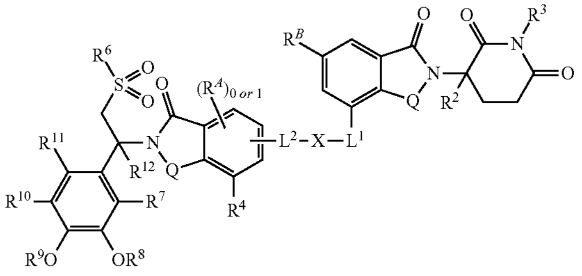

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $R^A$, $R^B$, $L^1$, $L^2$, Q, and X are each as defined herein.

In one embodiment, provided herein is a compound of Formula (XXII):

(XXII)

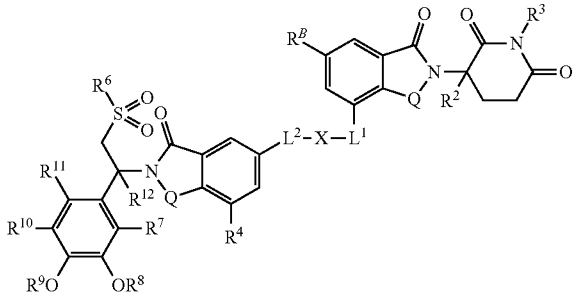

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $R^B$, $L^1$, $L^2$, Q, and X are each as defined herein.

In another embodiment, provided herein is a compound of Formula (XXIII):

(XXIII)

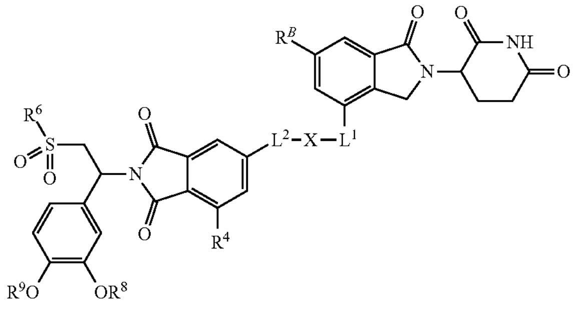

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^1$, $L^2$, and X are each as defined herein.

In yet another embodiment, provided herein is a compound of Formula (XXIV):

(XXIV)

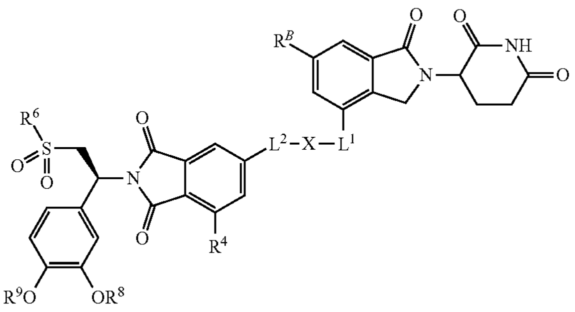

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^1$, $L^2$, and X are each as defined herein.

In yet another embodiment, provided herein is a compound of Formula (XXV):

(XXV)

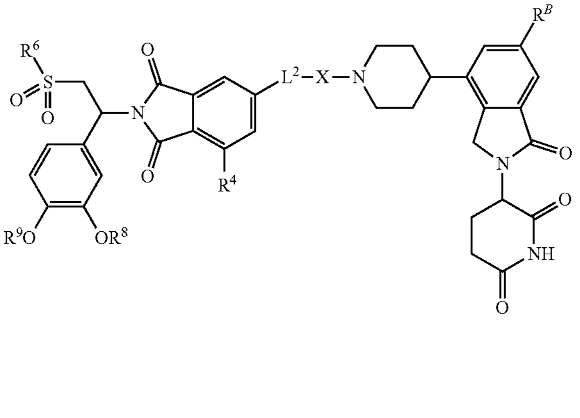

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^2$, and X are each as defined herein.

In still another embodiment, provided herein is a compound of Formula (XXVI):

(XXVI)

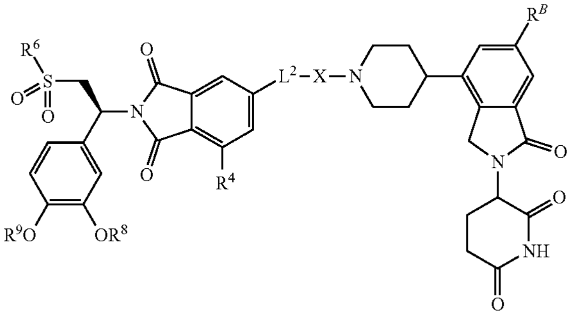

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^2$, and X are each as defined herein.

In one embodiment, provided herein is a compound of Formula (XXVII):

(XXVII)

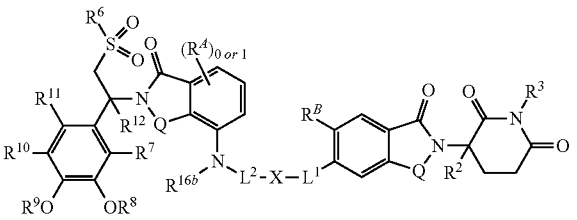

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^6$, $R^7$, $R^8$, $R^9$, $R^{10}$, $R^{11}$, $R^{12}$, $R^{16b}$, $R^A$, $R^B$, $L^1$, $L^2$, Q, and X are each as defined herein.

In another embodiment, provided herein is a compound of Formula (XXVIII):

(XXVIII)

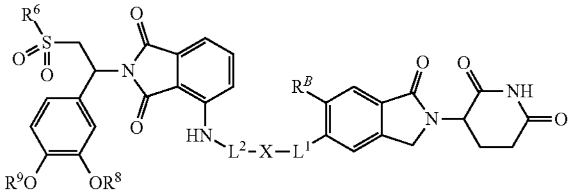

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^1$, $L^2$, and X are each as defined herein.

In yet another embodiment, provided herein is a compound of Formula (XXIX):

(XXIX)

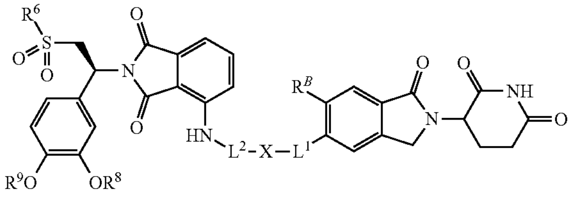

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^1$, $L^2$, and X are each as defined herein.

In yet another embodiment, provided herein is a compound of Formula (XXX):

(XXX)

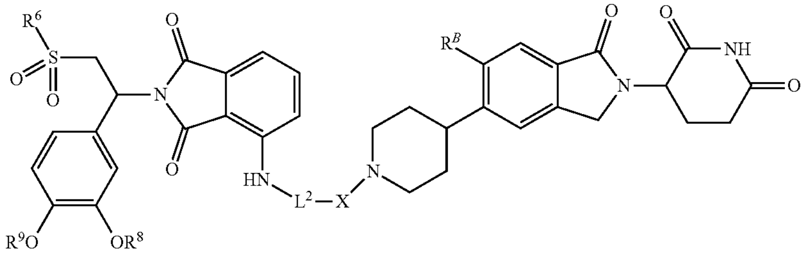

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^2$, and X are each as defined herein.

In still another embodiment, provided herein is a compound of Formula (XXXI):

(XXXI)

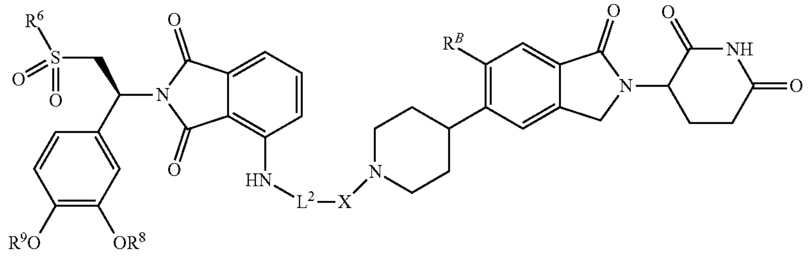

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $R^B$, $L^2$, and X are each as defined herein.

In one embodiment, provided herein is a compound of Formula (XXXII):

(XXXII)

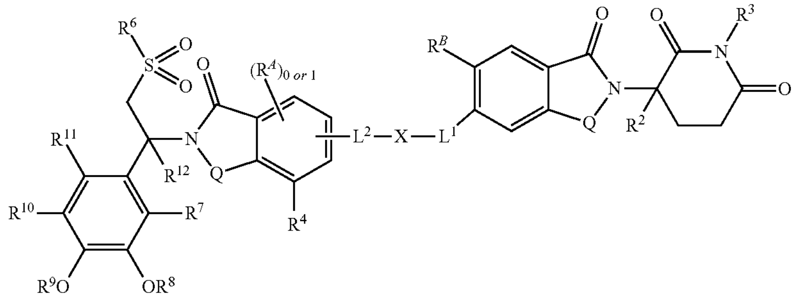

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $R^B$, $L^1$, $L^2$, Q, and X are each as defined herein.

In one embodiment, provided herein is a compound of Formula (XXXIII):

(XXXIII)

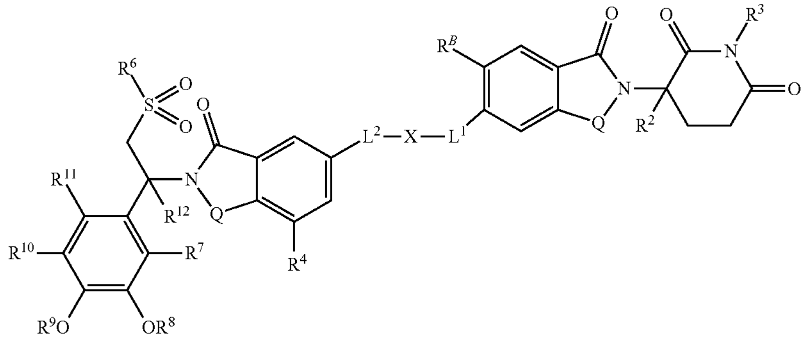

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^4$, $R^6$, $R^7$, $R^8$, $R^9$, $R^{10}$, $R^{11}$, $R^{12}$, $R^B$, $L^1$, $L^2$, Q, and X are each as defined herein.

In another embodiment, provided herein is a compound of Formula (XXXIV):

(XXXIV)

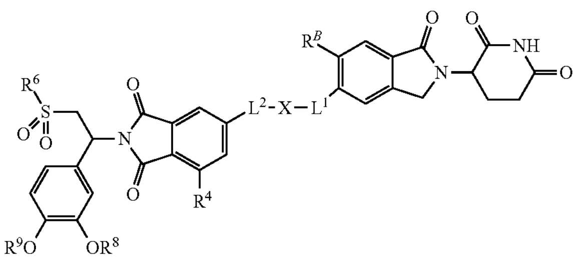

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^1$, $L^2$, and X are each as defined herein.

In yet another embodiment, provided herein is a compound of Formula (XXXV):

(XXXV)

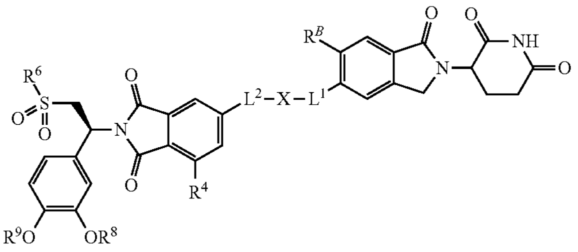

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^1$, $L^2$, and X are each as defined herein.

In yet another embodiment, provided herein is a compound of Formula (XXXVI):

(XXXVI)

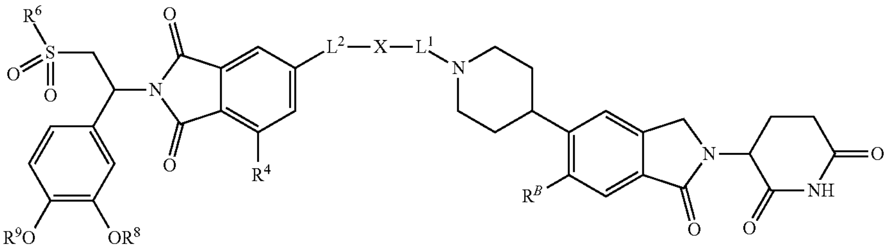

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^2$, and X are each as defined herein.

In still another embodiment, provided herein is a compound of Formula (XXXVII):

(XXXVII)

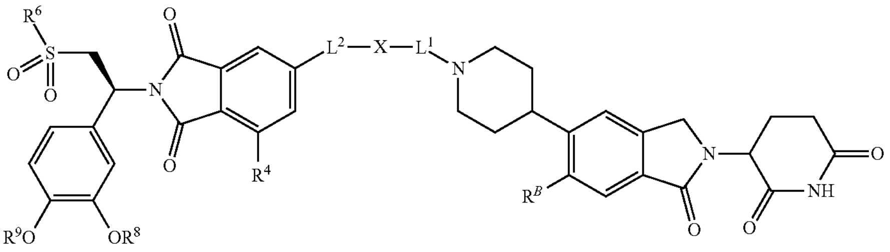

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $R^B$, $L^2$, and X are each as defined herein.

In one embodiment, provided herein is a compound of Formula (XXXVIII):

(XXXVIII)

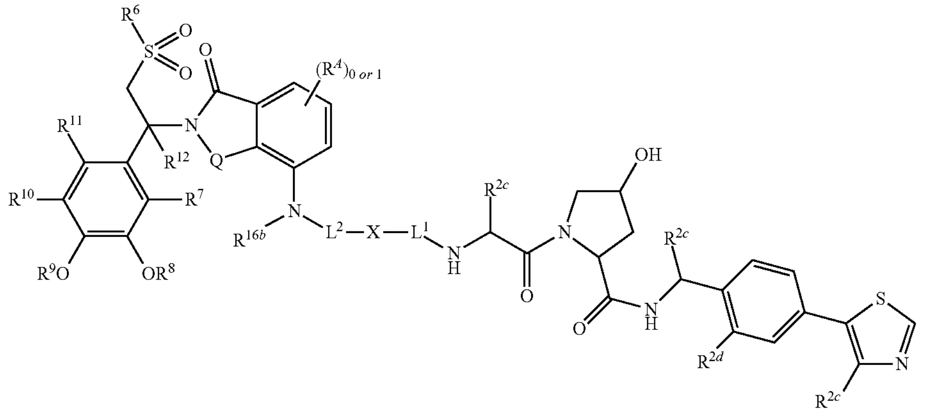

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^7$, $R^8$, $R^9$, $R^{10}$, $R^{11}$, $R^{12}$, $R^{2c}$, $R^{2d}$, $R^{16b}$, $R^A$, $L^1$, $L^2$, Q, and X are each as defined herein.

In another embodiment, provided herein is a compound of Formula (XXXIX):

(XXXIX)

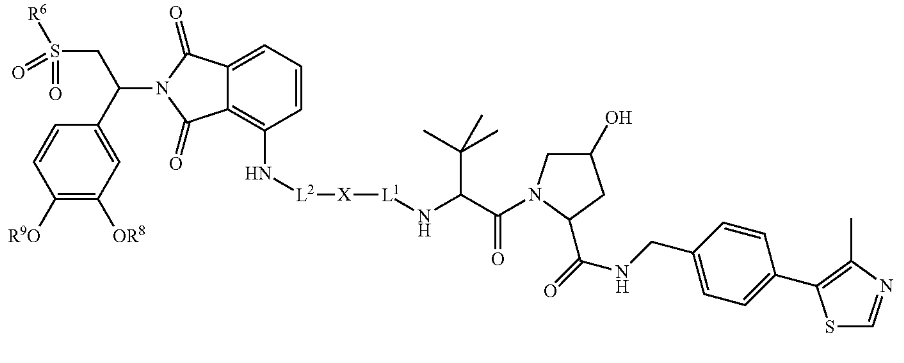

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^1$, $L^2$, and X are each as defined herein.

In yet another embodiment, provided herein is a compound of Formula (XL):

(XL)

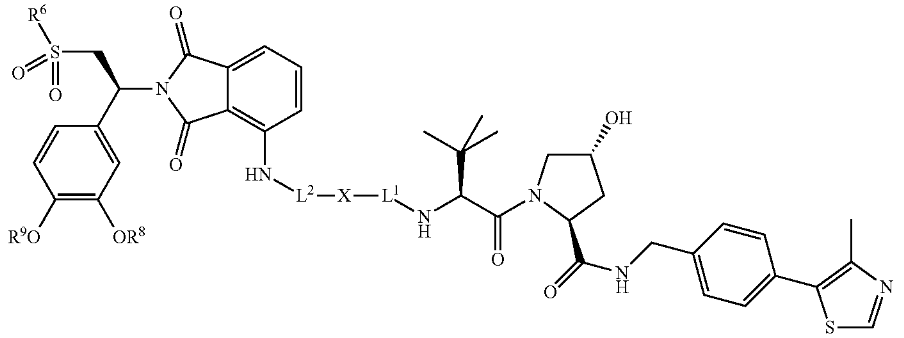

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^6$, $R^8$, $R^9$, $L^1$, $L^2$, and X are each as defined herein.

In one embodiment, provided herein is a compound of Formula (XLI):

(XLI)

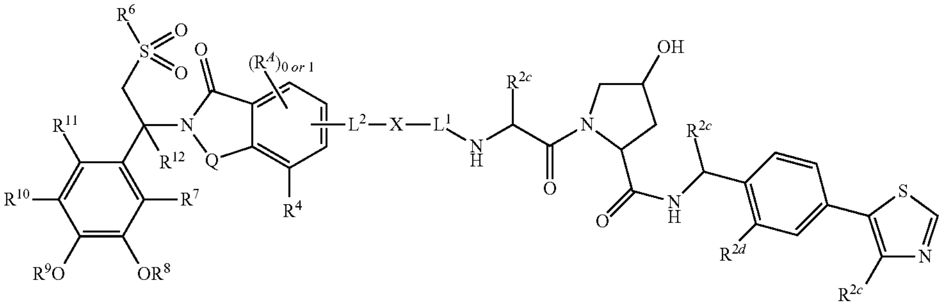

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^7$, $R^8$, $R^9$, $R^{10}$, $R^{11}$, $R^{12}$, $R^{2c}$, $R^{2d}$, $R^A$, $L^1$, $L^2$, Q, and X are each as defined herein.

In one embodiment, provided herein is a compound of Formula (XLII):

(XLII)

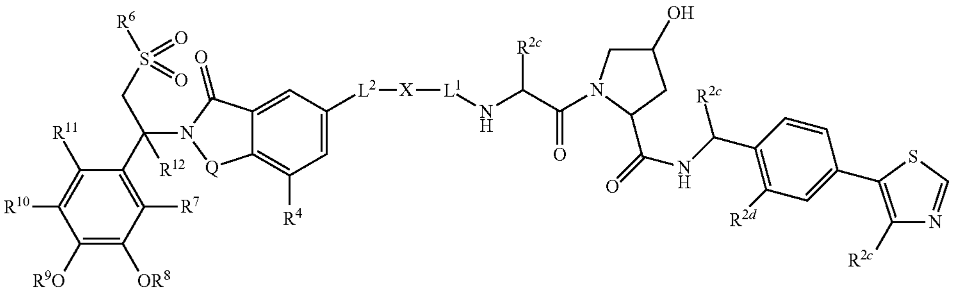

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^7$, $R^8$, $R^9$, $R^{10}$, $R^{11}$, $R^{12}$, $R^{2c}R^{2d}$, $L^1$, $L^2$, Q, and X are each as defined herein.

In another embodiment, provided herein is a compound of Formula (XLIII):

-continued

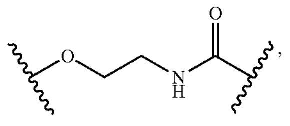

(XLIII)

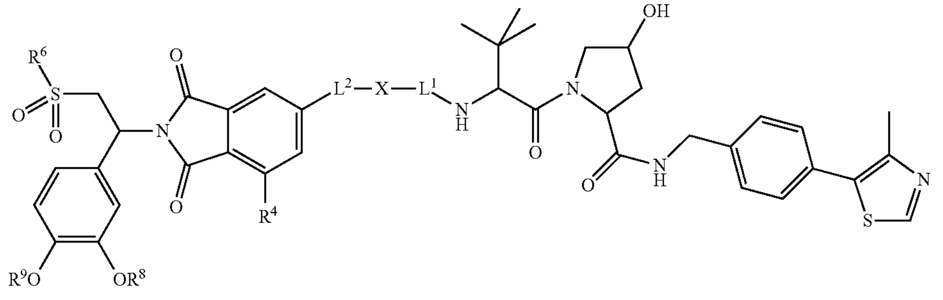

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^1$, $L^2$, and X are each as defined herein.

In yet another embodiment, provided herein is a compound of Formula (XLIV):

-continued

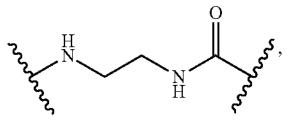

(XLIV)

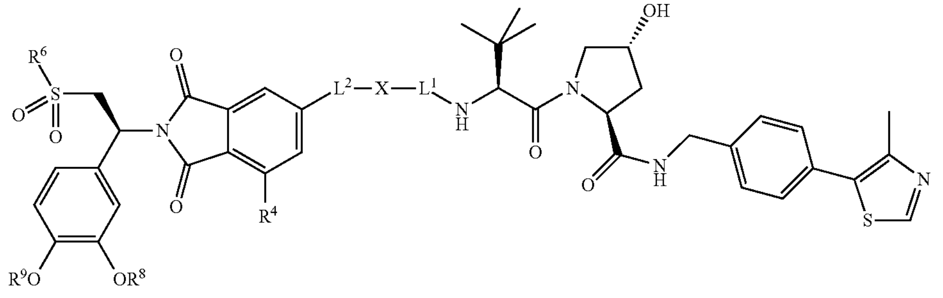

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^6$, $R^8$, $R^9$, $L^1$, $L^2$, and X are each as defined herein.

In certain embodiments, in any one of Formulae (II) to (XLIV), $L^1$, if present, is a bond, —NH—, pyrrolidin-1,3-diyl, piperidin-1,3-diyl, piperidin-1,4-diyl,

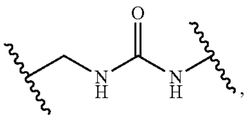

-continued

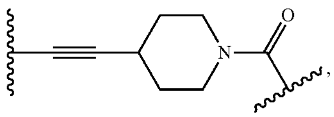

or

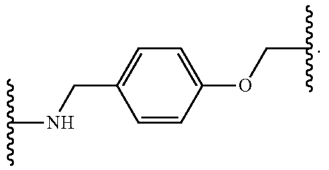

In certain embodiments, in any one of Formulae (II) to (XIL), $L^1$, if present, is a bond, —NH—, piperidin-1,4-diyl,

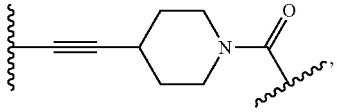
, or

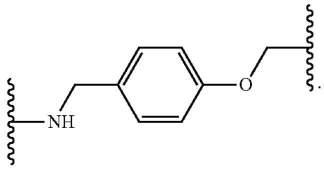
.

In certain embodiments, in any one of Formulae (II) to (XLIV) and (IIa) to (IId), $L^2$ is a bond, —O—, —NH—, or —C(═O)NH—.

In certain embodiments, in any one of Formulae (II) to (XLIV) and (IIa) to (IId), X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl,

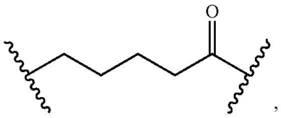
,

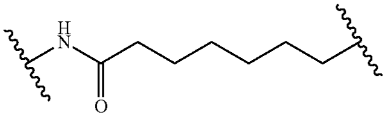
,

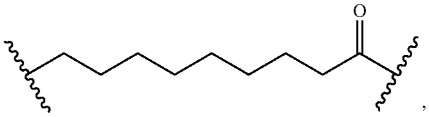
,

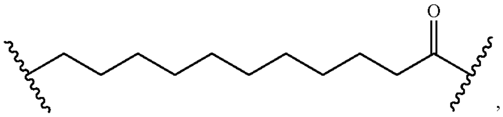
,

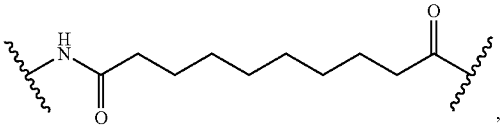
,

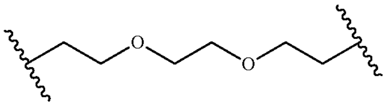
,

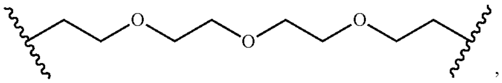
,

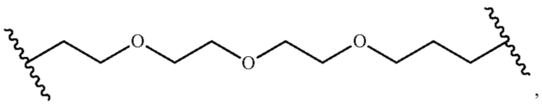
,

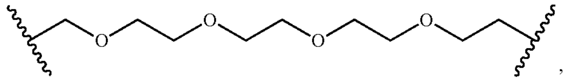
,

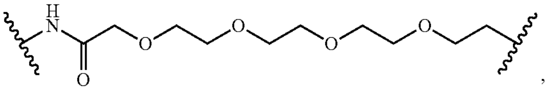
,

-continued

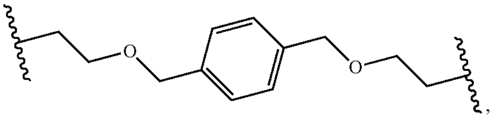
, or

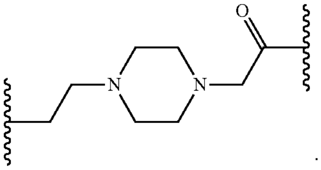
.

In certain embodiments, in any one of Formulae (II) to (XLIV) and (IIa) to (IId), $L^1$, if present, is a bond, —NH—, pyrrolidin-1,3-diyl, piperidin-1,3-diyl, piperidin-1,4-diyl,

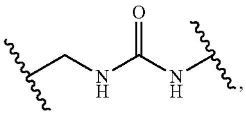
,

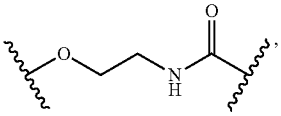
,

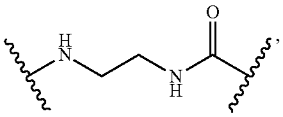
,

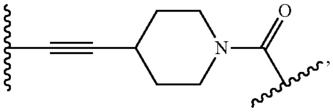
, or

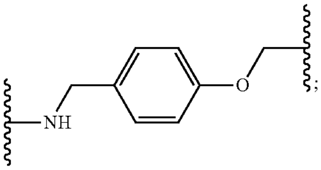
;

$L^2$ is a bond, —O—, —NH—, or —C(═O)NH—; and X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl

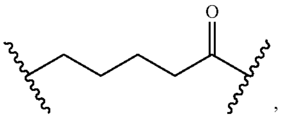
,

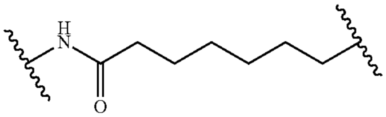
,

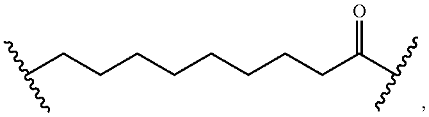
,

-continued
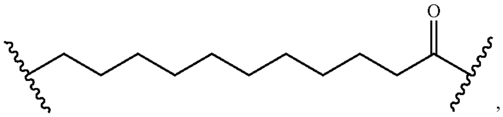,
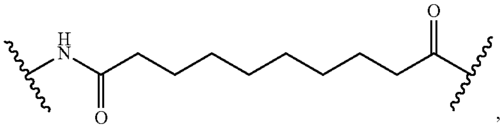,
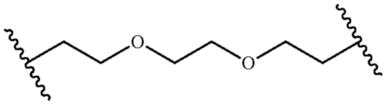,
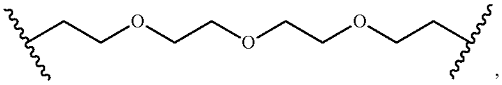,
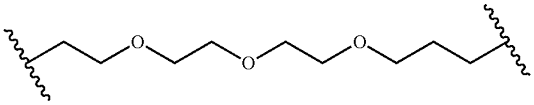,
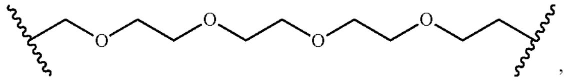,
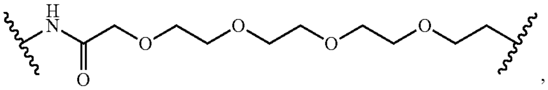,
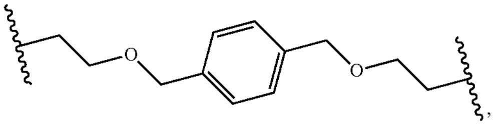, or
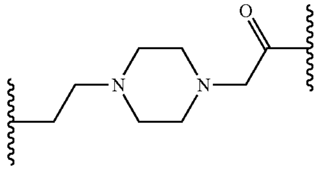.
In certain embodiments, in any one of Formulae (II) to (XLIV) and (IIa) to (IId), $L^1$, if present, is a bond, —NH—, piperidin-1,4-diyl,
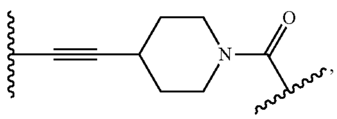, or
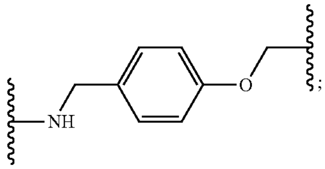;
$L^2$ is a bond, —O—, —NH—, or —C(═O)NH—; and X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-1,7-diyl,
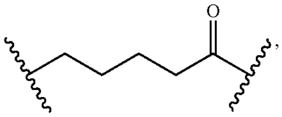,
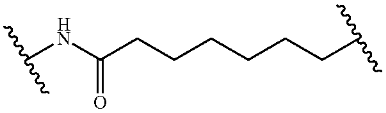,
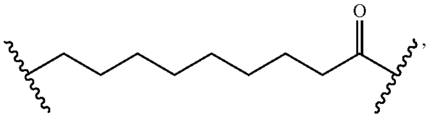,
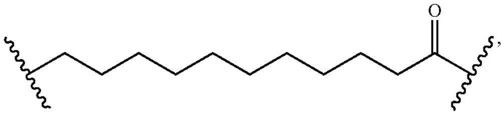,
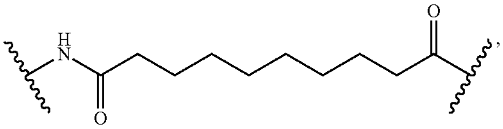,
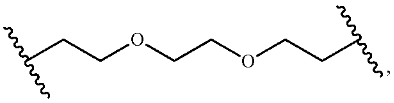,
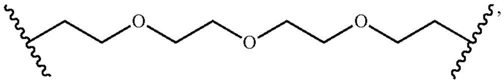,
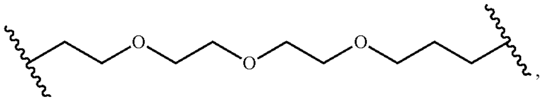,
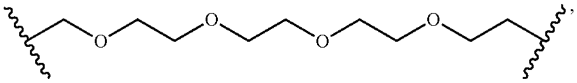,
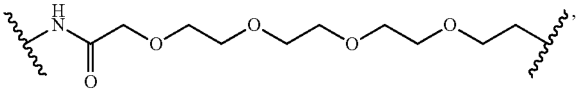,
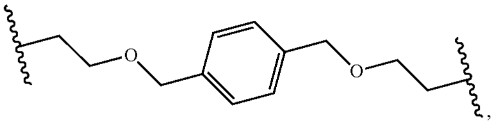, or
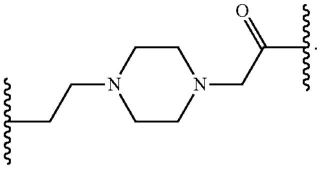.
In certain embodiments, in Formula (II), (IIa), (IIb), (IIc), or (IId), $R^W$ is

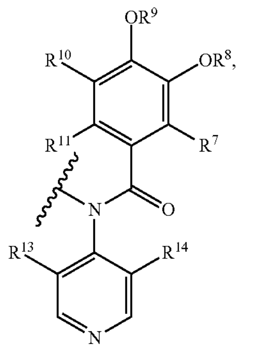

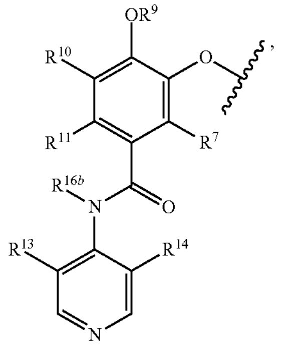

or

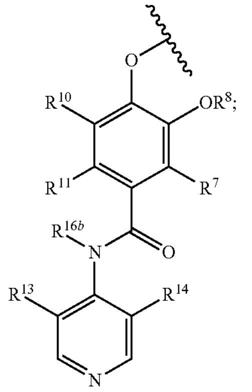

wherein each $R^7$, $R^8$, $R^9$, $R^{10}$, $R^{11}$, $R^{13}$, $R^{14}$, and $R^{16b}$ is as defined herein. In certain such embodiments, each $R^{13}$ and $R^{14}$ is independently halogen or $C_1$-$C_6$ alkyl. In certain such embodiments, both $R^{13}$ and $R^{14}$ are halogen (e.g., fluoro or chloro). In certain such embodiments, each of $R^7$, $R^{10}$ and $R^{11}$ is H. In certain such embodiments, each $R^8$ and $R^9$ is independently $C_1$-$C_6$ alkyl, $C_1$-$C_6$ haloalkyl, optionally substituted $C_3$-$C_7$ cycloalkyl, or optionally substituted ($C_3$-$C_7$ cycloalkyl)$C_1$-$C_6$ alkyl. In certain such embodiments, each of $R^{13}$ and $R^{14}$ is independently halogen (e.g., chloro or fluoro); $R^8$ is ($C_3$-$C_7$ cycloalkyl)$C_1$-$C_6$ alkyl (e.g., —$CH_2$-cyclopropyl); and $R^9$ is $C_1$-$C_6$ haloalkyl (e.g., —$CF_3$, —$CHF_2$, or —$CH_2F$). In certain embodiments, in Formula (II), (IIa), (IIb), (IIc), or (IId), $R^W$ is

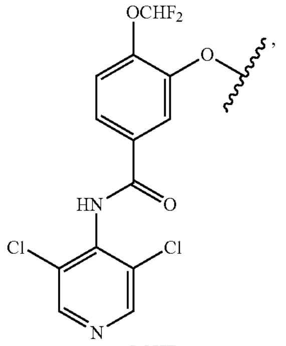

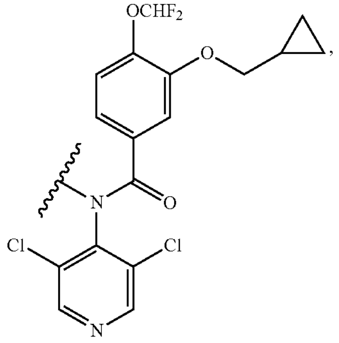

or

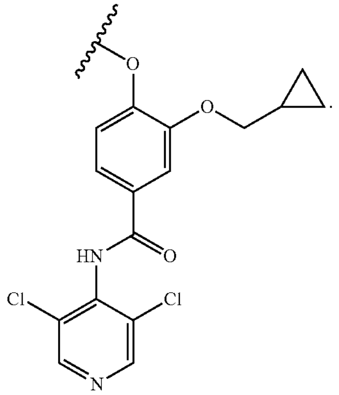

In one embodiment, provided herein is a compound of Formula (XLV):

(XLV)

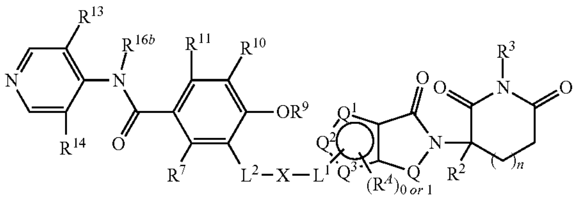

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^9$, $R^{10}$, $R^{11}$, $R^{13}$, $R^{14}$, $R^{16b}$, $R^A$, $L^1$, $L^2$, Q, $Q^1$, $Q^2$, $Q^3$, X, and n are each as defined herein.

In another embodiment, provided herein is a compound of Formula (XLVI):

(XLVI)

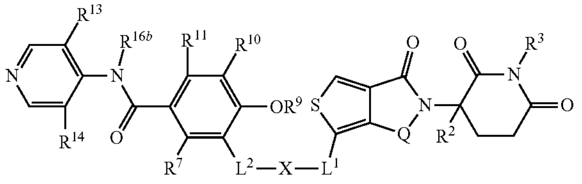

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^9$, $R^{10}$, $R^{11}$, $R^{13}$, $R^{14}$, $R^{16b}$, $L^1$, $L^2$, Q, and X are each as defined herein.

In yet another embodiment, provided herein is a compound of Formula (XLVII):

(XLVII)

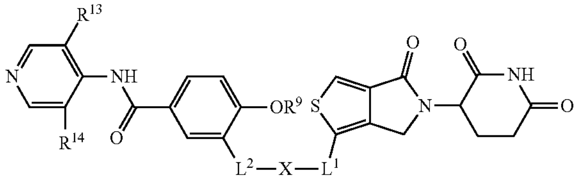

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $L^1$, $L^2$, and X are each as defined herein.

In still another embodiment, provided herein is a compound of Formula (XLVIII):

(XLVIII)

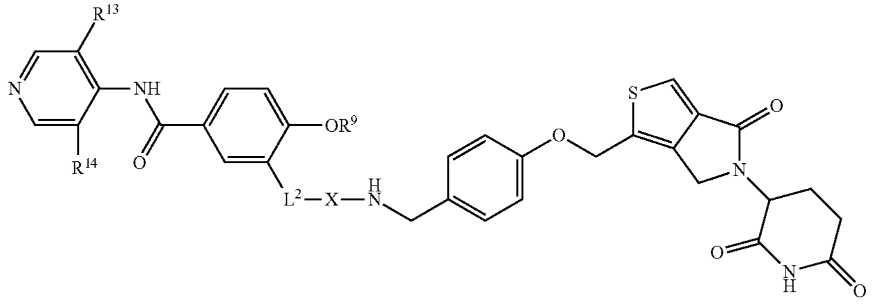

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $L^2$, and X are each as defined herein.

In one embodiment, provided herein is a compound of Formula (XLIX):

(XLIX)

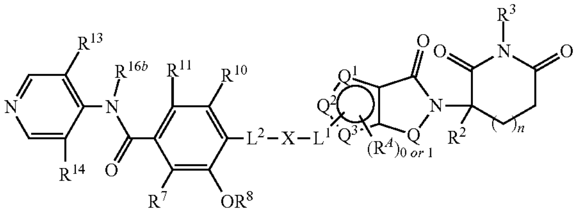

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^8$, $R^{10}$, $R^{11}$, $R^{13}$, $R^{14}$, $R^{16b}$, $R^A$, $L^1$, $L^2$, Q, $Q^1$, $Q^2$, $Q^3$, X, and n are each as defined herein.

In another embodiment, provided herein is a compound of Formula (L):

(L)

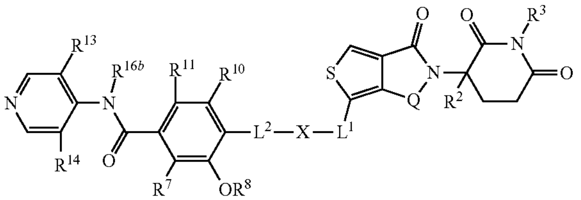

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^8$, $R^{10}$, $R^{11}$, $R^{13}$, $R^{14}$, $R^{16b}$, $L^1$, $L^2$, Q, and X are each as defined herein.

In yet another embodiment, provided herein is a compound of Formula (LI):

(LI)

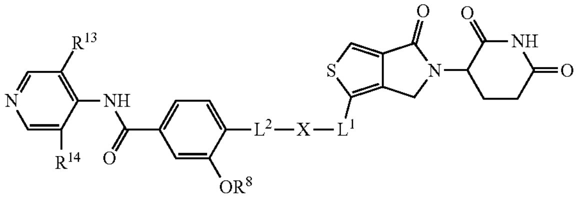

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $L^1$, $L^2$, and X are each as defined herein.

In still another embodiment, provided herein is a compound of Formula (LII):

(LII)

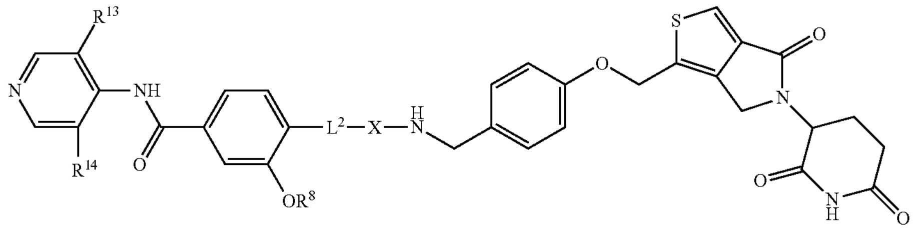

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $L^2$, and X are each as defined herein.

In one embodiment, provided herein is a compound of Formula (LIII):

(LIII)

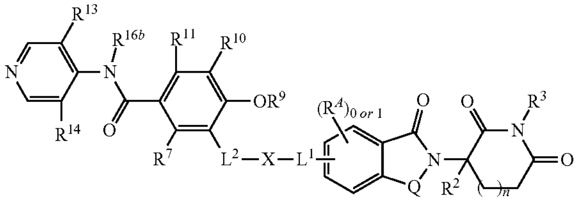

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^9$, $R^{10}$, $R^{11}$, $R^{13}$, $R^{14}$, $R^{16b}$, $R^A$, $L^1$, $L^2$, Q, X, and n are each as defined herein.

In one embodiment, provided herein is a compound of Formula (LIV):

(LIV)

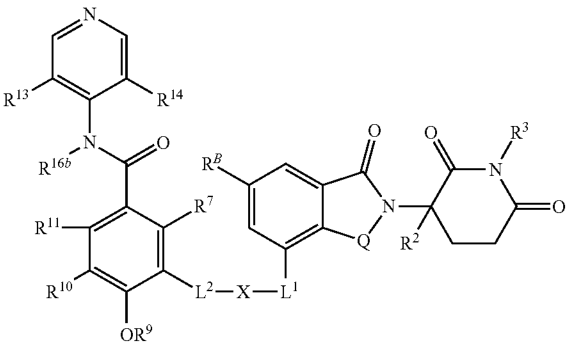

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^9$, $R^{10}$, $R^{11}$, $R^{13}$, $R^{14}$, $R^{16b}$, $R^B$, $L^1$, $L^2$, Q, and X are each as defined herein.

In another embodiment, provided herein is a compound of Formula (LV):

(LV)

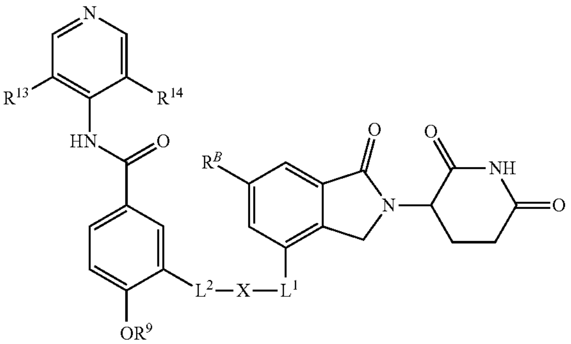

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $R^B$, $L^1$, $L^2$, and X are each as defined herein.

In yet another embodiment, provided herein is a compound of Formula (LVI):

(LVI)

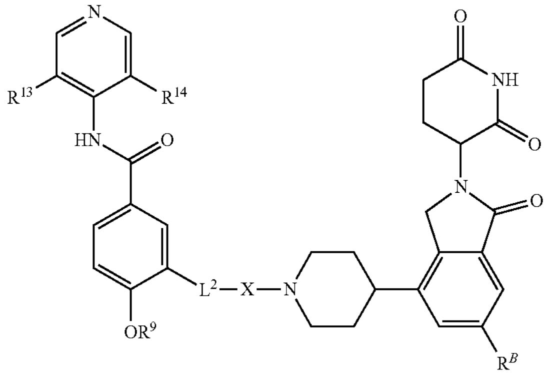

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $R^B$, $L^2$, and X are each as defined herein.

In one embodiment, provided herein is a compound of Formula (LVII):

(LVII)

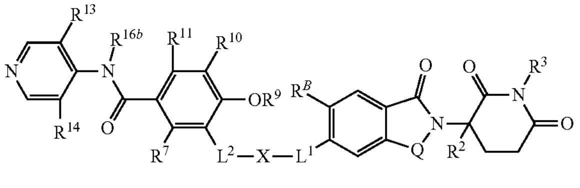

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^9$, $R^{10}$, $R^{11}$, $R^{13}$, $R^{14}$, $R^{16b}$, $R^B$, $L^1$, $L^2$, Q, and X are each as defined herein.

In another embodiment, provided herein is a compound of Formula (LVIII):

(LVIII)

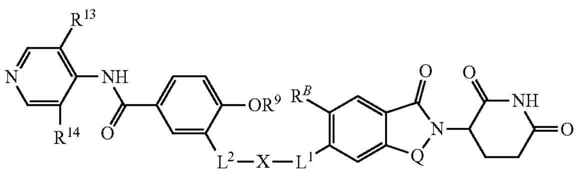

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $R^B$, $L^1$, $L^2$, and X are each as defined herein.

In yet another embodiment, provided herein is a compound of Formula (LIX):

(LIX)

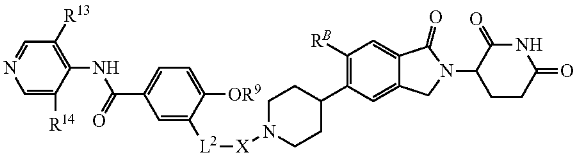

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $R^B$, $L^2$, and X are each as defined herein.

In one embodiment, provided herein is a compound of Formula (LX):

(LX)

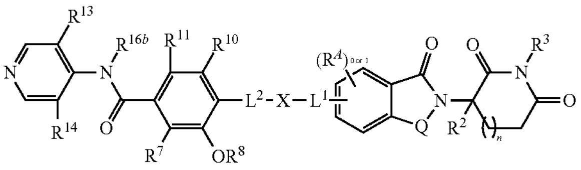

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^8$, $R^{10}$, $R^{11}$, $R^{13}$, $R^{14}$, $R^{16b}$, $R^A$, $L^1$, $L^2$, Q, X, and n are each as defined herein.

In one embodiment, provided herein is a compound of Formula (LXI):

(LXI)

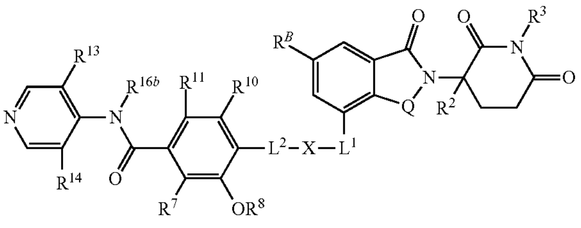

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^8$, $R^{10}$, $R^{11}$, $R^{13}$, $R^{14}$, $R^{16b}$, $R^B$, $L^1$, $L^2$, Q, and X are each as defined herein.

In another embodiment, provided herein is a compound of Formula (LXII):

(LXII)

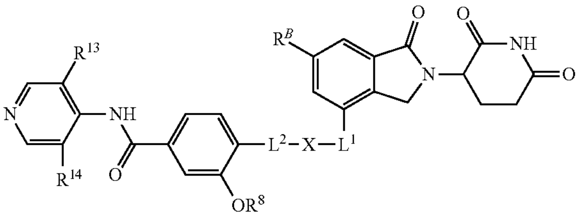

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $R^B$, $L^1$, $L^2$, and X are each as defined herein.

In yet another embodiment, provided herein is a compound of Formula (LXIII):

(LXIII)

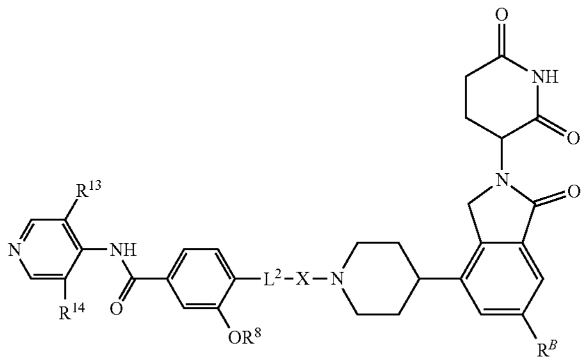

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $L^2$, and X are each as defined herein.

In one embodiment, provided herein is a compound of Formula (LXIV):

(LXIV)

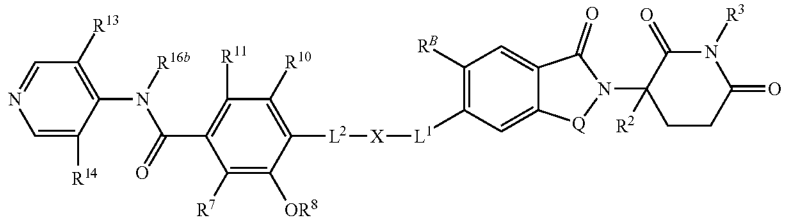

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^2$, $R^3$, $R^7$, $R^8$, $R^{10}$, $R^{11}$, $R^{13}$, $R^{14}$, $R^{16b}$, $R^B$, $L^1$, $L^2$, Q, and X are each as defined herein.

In another embodiment, provided herein is a compound of Formula (LXV):

(LXIV)

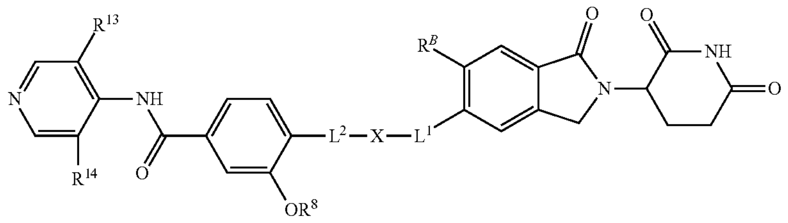

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $R^B$, $L^1$, $L^2$, and X are each as defined herein.

In yet another embodiment, provided herein is a compound of Formula (LXVI):

(LXVI)

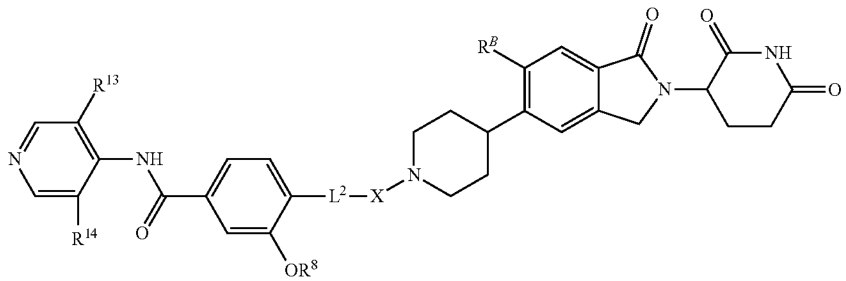

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $R^B$, $L^2$, and X are each as defined herein.

In one embodiment, provided herein is a compound of Formula (LXVII):

(LXVII)

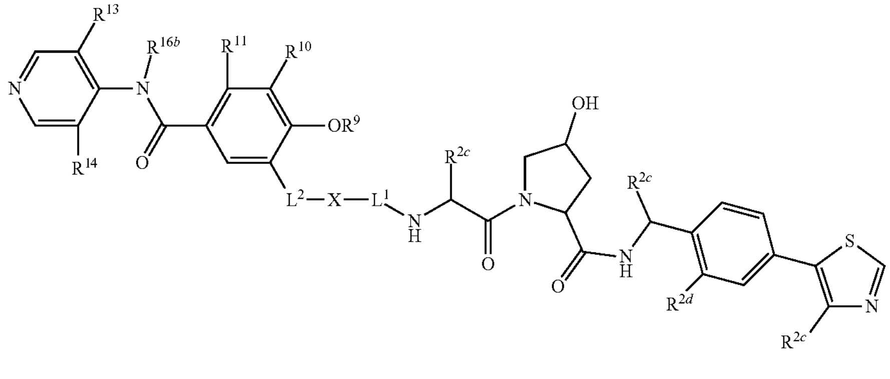

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^7$, $R^9$, $R^{10}$, $R^{11}$, $R^{13}$, $R^{14}$, $R^{2c}$, $R^{2d}$, $R^{16b}$, $L^1$, $L^2$, and X are each as defined herein.

In another embodiment, provided herein is a compound of Formula (LXVIII):

(LXVIII)

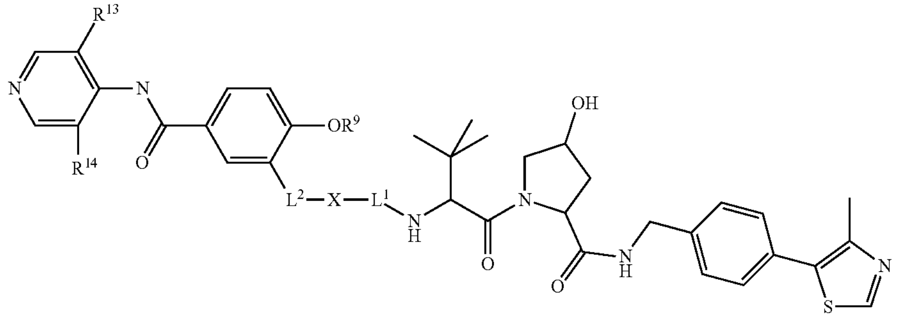

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $L^1$, $L^2$, and X are each as defined herein.

In yet another embodiment, provided herein is a compound of Formula (LXIX):

(LXIX)

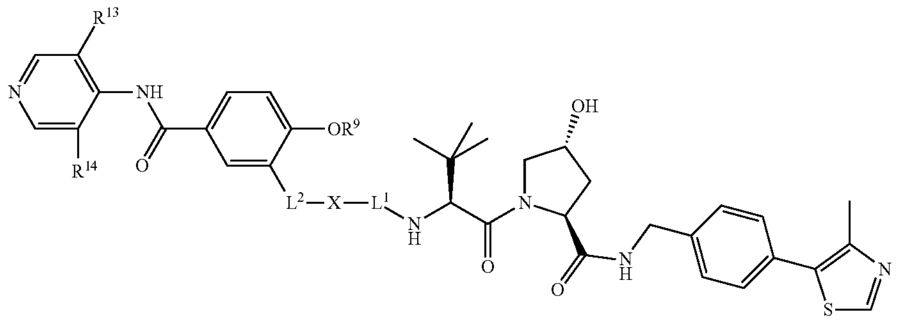

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^9$, $R^{13}$, $R^{14}$, $L^1$, $L^2$, and X are each as defined herein.

In one embodiment, provided herein is a compound of Formula (LXX):

(LXX)

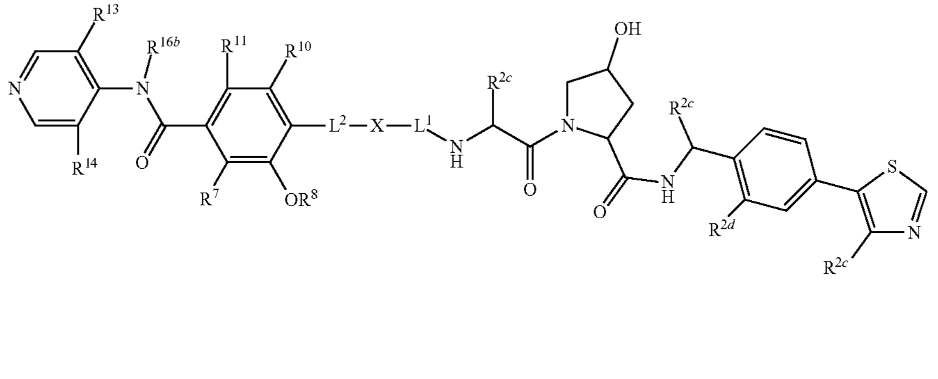

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^7$, $R^8$, $R^{10}$, $R^{11}$, $R^{13}$, $R^{14}$, $R^{2c}$, $R^{2d}$, $R^{16b}$, $L^1$, $L^2$, and X are each as defined herein.

In another embodiment, provided herein is a compound of Formula (LXXI):

(LXXI)

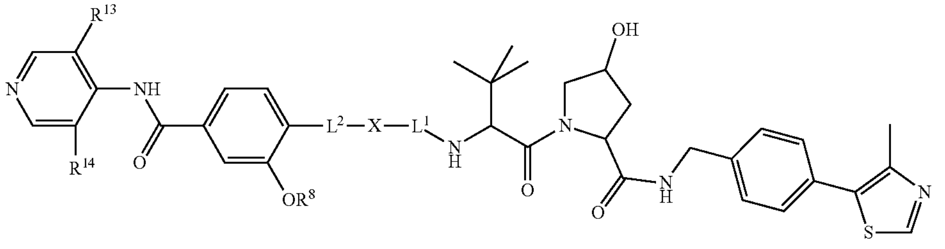

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $L^1$, $L^2$, and X are each as defined herein.

In yet another embodiment, provided herein is a compound of Formula (LXXII):

(LXXII)

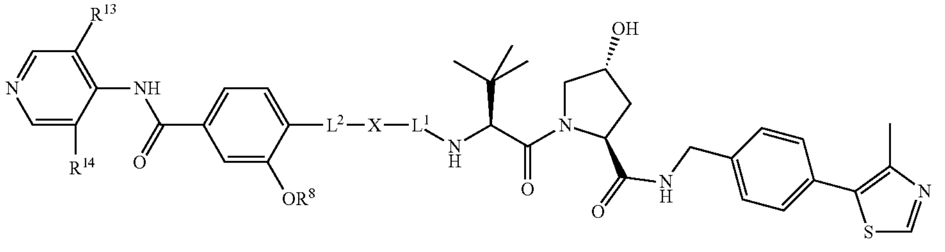

or a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^8$, $R^{13}$, $R^{14}$, $L^1$, $L^2$, and X are each as defined herein.

In certain embodiments, in any one of Formulae (XLV) to (LXXII), $R^8$ is optionally substituted $C_1$-$C_6$ alkyl, $C_1$-$C_6$ haloalkyl, or optionally substituted ($C_3$-$C_7$ cycloalkyl)$C_1$-$C_6$ alkyl. In certain embodiments, in any one of Formulae (XLV) to (LXXII), $R^8$ is optionally substituted $C_1$-$C_6$ alkyl. In certain embodiments, in any one of Formulae (XLV) to (LXXII), $R^8$ is optionally substituted methyl. In certain embodiments, in any one of Formulae (XLV) to (LXXII), $R^8$ is methyl. In certain embodiments, in any one of Formulae (XLV) to (LXXII), $R^8$ is $C_1$-$C_6$ haloalkyl. In certain embodiments, in any one of Formulae (XLV) to (LXXII), $R^8$ is difluoromethyl or trifluoromethyl. In certain embodiments, in any one of Formulae (XLV) to (LXXII), $R^8$ is optionally substituted ($C_3$-$C_7$ cycloalkyl)$C_1$-$C_6$ alkyl. In certain embodiments, in any one of Formulae (XLV) to (LXXII), $R^8$ is optionally substituted ($C_3$-$C_7$ cycloalkyl)methyl. In certain embodiments, in any one of Formulae (XLV) to (LXXII), $R^8$ is cyclopropylmethyl.

In certain embodiments, in any one of Formulae (XLV) to (LXXII), $R^9$ is optionally substituted $C_1$-$C_6$ alkyl, $C_1$-$C_6$ haloalkyl, or optionally substituted ($C_3$-$C_7$ cycloalkyl)$C_1$-$C_6$ alkyl. In certain embodiments, in any one of Formulae (XLV) to (LXXII), $R^9$ is optionally substituted $C_1$-$C_6$ alkyl. In certain embodiments, in any one of Formulae (XLV) to (LXXII), $R^9$ is optionally substituted methyl. In certain embodiments, in any one of Formulae (XLV) to (LXXII), $R^9$ is methyl. In certain embodiments, in any one of Formulae (XLV) to (LXXII), $R^9$ is $C_1$-$C_6$ haloalkyl. In certain embodiments, in any one of Formulae (XLV) to (LXXII), $R^9$ is difluoromethyl or trifluoromethyl. In certain embodiments, in any one of Formulae (XLV) to (LXXII), $R^9$ is optionally substituted ($C_3$-$C_7$ cycloalkyl)$C_1$-$C_6$ alkyl. In certain embodiments, in any one of Formulae (XLV) to (LXXII), $R^9$ is optionally substituted ($C_3$-$C_7$ cycloalkyl)methyl. In certain embodiments, in any one of Formulae (XLV) to (LXXII), $R^9$ is cyclopropylmethyl.

In certain embodiments, in any one of Formulae (XLV) to (LXXII), $R^{13}$ is halogen or optionally substituted $C_1$-$C_6$ alkyl. In certain embodiments, in any one of Formulae (XLV) to (LXXII), $R^{13}$ is halogen. In certain embodiments, in any one of Formulae (XLV) to (LXXII), $R^{13}$ is fluoro, chloro, or bromo. In certain embodiments, in any one of Formulae (XLV) to (LXXII), $R^{13}$ is chloro. In certain embodiments, in any one of Formulae (XLV) to (LXXII), $R^{13}$ is optionally substituted $C_1$-$C_6$ alkyl. In certain embodiments, in any one of Formulae (XLV) to (LXXII), $R^{13}$ is methyl or trifluoromethyl.

In certain embodiments, in any one of Formulae (XLV) to (LXXII), $R^{14}$ is halogen or optionally substituted $C_1$-$C_6$ alkyl. In certain embodiments, in any one of Formulae (XLV) to (LXXII), $R^{14}$ is halogen. In certain embodiments, in any one of Formulae (XLV) to (LXXII), $R^{14}$ is fluoro, chloro, or bromo. In certain embodiments, in any one of Formulae (XLV) to (LXXII), $R^{14}$ is chloro. In certain embodiments, in any one of Formulae (XLV) to (LXXII), $R^{14}$ is optionally substituted $C_1$-$C_6$ alkyl. In certain embodiments, in any one of Formulae (XLV) to (LXXII), $R^{14}$ is methyl or trifluoromethyl.

In certain embodiments, in any one of Formulae (XLV) to (LXXII), $L^1$, if present, is a bond, —NH—, pyrrolidin-1,3-diyl, piperidin-1,3-diyl, piperidin-1,4-diyl,

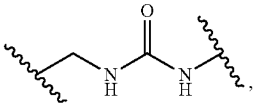

,

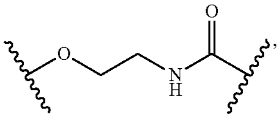

,

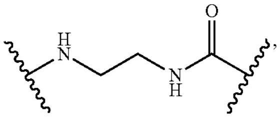

,

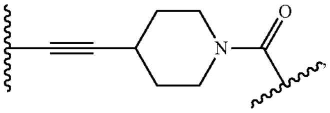

, or

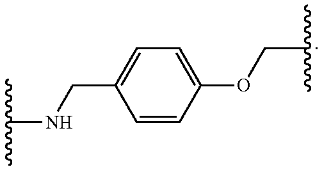

.

In certain embodiments, in any one of Formulae (II) to (XIL), $L^1$, if present, is a bond, —NH—, piperidin-1,4-diyl,

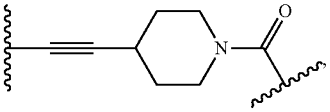

, or

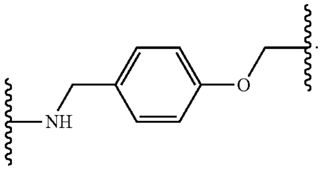

.

In certain embodiments, in any one of Formulae (XLV) to (LXXII), $L^2$ is a bond, —O—, —NH—, or —C(═O)NH—.

In certain embodiments, in any one of Formulae (XLV) to (LXXII), X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl,

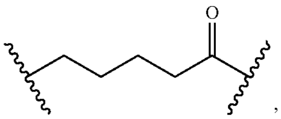

,

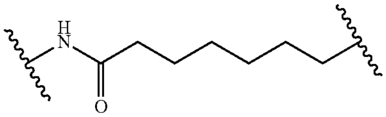

,

-continued

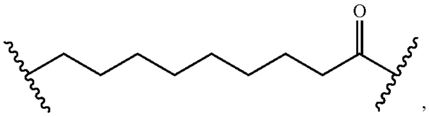

,

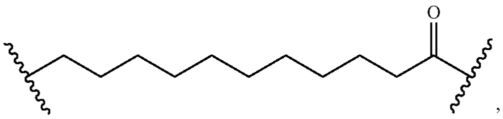

,

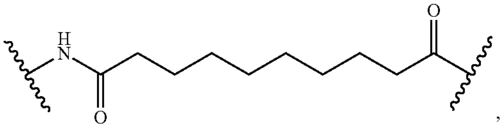

,

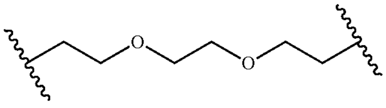

,

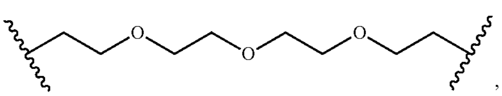

,

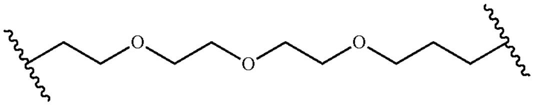

,

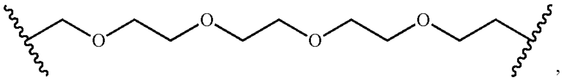

,

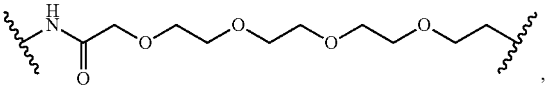

,

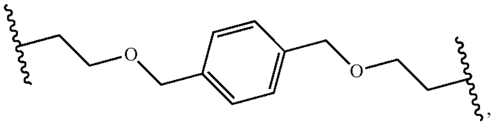

, or

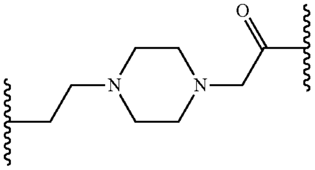

.

In certain embodiments, in any one of Formulae (XLV) to (LXXII), $L^1$, if present, is a bond, —NH—, pyrrolidin-1,3-diyl, piperidin-1,3-diyl, piperidin-1,4-diyl,

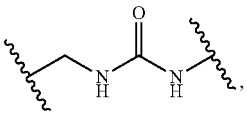

,

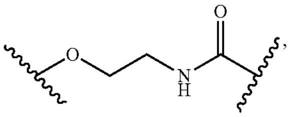

,

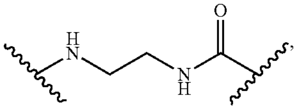

,

-continued

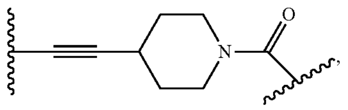

, or

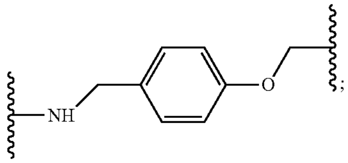

;

$L^2$ is a bond, —O—, —NH—, or —C(═O)NH—; and X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl,

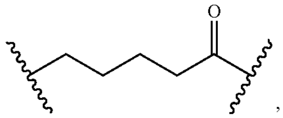

,

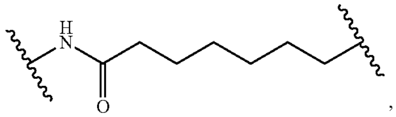

,

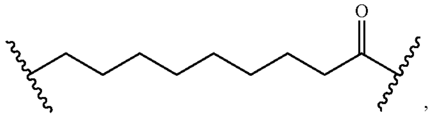

,

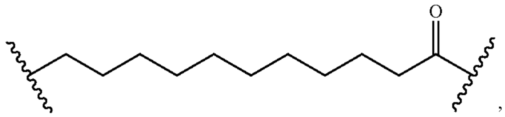

,

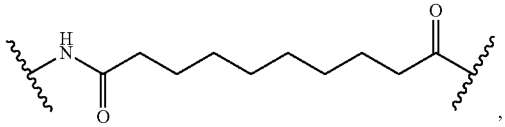

,

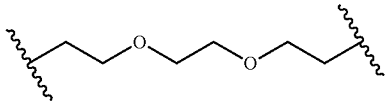

,

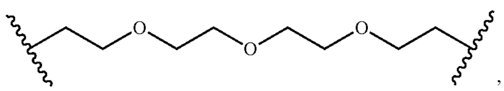

,

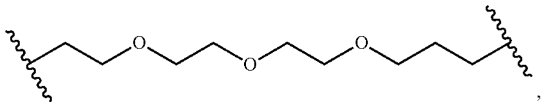

,

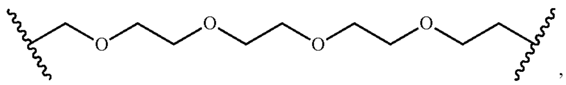

,

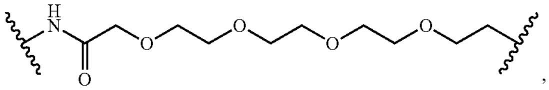

,

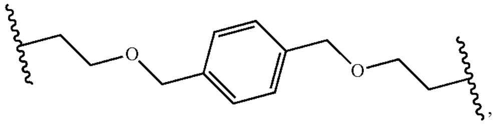

, or

-continued

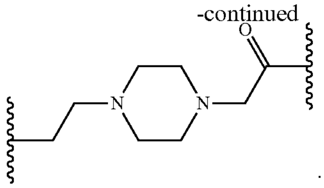

.

In certain embodiments, in any one of Formulae (XLV) to (LXXII), $L^1$, if present, is a bond, —NH—, piperidin-1,4-diyl,

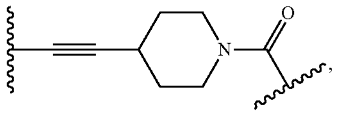

, or

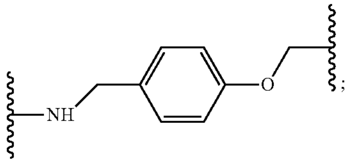

;

$L^2$ is a bond, —O—NH—, or —C(═O)NH—; and X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl,

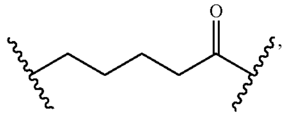

,

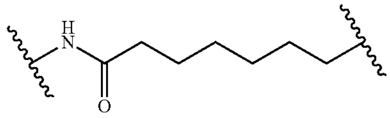

,

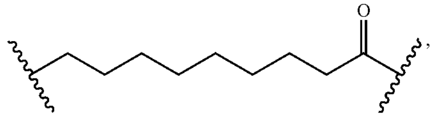

,

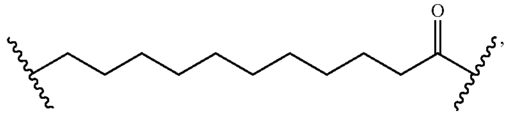

,

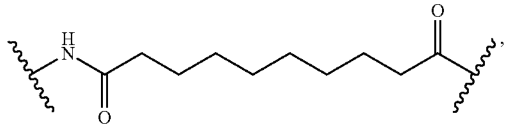

,

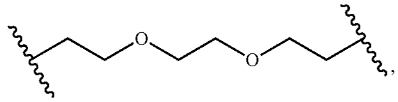

,

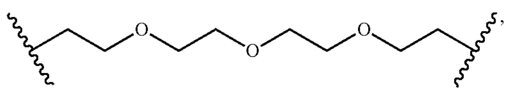

,

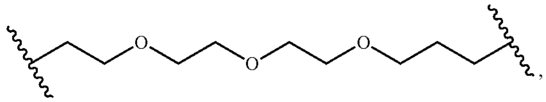

,

-continued

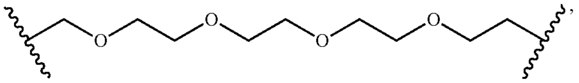

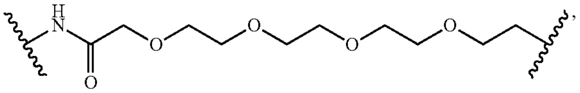

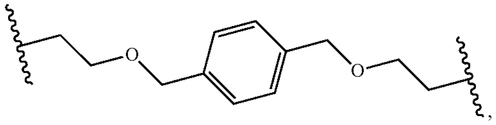

or

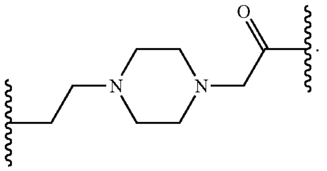

In certain embodiments, in Formula (II), (IIa), (IIb), (IIc), or (IId), $R^W$ is

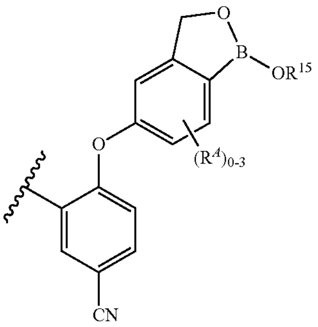

or

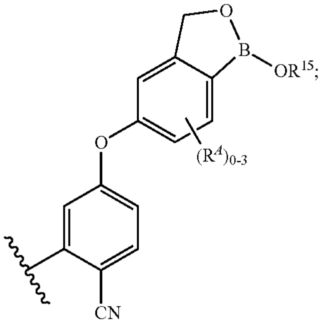

wherein each $R^{15}$ and $R^A$ is as defined herein. In certain such embodiments, each $R^A$ is independently absent, halogen, or $C_1$-$C_6$ alkyl. In certain such embodiments, $R^{15}$ is H.

In certain embodiments, in Formula (II), (IIa), (IIb), (IIc), or (IId), $R^W$ is

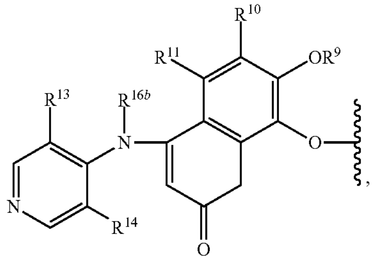

wherein $R^9$, $R^{10}$, $R^{11}$, $R^{13}$, $R^{14}$, and $R^{16b}$ are each as defined herein. In certain such embodiments, each $R^{13}$ and $R^{14}$ is independently halogen or $C_1$-$C_6$ alkyl; and each $R^{10}$ and $R^{11}$ is H. In certain such embodiments, each of $R^{13}$ and $R^{14}$ is independently halogen (e.g., chloro or fluoro); and $R^9$ is $C_1$-$C_6$ alkyl (e.g., methyl or ethyl). In certain embodiments, $R^W$ is

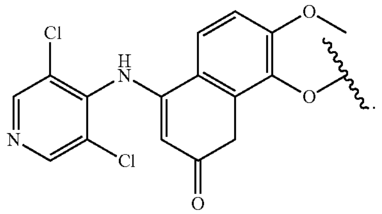 [SMILES: *Oc1c(OC)ccc2c1CC(=O)C=C2Nc1c(Cl)cncc1Cl]

In certain embodiments, in Formula (II), $R^1$ is

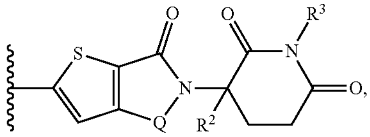

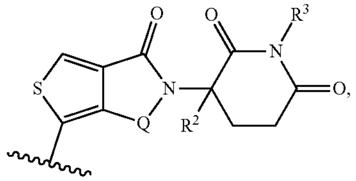

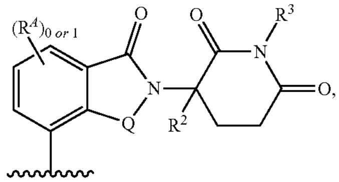

or

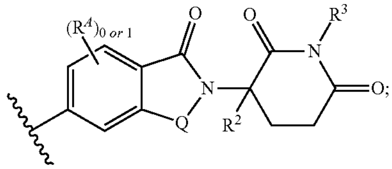

and $-L^1$-X-$L^2$- is one listed in Table A. In certain embodiments, in Formula (II), $R^1$ is -continued
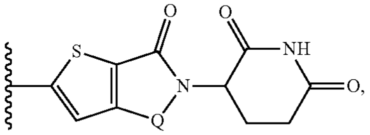
,
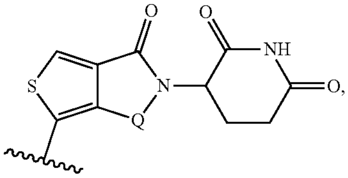
,
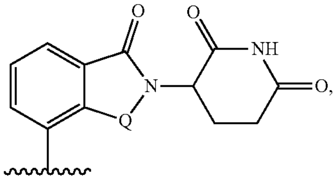
,
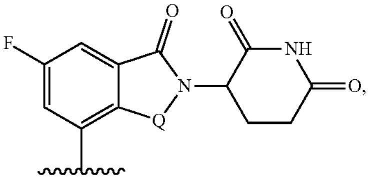
,
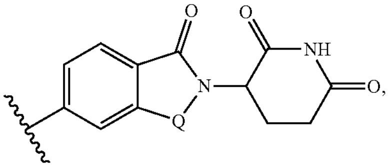
,
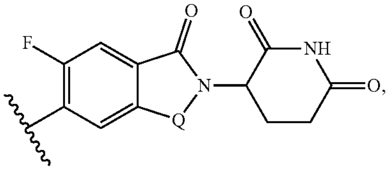
,
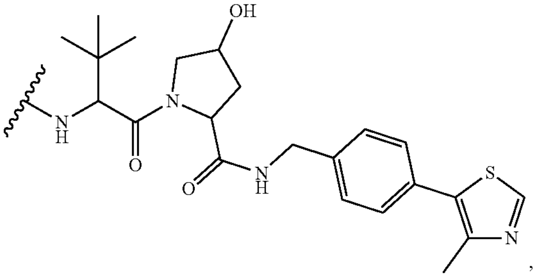
,
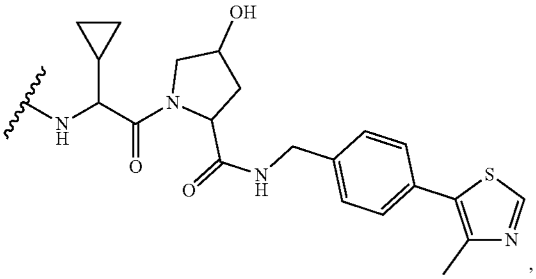
,
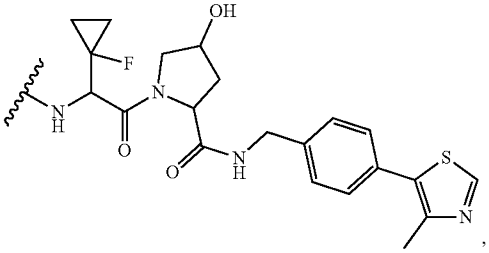
, or
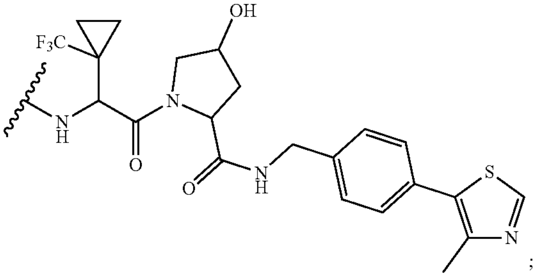
;
and -$L^1$-X-$L^2$- is one listed in Table A; and $R^W$ is as defined herein.
TABLE A
| —$L^1$—X—$L^2$— |
|---|
| —$NH(CH_2)_2NHC({=}O)(CH_2CH_2O)_3$— |
| —$NH(CH_2)_2NHC({=}O)CH_2CH_2OCH_2CH_2$— |
| —$NH(CH_2CH_2O)_3CH_2CH_2$— |
| —$NH(CH_2CH_2O)_2CH_2CH_2$— |
| —$NH(CH_2CH_2O)_4$— |
| —$NH(CH_2CH_2O)_3$— |
| —$NH(CH_2)_{1-3}(OCH_2CH_2)_3$— |
| —$NH(CH_2)_{1-3}(OCH_2CH_2)_3O$— |
| —$NH(CH_2)_{1-3}(OCH_2CH_2)_3$—$C({=}O)$— |
| —$NH(CH_2)_6O$— |
| —$NH(CH_2)_7O$— |
| —$NH(CH_2)_8O$— |
| —$O(CH_2)_2NHC({=}O)(CH_2CH_2O)_3$— |
| —$O(CH_2)_2NHC({=}O(CH_2CH_2O)_2CH_2CH_2$— |

TABLE A-continued
| —$L^1$—X—$L^2$— |
| --- |
| —$O(CH_2)_2NHC(=O)CH_2CH_2OCH_2CH_2$— |
| —$CH_2NHC(O)NH(CH_2)_5NHC(O)CH_2$— |
| 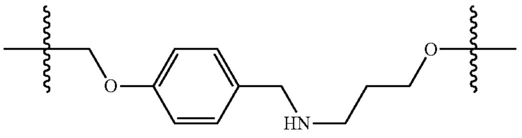 |
| 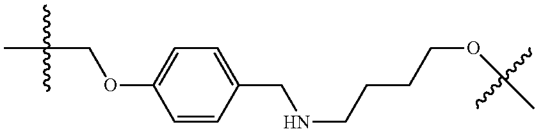 [SMILES: *COc1ccc(CNCCCCO*)cc1] |
| 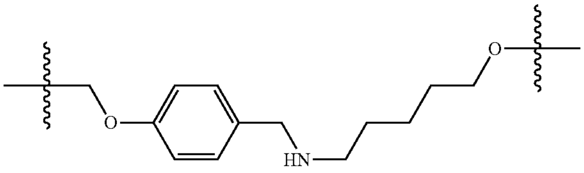 [SMILES: *COc1ccc(CNCCCCCO*)cc1] |
| 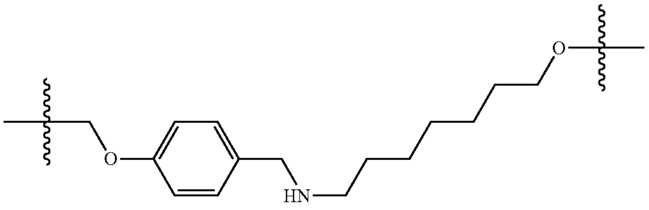 [SMILES: *COc1ccc(CNCCCCCCCO*)cc1] |
| 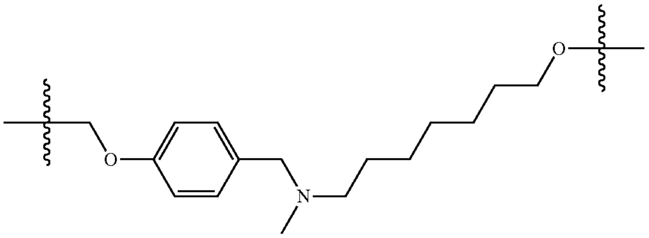 [SMILES: *COc1ccc(CN(C)CCCCCCCO*)cc1] |
| 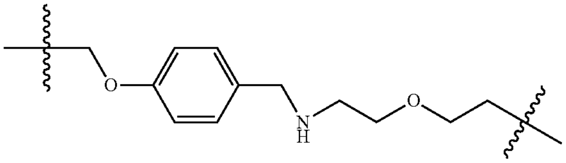 [SMILES: *CCOCCNCc1ccc(OC*)cc1] |
| 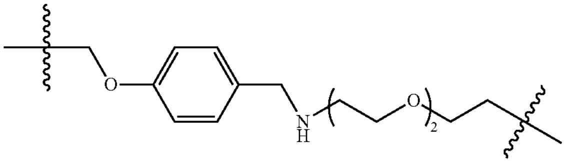 |
| 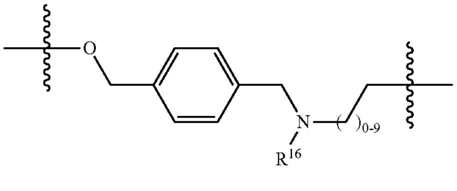 |

TABLE A-continued
| —$L^1$—X—$L^2$— |
| --- |
| 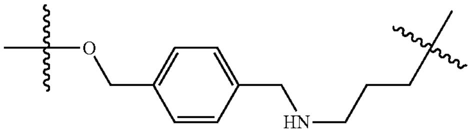 |
| 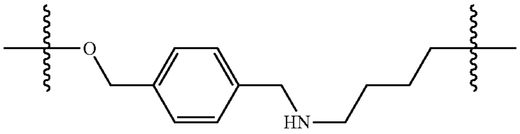 |
| 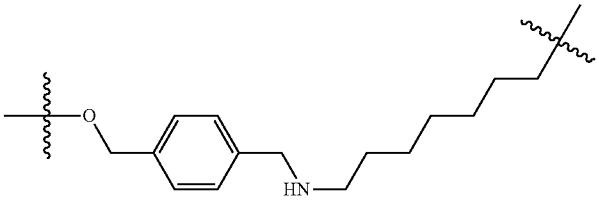 [SMILES: *CCCCCCCNCc1ccc(CO*)cc1] |
| 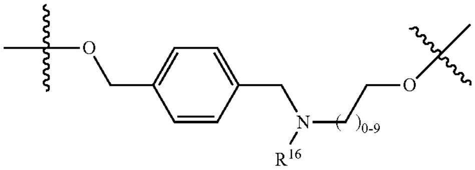 |
| 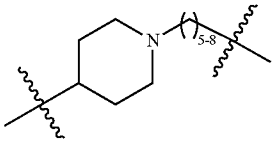 |
| 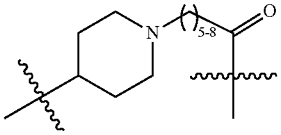 |
| 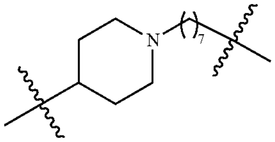 |
| 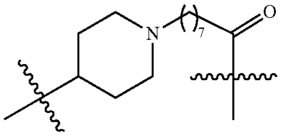 |
| 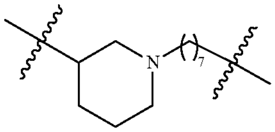 |
| 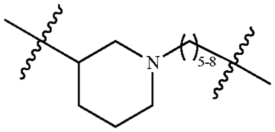 |

TABLE A-continued
| $-L^1-X-L^2-$ |
| --- |
| 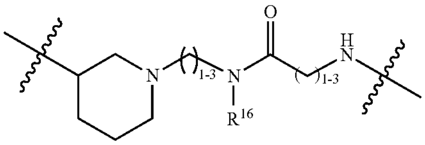 |
| 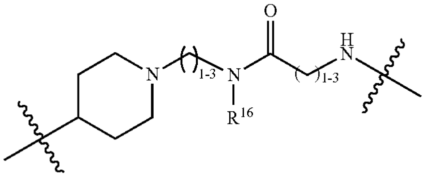 |
| 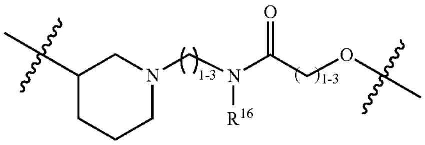 |
| 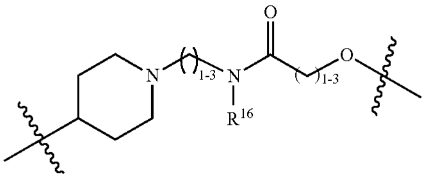 |
| 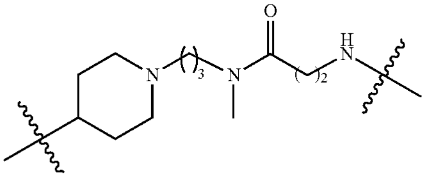 |
| 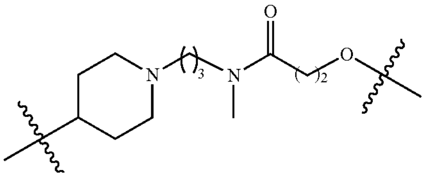 |
| 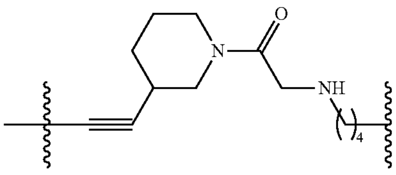 |
| $-C(O)(CH_2)_{4\text{-}10}-O-$ |
| $-C(O)(CH_2)_6-O-$ |
| $-C(O)(CH_2)_8-O-$ |
| $-C(O)(CH_2)_{10}-O-$ |
| $-C(O)(CH_2)_{4\text{-}10}-$ |
| $-C(O)(CH_2)_6-$ |
| $-C(O)(CH_2)_8-$ |
| $-C(O)(CH_2)_{10}-$ |

TABLE A-continued
| $—L^1—X—L^2—$ |
| --- |
| 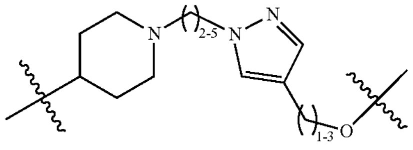 |
| 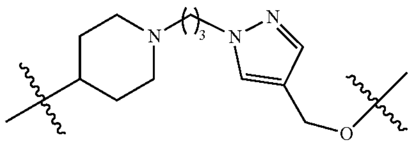 |
| 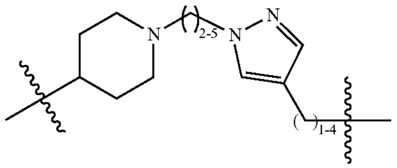 |
| 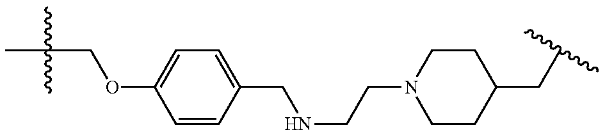 [SMILES: *COc1ccc(CNCCN2CCC(C*)CC2)cc1] |
| 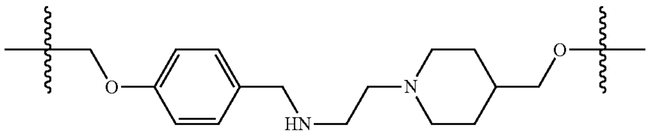 [SMILES: *COc1ccc(CNCCN2CCC(CO*)CC2)cc1] |
| 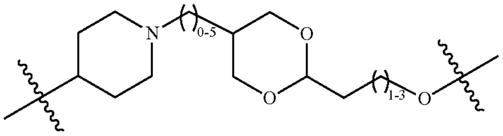 |
| 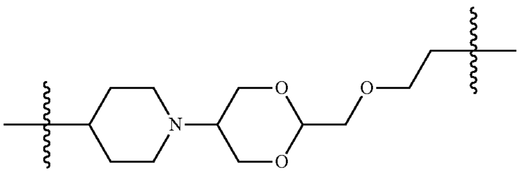 [SMILES: *CCOCC1OCC(N2CCC(*)CC2)CO1] |
| 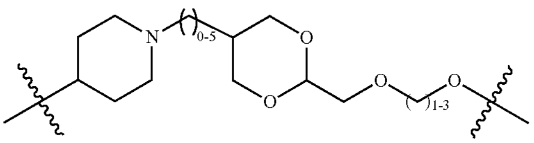 |
| $—NH(CH_2)_2NHC(=O)(CH_2CH_2O)_2CH_2CH_2—$ |
| $—CH_2NHC(O)NH(CH_2)_7O—$ |
| 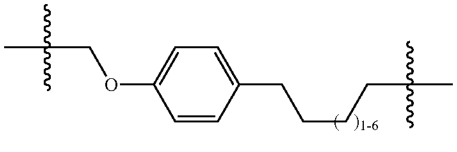 |

TABLE A-continued
| $-L^1-X-L^2-$ |
| --- |
| 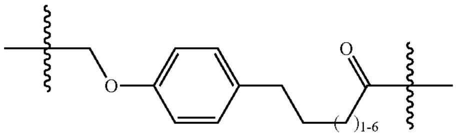 |
| 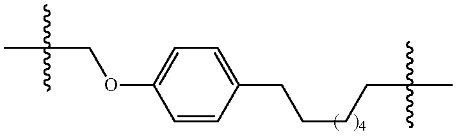 |
| 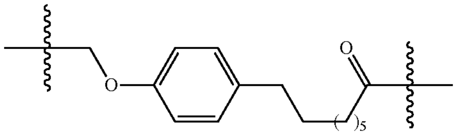 |
| 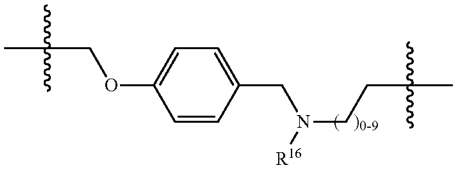 |
| 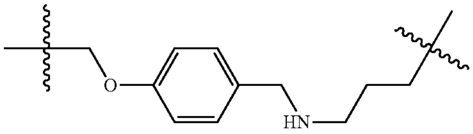 [SMILES: *CCCNCc1ccc(OC*)cc1] |
| 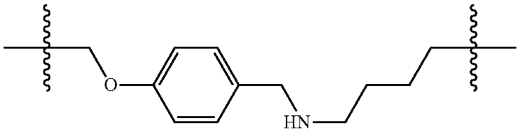 |
| 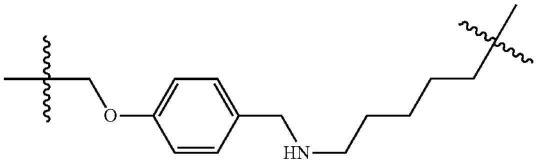 [SMILES: *CCCCCNCc1ccc(OC*)cc1] |
| 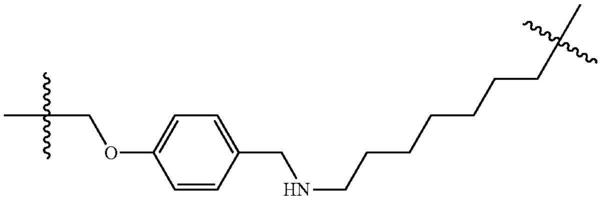 [SMILES: *CCCCCCCNCc1ccc(OC*)cc1] |
| 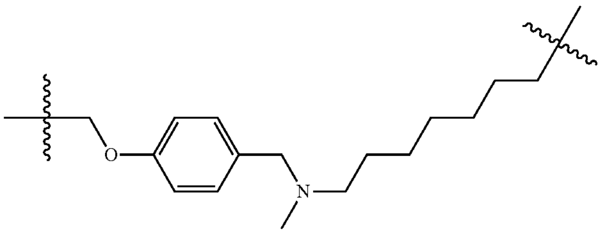 [SMILES: *CCCCCCCN(C)Cc1ccc(OC*)cc1] |

TABLE A-continued
| —$L^1$—X—$L^2$— |
| --- |
| 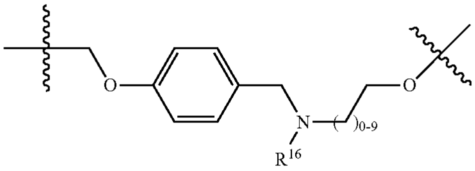 |
| 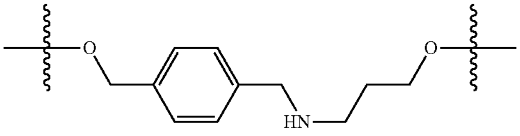 |
| 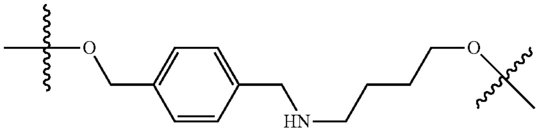 [SMILES: *OCCCCNCc1ccc(CO*)cc1] |
| 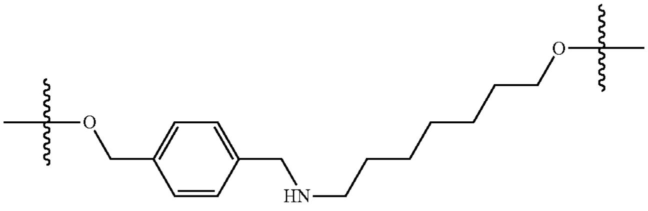 [SMILES: *OCCCCCCCNCc1ccc(CO*)cc1] |
| 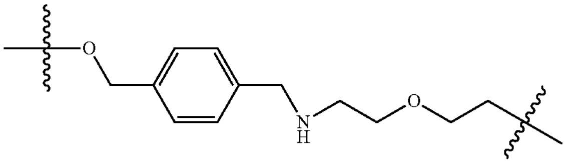 [SMILES: *CCOCCNCc1ccc(CO*)cc1] |
| 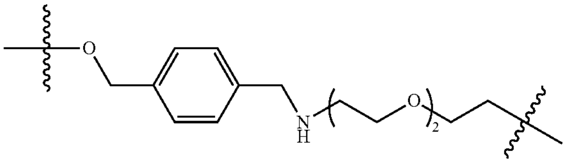 |
| 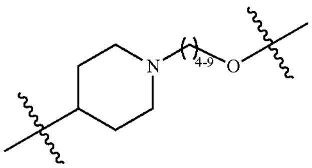 |
| 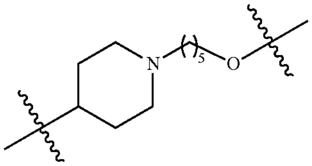 |
| 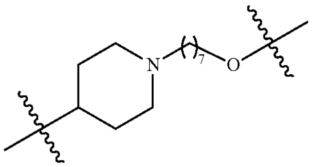 |

TABLE A-continued
| —L¹—X—L²— |
| --- |
| 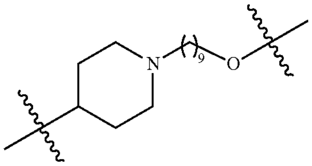 |
| 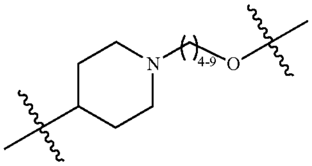 |
| 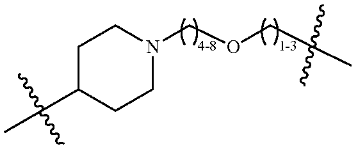 |
| 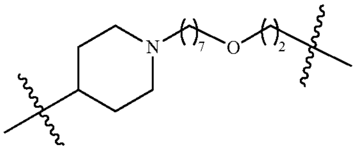 |
| 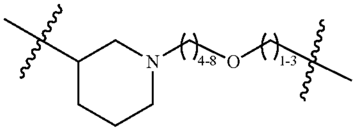 |
| 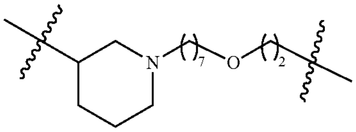 |
| 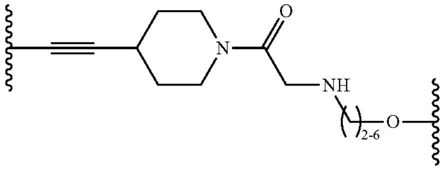 |
| 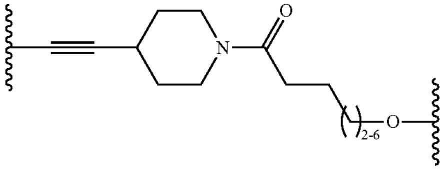 |
| 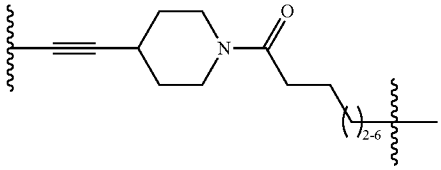 |

TABLE A-continued
| —$L^1$—X—$L^2$— |
| --- |
| 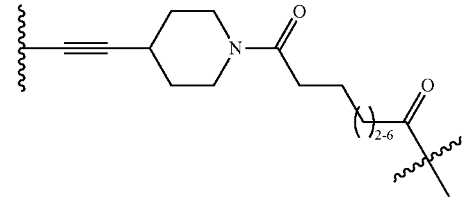 |
| 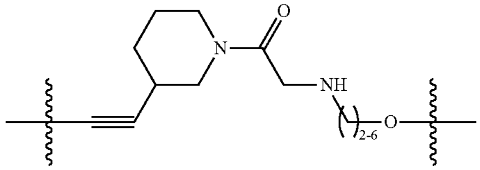 |
| 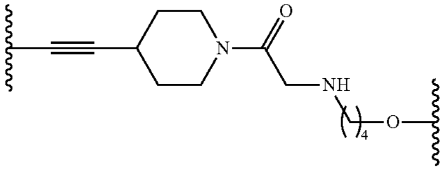 |
| 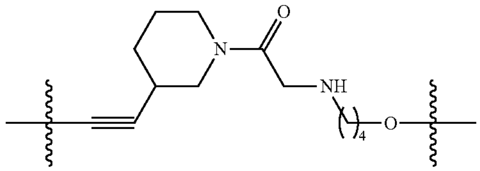 |
| 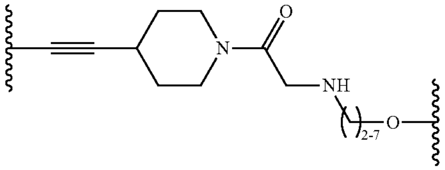 |
| 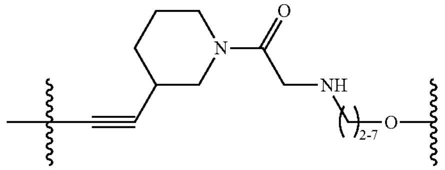 |
| 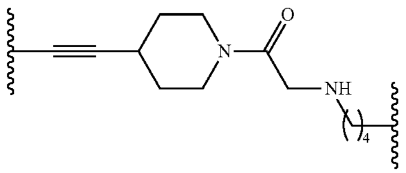 |
| 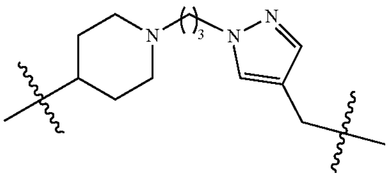 |

TABLE A-continued
| —$L^1$—X—$L^2$— |
| --- |
| 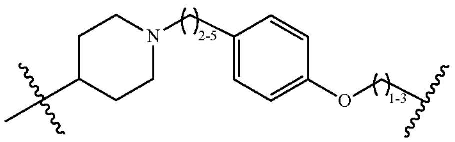 |
| 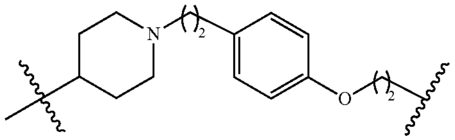 |
| 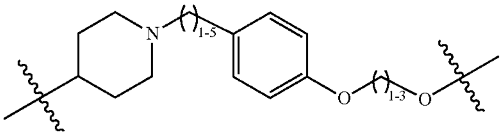 |
| 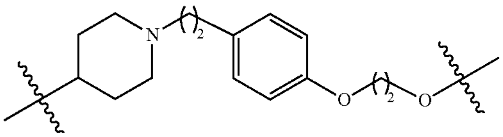 |
| 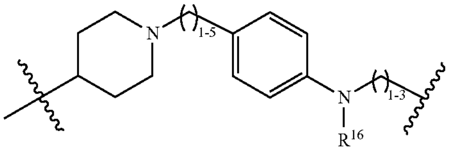 |
| 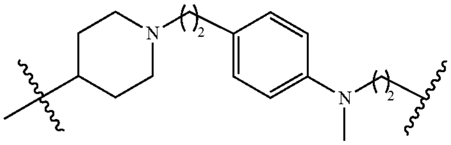 |
| 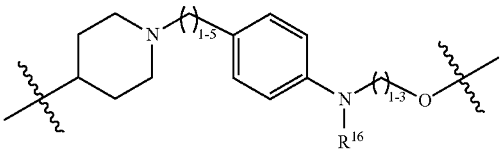 |
| 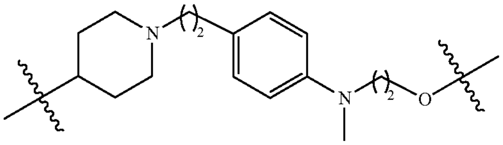 |
| 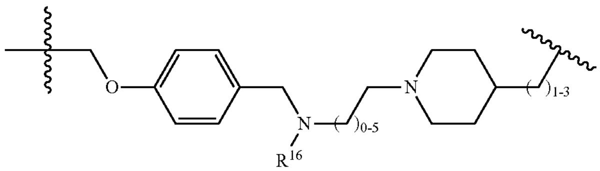 |
| 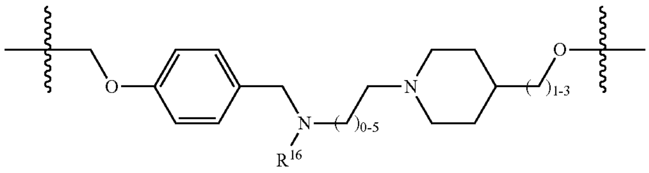 |

TABLE A-continued

| —$L^1$—X—$L^2$— |
| --- |
| 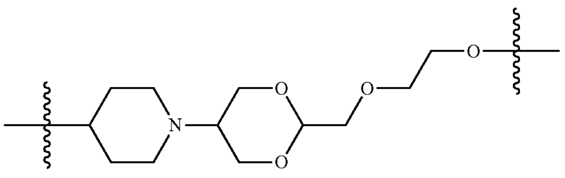 [SMILES: *OCCOCC1OCC(N2CCC(*)CC2)CO1] |
| 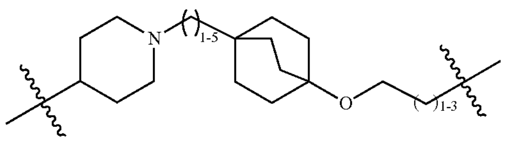 |
| 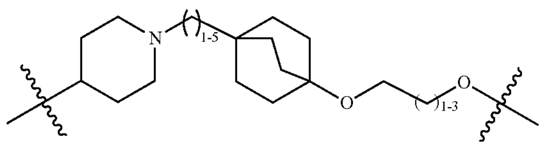 |
| 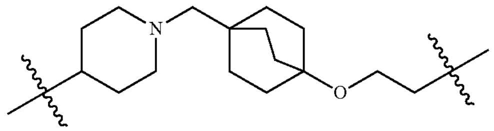 [SMILES: *CCOC12CCC(CN3CCC(*)CC3)(CC1)CC2] |
| 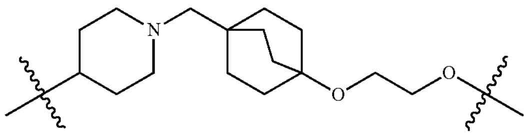 [SMILES: *OCCOC12CCC(CN3CCC(*)CC3)(CC1)CC2] |

In one embodiment, provided herein is:

8-(4-(2-(2,6-dioxopiperidin-3-yl)-6-fluoro-1-oxoisoindolin-4-yl)piperidin-1-yl)-N-(2-((S)-1-(3-ethoxy-4-methoxy-phenyl)-2-(methylsulfonyl)ethyl)-1,3-dioxoisoindolin-4-yl)octanamide B1 (compound No. A);

N-(6-(7-(4-(2-(2,6-dioxopiperidin-3-yl)-6-fluoro-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B2 (compound No. B);

3-(cyclopropylmethoxy)-N-(3,5-dichloropyridin-4-yl)-4-(difluoromethoxy)-N-(7-(4-(2-(2,6-dioxopiperidin-3-yl)-6-fluoro-1-oxoisoindolin-4-yl)piperidin-1-yl)heptyl)benzamide B3 (compound No. C);

N-(3,5-dichloropyridin-4-yl)-4-(difluoromethoxy)-3-((7-(4-(2-(2,6-dioxopiperidin-3-yl)-6-fluoro-1-oxoisoindolin-4-yl)piperidin-1-yl)heptyl)oxy)benzamide B4 (compound No. D);

3-(7-(4-(2-(2,6-dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B5 (compound No. E);

2-(7-(4-(2-(2,6-dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B6 (compound No. F);

3-(4-(1-(7-((4-((3,5-dichloropyridin-4-yl)amino)-7-methoxy-2-oxo-2H-chromen-8-yl)oxy)heptyl)piperidin-4-yl)-6-fluoro-1-oxoisoindolin-2-yl)piperidine-2,6-dione B7 (compound No. G);

3-(2-(2-(3-((2-(2,6-dioxopiperidin-3-yl)-1-oxoisoindolin-4-yl)amino)propoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B8 (compound No. H);

N-(6-(2-(2-(2-(3-((2-(2,6-dioxopiperidin-3-yl)-1-oxoisoindolin-4-yl)amino)propoxy)-ethoxy)ethoxy)ethyl)-2-((S)-1-(3-ethoxy-4-methoxyphenyl)-2-(methylsulfonyl)ethyl)-1,3-dioxoisoindolin-4-yl)acetamide B9 (compound No. I);

3-(cyclopropylmethoxy)-N-(3,5-dichloropyridin-4-yl)-4-(difluoromethoxy)-N-(2-(2-(2-(3-((2-(2,6-dioxopiperidin-3-yl)-1-oxoisoindolin-4-yl)amino)propoxy)ethoxy)ethoxy)-ethyl)benzamide B10 (compound No. J);

N-(3,5-dichloropyridin-4-yl)-4-(difluoromethoxy)-3-(2-(2-(2-(3-((2-(2,6-dioxopiperidin-3-yl)-1-oxoisoindolin-4-yl)amino)propoxy)ethoxy)ethoxy)ethoxy)benzamide B11 (compound No. K);

4-(2-(2-(2-(3-((2-(2,6-dioxopiperidin-3-yl)-1-oxoisoindolin-4-yl)amino)propoxy)-ethoxy)ethoxy)ethyl)-3-((1-hydroxy-1,3-dihydrobenzo[c][1,2]oxaborol-5-yl)oxy)benzonitrile B12 (compound No. L);

2-(2-(2-(2-(3-((2-(2,6-dioxopiperidin-3-yl)-1-oxoisoindolin-4-yl)amino)propoxy)-ethoxy)ethoxy)ethyl)-4-((1-hydroxy-1,3-dihydrobenzo[c][1,2]oxaborol-5-yl)oxy)benzonitrile B13 (compound No. M);

3-(4-((3-(2-(2-(2-((4-((3,5-dichloropyridin-4-yl)amino)-7-methoxy-2-oxo-2H-chromen-8-yl)oxy)ethoxy)ethoxy)ethoxy)propyl)amino)-1-oxoisoindolin-2-yl)piperidine-2,6-dione B14 (compound No. N);

6-(4-((2-(2,6-dioxopiperidin-3-yl)-1-oxoisoindolin-4-yl)ethynyl)piperidin-1-yl)-N-(2-((S)-1-(3-ethoxy-4-methoxyphenyl)-2-(methylsulfonyl)ethyl)-1,3-dioxoisoindolin-4-yl)-6-oxohexanamide B15 (compound No. O);

N-(6-(5-(4-((2-(2,6-dioxopiperidin-3-yl)-1-oxoisoindolin-4-yl)ethynyl)piperidin-1-yl)-5-oxopentyl)-2-((S)-1-(3-ethoxy-4-methoxyphenyl)-2-(methylsulfonyl)ethyl)-1,3-dioxoisoindolin-4-yl)acetamide B16 (compound No. P);

3-(cyclopropylmethoxy)-N-(3,5-dichloropyridin-4-yl)-4-(difluoromethoxy)-N-(5-(4-((2-(2,6-dioxopiperidin-3-yl)-1-oxoisoindolin-4-yl)ethynyl)piperidin-1-yl)-5-oxopentyl)benzamide B17 (compound No. Q);

N-(3,5-dichloropyridin-4-yl)-4-(difluoromethoxy)-3-((5-(4-((2-(2,6-dioxopiperidin-3-yl)-1-oxoisoindolin-4-yl)ethynyl)piperidin-1-yl)-5-oxopentyl)oxy)benzamide B18 (compound No. R);

4-(5-(4-((2-(2,6-dioxopiperidin-3-yl)-1-oxoisoindolin-4-yl)ethynyl)piperidin-1-yl)-5-oxopentyl)-3-((1-hydroxy-1,3-dihydrobenzo[c][1,2]oxaborol-5-yl)oxy)benzonitrile B19 (compound No. S);

2-(5-(4-((2-(2,6-dioxopiperidin-3-yl)-1-oxoisoindolin-4-yl)ethynyl)piperidin-1-yl)-5-oxopentyl)-4-((1-hydroxy-1,3-dihydrobenzo[c][1,2]oxaborol-5-yl)oxy)benzonitrile B20 (compound No. T);

3-(4-((1-(5-((4-((3,5-dichloropyridin-4-yl)amino)-7-methoxy-2-oxo-2H-chromen-8-yl)oxy)pentanoyl)piperidin-4-yl)ethynyl)-1-oxoisoindolin-2-yl)piperidine-2,6-dione B21 (compound No. U);

8-(4-(2-(2,6-dioxopiperidin-3-yl)-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)octanamide B22 (compound No. V);

N-(6-(7-(4-(2-(2,6-dioxopiperidin-3-yl)-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B23 (compound No. W);

3-(cyclopropylmethoxy)-N-(3,5-dichloropyridin-4-yl)-4-(difluoromethoxy)-N-(7-(4-(2-(2,6-dioxopiperidin-3-yl)-1-oxoisoindolin-4-yl)piperidin-1-yl)heptyl)benzamide B24 (compound No. X);

N-(3,5-dichloropyridin-4-yl)-4-(difluoromethoxy)-3-((7-(4-(2-(2,6-dioxopiperidin-3-yl)-1-oxoisoindolin-4-yl)piperidin-1-yl)heptyl)oxy)benzamide B25 (compound No. Y);

3-(7-(4-(2-(2,6-dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B26 (compound No. Z);

2-(7-(4-(2-(2,6-dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B27 (compound No. AA);

3-(4-(1-(7-((4-((3,5-dichloropyridin-4-yl)amino)-7-methoxy-2-oxo-2H-chromen-8-yl)oxy)heptyl)piperidin-4-yl)-1-oxoisoindolin-2-yl)piperidine-2,6-dione B28 (compound No. AB);

8-(4-((5-(2,6-dioxopiperidin-3-yl)-4-oxo-5,6-dihydro-4H-thieno[3,4-c]pyrrol-1-yl)methoxy)phenyl)-N-(2-((S)-1-(3-ethoxy-4-methoxyphenyl)-2-(methylsulfonyl)ethyl)-1,3-dioxoisoindolin-4-yl)octanamide B29 (compound No. AC);

N-(6-(7-(4-((5-(2,6-dioxopiperidin-3-yl)-4-oxo-5,6-dihydro-4H-thieno[3,4-c]pyrrol-1-yl)methoxy)phenyl)heptyl)-2-((S)-1-(3-ethoxy-4-methoxyphenyl)-2-(methylsulfonyl)ethyl)-1,3-dioxoisoindolin-4-yl)acetamide B30 (compound No. AD);

3-(cyclopropylmethoxy)-N-(3,5-dichloropyridin-4-yl)-4-(difluoromethoxy)-N-(7-(4-((5-(2,6-dioxopiperidin-3-yl)-4-oxo-5,6-dihydro-4H-thieno[3,4-c]pyrrol-1-yl)methoxy)phenyl)-heptyl)benzamide B31 (compound No. AE);

N-(3,5-dichloropyridin-4-yl)-4-(difluoromethoxy)-3-((7-(4-((5-(2,6-dioxopiperidin-3-yl)-4-oxo-5,6-dihydro-4H-thieno[3,4-c]pyrrol-1-yl)methoxy)phenyl)heptyl)oxy)benzamide B32 (compound No. AF);

3-(7-(4-((5-(2,6-dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B33 (compound No. AG);

2-(7-(4-((5-(2,6-dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B34 (compound No. AH);

3-(1-((4-(7-((4-((3,5-dichloropyridin-4-yl)amino)-7-methoxy-2-oxo-2H-chromen-8-yl)oxy)heptyl)phenoxy)methyl)-4-oxo-4H-thieno[3,4-c]pyrrol-5(6H)-yl)piperidine-2,6-dione B35 (compound No. AI);

(2S,4R)-1-((S)-2-((8-((2-((S)-1-(3-ethoxy-4-methoxyphenyl)-2-(methylsulfonyl)-ethyl)-1,3-dioxoisoindolin-4-yl)amino)-8-oxooctyl)amino)-3,3-dimethylbutanoyl)-4-hydroxy-N-(4-(4-methylthiazol-5-yl)benzyl)pyrrolidine-2-carboxamide B36 (compound No. AJ);

(2S,4R)-1-((S)-2-((7-(7-acetamido-2-((S)-1-(3-ethoxy-4-methoxyphenyl)-2-(methylsulfonyl)ethyl)-1,3-dioxoisoindolin-5-yl)heptyl)amino)-3,3-dimethylbutanoyl)-4-hydroxy-N-(4-(4-methylthiazol-5-yl)benzyl)pyrrolidine-2-carboxamide B37 (compound No. AK);

(2S,4R)-1-((S)-2-((7-(3-(cyclopropylmethoxy)-N-(3,5-dichloropyridin-4-yl)-4-(difluoromethoxy)benzamido)heptyl)amino)-3,3-dimethylbutanoyl)-4-hydroxy-N-(4-(4-methylthiazol-5-yl)benzyl)pyrrolidine-2-carboxamide B38 (compound No. AL);

(2S,4R)-1-((S)-2-((7-(5-((3,5-dichloropyridin-4-yl)carbamoyl)-2-(difluoromethoxy)-phenoxy)heptyl)amino)-3,3-dimethylbutanoyl)-4-hydroxy-N-(4-(4-methylthiazol-5-yl)benzyl)-pyrrolidine-2-carboxamide B39 (compound No. AM);

(2S,4R)-1-((S)-2-((7-(5-cyano-2-((1-hydroxy-1,3-dihydrobenzo[c][1,2]oxaborol-5-yl)oxy)phenyl)heptyl)amino)-3,3-dimethylbutanoyl)-4-hydroxy-N-(4-(4-methylthiazol-5-yl)benzyl)pyrrolidine-2-carboxamide B40 (compound No. AN);

(2S,4R)-1-((S)-2-((7-(3-cyano-5-((1-hydroxy-1,3-dihydrobenzo[c][1,2]oxaborol-5-yl)oxy)phenyl)heptyl)amino)-3,3-dimethylbutanoyl)-4-hydroxy-N-(4-(4-methylthiazol-5-yl)benzyl)pyrrolidine-2-carboxamide B41 (compound No. AO); or (2S,4R)-1-((S)-2-((7-((4-((3,5-dichloropyridin-4-yl)amino)-7-methoxy-2-oxo-2H-chromen-8-yl)oxy)heptyl)amino)-3,3-dimethylbutanoyl)-4-hydroxy-N-(4-(4-methylthiazol-5-yl)benzyl)pyrrolidine-2-carboxamide B42 (compound No. AP);

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is:

3-(2-(2-(2-((2-(2,6-dioxopiperidin-3-yl)-1,3-dioxoisoindolin-4-yl)amino)ethoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B43;

7-((4-((5-((S)-2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)heptanamide B44;

N-(3,5-dichloropyridin-4-yl)-4-(difluoromethoxy)-3-((9-(4-(2-(2,6-dioxopiperidin-3-yl)-6-fluoro-1-oxoisoindolin-4-yl)piperidin-1-yl)nonyl)oxy)benzamide B45;

N-(3,5-dichloropyridin-4-yl)-4-(difluoromethoxy)-3-((5-(4-(2-(2,6-dioxopiperidin-3-yl)-6-fluoro-1-oxoisoindolin-4-yl)piperidin-1-yl)pentyl)oxy)benzamide B46;

N-(6-(7-(4-(2-(2,6-dioxopiperidin-3-yl)-6-fluoro-1-oxoisoindolin-4-yl)piperidin-1-yl)hept-1-yn-1-yl)-2-((S)-1-(3-ethoxy-4-methoxyphenyl)-2-(methylsulfonyl)ethyl)-1,3-dioxoisoindolin-4-yl)acetamide B47;

14-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)-3,6,9,12-tetraoxatetradecan-1-amide B48;

3-(6-fluoro-4-(1-(7-(2-methoxy-5-(1-oxoisoindolin-2-yl)phenoxy)heptyl)piperidin-4-yl)-1-oxoisoindolin-2-yl)piperidine-2,6-dione B49;

3-(4-(1-(7-(2-(cyclopentyloxy)-4-(1-oxoisoindolin-2-yl)phenoxy)heptyl)piperidin-4-yl)-6-fluoro-1-oxoisoindolin-2-yl)piperidine-2,6-dione B50;

2-(3-((7-(4-(2-(2,6-dioxopiperidin-3-yl)-6-fluoro-1-oxoisoindolin-4-yl)piperidin-1-yl)heptyl)oxy)-4-methoxyphenyl)isoindoline-1,3-dione B51;

5-amino-2-(3-((7-(4-(2-(2,6-dioxopiperidin-3-yl)-6-fluoro-1-oxoisoindolin-4-yl)piperidin-1-yl)heptyl)oxy)-4-methoxyphenyl)isoindoline-1,3-dione B52;

3-(6-fluoro-4-(1-(7-(2-methoxy-5-(5-oxopyrrolidin-3-yl)phenoxy)heptyl)piperidin-4-yl)-1-oxoisoindolin-2-yl)piperidine-2,6-dione B53;

2-(3-(cyclopentyloxy)-4-methoxyphenyl)-5-((7-(4-(2-(2,6-dioxopiperidin-3-yl)-6-fluoro-1-oxoisoindolin-4-yl)piperidin-1-yl)heptyl)amino)isoindoline-1,3-dione B54;

3-(6-fluoro-5-(1-(7-(2-methoxy-5-(5-oxopyrrolidin-3-yl)phenoxy)heptyl)piperidin-4-yl)-1-oxoisoindolin-2-yl)piperidine-2,6-dione B55;

3-(4-(1-(7-((2-(3-(cyclopentyloxy)-4-methoxyphenyl)-3-oxoisoindolin-5-yl)amino)heptyl)piperidin-4-yl)-6-fluoro-1-oxoisoindolin-2-yl)piperidine-2,6-dione B56;

3-(4-(1-(7-(2-(cyclopentyloxy)-4-(5-oxopyrrolidin-3-yl)phenoxy)heptyl)piperidin-4-yl)-6-fluoro-1-oxoisoindolin-2-yl)piperidine-2,6-dione B57;

5-amino-2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B58;

2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B59;

3-(4-(1-(7-(5-(6-amino-1-oxoisoindolin-2-yl)-2-methoxyphenoxy)heptyl)piperidin-4-yl)-6-fluoro-1-oxoisoindolin-2-yl)piperidine-2,6-dione B60;

N-(3,5-dichloropyridin-4-yl)-4-(difluoromethoxy)-3-((7-(4-(2-(2,6-dioxopiperidin-3-yl)-6-fluoro-1-oxoisoindolin-5-yl)piperidin-1-yl)heptyl)oxy)benzamide B61;

3-(4-(1-(7-(5-(6-amino-1-oxoisoindolin-2-yl)-2-methoxyphenoxy)heptyl)piperidin-4-yl)-6-fluoro-1-oxoisoindolin-2-yl)piperidine-2,6-dione B62;

$N^1$-(2-((S)-1-(3-ethoxy-4-methoxyphenyl)-2-(methylsulfonyl)ethyl)-1,3-dioxoisoindolin-4-yl)-$N^{10}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide B63;

3-((4-((2-((2-(2,6-dioxopiperidin-3-yl)-1,3-dioxoisoindolin-4-yl)amino)ethoxy)-methyl)benzyl)oxy)-N-(2-((S)-1-(3-ethoxy-4-methoxyphenyl)-2-(methylsulfonyl)ethyl)-1,3-dioxoisoindolin-4-yl)propanamide B64;

5-(3-((7-(4-(2-(2,6-dioxopiperidin-3-yl)-6-fluoro-1-oxoisoindolin-4-yl)piperidin-1-yl)heptyl)oxy)-4-methoxyphenyl)-4H-thieno[2,3-c]pyrrole-4,6(5H)-dione B65;

2-(2,6-dioxopiperidin-3-yl)-4-((7-(2-methoxy-5-(5-oxopyrrolidin-3-yl)phenoxy)-heptyl)amino)isoindoline-1,3-dione B66;

(2S,4R)-4-hydroxy-1-((2S)-2-(9-(2-methoxy-5-(5-oxopyrrolidin-3-yl)phenoxy)-nonanamido)-3,3-dimethylbutanoyl)-N-(4-(4-methylthiazol-5-yl)benzyl)pyrrolidine-2-carboxamide B67;

(2S,4R)-1-((S)-2-(9-(5-((3,5-dichloropyridin-4-yl)carbamoyl)-2-(difluoromethoxy)phenoxy)nonanamido)-3,3-dimethylbutanoyl)-4-hydroxy-N-(4-(4-methylthiazol-5-yl)benzyl)pyrrolidine-2-carboxamide B68;

N-(6-(3-(4-(2-(2,6-dioxopiperidin-3-yl)-6-fluoro-1-oxoisoindolin-4-yl)piperidin-1-yl)propyl)-2-((S)-1-(3-ethoxy-4-methoxyphenyl)-2-(methylsulfonyl)ethyl)-1,3-dioxoisoindolin-4-yl)acetamide B69;

9-((4-((5-(2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)nonanamide B70;

12-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)dodecanamide B71;

N-(3,5-dichloropyridin-4-yl)-4-(difluoromethoxy)-3-((7-((2-(2,6-dioxopiperidin-3-yl)-1,3-dioxoisoindolin-4-yl)amino)heptyl)oxy)benzamide B72;

N-(3,5-dichloropyridin-4-yl)-4-(difluoromethoxy)-3-((12-(4-(2-(2,6-dioxopiperidin-3-yl)-6-fluoro-1-oxoisoindolin-4-yl)piperidin-1-yl)dodecyl)oxy)benzamide B73;

N-(3,5-dichloropyridin-4-yl)-3-(difluoromethoxy)-4-(2-(2-(2-(2-((2-(2,6-dioxopiperidin-3-yl)-1,3-dioxoisoindolin-4-yl)amino)ethoxy)ethoxy)ethoxy)ethoxy)benzamide B74;

9-(4-(2-(2,6-dioxopiperidin-3-yl)-6-fluoro-1-oxoisoindolin-5-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B75;

(2S,4R)-1-((S)-2-(11-(5-((3,5-dichloropyridin-4-yl)carbamoyl)-2-(difluoromethoxy)-phenoxy)undecanamido)-3,3-dimethylbutanoyl)-4-hydroxy-N-(4-(4-methylthiazol-5-yl)benzyl)pyrrolidine-2-carboxamide B76;

9-(4-(2-(2,6-dioxopiperidin-3-yl)-6-fluoro-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B77;

5-((4-((5-(2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)pentanamide B78;

N-(6-(12-(4-(2-(2,6-dioxopiperidin-3-yl)-6-fluoro-1-oxoisoindolin-4-yl)piperidin-1-yl)dodecyl)-2-((S)-1-(3-ethoxy-4-methoxyphenyl)-2-(methylsulfonyl)ethyl)-1,3-dioxoisoindolin-4-yl)acetamide B79;

3-(6-fluoro-4-(1-(7-(2-methoxy-5-(4-oxo-4,6-dihydro-5H-thieno[2,3-c]pyrrol-5-yl)phenoxy)heptyl)piperidin-4-yl)-1-oxoisoindolin-2-yl)piperidine-2,6-dione B80;

3-(cyclopropylmethoxy)-N-(3,5-dichloropyridin-4-yl)-4-(2-(2-(2-(3-((2-(2,6-dioxopiperidin-3-yl)-1-oxoisoindolin-4-yl)amino)propoxy)ethoxy)ethoxy)ethoxy)benzamide B81;

3-(cyclopropylmethoxy)-N-(3,5-dichloropyridin-4-yl)-4-((7-(4-(2-(2,6-dioxopiperidin-3-yl)-6-fluoro-1-oxoisoindolin-4-yl)piperidin-1-yl)heptyl)oxy)benzamide B82;

N-(3,5-dichloropyridin-4-yl)-4-(difluoromethoxy)-3-(3-(4-(2-(2,6-dioxopiperidin-3-yl)-6-fluoro-1-oxoisoindolin-4-yl)piperidin-1-yl)propoxy)benzamide B83;

3-(cyclopropylmethoxy)-N-(3,5-dichloropyridin-4-yl)-4-((9-(4-(2-(2,6-dioxopiperidin-3-yl)-6-fluoro-1-oxoisoindolin-4-yl)piperidin-1-yl)nonyl)oxy)benzamide B84;

3-((9-(4-(2-(1-acetamido-1-oxopropan-2-yl)-6-fluoro-1-oxoisoindolin-4-yl)piperidin-1-yl)nonyl)oxy)-N-(3,5-dichloropyridin-4-yl)-4-(difluoromethoxy)benzamide B85;

(2S,4R)-1-((S)-2-(9-(2-(cyclopropylmethoxy)-5-((3,5-dichloropyridin-4-yl)carbamoyl)phenoxy)nonanamido)-3,3-dimethylbutanoyl)-4-hydroxy-N-(4-(4-methylthiazol-5-yl)benzyl)pyrrolidine-2-carboxamide B86;

5-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)-4H-thieno[2,3-c]pyrrole-4,6(5H)-dione B87;

N-(6-(7-(1-(2-(2,6-dioxopiperidin-3-yl)-1,3-dioxoisoindolin-4-yl)piperidin-4-yl)heptyl)-2-((S)-1-(3-ethoxy-4-methoxyphenyl)-2-(methylsulfonyl)ethyl)-1,3-dioxoisoindolin-4-yl)acetamide B88;

3-(2-(2-((2-(2,6-dioxopiperidin-3-yl)-1,3-dioxoisoindolin-4-yl)amino)ethoxy)ethoxy)-N-(2-((S)-1-(3-ethoxy-4-methoxyphenyl)-2-(methylsulfonyl)ethyl)-1,3-dioxoisoindolin-4-yl)propanamide B89;

N-(3,5-dichloropyridin-4-yl)-4-(difluoromethoxy)-3-((7-(1-(2-(2,6-dioxopiperidin-3-yl)-1,3-dioxoisoindolin-4-yl)piperidin-4-yl)heptyl)oxy)benzamide B90;

3-(4-(1-(7-(2-(cyclopentyloxy)-4-(4-oxo-4,6-dihydro-5H-thieno[2,3-c]pyrrol-5-yl)phenoxy)heptyl)piperidin-4-yl)-6-fluoro-1-oxoisoindolin-2-yl)piperidine-2,6-dione B91; or N-(3,5-dichloropyridin-4-yl)-4-(difluoromethoxy)-3-((7-((4-((5-(2,6-dioxopiperidin-3-yl)-4-oxo-5,6-dihydro-4H-thieno[3,4-c]pyrrol-1-yl)methoxy)benzyl)amino)heptyl)oxy)benzamide B92;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Uses or Methods of Treatment

In one embodiment, provided herein is a method of treating, preventing, or ameliorating one or more symptoms of a disease, disorder, or condition associated with a PDE4 in a subject, comprising administering to the subject in need thereof a therapeutically effective amount of a compound of Formula (I) or (II), or a pharmaceutically acceptable salt thereof.

In certain embodiments, the disease, disorder, or condition associated with a PDE4 is an inflammatory disease.

In certain embodiments, the PDE4 is a PDE4A. In certain embodiments, the PDE4 is a PDE4B. In certain embodiments, the PDE4 is a PDE4C. In certain embodiments, the PDE4 is a PDE4D. In certain embodiments, the PDE4 is a PDE4D. In certain embodiments, the PDE4 is a PDE4D short isoform.

In another embodiment, provided herein is a method of treating, preventing, or ameliorating one or more symptoms of an inflammatory disease in a subject, comprising administering to the subject in need thereof a therapeutically effective amount of a compound of Formula (I) or (II), or a pharmaceutically acceptable salt thereof.

In certain embodiments, the inflammatory disease is arthritis, ankylosing spondylitis, osteoarthritis, rheumatoid arthritis, Behcet's disease, an inflammatory bowel disease, Crohn's disease, ulcerative colitis, psoriasis, psoriatic arthritis, atopic dermatitis, contact dermatitis, or COPD. In certain embodiments, the inflammatory disease is psoriasis. In some embodiments, the inflammatory disease is psoriatic arthritis. In certain embodiments, the inflammatory disease is atopic dermatitis. In certain embodiments, the inflammatory disease is contact dermatitis.

In yet another embodiment, provided herein is a method of treating, preventing, or ameliorating one or more symptoms of psoriasis, psoriatic arthritis, or atopic dermatitis in a subject, comprising administering to the subject in need thereof a therapeutically effective amount of a compound of Formula (I) or (II), or a pharmaceutically acceptable salt thereof.

In certain embodiments, the subject is a mammal. In certain embodiments, the subject is a human.

In yet another embodiment, provided herein is a method of inhibiting the activity of a phosphodiesterase 4 (PDE4), comprising contacting the PDE4 with an effective amount of a compound of Formula (I) or (II), or a pharmaceutically acceptable salt thereof.

In certain embodiments, the PDE4 is a PDE4A. In certain embodiments, the PDE4 is a PDE4B. In certain embodiments, the PDE4 is a PDE4C. In certain embodiments, the PDE4 is a PDE4D. In certain embodiments, the PDE4 is a PDE4D. In certain embodiments, the PDE4 is a PDE4D short isoform.

In still another embodiment, provided herein is a method of decreasing expression of a protein selected from TNF-α, INF-γ, IL-2, IL-17, and IL-23, comprising contacting the protein with an effective amount of a compound of Formula (I) or Formula (II), or a pharmaceutically acceptable salt thereof. In certain embodiments, the protein is TNF-α.

Dosing Regimes

In certain embodiments, therapeutically effective amount is ranging from about 1 mg to about 5 grams; from about 2 mg to about 2 gram; from about 5 mg to about 1 gram; from about 10 mg to about 800 mg; from about 20 mg to about 600 mg; from about 30 mg to about 400 mg; from about 40 mg to about 200 mg; from about 50 mg to about 100 mg of a compound provided herein each day. In certain embodiments, therapeutically effective amount is ranging from about 1 mg to about 5 grams; from about 2 mg to about 2 gram; from about 5 mg to about 1 gram; from about 10 mg to about 800 mg; from about 20 mg to about 600 mg; from about 30 mg to about 400 mg; from about 40 mg to about 200 mg; from about 50 mg to about 100 mg of a compound provided herein each day each week. In certain embodiments, from about 1 mg to about 5 grams; from about 2 mg to about 2 gram; from about 5 mg to about 1 gram; from about 10 mg to about 800 mg; from about 20 mg to about 600 mg; from about 30 mg to about 400 mg; from about 40 mg to about 200 mg; from about 50 mg to about 100 mg of a compound provided herein each cycle of treatment.

In certain embodiments, a compound provided herein is administered at least once per day, at least twice per day, at least three times per day, or at least four times per day. In certain embodiments, each cycle of treatment lasts 1, 2, 3, 4, 5, 6, 7, 8, 9, 10, 11, 12, 13, or 14 days. In certain embodiments, each cycle of treatment has at least 1, 2, 3, 4, 5, 6, or 7 days between administrations of a compound provided herein.

Pharmaceutical Compositions

In certain embodiments, provided herein is a pharmaceutical composition, comprising a compound provided herein, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable carrier or excipient.

In certain embodiments, a pharmaceutical composition provided herein is formulated for intravenous injection, subcutaneous injection, oral administration, buccal administration, inhalation, nasal administration, topical administration, transdermal administration, ophthalmic administration, or otic administration. In certain embodiments, a pharmaceutical composition provided herein is formulated in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

In certain embodiments, a pharmaceutical composition provided herein is formulated as a gel, salve, ointment, cream, emulsion, or paste for topical application to the skin. In certain embodiments, a pharmaceutical composition provided herein is formulated for oral administration.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); mmol (millimoles); h (hour or hours); min (minute or minutes); ACN (acetonitrile); AcOH (acetic acid); DCM (dichloromethane); DMF (dimethylformamide); DMSO (dimethyl sulfoxide); EtOH (ethanol); MeOH (methanol); EtOAc (ethyl acetate); PE (petroleum ether); THF (tetrahydrofuran); $Ac_2O$ (acetic anhydride); CDI (1,1'-carbonyldiimidazole); DIBAL-H (diisobutylaluminum hydride); DIPEA (N,N-diisopropylethylamine); HATU (1-(bis(dimethylamino)methylene)-1H-1,2,3-triazolo[4,5-b] pyridinium 3-oxide hexafluorophosphate); HOBt (1-hydroxybenzotriazole); TEA (triethylamine); TFA (trifluoroacetic acid); HPLC (high-performance liquid chromatography); MS (mass spectrometry); NMR (nuclear magnetic resonance); and TLC (thin-layer chromatography).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Synthesis of (S)-1-Amino-5-(1-(3-ethoxy-4-methoxyphenyl)-2-(methylsulfonyl)ethyl)-4H-thieno[3,4-c]pyrrole-4,6(5H)-dione

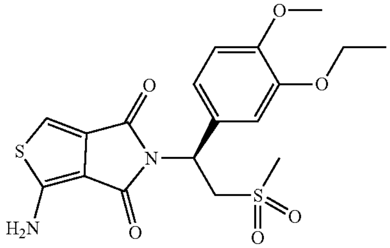 [SMILES: CCOc1cc([C@@H](CS(C)(=O)=O)N2C(=O)c3csc(N)c3C2=O)ccc1OC]

A solution of thiophene-3,4-dicarboxylic acid (25.0 g, 145 mmol) in $Ac_2O$ (250 mL) was heated to 110° C. for 16 h. The mixture was then concentrated to give thieno[3,4-c]-furan-1,3-dione (22.0 g, crude) as a solid.

Thieno[3,4-c]furan-1,3-dione (22.0 g, 143 mmol) was added to nitric acid (95%, 90 mL) over 1 h at 0-5° C. After stirred at room temperature for 1 h, the reaction mixture was poured into ice water and extracted with EtOAc. The combined organic layers were dried over anhydrous $Na_2SO_4$, filtered, and concentrated to give 2-nitrothiophene-3,4-dicarboxylic acid (20.8 g) in 66% yield as a solid.

A solution of 2-nitrothiophene-3,4-dicarboxylic acid (6.0 g, 27.6 mmol) in $Ac_2O$ (60 mL) was heated to 140° C. for 3 h. The mixture was concentrated to give 4-nitrothieno[3,4-c]-furan-1,3-dione (5.5 g, crude) as a solid.

A mixture of 4-nitrothieno[3,4-c]furan-1,3-dione (5.5 g, 27.64 mmol) and (S)-1-(3-ethoxy-4-methoxyphenyl)-2-(methylsulfonyl)ethanamine (7.54 g, 27.64 mmol) in THF (250 mL) was stirred at room temperature for 16 h. CDI (5.37 g, 33.1 mmol) was then added. After refluxed for 3 h, the mixture was concentrated and purified on silica gel eluting with EtOAc/PE from 30% to 50% to give (S)-5-(1-(3-ethoxy-4-methoxyphenyl)-2-(methylsulfonyl)ethyl)-1-nitro-4H-thieno[3,4-c]-pyrrole-4,6(5H)-dione (10.0 g) in 79% yield as a solid.

A mixture of (S)-5-(1-(3-ethoxy-4-methoxyphenyl)-2-(methylsulfonyl)ethyl)-1-nitro-4H-thieno[3,4-c]-pyrrole-4,6(5H)-dione (1.0 g, 2.2 mmol), ammonium chloride (706 mg, 13.2 mmol), and iron powder (740 mg, 13.2 mmol) in THF/water (50 mL/10 mL) was refluxed for 1 h. The mixture was then filtered, concentrated, and purified on silica gel eluting with EtOAc/PE from 40% to 70% to give (S)-1-amino-5-(1-(3-ethoxy-4-methoxyphenyl)-2-(methylsulfonyl)ethyl)-4H-thieno[3,4-c]pyrrole-4,6(5H)-dione (Intermediate 1) (300 mg) in 32% yield as a solid. MS (ESI) m/z: 424.9 $[M+H]^+$.

The following compounds were prepared similarly.

(S)-1-Amino-5-(1-(3-cyclopropoxy-4-methoxyphenyl)-2-(methylsulfonyl)ethyl)-4H-thieno[3,4-c]pyrrole-4,6(5H)-dione.

(R)-1-Amino-5-(1-(3-cyclopropoxy-4-methoxyphenyl)-2-(methylsulfonyl)ethyl)-4H-thieno[3,4-c]pyrrole-4,6(5H)-dione.

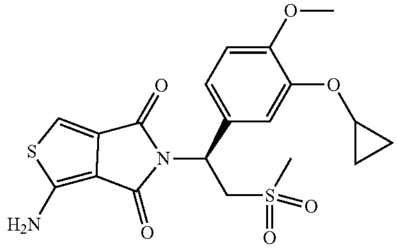

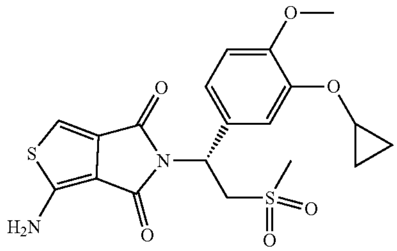

(S)-1-Amino-5-(1-(3-cyclopropoxy-4-methoxyphenyl)-2-(methylsulfonyl)ethyl)-4H-thieno[3,4-c]pyrrole-4,6(5H)-dione.

(R)-1-Amino-5-(1-(3-cyclopropoxy-4-methoxyphenyl)-2-(methylsulfonyl)ethyl)-4H-thieno[3,4-c]pyrrole-4,6(5H)-dione.

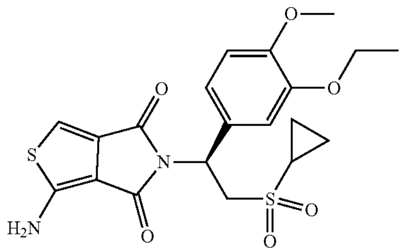

-continued

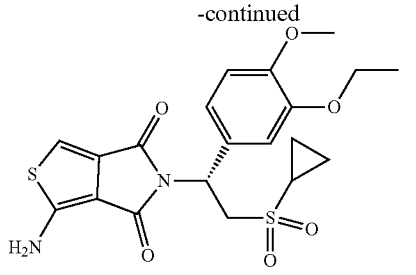

Example 2

Synthesis of (S)-3-Amino-5-(1-(3-ethoxy-4-methoxyphenyl)-2-(methylsulfonyl)ethyl)-4H-thieno[2,3-c]pyrrol-6(5H)-one

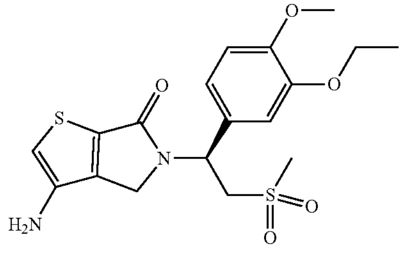 [SMILES: CCOc1cc([C@@H](CS(C)(=O)=O)N2Cc3c(N)csc3C2=O)ccc1OC]

To a stirred solution of methyl 4-bromo-3-(bromomethyl)thiophene-2-carboxylate (628 mg, 2 mmol) and (S)-1-(3-ethoxy-4-methoxyphenyl)-2-(methylsulfonyl)ethanamine (819 mg, 3.0 mmol) in ACN (20 mL) was added $Cs_2CO_3$ (358 mg, 1.1 mmol). After stirred at room temperature overnight, the mixture was concentrated and purified on silica gel eluting with EtOAc/PE (1:1) to give (S)-methyl-4-bromo-3-(((1-(3-ethoxy-4-methoxyphenyl)-2-(methylsulfonyl)ethyl)amino)-methyl)thiophene-2-carboxylate (905 mg) in 90% yield as a solid. MS (ESI) m/z: 505.9 $[M+H]^+$.

To a stirred solution of (S)-methyl-4-bromo-3-(((1-(3-ethoxy-4-methoxyphenyl)-2-(methylsulfonyl)ethyl)amino)methyl)thiophene-2-carboxylate (740 mg, 1.46 mmol) in THF (8 mL) and MeOH (8 mL) was added a solution of lithium hydroxide (614 mg, 14.6 mmol) in water (8 mL). After stirred at room temperature for 8 h, the mixture was concentrated, acidified to pH 4 with 2 N HCl, and then extracted with DCM. The combined organic layers were washed with brine, dried over anhydrous $Na_2SO_4$, and concentrated to give (S)-4-bromo-3-(((1-(3-ethoxy-4-methoxyphenyl)-2-(methylsulfonyl)ethyl)amino)methyl)thiophene-2-carboxylic acid (638 mg) in 89% yield as a solid. MS (ESI) m/z: 491.9 $[M+H]^+$.

To a stirred solution of (S)-4-bromo-3-(((1-(3-ethoxy-4-methoxyphenyl)-2-(methylsulfonyl)ethyl)amino)methyl)thiophene-2-carboxylic acid (628 mg, 1.27 mmol) in DCM (20 mL) was added oxalyl chloride (486 mg, 3.8 mmol) dropwise, followed by addition of 2 drops of DMF. The mixture was stirred at room temperature overnight, and then concentrated and purified on silica gel eluting with DCM/MeOH (10:1) to give (S)-4-bromo-5-(1-(3-ethoxy-4-methoxy-phenyl)-2-(methylsulfonyl)ethyl)-4H-thieno[2,3-c]pyrrol-6(5H)-one (398 mg) in 66% yield as a solid. MS (ESI) m/z: 473.9 $[M+H]^+$.

To a stirred solution of (S)-4-bromo-5-(1-(3-ethoxy-4-methoxy-phenyl)-2-(methyl-sulfonyl)ethyl)-4H-thieno[2,3-c]pyrrol-6(5H)-one (364 mg, 0.77 mmol) and diphenyl-methanimine (183 mg, 1.01 mmol) in 1,4-dioxane (3.5 mL) and toluene (3.5 mL) were added $Cs_2CO_3$ (511 mg, 1.56 mmol), tris(dibenzylideneacetone)dipalladium (73 mg, 0.08 mmol), and Xantphos (110 mg, 0.21 mmol). After $N_2$ purge and stirred at 108° C. (microwave) for 16 h, the mixture was diluted with water and EtOAc. The organic layer was separated, washed with brine, dried over anhydrous $Na_2SO_4$, filtered, concentrated, and purified using prep-TLC eluting with petroleum/EtOAc (1:1) to give (S)-4-((diphenylmethylene)amino)-5-(1-(3-ethoxy-4-methoxyphenyl)-2-(methylsulfonyl)ethyl)-4H-thieno[2,3-c]pyrrol-6(5H)-one (140 mg) in 32% yield as a solid. MS (ESI) m/z: 575.0 $[M+H]^+$.

To a stirred solution of (S)-4-((diphenylmethylene)amino)-5-(1-(3-ethoxy-4-methoxyphenyl)-2-(methylsulfonyl)ethyl)-4H-thieno[2,3-c]pyrrol-6(5H)-one (140 mg, 0.24 mmol) in EtOAc (5 mL) was added a solution of HCl in EtOAc (2.5 mL). The mixture was stirred at room temperature for 20 min, and then concentrated and washed with petroleum to give (S)-4-amino-5-(1-(3-ethoxy-4-methoxyphenyl)-2-(methylsulfonyl)ethyl)-4H-thieno[2,3-c]pyrrol-6(5H)-one (Intermediate 2) (130 mg, crude) as a solid, which was used directly without further purification. MS (ESI) m/z: 411.0 $[M+H]^+$.

Example 3

Synthesis of (S)—N-(5-(1-(3-Ethoxy-4-methoxyphenyl)-2-(methylsulfonyl)ethyl)-4-oxo-5,6-dihydro-4H-thieno[3,4-c]pyrrol-1-yl)-2,2,2-trifluoroacetamide A1

A1

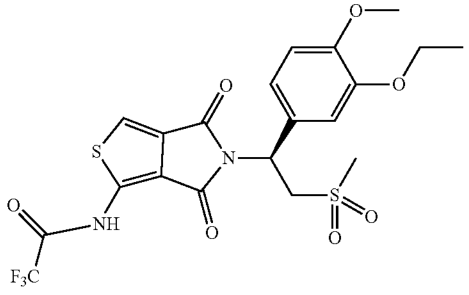

To a solution of Intermediate 1 (100 mg, 0.236 mmol) in pyridine (5 mL) was added trifluoroacetic anhydride (0.2 mL) in ACN (1 mL) at 0° C. After stirred at room temperature for 4 h, the mixture was diluted with water and then extracted with EtOAc. The combined organic layers were washed with HCl (1N), dried over anhydrous $Na_2SO_4$, filtered, concentrated, and purified on silica gel eluting with EtOAc/PE from 40% to 70% to give compound A1 (19 mg) in 16% yield as a white solid. MS (ESI) m/z: 520.5 $[M+H]^+$.

The following compounds were prepared similarly according to the synthetic procedures or methodologies exemplified herein.

(S)—N-(5-(1-(3-Ethoxy-4-methoxyphenyl)-2-(methylsulfonyl)ethyl)-6-oxo-5,6-dihydro-4H-thieno[2,3-c]pyrrol-3-yl)-2-methoxyacetamide A2. MS (ESI) m/z: 483.1 $[M+H]^+$.

(S)—N-(5-(1-(3-Ethoxy-4-methoxyphenyl)-2-(methylsulfonyl)ethyl)-6-oxo-5,6-dihydro-4H-thieno[2,3-c]pyrrol-3-yl)cyclopropanecarboxamide A3. MS (ESI) m/z: 479.1 $[M+H]^+$.

A2

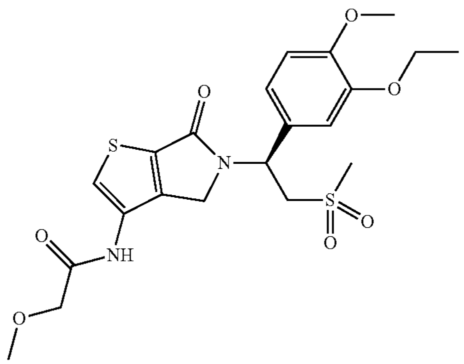

A3

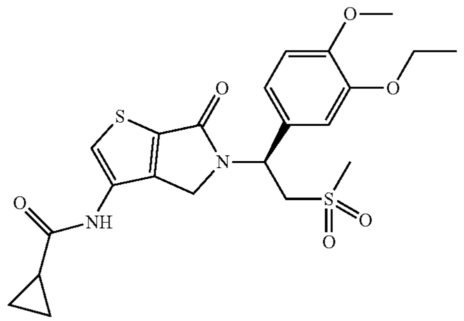

(S)—N-(5-(1-(3-Cyclopropoxy-4-methoxyphenyl)-2-(methylsulfonyl)ethyl)-4,6-dioxo-5,6-dihydro-4H-thieno[3,4-c]pyrrol-1-yl)acetamide A4. MS (ESI) m/z: 479.1 $[M+H]^+$.

(R)—N-(5-(1-(3-Cyclopropoxy-4-methoxyphenyl)-2-(methylsulfonyl)ethyl)-4,6-dioxo-5,6-dihydro-4H-thieno[3,4-c]pyrrol-1-yl)acetamide A5. MS (ESI) m/z: 478.9 $[M+H]^+$.

(S)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)acetamide A6. MS (ESI) m/z: 493.0 $[M+H]^+$.

A4

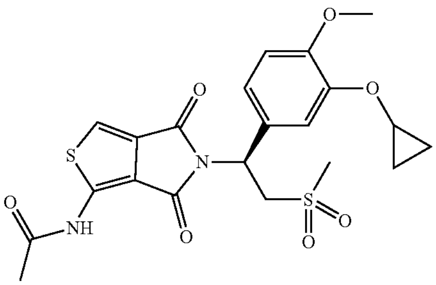

-continued

A5

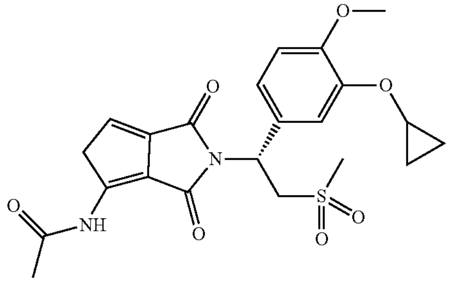

A6

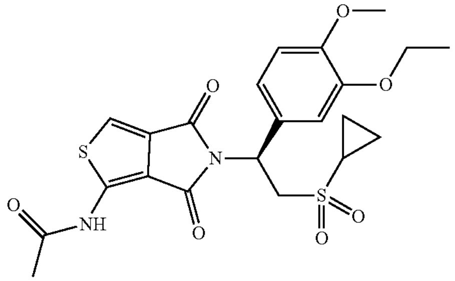

(S)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)-2,2,2-trifluoroacetamide A7. MS (ESI) m/z: 546.6 $[M+H]^+$.

(R)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)-2,2,2-trifluoroacetamide A8. MS (ESI) m/z: 546.8 $[M+H]^+$.

(R)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)-2-methoxyacetamide A9. MS (ESI) m/z: 523.0 $[M+H]^+$.

A7

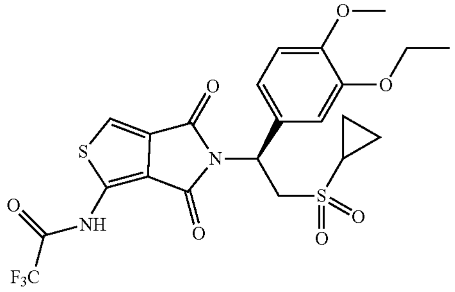

A8

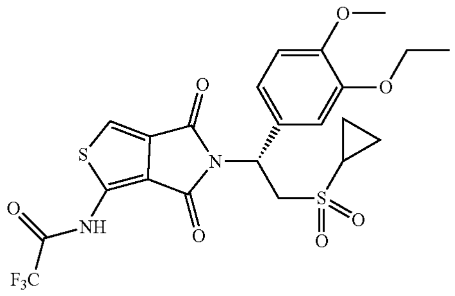

-continued

A9

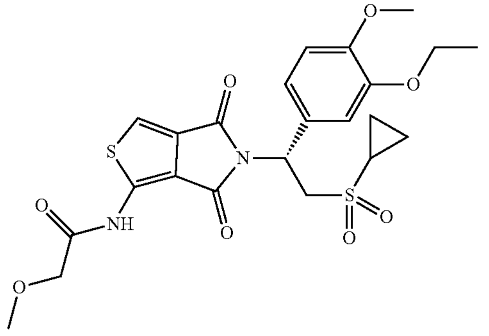

(R)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)acetamide A10. MS (ESI) m/z: 493.0 $[M+H]^+$.

(S)—N-(5-(2-(Cyclopropylsulfonyl)-1-(3-ethoxy-4-methoxyphenyl)ethyl)-4,6-dioxo-5,6-dihydro-4H-thieno[3,4-c]pyrrol-1-yl)-2-methoxyacetamide A11. MS (ESI) m/z: 523.1 $[M+H]^+$.

A10

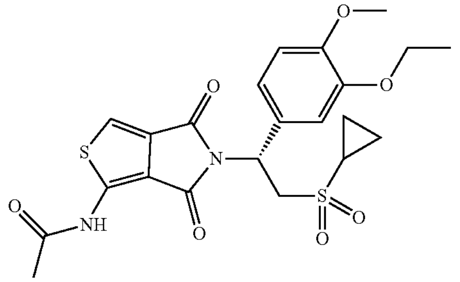

-continued

A11

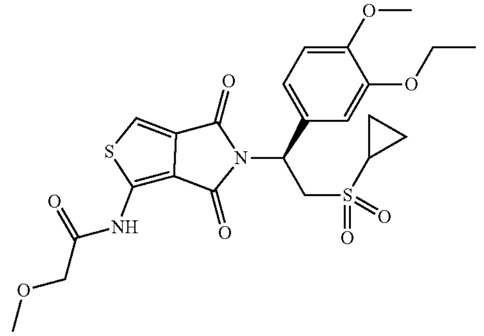

Example 4

Synthesis of N-(6-(7-(4-(2-(2,6-Dioxopiperidin-3-yl)-6-fluoro-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B2 and N-(6-(7-(4-(2-(2,6-Dioxopiperidin-3-yl)-6-fluoro-1-oxoisoindolin-4-yl)piperidin-1-yl)hept-1-yn-1-yl)-2-((S)-1-(3-ethoxy-4-methoxyphenyl)-2-(methylsulfonyl)ethyl)-1,3-dioxoisoindolin-4-yl)acetamide B47

B2

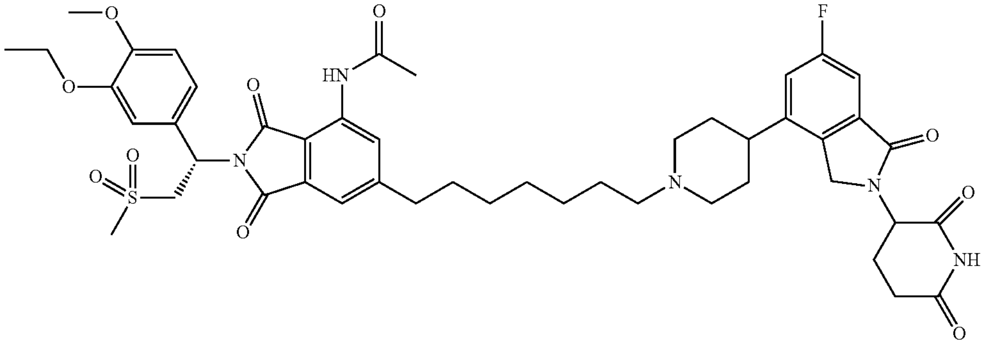

-continued

B47

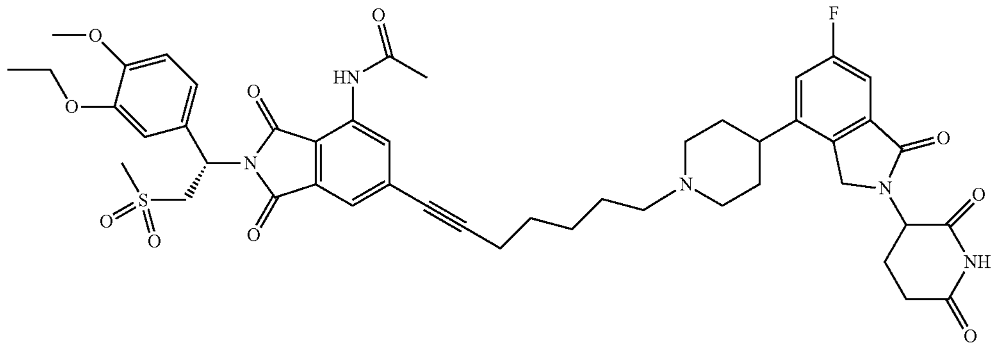

To a solution of 2-methyl-3-nitrobenzoic acid (5.00 g, 27.6 mmol) in $H_2SO_4$ (25 mL) at 60° C. was added N-iodosuccinimide (7.458 g, 33.1 mmol) in portions. The mixture was stirred at 60° C. for 2 h and then poured into 150 g of ice. The mixture was filtered, washed with water and petroleum ether, and concentrated to afford 5-iodo-2-methyl-3-nitrobenzoic acid (8.302 g) in 98% yield. MS (ESI) m/z: 306.2 $[M-H]^-$.

To a suspension of 5-iodo-2-methyl-3-nitrobenzoic acid (3.0 g, 10 mmol) in water (78 mL) was added NaOH (2M solution, 5.2 mL, 2.6 mmol), followed by addition of $KMnO_4$ (6.32 g, 40 mmol) at 60° C. After refluxed overnight, the mixture was cooled to 80° C., filtered, and washed with hot water. The filtrate was acidified to pH 1 with conc. HCl, filtered, and concentrated to afford 5-iodo-3-nitrophthalic acid (5.2 g) in a quantitative yield. MS (ESI) m/z: 335.9 $[M-H]^-$.

A solution of 5-iodo-3-nitrophthalic acid (5.2 g, 10 mmol) in acetic anhydride (20 mL) was heated to 140° C. and stirred for 3 h. The mixture was concentrated to give 6-iodo-4-nitroisobenzofuran-1,3-dione (5.0 g, crude).

To a solution of 6-iodo-4-nitroisobenzofuran-1,3-dione (5.0 g, crude) in acetic acid (20 mL) was added (S)-1-(3-ethoxy-4-methoxyphenyl)-2-(methylsulfonyl)ethanamine (4.1 g, 15 mmol). After stirred at 60° C. for 3 h, the mixture was concentrated and water/EtOH (4:1) was added. The resulting solid was collected by filtration and washed with petroleum ether to afford (S)-2-(1-(3-ethoxy-4-methoxyphenyl)-2-(methylsulfonyl)ethyl)-6-iodo-4-nitroisoindoline-1,3-dione (2.3 g) in 40% yield. MS (ESI) m/z: 574.9 $[M+H]^+$.

To a solution of (S)-2-(1-(3-ethoxy-4-methoxyphenyl)-2-(methylsulfonyl)ethyl)-6-iodo-4-nitroisoindoline-1,3-dione (2.3 g, 4 mmol) in EtOH (40 mL) and water (20 mL) were added $NH_4Cl$ (1.08 g, 20 mmol) and iron powder (1.12 g, 20 mmol). After refluxed for 1 h, the mixture was filtered through celite, washed with ethyl acetate, concentrated, and purified using silica gel eluting with methanol in dichloromethane from 0% to 5% to give (S)-4-amino-2-(1-(3-ethoxy-4-methoxyphenyl)-2-(methylsulfonyl)ethyl)-6-iodoisoindoline-1,3-dione (1.366 g) in 63% yield. MS (ESI) m/z: 562.2 $[M+NH_4]^+$.

To a solution of (S)-4-amino-2-(1-(3-ethoxy-4-methoxyphenyl)-2-(methylsulfonyl)-ethyl)-6-iodoisoindoline-1,3-dione (1.366 g, 2.5 mmol) in dichloromethane (10 mL) were added triethylamine (0.7 mL, 5 mmol) and acetyl chloride (234 mg, 3 mmol) at 0° C. The mixture was stirred at room temperature for 3 h and then concentrated. The residue was purified using silica gel eluting with ethyl acetate in petroleum ether from 50% to 85% to give (S)—N-(2-(1-(3-ethoxy-4-methoxyphenyl)-2-(methylsulfonyl)ethyl)-6-iodo-1,3-dioxoisoindolin-4-yl)acetamide (700 mg) in 48% yield. MS (ESI) m/z: 587.5 $[M+H]^+$.

To a solution of (S)—N-(2-(1-(3-ethoxy-4-methoxyphenyl)-2-(methylsulfonyl)ethyl)-6-iodo-1,3-dioxoisoindolin-4-yl)acetamide (450 mg, 0.77 mmol) and 3-(6-fluoro-4-(1-(hept-6-yn-1-yl)piperidin-4-yl)-1-oxoisoindolin-2-yl)piperidine-2,6-dione (828 mg, 1.89 mmol) in N,N-dimethylformamide (10 mL) were added $Pd(PPh_3)_2Cl_2$ (112 mg, 0.16 mmol), CuI (30 mg, 0.16 mmol), and triethylamine (191 mg, 1.89 mmol) under $N_2$. After the mixture was stirred at 80° C. for 5 h, 1N HCl was added and the mixture was extracted with ethyl acetate. The combined organic layers were washed with brine, dried over anhydrous $Na_2SO_4$, filtered, and concentrated. The residue was purified using silica gel eluting with methanol in dichloromethane from 3% to 10% and further purified using prep-HPLC to afford N-(6-(7-(4-(2-(2,6-dioxopiperidin-3-yl)-6-fluoro-1-oxoisoindolin-4-yl)piperidin-1-yl)hept-1-yn-1-yl)-2-((S)-1-(3-ethoxy-4-methoxyphenyl)-2-(methylsulfonyl)ethyl)-1,3-dioxoisoindolin-4-yl)acetamide B47 (45 mg) in 7% yield. $^1$H NMR (400 MHz, DMSO-$d_6$) δ 11.02 (s, 1H), 9.70 (s, 1H), 8.44 (s, 1H), 7.49 (s, 1H), 7.36 (d, J=8.8 Hz, 2H), 7.06 (s, 1H), 6.98-6.90 (m, 2H), 5.79-5.73 (m, 1H), 5.14 (dd, J=4.4, 12.4 Hz, 1H), 4.53-4.28 (m, 3H), 4.17-4.12 (m, 1H), 4.01 (q, J=7.6 Hz, 2H), 3.73 (s, 3H), 3.01 (s, 3H), 2.97-2.54 (m, 2H), 2.67-2.54 (m, 2H), 2.43-2.32 (m, 2H), 2.19 (s, 3H), 2.03-1.95 (m, 3H), 1.80-1.73 (m, 4H), 1.65-1.45 (m, 6H), 1.32 (t, J=6.0 Hz, 3H), 1.26-1.21 (m, 4H); MS (ESI) m/z: 898.3 $[M+H]^+$.

To a solution of N-(6-(7-(4-(2-(2,6-dioxopiperidin-3-yl)-6-fluoro-1-oxoisoindolin-4-yl)piperidin-1-yl)hept-1-yn-1-yl)-2-((S)-1-(3-ethoxy-4-methoxyphenyl)-2-(methylsulfonyl)ethyl)-1,3-dioxoisoindolin-4-yl)acetamide (50 mg, 0.06 mmol) in THF (3 mL) and MeOH (3 mL) was added Pd/C (5 mg, 0.04 mmol). After stirred under $H_2$ for 20 h, the mixture was filtered and washed with ethyl acetate. The filtrate was concentrated and the residue was purified using prep-HPLC to afford N-(6-(7-(4-(2-(2,6-dioxopiperidin-3-yl)-6-fluoro-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B2 (12 mg) in 24% yield. $^1$H NMR (400 MHz, DMSO-$d_6$) δ 11.01 (s, 1H), 9.64 (s, 1H), 8.28 (s, 1H), 7.46-7.31 (m, 3H), 7.06 (s, 1H), 6.98-6.90 (m, 2H), 5.76 (dd, J=4.0, 10.4 Hz, 1H), 5.13 (dd, J=5.2, 13.2 Hz, 1H), 4.52-4.31 (m, 3H), 4.15-4.10 (m, 1H), 4.01 (q, J=6.8 Hz, 2H), 3.73 (s, 3H), 3.01 (s, 3H), 2.96-2.89 (m, 3H), 2.76-2.65 (m, 2H), 2.64-2.54 (m, 2H), 2.46-2.39 (m, 1H), 2.29-2.21 (m, 2H), 2.18 (s, 3H), 2.06-1.86 (m, 4H), 1.78-1.64 (m, 4H), 1.63-1.52 (m, 2H), 1.46-1.36 (m, 2H), 1.35-1.18 (m, 8H); MS (ESI) m/z: 902.3 $[M+H]^+$.

Example 5

Synthesis of N-(3,5-Dichloropyridin-4-yl)-4-(difluoromethoxy)-3-((7-(4-(2-(2,6-dioxopiperidin-3-yl)-6-fluoro-1-oxoisoindolin-4-yl)piperidin-1-yl)heptyl)oxy)benzamide B4

B4

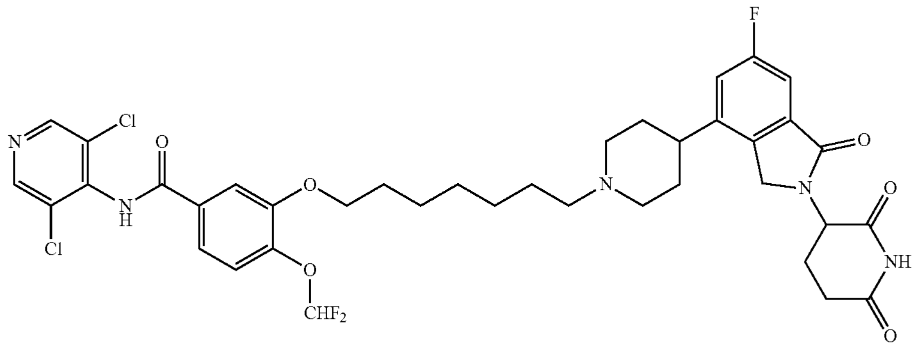

To a solution of methyl 4-(difluoromethoxy)-3-hydroxybenzaldehyde (1.0 g, 5.32 mmol) in ACN (14 mL) were added $K_2CO_3$ (2.20 g, 15.96 mmol) and 7-iodo-N-methoxy-N-methylheptanamide (2.39 g, 7.92 mmol). After stirred at 80° C. for 2 h, the mixture was diluted with $H_2O$ and extracted with EtOAc. The combined organic layers were dried over anhydrous $Na_2SO_4$, filtered, and concentrated. The residue was purified using silica gel with ethyl acetate in petroleum ether from 0% to 50% to give 7-(2-(difluoromethoxy)-5-formylphenoxy)-N-methoxy-N-methylheptanamide (1.8 g) in 94% yield. MS (ESI) m/z: 360.3 $[M+H]^+$.

To a solution of 7-(2-(difluoromethoxy)-5-formylphenoxy)-N-methoxy-N-methylheptanamide (1.8 g, 5.01 mmol) in acetic acid (40 mL) were added sulfamic acid (1.46 g, 15.04 mmol) and a solution of sodium chlorite (1.36 g, 15.04 mmol) in $H_2O$ (13 mL) dropwise. After stirred at 35° C. for 2 h, the mixture was diluted with $H_2O$ and filtered to give 4-(difluoromethoxy)-3-((7-(methoxy(methyl)amino)-7-oxoheptyl)oxy)benzoic acid (1.88 g) in 90% yield. MS (ESI) m/z: 376.3 $[M+H]^+$.

To a solution of 4-(difluoromethoxy)-3-((7-(methoxy(methyl)amino)-7-oxoheptyl)oxy)benzoic acid (500 mg, 1.333 mmol) in dichloromethane (8 mL) in 0° C. were added oxalyl chloride (250 mg, 2.00 mmol) and DMF (1 drop). After stirred at room temperature for 1 h, the mixture was concentrated to give 4-(difluoromethoxy)-3-((7-(methoxy(methyl)amino)-7-oxoheptyl)oxy)benzoyl chloride (crude).

To a solution of 3,5-dichloropyridin-4-amine (464 mg, 2.67 mmol) in tetrahydrofuran (6 mL) in 0° C. was added sodium hydride (64 mg, 2.67 mmol). After the mixture was stirred at 0° C. for 30 min, N-(3,5-dichloropyridin-4-yl)-4-(difluoromethoxy)-3-((7-(methoxy(methyl)amino)-7-oxoheptyl)oxy)benzamide (524 mg, 1.33 mmol) was added. After stirred at room temperature for 2 h, the mixture was diluted with $H_2O$ and extracted with ethyl acetate. The combined organic layers were dried over anhydrous $Na_2SO_4$, filtered, and concentrated. The residue was purified using silica gel eluting with ethyl acetate in petroleum ether from 0% to 40% to give N-(3,5-dichloropyridin-4-yl)-4-(difluoromethoxy)-3-((7-(methoxy(methyl)amino)-7-oxoheptyl)oxy)-benzamide (254 mg) in 37% yield. MS (ESI) m/z: 520.1 $[M+H]^+$.

To a solution of N-(3,5-dichloropyridin-4-yl)-4-(difluoromethoxy)-3-((7-(methoxy(methyl)amino)-7-oxoheptyl)oxy)benzamide (50 mg, 0.096 mmol) in tetrahydrofuran (3 mL) at −78° C. under nitrogen was added lithium aluminum hydride (0.14 mL, 1M in tetrahydrofuran) dropwise. After stirred at this temperature for 1 h, the reaction was quenched with ammonium chloride (5 mL) and the reaction mixture was extracted with ethyl acetate. The combined organic layers were dried over anhydrous sodium sulfate, filtered, and concentrated to give N-(3,5-dichloropyridin-4-yl)-4-(difluoromethoxy)-3-((7-oxoheptyl)oxy)benzamide (40 mg, crude). MS (ESI) m/z: 461.1$[M+H]^+$.

To a solution of 3-(6-fluoro-1-oxo-4-(piperidin-4-yl)isoindolin-2-yl)piperidine-2,6-dione (42 mg, 0.010 mmol) in dichloromethane/methanol (4 mL/1 mL) was added N,N-diisopropylethylamine (12 mg, 0.10 mmol) at 0° C., followed by addition of N-(3,5-dichloropyridin-4-yl)-4-(difluoromethoxy)-3-((7-oxoheptyl)oxy)benzamide (40 mg, crude, 0.10 mmol), $NaBH_3CN$ (12 mg, 0.19 mmol), and acetic acid (1 drop). The mixture was stirred at room temperature overnight and then concentrated. The residue was purified using prep-HPLC eluting with water (0.1% TFA) in ACN (0.1% TFA) at a gradient of 95 to 5% to give N-(3,5-dichloropyridin-4-yl)-4-(difluoromethoxy)-3-((7-(4-(2-(2,6-dioxopiperidin-3-yl)-6-fluoro-1-oxoisoindolin-4-yl)piperidin-1-yl)heptyl)oxy)benzamide B4 (17.2 mg) in 23% yield. $^1H$ NMR (400 MHz, DMSO-$d_6$) δ 11.00 (s, 1H), 10.66 (brs, 1H), 8.77 (s, 2H), 7.73 (d, J=2.0 Hz, 1H), 7.66 (dd, J=2.0, 8.4 Hz, 1H), 7.40-7.07 (m, 4H), 5.14 (dd, J=4.8, 13.2 Hz, 1H), 4.53-4.32 (m, 2H), 4.13 (t, J=6.4 Hz, 2H), 3.52-3.49 (m, 2H), 3.01-2.88 (m, 3H), 2.62-2.58 (m, 2H), 2.45-2.35 (m, 2H), 2.07-1.99 (m, 3H), 1.81-1.70 (m, 5H), 1.51-1.27 (m, 8H); MS (ESI) m/z: 790.3 $[M+H]^+$.

Example 6

Synthesis of N-(6-(5-(4-((2-(2,6-Dioxopiperidin-3-yl)-1-oxoisoindolin-4-yl)ethynyl)piperidin-1-yl)-5-oxopentyl)-2-((S)-1-(3-ethoxy-4-methoxyphenyl)-2-(methylsulfonyl)ethyl)-1,3-dioxoisoindolin-4-yl) acetamide B16

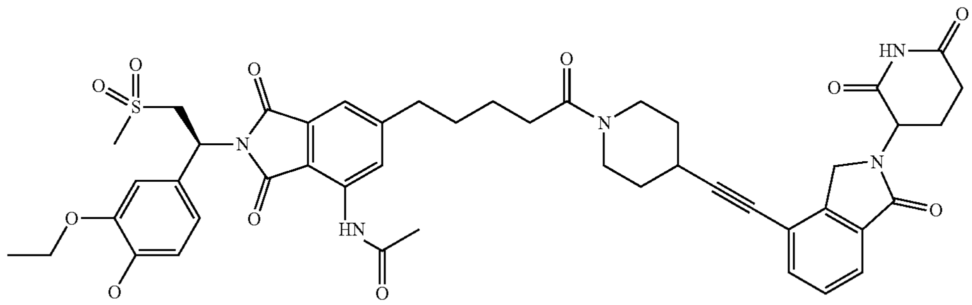

B16

To a solution of pent-4-ynoic acid (1.0 g, 10.20 mmol) in methanol (15 mL) was added $H_2SO_4$ (1.0 g, 10.20 mmol). After stirred at 70° C. for 16 h, the reaction was quenched by $NaHCO_3$ (aq.) (10 mL) and the reaction mixture was extracted with ethyl acetate. The combined organic layers were dried over anhydrous $Na_2SO_4$, filtered, and concentrated. The residue was purified using silica gel eluting with petroleum ether/ethyl acetate (20:1) to give methyl pent-4-ynoate (464 mg) in 46% yield.

To a solution of methyl pent-4-ynoate (191 mg, 1.7 mmol) in tetrahydrofuran (20 mL) were added (S)—N-(2-(1-(3-ethoxy-4-methoxyphenyl)-2-(methylsulfonyl)ethyl)-6-iodo-1,3-dioxoisoindolin-4-yl)acetamide (400 mg, 0.68 mmol), CuI (26 mg, 0.14 mmol), triethylamine (206 mg, 2.04 mmol), and $Pd(PPh_3)_2Cl_2$ (98 mg, 0.14 mmol). The mixture was stirred at 70° C. under $N_2$ atmosphere for 16 h and then concentrated. The residue was diluted with $H_2O$ and extracted with ethyl acetate. The combined organic layers were dried over anhydrous $Na_2SO_4$, filtered, and concentrated. The residue was purified using prep-TLC eluting with DCM/MeOH (20:1) to give (S)-methyl 5-(7-acetamido-2-(1-(3-ethoxy-4-methoxyphenyl)-2-(methylsulfonyl)ethyl)-1,3-dioxoisoindolin-5-yl)pent-4-ynoate (212 mg) in 55% yield. MS (ESI) m/z: 571.2 $[M+H]^+$.

To a solution of (S)-methyl 5-(7-acetamido-2-(1-(3-ethoxy-4-methoxyphenyl)-2-(methylsulfonyl)ethyl)-1,3-dioxoisoindolin-5-yl)pent-4-ynoate (212 mg, 0.37 mmol) in MeOH (10 mL) was added Pd/C (212 mg). After stirred under $H_2$ atmosphere for 16 h, the mixture was filtered and washed with dichloromethane. The combined filtrates were concentrated. The residue was purified using prep-TLC eluting with DCM/MeOH (20:1) to give (S)-methyl 5-(7-acetamido-2-(1-(3-ethoxy-4-methoxyphenyl)-2-(methylsulfonyl)ethyl)-1,3-dioxoisoindolin-5-yl)pentanoate (199 mg) in 94% yield. MS (ESI) m/z: 575.2 $[M+H]^+$.

To a solution of (S)-methyl 5-(7-acetamido-2-(1-(3-ethoxy-4-methoxyphenyl)-2-(methylsulfonyl)ethyl)-1,3-dioxoisoindolin-5-yl)pentanoate (118 mg, 0.206 mmol) in tetrahydrofuran (10 mL) was added potassium trimethylsilanolate (79 mg, 0.618 mmol). The mixture was stirred at 0° C. for 3 h and then concentrated to afford (S)-5-(7-acetamido-2-(1-(3-ethoxy-4-methoxyphenyl)-2-(methylsulfonyl)ethyl)-1,3-dioxoisoindolin-5-yl)pentanoic acid. MS (ESI) m/z: 561.2 $[M+H]^+$.

To a solution of tert-butyl 4-((2-(2,6-dioxopiperidin-3-yl)-1-oxoisoindolin-4-yl)ethynyl)piperidine-1-carboxylate (89 mg, 0.197 mmol) in dichloromethane (8 mL) was added HCl-ethyl acetate (2 mL). The mixture was stirred for 1 h and then concentrated to give 3-(1-oxo-4-(piperidin-4-ylethynyl)isoindolin-2-yl)piperidine-2,6-dione HCl salt (75 mg), which was dissolved in N,N-dimethylformamide (1 mL). N,N-Diisopropylethylamine (76 mg, 0.591 mmol) was then added, followed by addition of a solution of (S)-5-(7-acetamido-2-(1-(3-ethoxy-4-methoxyphenyl)-2-(methylsulfonyl)ethyl)-1,3-dioxoisoindolin-5-yl)pentanoic acid (solution, 0.206 mmol), HOBt (40 mg, 0.296 mmol), and EDCI·HCl (57 mg, 0.296 mmol). After stirred overnight, the mixture was diluted with $H_2O$ and extracted with ethyl acetate. The combined organic layers were dried over anhydrous $Na_2SO_4$, filtered, and concentrated. The residue was purified using prep-TLC eluting with dichloromethane/methanol (10:1) and further purified using prep-HPLC to give N-(6-(5-(4-((2-(2,6-dioxopiperidin-3-yl)-1-oxoisoindolin-4-yl)ethynyl)piperidin-1-yl)-5-oxopentyl)-2-((S)-1-(3-ethoxy-4-methoxyphenyl)-2-(methylsulfonyl)ethyl)-1,3-dioxoisoindolin-4-yl)acetamide B16 (6.6 mg) in 4% yield. $^1H$ NMR (400 MHz, DMSO-$d_6$) δ 11.00 (s, 1H), 9.66 (s, 1H), 8.29 (s, 1H), 7.73 (d, J=7.2 Hz, 1H), 7.66 (d, J=7.6 Hz, 1H), 7.54 (d, J=7.6 Hz, 1H), 7.45 (s, 1H), 7.07 (s, 1H), 6.97-6.93 (m, 2H), 5.77 (dd, J=4.4, 10.4 Hz, 1H), 5.13 (dd, J=4.4, 12.8 Hz, 1H), 4.49-4.31 (m, 4H), 4.15-4.11 (m, 1H), 4.02 (q, J=7.2 Hz, 2H), 3.89-3.84 (m, 2H), 3.74 (s, 3H), 3.72-3.57 (m, 2H), 3.22-3.17 (m, 1H), 3.02 (s, 3H), 2.97-2.90 (m, 1H), 2.75 (t, J=6.8 Hz, 2H), 2.63-2.59 (m, 2H), 2.36-2.33 (m, 2H), 2.18 (s, 3H), 2.04-1.98 (m, 2H), 1.89-1.81 (m, 2H), 1.64-1.59 (m, 2H), 1.56-1.49 (m, 2H), 1.33 (t, J=7.2 Hz, 2H); MS (ESI) m/z: 894.3$[M+H]^+$.

Example 7

Synthesis of N-(3,5-Dichloropyridin-4-yl)-4-(difluoromethoxy)-3-((5-(4-((2-(2,6-dioxopiperidin-3-yl)-1-oxoisoindolin-4-yl)ethynyl)piperidin-1-yl)-5-oxopentyl)oxy)benzamide B18

B18

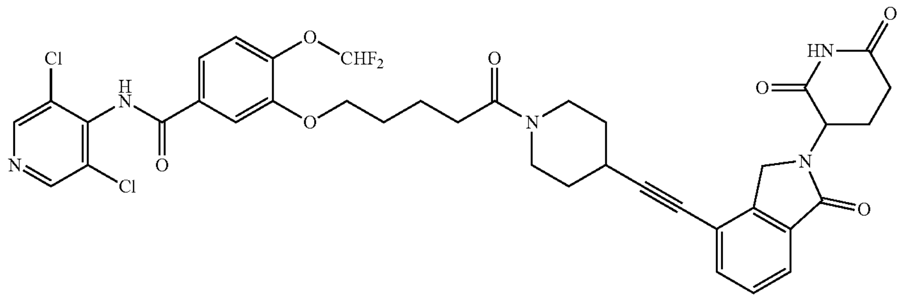

A solution of 3-(benzyloxy)-N-(3,5-dichloropyridin-4-yl)-4-(difluoromethoxy)-benzamide (110 mg, 0.271 mmol) in trifluoroacetic acid (6 mL) was stirred at 80° C. for 1 h and then concentrated to give N-(3,5-dichloropyridin-4-yl)-4-(difluoromethoxy)-3-hydroxybenzamide (crude). MS (ESI) m/z: 349.0 $[M+H]^+$.

To a solution of N-(3,5-dichloropyridin-4-yl)-4-(difluoromethoxy)-3-hydroxybenzamide (94 mg, 0.270 mmol) in acetonitrile (5 mL) were added potassium carbonate (112 mg, 0.810 mmol) and methyl 5-bromopentanoate (47 mg, 0.243 mmol). After heated at 80° C. overnight, the mixture was diluted with water and extracted with ethyl acetate. The combined organic layers were dried over anhydrous $Na_2SO_4$, filtered, and concentrated. The residue was purified using prep-TLC eluting with petroleum ether/ethyl acetate (3:1) to give methyl 5-(5-((3,5-dichloropyridin-4-yl)carbamoyl)-2-(difluoromethoxy)phenoxy)pentanoate (75 mg) in 60% yield. MS (ESI) m/z: 463.1 $[M+H]^+$.

To a solution of methyl 5-(5-((3,5-dichloropyridin-4-yl) carbamoyl)-2-(difluoromethoxy)phenoxy)pentanoate (75 mg, 0.162 mmol) in methanol (4 mL), tetrahydrofuran (2 mL), and water (1 mL) was added lithium hydroxide (14 mg, 0.325 mmol). After stirred for 12 h, the mixture was neutralized to pH 6 with 1N HCl and then extracted with ethyl acetate. The combined organic layers were concentrated to give 5-(5-((3,5-dichloropyridin-4-yl)carbamoyl)-2-(difluoromethoxy)phenoxy)pentanoic acid (72 mg) in 99% yield. MS (ESI) m/z: 449.2 $[M+H]^+$.

To a solution of 5-(5-((3,5-dichloropyridin-4-yl)carbamoyl)-2-(difluoromethoxy)-phenoxy)pentanoic acid (72 mg, 0.162 mmol) in N,N-dimethylformamide (5 mL) were added HATU (93 mg, 0.243 mmol), 3-(1-oxo-4-(piperidin-4-ylethynyl)isoindolin-2-yl)piperidine-2,6-dione (57 mg, 0.62 mmol), and ethyldiisopropylamine (63 mg, 0.486 mmol). The mixture was stirred overnight and then concentrated. The residue was purified using prep-HPLC to give N-(3,5-dichloropyridin-4-yl)-4-(difluoromethoxy)-3-((5-(4-((2-(2,6-dioxopiperidin-3-yl)-1-oxoisoindolin-4-yl)ethynyl)piperidin-1-yl)-5-oxopentyl)oxy)benzamide B18 (36.9 mg) in 29% yield. $^1H$ NMR (400 MHz, DMSO-$d_6$) δ 10.98 (s, 1H), 10.63 (s, 1H), 8.74 (s, 2H), 7.72-7.70 (m, 2H), 7.66-7.63 (m, 2H), 7.53 (t, J=7.6 Hz, 1H), 7.38-7.01 (m, 2H), 5.12 (dd, J=5.2, 13.6 Hz, 1H), 4.47-4.29 (m, 2H), 4.15 (t, J=6.4, 2H), 3.90-3.87 (m, 1H), 3.73-3.69 (m, 1H), 3.29 (s, 2H), 3.22-3.16 (m, 1H), 2.99-2.86 (m, 2H), 2.66-2.57 (m, 1H), 2.45-2.38 (m, 3H), 2.07-1.95 (m, 2H), 1.71-1.66 (m, 2H), 1.23 (s, 4H); MS (ESI) m/z: 782.2 $[M+H]^+$.

Example 8

Synthesis of 7-((4-((5-((S)-2,6-Dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)heptanamide B44

B44

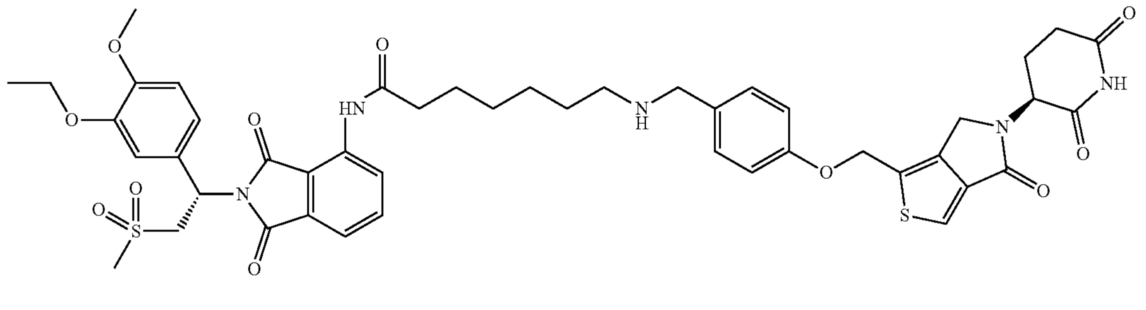

To a stirred solution of 7-(((benzyloxy)carbonyl)amino) heptanoic acid (500 mg, 1.79 mmol) in toluene (10 mL) was added thionyl chloride (1.1 g, 9.24 mmol). The mixture was stirred at 100° C. for 2 h and then concentrated to give benzyl (7-chloro-7-oxoheptyl)carbamate (crude).

To a stirred solution of benzyl (7-chloro-7-oxoheptyl) carbamate (1.79 mmol) in tetrahydrofuran (10 mL) was added (S)-4-amino-2-(1-(3-ethoxy-4-methoxyphenyl)-2-(methylsulfonyl)ethyl)isoindoline-1,3-dione (375 mg, 0.9 mmol). The mixture was stirred for 3 days and then concentrated. The residue was purified using silica gel eluting with ethyl acetate in petroleum ether from 20% to 50% to give (S)-benzyl (7-((2-(1-(3-ethoxy-4-methoxyphenyl)-2-(methylsulfonyl)ethyl)-1,3-dioxoisoindolin-4-yl)amino)-7-oxoheptyl)carbamate (565 mg) in 93% yield. MS (ESI) m/z: 680.2 $[M+H]^+$.

To a stirred solution of (S)-benzyl (7-((2-(1-(3-ethoxy-4-methoxyphenyl)-2-(methylsulfonyl)ethyl)-1,3-dioxoisoindolin-4-yl)amino)-7-oxoheptyl)carbamate (200 mg, 0.29 mmol) in methanol (5 mL) was added 10% Pd/C (200 mg). After stirred at room temperature overnight under hydrogen, the mixture was filtered and the filtrate was concentrated to give (S)-7-amino-N-(2-(1-(3-ethoxy-4-methoxyphenyl)-2-(methylsulfonyl)ethyl)-1,3-dioxoisoindolin-4-yl)heptanamide (135 mg) in 84% yield. MS (ESI) m/z: 546.2 $[M+H]^+$.

To a stirred solution of (S)-7-amino-N-(2-(1-(3-ethoxy-4-methoxyphenyl)-2-(methylsulfonyl)ethyl)-1,3-dioxoisoindolin-4-yl)heptanamide (135 mg, 0.25 mmol) and (S)-4-((5-(2,6-dioxopiperidin-3-yl)-4-oxo-5,6-dihydro-4H-thieno[3,4-c]pyrrol-1-yl)methoxy)benzaldehyde (95 mg, 0.25 mmol) in dichloromethane (4 mL) and methanol (1 mL) were added sodium cyanoborohydride (32 mg, 0.5 mmol) and acetic acid (2 drops). The mixture was stirred overnight then concentrated. The residue was purified using prep-TLC (dichloromethane/methanol (10:1) and further purified using prep-HPLC to give 7-((4-((5-((S)-2,6-dioxopiperidin-3-yl)-4-oxo-5,6-dihydro-4H-thieno[3,4-c]pyrrol-1-yl)methoxy) benzyl)amino)-N-(2-((S)-1-(3-ethoxy-4-methoxyphenyl)-2-(methylsulfonyl)ethyl)-1,3-dioxoisoindolin-4-yl) heptanamide B44 (8.0 mg). $^1$H NMR (400 MHz, DMSO-$d_6$) δ 10.99 (s, 1H), 9.66 (s, 1H), 8.66 (brs, 2H), 8.46 (d, J=8.4 Hz, 1H), 8.03 (s, 1H), 7.79 (t, J=8.0 Hz, 1H), 7.57 (d, J=7.2 Hz, 1H), 7.42 (d, J=8.8 Hz, 2H), 7.12-7.07 (m, 3H), 7.00-6.92 (m, 2H), 5.77 (dd, J=4.0, 10.4 Hz, 1H), 5.34 (s, 2H), 5.02 (dd, J=4.8, 13.2 Hz, 1H), 4.38-4.30 (m, 2H), 4.24-4.12 (m, 2H), 4.07 (t, J=4.8 Hz, 2H), 4.01 (q, J=6.4 Hz, 2H), 3.73 (s, 3H), 3.01 (s, 3H), 2.97-2.85 (m, 3H), 2.67-2.53 (m, 1H), 2.49-2.46 (m, 2H), 2.38-2.28 (m, 1H), 2.02-1.97 (m, 1H), 1.66-1.58 (m, 4H), 1.38-1.30 (m, 7H); MS (ESI) m/z: 914.2 $[M+H]^+$.

Example 9

Synthesis of 14-((2-(2,6-Dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)-3,6,9,12-tetraoxatetradecan-1-amide B48

B48

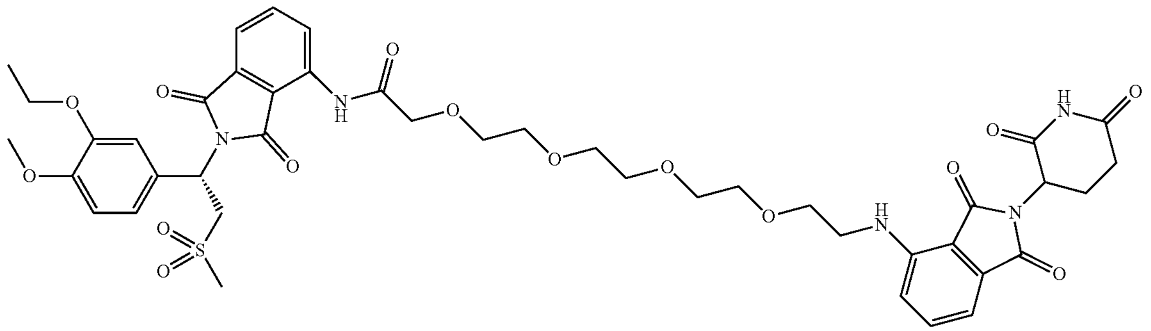

To a stirred solution of 2,2-dimethyl-4-oxo-3,8,11,14,17-pentaoxa-5-azanonadecan-19-oic acid (300 mg, 0.85 mmol) in dichloromethane (10 mL) were added oxalyl chloride (130 mg, 1.02 mmol) and 1 drop of N,N-dimethylformamide. The mixture was stirred for 2 h and then concentrated to give tert-butyl (14-chloro-14-oxo-3,6,9,12-tetraoxatetradecyl)carbamate (300 mg, crude).

To a stirred solution of tert-butyl (14-chloro-14-oxo-3,6,9,12-tetraoxatetradecyl)-carbamate (0.85 mmol) in tetrahydrofuran (10 mL) was added (S)-4-amino-2-(1-(3-ethoxy-4-methoxyphenyl)-2-(methylsulfonyl)ethyl)isoindoline-1,3-dione (120 mg, 0.287 mmol). The mixture was stirred overnight and then concentrated. The residue was purified using prep-TLC eluting with dichloromethane/methanol (20:1) to give (S)-14-amino-N-(2-(1-(3-ethoxy-4-methoxyphenyl)-2-(methylsulfonyl)ethyl)-1,3-dioxoisoindolin-4-yl)-3,6,9,12-tetraoxatetradecan-1-amide (90 mg) in 48% yield. MS (ESI) m/z: 652.2 $[M+H]^+$.

To a stirred solution of (S)-14-amino-N-(2-(1-(3-ethoxy-4-methoxyphenyl)-2-(methylsulfonyl)ethyl)-1,3-dioxoisoindolin-4-yl)-3,6,9,12-tetraoxatetradecan-1-amide (90 mg, 0.14 mmol) and 2-(2,6-dioxopiperidin-3-yl)-4-fluoroisoindoline-1,3-dione (41 mg, 0.15 mmol) in 1-methyl-2-pyrrolidinone (3 mL) was added ethyldiisopropylamine (54 mg, 0.42 mmol). The mixture was stirred at 150° C. for 1 h under microwave. Water was added and the mixture was extracted with dichloromethane. The combined organic layers were washed with brine, dried over anhydrous sodium sulfate, filtered, and concentrated. The residue was purified using prep-HPLC to give 14-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)-3,6,9,12-tetraoxatetradecan-1-amide B48 (9.8 mg) in 8% yield. $^1$H NMR (400 MHz, DMSO-$d_6$) δ 11.09 (s, 1H), 10.35 (s, 1H), 8.67 (d, J=8.8 Hz, 1H), 7.81 (t, J=8.0 Hz, 1H), 7.58-7.52 (m, 2H), 7.10-7.08 (m, 2H), 7.02-6.91 (m, 3H), 6.56 (t, J=5.2 Hz, 1H), 5.78 (dd, J=4.0, 10.4 Hz, 1H), 5.04 (dd, J=5.2, 12.4 Hz, 1H), 4.35-4.12 (m, 4H), 4.01 (q, J=7.2 Hz, 2H), 3.76-3.72 (m, 5H), 3.68-3.64 (m, 2H), 3.58-3.55 (m, 2H), 3.54-3.52 (m, 2H), 3.49-3.46 (m, 8H), 3.01 (s, 3H), 2.88-2.82 (m, 1H), 2.60-2.53 (m, 2H), 2.04-1.99 (m, 1H), 1.31 (t, J=7.2 Hz, 3H); MS (ESI) m/z: 908.2 $[M+H]^+$.

Example 10

Synthesis of 2-(3-(Cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B59

B59

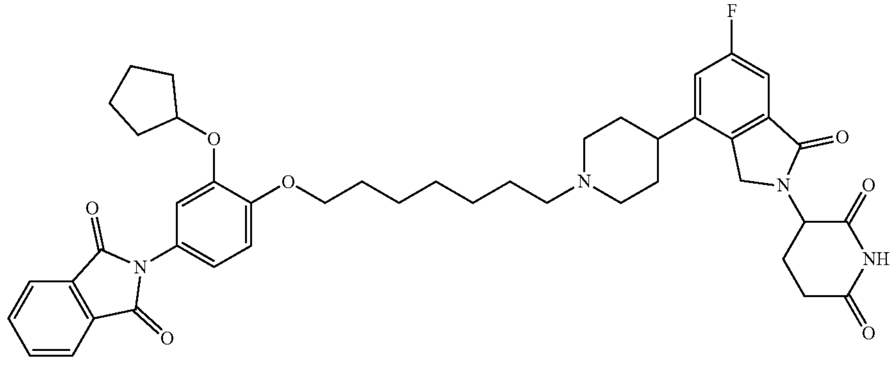

To a solution of 1-(benzyloxy)-2-(cyclopentyloxy)-4-nitrobenzene (1.0 g, 3.19 mmol) in acetic acid (4 mL) was added hydrogen bromide (2 mL, 33% in AcOH). The mixture was stirred for 3 h and then concentrated to give 2-(cyclopentyloxy)-4-nitrophenol (500 mg, crude). MS (ESI) m/z: 224.1[M+H]$^+$.

To a solution of 2-(cyclopentyloxy)-4-nitrophenol (400 mg, 1.79 mmol) in N,N-dimethylformamide (5 mL) at 80° C. were added 7-iodo-N-methoxy-N-methylheptanamide (803 mg, 2.69 mmol) and potassium carbonate (494 mg, 3.58 mmol). After stirred at 80° C. overnight, the mixture was diluted with $H_2O$ and extracted with ethyl acetate. The combined organic layers were dried over anhydrous sodium sulfate, filtered, and concentrated. The residue was purified using silica gel eluting with methanol in dichloromethane from 0% to 5% to give 7-(2-(cyclopentyloxy)-4-nitrophenoxy)-N-methoxy-N-methylheptanamide (604 mg) in 86% yield. MS (ESI) m/z: 395.2[M+H]$^+$.

To a solution of 7-(2-(cyclopentyloxy)-4-nitrophenoxy)-N-methoxy-N-methylheptanamide (400 mg, 1.0 mmol) in tetrahydrofuran (5 mL) at −75° C. under nitrogen was added lithium aluminum hydride (1.5 mL, 1 M in tetrahydrofuran) dropwise. After stirred at this temperature for 1 h, the reaction was quenched with ammonium chloride (5 mL) and the reaction mixture was extracted with ethyl acetate. The combined organic layers were dried over anhydrous sodium sulfate, filtered, and concentrated to give 7-(2-(cyclopentyloxy)-4-nitrophenoxy)heptanal (350 mg, crude). MS (ESI) m/z: 336.2[M+H]$^+$.

To a solution of 7-(2-(cyclopentyloxy)-4-nitrophenoxy)heptanal (335 mg, 1 mmol, crude) in dichloromethane (5 mL) was added 3-(6-fluoro-1-oxo-4-(piperidin-4-yl)isoindolin-2-yl)piperidine-2,6-dione (414 mg, crude, 1.2 mmol), followed by addition of sodium cyanoborohydride (126 mg, 2.0 mmol). The mixture was stirred for 2 h and then concentrated. The residue was purified using silica gel eluting with methanol in dichloromethane from 0% to 5% to give 3-(4-(1-(7-(2-(cyclopentyloxy)-4-nitrophenoxy)heptyl)piperidin-4-yl)-6-fluoro-1-oxoisoindolin-2-yl)piperidine-2,6-dione (664 mg, crude). MS (ESI) m/z: 665.3[M+H]$^+$.

To a solution of 3-(4-(1-(7-(2-(cyclopentyloxy)-4-nitrophenoxy)heptyl)piperidin-4-yl)-6-fluoro-1-oxoisoindolin-2-yl)piperidine-2,6-dione (800 mg, crude) in tetrahydrofuran (20 mL) was added Pd/C (300 mg). After stirred under $H_2$ overnight, the mixture was filtered and the filtrate was concentrated to give 3-(4-(1-(7-(4-amino-2-(cyclopentyloxy)phenoxy)heptyl)piperidin-4-yl)-6-fluoro-1-oxoisoindolin-2-yl)piperidine-2,6-dione (700 mg) in 73% yield. MS (ESI) m/z: 635.3[M+H]$^+$.

To a stirred solution of 3-(4-(1-(7-(4-amino-2-(cyclopentyloxy)phenoxy)heptyl)-piperidin-4-yl)-6-fluoro-1-oxoisoindolin-2-yl)piperidine-2,6-dione (300 mg, 0.47 mmol) in acetic acid (15 mL) was added isobenzofuran-1,3-dione (84.2 mg, 0.57 mmol). The mixture was stirred at 90° C. for 4 h. Water was then added and the mixture was extracted with ethyl acetate. The combined organic layers were washed with brine, dried over anhydrous sodium sulfate, filtered, and concentrated. The residue was purified using prep-HPLC to give 2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)-isoindoline-1,3-dione B59 (11.3 mg) in 3% yield. $^1H$ NMR (400 MHz, DMSO-$d_6$) δ 11.04 (s, 1H), 9.39 (s, 1H), 7.96-7.89 (m, 4H), 7.43 (dd, J=2.0, 7.2 Hz, 1H), 7.31 (dd, J=1.6, 10.8 Hz, 1H), 7.14-7.01 (m, 2H), 6.93 (dd, J=2.0, 8.8 Hz, 1H), 5.16 (dd, J=4.8, 13.2 Hz, 1H), 4.85 (s, 1H), 4.56-4.36 (m, 2H), 4.02 (t, J=6.0 Hz, 2H), 3.61-3.51 (m, 3H), 3.02-2.89 (m, 6H), 2.66-2.61 (m, 1H), 2.40-2.29 (m, 1H), 2.07-1.85 (m, 6H), 1.77-1.71 (m, 6H), 1.60-1.55 (m, 2H), 1.48-1.37 (m, 6H); MS (ESI) m/z: 765.4 [M+H]$^+$.

Example 11

Synthesis of N-(3,5-Dichloropyridin-4-yl)-4-(difluoromethoxy)-3-((7-(4-(2-(2,6-dioxopiperidin-3-yl)-6-fluoro-1-oxoisoindolin-5-yl)piperidin-1-yl)heptyl)oxy)benzamide B61

B61

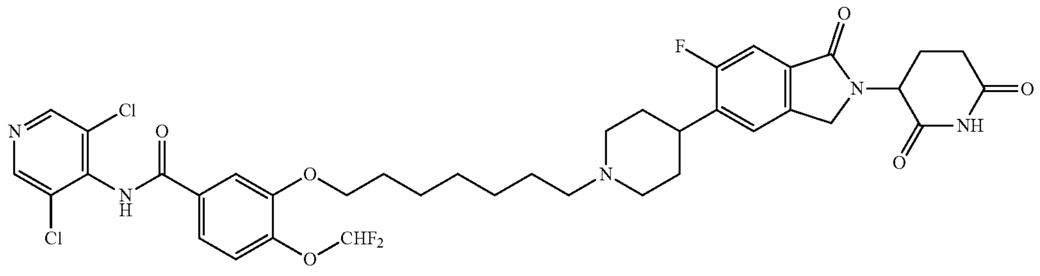

To a solution of N-(3,5-dichloropyridin-4-yl)-4-(difluoromethoxy)-3-((7-(methoxy(methyl)amino)-7-oxoheptyl)oxy)benzamide (80 mg, 0.154 mmol) in tetrahydrofuran (5 mL) at −78° C. under nitrogen was added lithium aluminum hydride (0.23 mL, 1 M in tetrahydrofuran) dropwise. After stirred at this temperature for 1 h, the reaction was quenched with ammonium chloride (5 mL) and the reaction mixture was extracted with ethyl acetate. The combined organic layers were dried over anhydrous sodium sulfate, filtered, and concentrated to give N-(3,5-dichloropyridin-4-yl)-4-(difluoromethoxy)-3-((7-oxoheptyl)oxy)benzamide (71 mg, crude). MS (ESI) m/z: 461.1[M+H]$^+$.

To a solution of tert-butyl 4-(2-(2,6-dioxopiperidin-3-yl)-6-fluoro-1-oxoisoindolin-5-yl)piperidine-1-carboxylate (60 mg, 0.135 mmol) in dichloromethane (3 mL) was added trifluoroacetic acid (1 mL). The mixture was stirred for 1 h and then concentrated. The residue was co-evaporated with toluene to give 3-(6-fluoro-1-oxo-5-(piperidin-4-yl)isoindolin-2-yl)piperidine-2,6-dione (47 mg, crude). MS (ESI) m/z: 346.1 [M+H]$^+$.

To a solution of 3-(6-fluoro-1-oxo-5-(piperidin-4-yl)isoindolin-2-yl)piperidine-2,6-dione (47 mg, 0.135 mmol) in dichloromethane (4 mL) and methanol (1 mL) at 0° C. was added N,N-diisopropylethylamine (35 mg, 0.27 mmol), followed by addition of N-(3,5-dichloropyridin-4-yl)-4-(difluoromethoxy)-3-((7-oxoheptyl)oxy)benzamide (71 mg, crude, 0.154 mmol), $NaBH_3CN$ (17 mg, 0.27 mmol), and acetic acid (1 drop). The mixture was stirred at room temperature for 8 h and then concentrated. The residue was purified using silica gel eluting with methanol in dichloromethane from 0% to 10% to give N-(3,5-dichloropyridin-4-yl)-4-(difluoromethoxy)-3-((7-(4-(2-(2,6-dioxopiperidin-3-yl)-6-fluoro-1-oxoisoindolin-5-yl)piperidin-1-yl)heptyl)oxy)benzamide B61 (28.0 mg) in 26.4% yield. $^1$HNMR (DMSO-$d_6$, 400 MHz) δ 10.99 (s, 1H), 10.66 (s, 1H), 8.76 (s, 2H), 7.72 (d, J=2.0 Hz, 1H), 7.65 (dd, J=1.6, 8.0 Hz, 1H), 7.61 (d, J=6.4 Hz, 1H), 7.46 (d, J=9.2 Hz, 1H), 7.38-7.01 (m, 2H), 5.10 (dd, J=4.8, 12.8 Hz, 1H), 4.32-4.26 (m, 2H), 4.13 (t, J=6.4 Hz, 2H), 2.99-2.96 (m, 2H), 2.94-2.83 (m, 2H), 2.67-2.58 (m, 1H), 2.43-2.36 (m, 1H), 2.36-2.28 (m, 3H), 2.03-1.98 (m, 3H), 1.79-1.72 (m, 6H), 1.48-1.44 (m, 4H), 1.38-1.29 (m, 4H); MS (ESI) m/z: 790.3 [M+H]$^+$.

Example 12

Synthesis of N$^1$-(2-((S)-1-(3-Ethoxy-4-methoxyphenyl)-2-(methylsulfonyl)ethyl)-1,3-dioxoisoindolin-4-yl)-N$^{10}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide B63

B63

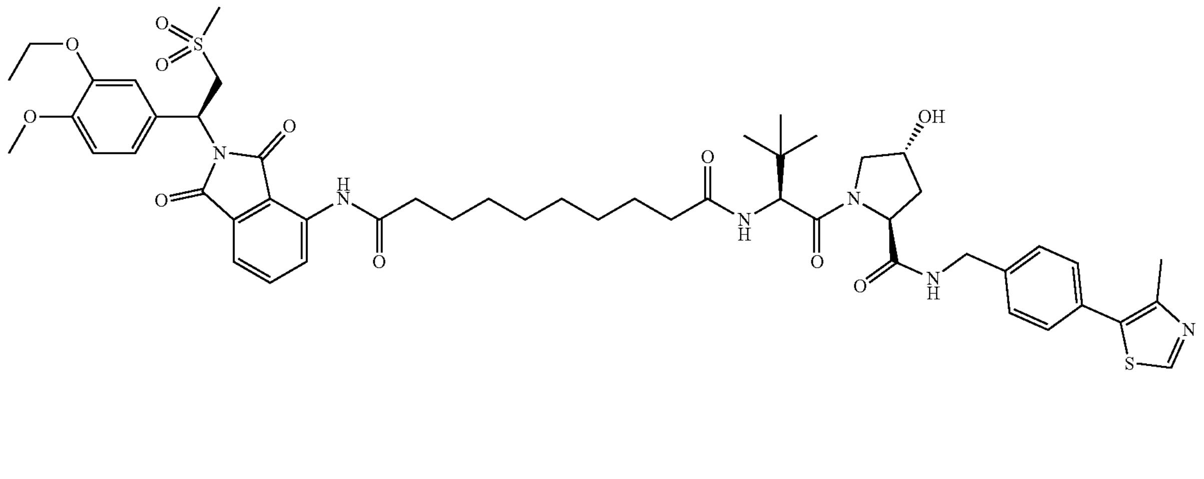

To a stirred solution of 10-(tert-butoxy)-10-oxodecanoic acid (370 mg, 1.43 mmol) in dichloromethane (10 mL) were added oxalyl chloride (182 mg, 1.43 mmol) and 2 drops of N,N-dimethylformamide. The mixture was stirred at 0° C. for 2 h and then concentrated to give tert-butyl 10-chloro-10-oxodecanoate (350 mg, crude).

To a stirred solution of tert-butyl 10-chloro-10-oxodecanoate (1.43 mmol) in tetrahydrofuran (10 mL) was added (S)-4-amino-2-(1-(3-ethoxy-4-methoxyphenyl)-2-(methylsulfonyl)ethyl)isoindoline-1,3-dione (200 mg, 0.47 mmol). The mixture was stirred for 2 days and then concentrated. The residue was purified using silica gel eluting with ethyl acetate in petroleum ether from 20% to 50% to give (S)-tert-butyl 10-((2-(1-(3-ethoxy-4-methoxyphenyl)-2-(methylsulfonyl)ethyl)-1,3-dioxoisoindolin-4-yl)amino)-10-oxodecanoate (207 mg) in 43% yield. MS (ESI) m/z: 659.3 [M+H]$^+$.

To a stirred solution of (S)-tert-butyl 10-((2-(1-(3-ethoxy-4-methoxyphenyl)-2-(methylsulfonyl)ethyl)-1,3-dioxoisoindolin-4-yl)amino)-10-oxodecanoate (100 mg, 0.15 mmol) in dichloromethane (4 mL) was added trifluoroacetic acid (1 mL). The mixture was stirred for 1 h and then concentrated to give (S)-10-((2-(1-(3-ethoxy-4-methoxyphenyl)-2-(methylsulfonyl)ethyl)-1,3-dioxoisoindolin-4-yl) amino)-10-oxodecanoic acid. MS (ESI) m/z: 603.2 [M+H]$^+$.

To a stirred solution of (S)-10-((2-(1-(3-ethoxy-4-methoxyphenyl)-2-(methylsulfonyl)ethyl)-1,3-dioxoisoindolin-4-yl)amino)-10-oxodecanoic acid (91 mg, 0.15 mmol) in N,N-dimethylformamide (3 mL) was added (2S,4R)-1-((S)-2-amino-3,3-dimethylbutanoyl)-4-hydroxy-N-(4-(4-methylthiazol-5-yl)benzyl)pyrrolidine-2-carboxamide (64.5 mg, 0.35 mmol), followed by addition of ethyldiisopropylamine (59 mg, 0.45 mmol), 1-hydroxybenzotriazole (31 mg, 0.22 mmol), and 1-(3-dimethylaminopropyl)-3-ethylcarbodiimide hydrochloride (44 mg, 0.22 mmol). The mixture was stirred overnight and then concentrated. The residue was purified using prep-HPLC to give $N^1$-(2-((S)-1-(3-ethoxy-4-methoxyphenyl)-2-(methylsulfonyl)ethyl)-1,3-dioxoisoindolin-4-yl)-$N^{10}$—((S)-1-((2S,4R)-4-hydroxy-2-((4-(4-methylthiazol-5-yl)benzyl)-carbamoyl)pyrrolidin-1-yl)-3,3-dimethyl-1-oxobutan-2-yl)decanediamide B63 (31.8 mg) in 20% yield. $^1$H NMR (400 MHz, DMSO-$d_6$) δ 9.66 (s, 1H), 8.98 (s, 1H), 8.56 (t, J=6.0 Hz, 1H), 8.46 (d, J=8.4 Hz, 1H), 7.85-7.76 (m, 2H), 7.56 (d, J=7.2 Hz, 1H), 7.43-7.37 (m, 4H), 7.08-7.07 (m, 1H), 6.99-6.92 (m, 2H), 5.77 (dd, J=4.0, 10.4 Hz, 1H), 5.11 (d, J=3.6 Hz, 1H), 4.54 (d, J=9.6 Hz, 1H), 4.46-4.12 (m, 6H), 4.02 (q, J=6.8 Hz, 2H), 3.73 (s, 3H), 3.68-3.62 (m, 2H), 3.01 (s, 3H), 2.47-2.44 (m, 5H), 2.29-2.22 (m, 1H), 2.13-2.10 (m, 1H), 2.02-2.00 (m, 1H), 1.93-1.86 (m, 1H), 1.62-1.44 (m, 4H), 1.33-1.25 (m, 11H), 0.92 (s, 9H); MS (ESI) m/z: 1015.4 [M+H]$^+$.

Example 13

Synthesis of 5-(3-((7-(4-(2-(2,6-Dioxopiperidin-3-yl)-6-fluoro-1-oxoisoindolin-4-yl)piperidin-1-yl) heptyl)oxy)-4-methoxyphenyl)-4H-thieno[2,3-c] pyrrole-4,6(5H)-dione B65

B65

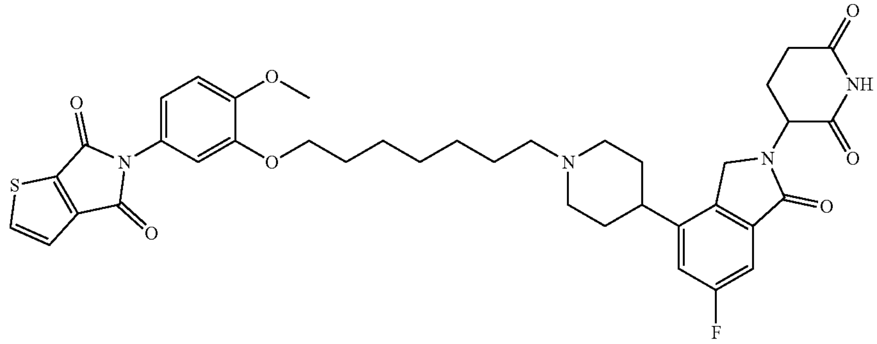

To a solution of methyl 2-methoxy-5-nitrophenol (400 mg, 2.37 mmol) in N,N-dimethylformaine (5 mL) were added 7-iodo-N-methoxyheptanamide (778 mg, 2.60 mmol) and $K_2CO_3$ (654 mg, 4.74 mmol). After stirred at 60° C. for 4 h, the mixture was diluted with $H_2O$ and extracted with ethyl acetate. The combined organic layers were dried over anhydrous $Na_2SO_4$, filtered, and concentrated. The residue was purified using silica gel eluting with ethyl acetate in petroleum ether from 0% to 50% to give N-methoxy-7-(2-methoxy-5-nitrophenoxy)-N-methylheptanamide (800 mg) in 72.1% yield. MS (ESI) m/z: 341.3[M+H]$^+$.

To a solution of N-methoxy-7-(2-methoxy-5-nitrophenoxy)-N-methylheptanamide (190 mg, 0.56 mmol) in tetrahydrofuran (4 mL) at −70° C. under nitrogen was added lithium aluminum hydride (0.8 mL, 1 M in tetrahydrofuran) dropwise. After stirred at this temperature for 1 h, the reaction was quenched with ammonium chloride (5 mL) and the reaction mixture was extracted with ethyl acetate. The combined organic layers were dried over anhydrous sodium sulfate, filtered, and concentrated to give 7-(2-methoxy-5-nitrophenoxy)heptanal (157 mg, crude). MS (ESI) m/z: 282.3 [M+H]$^+$.

To a solution of 3-(6-fluoro-1-oxo-4-(piperidin-4-yl) isoindolin-2-yl)piperidine-2,6-dione (96 mg, crude, 0.28 mmol) in dichloromethane (4 mL) and methanol (1 mL) was added N,N-diisopropylethylamine (35 mg, 0.28 mmol) at 0° C., followed by addition of 7-(2-methoxy-5-nitrophenoxy) heptanal (82 mg, crude, 0.28 mmol), $NaBH_3CN$ (35 mg, 0.56 mmol), and acetic acid (1 drop). The mixture was stirred at room temperature overnight and then concentrated. The residue was purified using silica gel eluting with methanol in dichloromethane from 0% to 10% to give 3-(6-fluoro-4-(1-(7-(2-methoxy-5-nitrophenoxy)heptyl)piperidin-4-yl)-1-oxoisoindolin-2-yl)piperidine-2,6-dione (101 mg) in 65% yield. MS (ESI) m/z: 611.6 [M+H]$^+$.

To a solution of 3-(6-fluoro-4-(1-(7-(2-methoxy-5-nitrophenoxy)heptyl)piperidin-4-yl)-1-oxoisoindolin-2-yl)piperidine-2,6-dione (101 mg, 0.17 mmol) in acetic acid (5 mL)

was added Fe powder (10 mg, 0.50 mmol). After stirred for 1 h, the mixture was filtered and the filtrate was concentrated to give 3-(4-(1-(7-(5-amino-2-methoxyphenoxy)heptyl)piperidin-4-yl)-6-fluoro-1-oxoisoindolin-2-yl)piperidine-2,6-dione (41 mg, crude). MS (ESI) m/z: 581.6 $[M+H]^+$.

To a solution of 3-(4-(1-(7-(5-amino-2-methoxyphenoxy)heptyl)piperidin-4-yl)-6-fluoro-1-oxoisoindolin-2-yl)piperidine-2,6-dione (41 mg, 0.068 mmol) in acetic acid (3 mL) was added thieno[2,3-c]furan-4,6-dione (10 mg, 0.068 mmol). The mixture was stirred at 90° C. overnight and then concentrated. Carbonyl diimidazole ((44 mg, 0.272 mmol) and tetrahydrofuran (4 mL) were added. The mixture was stirred at 75° C. for 2 h and then concentrated. The residue was purified using prep-HPLC to give 5-(3-((7-(4-(2-(2,6-dioxopiperidin-3-yl)-6-fluoro-1-oxoisoindolin-4-yl)piperidin-1-yl)heptyl)oxy)-4-methoxyphenyl)-4H-thieno[2,3-c]pyrrole-4,6(5H)-dione B65. $^1$H NMR (400 MHz, DMSO-$d_6$) δ 11.00 (s, 1H), 8.29 (d, J=4.8 Hz, 1H), 7.55 (d, J=4.8 Hz, 1H), 7.40 (dd, J=2.4, 10.8 Hz, 1H), 7.34 (dd, J=2.0, 7.2 Hz, 1H), 7.06-7.04 (m, 2H), 6.91 (dd, J=2.0 Hz, 8.4 Hz, 1H), 5.13 (dd, J=5.2, 13.2 Hz, 1H), 4.52-4.31 (m, 2H), 3.92 (t, J=6.4 Hz, 2H), 3.80 (s, 3H), 2.97-2.95 (m, 2H), 2.62-2.57 (m, 2H), 2.45-2.41 (m, 1H), 2.28 (t, J=7.2 Hz, 2H), 2.03-1.95 (m, 4H), 1.75-1.68 (m, 6H), 1.47-1.30 (m, 8H); MS (ESI) m/z: 717.3 $[M+H]^+$.

Example 14

Synthesis of (2S,4R)-1-((S)-2-(9-(5-((3,5-Dichloropyridin-4-yl)carbamoyl)-2-(difluoromethoxy)phenoxy)nonanamido)-3,3-dimethylbutanoyl)-4-hydroxy-N-(4-(4-methylthiazol-5-yl)benzyl)pyrrolidine-2-carboxamide B68 drous sodium sulfate, filtered, and concentrated to give 4-(difluoromethoxy)-3-((9-methoxy-9-oxononyl)oxy)benzoic acid (210 mg) in 89% yield. MS (ESI) m/z: 375.2 $[M+H]^+$.

To a solution of 4-(difluoromethoxy)-3-((9-methoxy-9-oxononyl)oxy)benzoic acid (100 mg, 0.27 mmol) in dichloromethane (10 mL) at 0° C. were added oxalyl chloride (51 mg, 0.41 mmol) and N,N-dimethylformamide (1drop). The mixture was stirred at 0° C. for 3 h and then concentrated to give methyl 9-(5-(chlorocarbonyl)-2-(difluoromethoxy)phenoxy)nonanoate (crude).

To a solution of 3,5-dichloropyridin-4-amine (65 mg, 0.41 mmol) in N,N-dimethylformamide (5 mL) at 0° C. was added NaH (21 mg, 0.54 mmol). After the mixture was stirred at this temperature for 30 min, a solution of methyl 9-(5-(chlorocarbonyl)-2-(difluoromethoxy)phenoxy)nonanoate (crude) in N,N-dimethylformamide (5 mL) was added. The reaction was stirred at 0° C. overnight and then quenched with water. The reaction mixture was extracted with ethyl acetate. The combined organic layers were dried over anhydrous sodium sulfate, filtered, and concentrated to give methyl 9-(5-((3,5-dichloropyridin-4-yl)carbamoyl)-2-(difluoromethoxy)phenoxy)nonanoate (50 mg, crude). MS (ESI) m/z: 519.2 $[M+H]^+$.

To a solution of methyl 9-(5-((3,5-dichloropyridin-4-yl)carbamoyl)-2-(difluoromethoxy)phenoxy)nonanoate (50 mg, 0.096 mmol) in tetrahydrofuran (5 mL) and water (5 mL) was added lithium hydroxide monohydrate (7.8 mg, 0.19 mmol). After stirred for 8 h, the mixture was acidified to pH 5 with 2N HCl and extracted with ethyl acetate. The combined organic layers were dried over anhydrous sodium sulfate, filtered, and concentrated to give 9-(5-((3,5-dichloropyridin-4-yl)carbamoyl)-2-(difluoromethoxy)phenoxy)nonanoic acid (37 mg, crude). MS (ESI) m/z: 504.1$[M+H]^+$.

B68

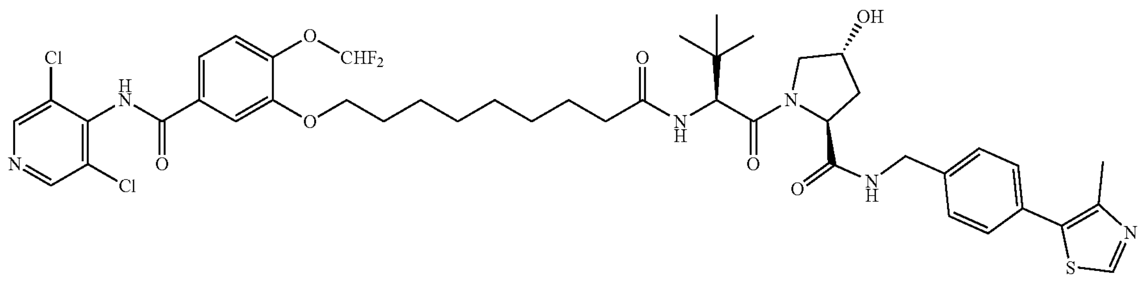

To a solution of 4-(difluoromethoxy)-3-hydroxybenzaldehyde (150 mg, 0.79 mmol) in acetonitrile (10 mL) were added methyl 9-bromononanoate (260 mg, 1.02 mmol) and potassium carbonate (330 mg, 2.3 mmol). After stirred at 80° C. overnight, the reaction was quenched with ammonium chloride (10 mL) and the reaction mixture was extracted with ethyl acetate. The combined organic layers were dried over anhydrous sodium sulfate, filtered, and concentrated to give methyl 9-(2-(difluoromethoxy)-5-formylphenoxy)nonanoate (217 mg, crude). MS (ESI) m/z: 359.1$[M+H]^+$.

To a solution of methyl 9-(2-(difluoromethoxy)-5-formylphenoxy)nonanoate (200 mg, 0.55 mmol) in acetic acid (10 mL) and water (10 mL) at 0° C. were added sulfamic acid (150 mg, 1.66 mmol) and sodium hypochlorite (162 mg, 1.67 mmol). After stirred at 0° C. for 30 min, the mixture was diluted with water and extracted with ethyl acetate. The combined organic layers were dried over anhy- To a solution of 9-(5-((3,5-dichloropyridin-4-yl)carbamoyl)-2-(difluoromethoxy)-phenoxy)nonanoic acid (37 mg, 0.073 mmol) in N,N-dimethylformamide (10 mL) at room temperature were added (2S,4R)-1-((S)-2-amino-3,3-dimethylbutanoyl)-4-hydroxy-N-(4-(4-methylthiazol-5-yl)benzyl)pyrrolidine-2-carboxamide (34.2 mg, 0.073 mmol), N,N-diisopropylethylamine (28.3 mg, 0.219 mmol), HOBt (19.7 mg, 0.146 mmol), and EDCI·HCl (28.1 mg, 0.146 mmol). After stirred overnight, the mixture was diluted with $H_2O$ and extracted with ethyl acetate. The combined organic layers were dried over anhydrous sodium sulfate, filtered, and concentrated. The residue was purified using prep-HPLC to give (2S,4R)-1-((S)-2-(9-(5-((3,5-dichloropyridin-4-yl)carbamoyl)-2-(difluoromethoxy)phenoxy)nonanamido)-3,3-dimethylbutanoyl)-4-hydroxy-N-(4-(4-methylthiazol-5-yl)benzyl)pyrrolidine-2-carboxamide B68 (12 mg). $^1$H NMR (400 MHz, DMSO-$d_6$) δ 10.66 (s, 1H), 8.98 (s, 1H), 8.76 (s 2H), 8.56 (t, J=5.2 Hz, 1H), 7.84 (d, J=9.2 Hz, 1H), 7.71 (s, 1H), 7.65 (d, J=7.6 Hz, 1H), 7.42-7.36 (m, 5H), 7.18 (t, J=74.0 Hz, 1H), 5.13 (d, J=3.6 Hz, 1H), 4.53 (d, J=9.6 Hz, 1H), 4.46-4.40 (m, 2H), 4.34 (s, 1H), 4.24-4.19 (m, 1H), 4.11 (t, J=6.0 Hz, 2H), 3.68-3.62 (m, 2H), 2.44 (s, 3H), 2.29-2.22 (m, 1H), 2.14-2.08 (m, 1H), 2.05-1.99 (m, 1H), 1.92-1.86 (m, 1H), 1.78-1.73 (m, 2H), 1.53-1.43 (m, 4H), 1.29-1.23 (m, 6H), 0.92 (s, 9H); MS (ESI) m/z: 917.3[M+H]$^+$.

Example 15

Synthesis of N-(6-(3-(4-(2-(2,6-Dioxopiperidin-3-yl)-6-fluoro-1-oxoisoindolin-4-yl)piperidin-1-yl)propyl)-2-((S)-1-(3-ethoxy-4-methoxyphenyl)-2-(methylsulfonyl)ethyl)-1,3-dioxoisoindolin-4-yl)acetamide B69

B69

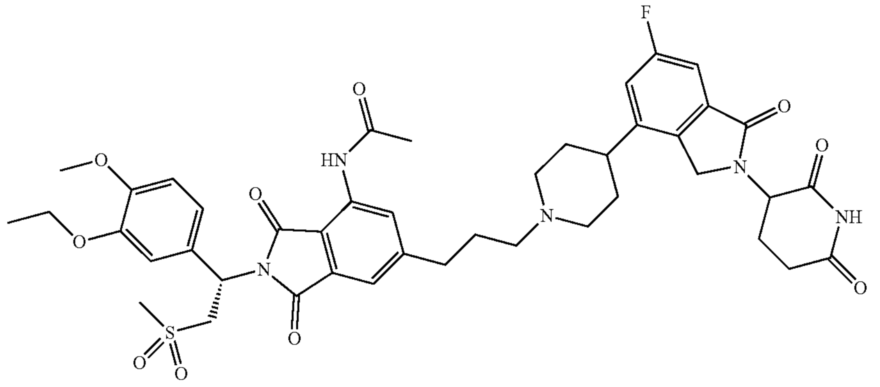

To a solution of (S)—N-(2-(1-(3-ethoxy-4-methoxyphenyl)-2-(methylsulfonyl)ethyl)-6-iodo-1,3-dioxoisoindolin-4-yl)acetamide (100 mg, 0.17 mmol) and 3-(6-fluoro-1-oxo-4-(1-(prop-2-yn-1-yl)piperidin-4-yl)isoindolin-2-yl)piperidine-2,6-dione (130 mg, 0.34 mmol) in 5 mL of THF were added $Pd(PPh_3)_2Cl_2$ (24 mg, 0.034 mmol), CuI (6.5 mg, 0.034 mmol), and triethylamine (52 mg, 0.51 mmol) under $N_2$. After stirred at 70° C. for 3 h, the mixture was concentrated and purified using prep-TLC eluting with ethyl acetate to afford N-(6-(3-(4-(2-(2,6-dioxopiperidin-3-yl)-6-fluoro-1-oxoisoindolin-4-yl)piperidin-1-yl)prop-1-yn-1-yl)-2-((S)-1-(3-ethoxy-4-methoxyphenyl)-2-(methylsulfonyl)ethyl)-1,3-dioxoisoindolin-4-yl)acetamide (95 mg) in 66% yield. MS (ESI) m/z: 842.2 [M+H]$^+$.

To a mixture of N-(6-(3-(4-(2-(2,6-dioxopiperidin-3-yl)-6-fluoro-1-oxoisoindolin-4-yl)piperidin-1-yl)prop-1-yn-1-yl)-2-((S)-1-(3-ethoxy-4-methoxyphenyl)-2-(methylsulfonyl)ethyl)-1,3-dioxoisoindolin-4-yl)acetamide (95 mg, 0.11 mmol) in 2 mL of THF was added Pd/C (10 mg). After stirred under $H_2$ for 48 h, the mixture was filtered and washed with ethyl acetate. The filtrate was concentrated and the residue purified using prep-HPLC to afford N-(6-(3-(4-(2-(2,6-dioxopiperidin-3-yl)-6-fluoro-1-oxoisoindolin-4-yl)piperidin-1-yl)propyl)-2-((S)-1-(3-ethoxy-4-methoxyphenyl)-2-(methylsulfonyl)ethyl)-1,3-dioxoisoindolin-4-yl)acetamide B69 (31 mg) in 32% yield. $^1H$ NMR (400 MHz, DMSO-$d_6$) δ 11.01 (s, 1H), 9.64 (s, 1H), 8.28 (s, 1H), 7.47 (s, 1H), 7.40 (dd, J=2.0, 11.2 Hz, 1H), 7.34 (dd, J=2.0, 7.2 Hz, 1H), 7.06 (s, 1H), 6.98-6.90 (m, 2H), 5.75 (dd, J=4.4, 10.4 Hz, 1H), 5.13 (dd, J=4.8, 13.2 Hz, 1H), 4.52-4.33 (m, 3H), 4.15-4.09 (m, 1H), 4.01 (q, J=6.8 Hz, 2H), 3.73 (s, 3H), 3.01 (s, 3H), 2.96-2.89 (m, 3H), 2.76-2.65 (m, 2H), 2.64-2.54 (m, 2H), 2.46-2.39 (m, 1H), 2.29-2.21 (m, 2H), 2.18 (s, 3H), 2.06-1.86 (m, 3H), 1.78-1.64 (m, 4H), 1.63-1.52 (m, 2H), 1.32 (t, J=6.8 Hz, 3H)); MS (ESI) m/z: 846.1 [M+H]$^+$.

Example 16

Synthesis of 12-((2-(2,6-Dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)dodecanamide B71

B71

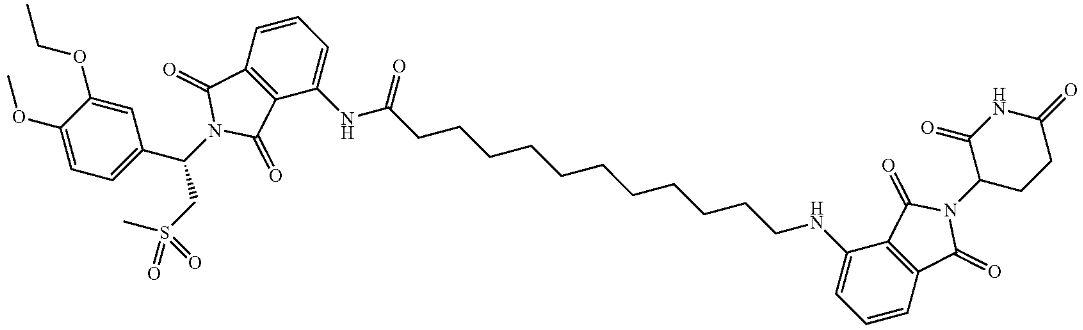

To a stirred solution of 12-aminododecanoic acid (1 g, 4.65 mmol) in 2N sodium hydroxide (15 mL) at 0° C. was added benzyl chloroformate (951 mg, 5.58 mmol) in 2N sodium hydroxide (15 mL). After stirred at 0° C. for 2 h, the mixture was diluted with $H_2O$ and extracted with methyl tert-butyl ether. The aqueous layer was acidified to pH 3-4 with 1N hydrochloric acid and extracted with methyl tert-butyl ether. The organic layers were combined, dried over anhydrous sodium sulfate, filtered, and concentrated to give 12-(((benzyloxy)carbonyl)-amino)dodecanoic acid (700 mg) in 43% yield. MS (ESI) m/z: 350.2 $[M+H]^+$.

To a stirred solution of 12-(((benzyloxy)carbonyl)amino) dodecanoic acid (700 mg, 2 mmol) in toluene (7 mL) was added thionyl chloride (1.19 g, 10 mmol). The mixture was stirred at 100° C. for 2 h and then concentrated to give benzyl (12-chloro-12-oxododecyl)carbamate (1.2 g, crude).

To a stirred solution of benzyl (12-chloro-12-oxododecyl) carbamate (1.2 g, 2 mmol) in tetrahydrofuran (4 mL) were added (S)-4-amino-2-(1-(3-ethoxy-4-methoxyphenyl)-2-(methylsulfonyl)ethyl)isoindoline-1,3-dione (418 mg, 1 mmol) and triethylamine (4 mL). The mixture was stirred for 3 days and then concentrated. The residue was purified using silica gel eluting with ethyl acetate in petroleum ether from 0 to 50% to give (S)-benzyl (12-((2-(1-(3-ethoxy-4-methoxyphenyl)-2-(methylsulfonyl)ethyl)-1,3-dioxoisoindolin-4-yl)amino)-12-oxododecyl)-carbamate (441 mg) in 59% yield. MS (ESI) m/z: 750.2 $[M+H]^+$.

To a stirred solution of (S)-benzyl (12-((2-(1-(3-ethoxy-4-methoxyphenyl)-2-(methylsulfonyl)ethyl)-1,3-dioxoisoindolin-4-yl)amino)-12-oxododecyl)carbamate (441 mg, 0.59 mmol) in methanol (9 mL) and dichloromethane (1 mL) was added Pd/C (200 mg). After stirred overnight under hydrogen, the mixture was filtered and the filtrate was concentrated to give (S)-12-amino-N-(2-(1-(3-ethoxy-4-methoxyphenyl)-2-(methylsulfonyl)ethyl)-1,3-dioxoisoindolin-4-yl)dodecanamide (350 mg) in 96% yield. MS (ESI) m/z: 616.2 $[M+H]^+$.

To a stirred solution of (S)-12-amino-N-(2-(1-(3-ethoxy-4-methoxyphenyl)-2-(methylsulfonyl)ethyl)-1,3-dioxoisoindolin-4-yl)dodecanamide (180 mg, 0.29 mmol) in N,N-dimethylformamide (3 mL) were added 2-(2,6-dioxopiperidin-3-yl)-4-fluoroisoindoline-1,3-dione (96 mg, 0.35 mmol) and N,N-diisopropylethylamine (112 mg, 0.87 mmol). After stirred at 150° C. for 1 h under microwave, the mixture was diluted with water and extracted with ethyl acetate. The combined organic layers were dried over anhydrous sodium sulfate, filtered, and concentrated. The residue was purified using prep-TLC eluting with petroleum ether/ethyl acetate (1:2) and further purified using prep-HPLC to give 12-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)dodecanamide B71 (27.3 mg). $^1H$ NMR (400 MHz, DMSO-$d_6$) δ 11.11 (s, 1H), 9.66 (s, 1H), 8.48 (d, J=8.4 Hz, 1H), 7.79 (t, J=7.6 Hz, 1H), 7.59-7.55 (m, 2H), 7.10-7.06 (m, 2H), 7.03-6.99 (m, 2H), 6.94 (d, J=8.0 Hz, 1H), 6.51 (t, J=5.2 Hz, 1H), 5.80 (dd, J=3.6, 10.0 Hz, 1H), 5.06 (dd, J=5.2, 12.8 Hz, 1H), 4.39-4.34 (m, 1H), 4.16 (dd, J=3.6, 14.4 Hz, 1H), 4.01 (q, J=6.8 Hz, 2H), 3.74 (s, 3H), 3.29-3.26 (m, 2H), 3.03 (s, 3H), 2.93-2.86 (m, 1H), 2.63-2.55 (m, 2H), 2.48-2.45 (m, 2H), 2.08-2.02 (m, 1H), 1.63-1.54 (m, 4H), 1.35-1.25 (m, 17H); MS (ESI) m/z: 872.4 $[M+H]^+$.

Example 17

Synthesis of 9-(4-(2-(2,6-Dioxopiperidin-3-yl)-6-fluoro-1-oxoisoindolin-5-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B75

B75

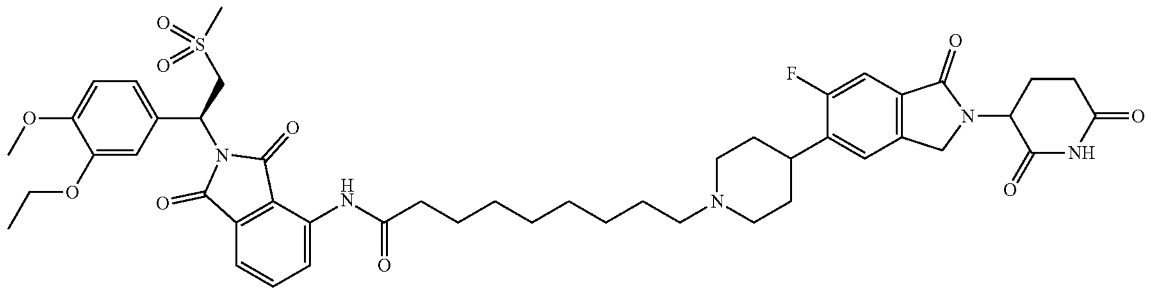

To a solution of 9-methoxy-9-oxononanoic acid (800 mg, 3.95 mmol) in dichloromethane (15 mL) was added oxalyl chloride (753 mg, 5.93 mmol), followed by addition DMF (1 drop). The mixture was stirred for 2 h and then concentrated to give methyl 9-chloro-9-oxononanoate (869 mg, crude).

To a solution of (S)-4-amino-2-(1-(3-ethoxy-4-methoxyphenyl)-2-(methylsulfonyl)-ethyl)isoindoline-1,3-dione (823 mg, 1.97 mmol) in pyridine (10 mL) at 0° C. was added methyl 9-chloro-9-oxononanoate (869 mg, 3.95 mmol, crude). The mixture was stirred at room temperature overnight and then concentrated. The residue was purified using silica gel eluting with ethyl acetate in petroleum ether from 10% to 50% to give (S)-methyl 9-((2-(1-(3-ethoxy-4-methoxyphenyl)-2-(methylsulfonyl)ethyl)-1,3-dioxoisoindolin-4-yl)amino)-9-oxononanoate (659 mg) in 56% yield. MS (ESI) m/z: 603.2 $[M+H]^+$.

To a solution of (S)-methyl 9-((2-(1-(3-ethoxy-4-methoxyphenyl)-2-(methylsulfonyl)-ethyl)-1,3-dioxoisoindolin-4-yl)amino)-9-oxononanoate (659 mg, 1.09 mmol) in toluene (15 mL) at −70° C. under $N_2$ was added DIBAL-H (2.19 mL, 1 M in THF). After stirred at this temperature for 30 min, the reaction was quenched with sat. $NH_4Cl$ (5 mL) and the reaction mixture was extracted with ethyl acetate. The combined organic layers were dried over anhydrous $Na_2SO_4$, filtered, and concentrated to give (S)—N-(2-(1-(3-ethoxy-4-methoxyphenyl)-2-(methylsulfonyl)ethyl)-1,3-dioxoisoindolin-4-yl)-9-oxononanamide (218 mg) in 35% yield. MS (ESI) m/z: 573.2$[M+H]^+$.

To a solution of (S)—N-(2-(1-(3-ethoxy-4-methoxyphenyl)-2-(methylsulfonyl)ethyl)-1,3-dioxoisoindolin-4-yl)-9-oxononanamide (218 mg, 0.13 mmol) in dichloromethane/methanol (8 mL/2 mL) were added 3-(6-fluoro-1-oxo-5-(piperidin-4-yl)isoindolin-2-yl)piperidine-2,6-dione (62 mg, 0.18 mmol) and N,N-diisopropylethylamine (23 mg, 0.18 mmol), followed by addition of $NaBH_3CN$ (16 mg, 0.266 mmol). The mixture was stirred overnight and then concentrated. The residue was purified using silica gel eluting with methanol in dichloromethane from 0% to 10% and further purified using prep-HPLC to give 9-(4-(2-(2,6-dioxopiperidin-3-yl)-6-fluoro-1-oxoisoindolin-5-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B75 (43.4 mg) in 36% yield. $^1H$ NMR (400 MHz, DMSO-$d_6$) δ 10.99 (s, 1H), 9.67 (s, 1H), 8.46 (d, J=8.4 Hz, 1H), 7.78 (t, J=8.0 Hz, 1H), 7.59 (d, J=5.6 Hz, 1H), 7.56 (d, J=7.6 Hz, 1H), 7.46 (d, J=8.8 Hz, 1H), 7.08 (d, J=1.6 Hz, 1H), 6.99-6.92 (m, 2H), 5.77 (dd, J=4.4, 10.4 Hz, 1H), 5.11 (dd, J=4.8, 13.2 Hz, 1H), 4.43-4.26 (m, 3H), 4.15 (dd, J=4.4, 14.4 Hz, 1H), 4.02 (q, J=6.8 Hz, 2H), 3.73 (s, 3H), 3.01 (s, 3H), 2.97-2.84 (m, 4H), 2.61-2.57 (m, 1H), 2.47-2.45 (m, 2H), 2.41-2.36 (m, 1H), 2.27 (t, J=6.8 Hz, 2H), 2.01-1.90 (m, 3H), 1.71-1.61 (m, 6H), 1.44-1.41 (m, 2H), 1.34-1.30 (m, 12H); MS (ESI) m/z: 902.4 $[M+H]^+$.

Example 18

Synthesis of (2S,4R)-1-((S)-2-(11-(5-((3,5-Dichloropyridin-4-yl)carbamoyl)-2-(difluoromethoxy)phenoxy)undecanamido)-3,3-dimethylbutanoyl)-4-hydroxy-N-(4-(4-methylthiazol-5-yl)benzyl)pyrrolidine-2-carboxamide B76

B76

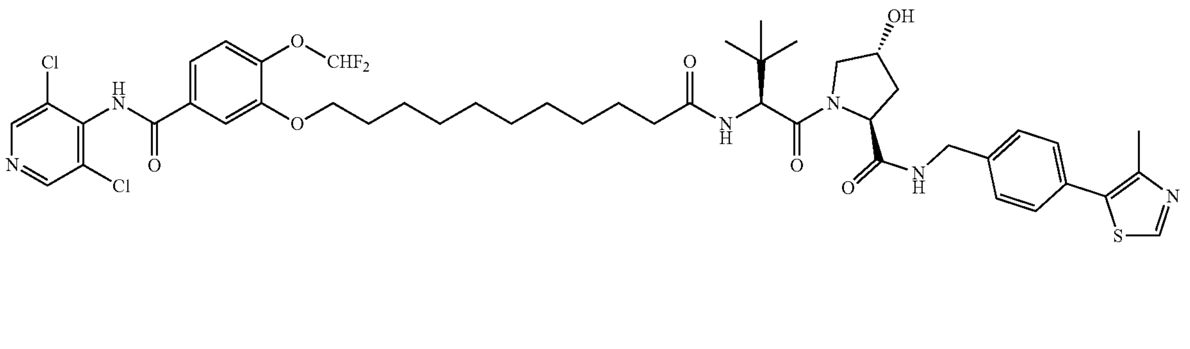

A solution of 3-(benzyloxy)-N-(3,5-dichloropyridin-4-yl)-4-(difluoromethoxy)-benzamide (120 mg, 0.274 mmol) in trifluoroacetic acid (6 mL) was heated at 80° C. for 1 h and then concentrated to give N-(3,5-dichloropyridin-4-yl)-4-(difluoromethoxy)-3-hydroxybenzamide (crude). MS (ESI) m/z: 349.0 $[M+H]^+$.

To a solution of N-(3,5-dichloropyridin-4-yl)-4-(difluoromethoxy)-3-hydroxybenzamide (95 mg, 0.273 mmol) in acetonitrile (6 mL) were added potassium carbonate (113 mg, 0.819 mmol) and tert-butyl 11-bromoundecanoate (96 mg, 0.30 mmol). After heated at 80° C. overnight, the mixture was diluted with water and extracted with ethyl acetate. The combined organic layers were concentrated. The residue was purified using silica gel eluting with ethyl acetate in petroleum from 0% to 20% to give tert-butyl 11-(5-((3,5-dichloropyridin-4-yl)carbamoyl)-2-(difluoromethoxy)phenoxy)undecanoate (86 mg) in 54% yield. MS (ESI) m/z: 533.2 $[M-56+H]^+$.

To a solution of tert-butyl 11-(5-((3,5-dichloropyridin-4-yl)carbamoyl)-2-(difluoromethoxy)phenoxy)undecanoate (86 mg, 0.146 mmol) in dichloromethane (6 mL) was trifluoroacetic acid (2 mL). The mixture was stirred for 12 h and then concentrated to give 11-(5-((3,5-dichloropyridin-4-yl)carbamoyl)-2-(difluoromethoxy)phenoxy)undecanoic acid (70 mg, crude). MS (ESI) m/z: 533.2 $[M+H]^+$.

To a solution of 11-(5-((3,5-dichloropyridin-4-yl)carbamoyl)-2-(difluoromethoxy)-phenoxy)undecanoic acid (77.8 mg, 0.146 mmol) in N,N-dimethylformamide (6 mL) were added ethyldiisopropylamine (57 mg, 0.438 mmol), (2S,4R)-1-((S)-2-amino-3,3-dimethylbutanoyl)-4-hydroxy-N-(4-(4-methylthiazol-5-yl)benzyl)pyrrolidine-2-carboxamide (68 mg, 0.146 mmol), 1-hydroxybenzotriazole (30 mg, 0.219 mmol), and 1-(3-dimethylaminopropyl)-3-ethylcarbodiimide hydrochloride (42 mg, 0.219 mmol). The mixture was stirred overnight and then concentrated. The residue was purified using prep-TLC eluting with dichloromethane/methanol (15:1) and further purified using prep-HPLC to give (2S,4R)-1-((S)-2-(11-(5-((3,5-dichloropyridin-4-yl)carbamoyl)-2-(difluoromethoxy)phenoxy)undecanamido)-3,3-dimethylbutanoyl)-4-hydroxy-N-(4-(4-methyl-thiazol-5-yl)benzyl)pyrrolidine-2-carboxamide B76 (30.3 mg) in 22% yield. $^1$H NMR (400 MHz, DMSO-$d_6$) δ 10.64 (s, 1H), 8.97 (s, 1H), 8.76 (s, 2H), 8.54 (t, J=5.6 Hz, 1H), 7.83 (d, J=10.0 Hz, 1H), 7.72 (s, 1H), 7.66 (d, J=8.0 Hz, 1H), 7.42-6.99 (m, 6H), 5.11 (d, J=3.6 Hz, 1H), 4.54 (d, J=8.8 Hz, 1H), 4.52-4.12 (m, 4H), 4.11 (t, J=6.4 Hz, 2H), 3.65 (s, 2H), 2.44 (s, 3H), 2.27-2.23 (m, 1H), 2.13-1.89 (m, 3H), 1.77-1.74 (m, 2H), 1.47-1.41 (m, 4H), 1.25-1.23 (m, 10H), 0.92 (s, 9H); MS (ESI) m/z: 945.1 $[½M+H]^+$, 473.3 $[½M+H]^+$.

Example 19

Synthesis of 5-((4-((5-(2,6-Dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)pentanamide B78

B78

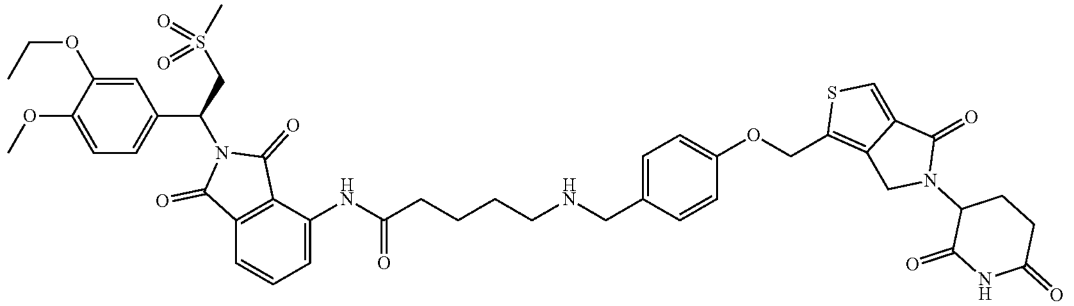

To a stirred solution of 5-bromopentanoic acid (300 mg, 1.66 mmol) in toluene (6 mL) was added thionyl chloride (988 mg, 8.3 mmol). The mixture was stirred at 100° C. for 2 h and then concentrated to give 5-bromopentanoyl chloride (320 mg, crude).

To a stirred solution of 5-bromopentanoyl chloride (1.66 mmol, crude) in tetrahydrofuran (10 mL) was added (S)-4-amino-2-(1-(3-ethoxy-4-methoxyphenyl)-2-(methylsulfonyl)ethyl)isoindoline-1,3-dione (150 mg, 0.36 mmol). The mixture was stirred overnight and then concentrated. The residue was purified using prep-TLC eluting with petroleum/ethyl acetate (1:1) to give (S)-5-bromo-N-(2-(1-(3-ethoxy-4-methoxyphenyl)-2-(methylsulfonyl)ethyl)-1,3-dioxoisoindolin-4-yl)pentanamide (200 mg) in 96% yield. MS (ESI) m/z: 581.2 $[M+H]^+$, 598.2 $[M+NH_4]^+$.

To a stirred solution of (S)-5-bromo-N-(2-(1-(3-ethoxy-4-methoxyphenyl)-2-(methylsulfonyl)ethyl)-1,3-dioxoisoindolin-4-yl)pentanamide (200 mg, 0.34 mmol) in N,N-dimethylformamide (4 mL) were added sodium azide (45 mg, 0.68 mmol) and potassium iodide (6 mg, 0.034 mmol). After stirred at 55° C. overnight, the reaction was quenched with water and the reaction mixture was extracted with ethyl acetate. The combined organic layers were washed with brine, dried over anhydrous sodium sulfate, filtered, and concentrated to give (S)-5-azido-N-(2-(1-(3-ethoxy-4-methoxyphenyl)-2-(methylsulfonyl)ethyl)-1,3-dioxoisoindolin-4-yl)pentanamide (120 mg, crude). MS (ESI) m/z: 561.2 $[M+NH_4]^+$.

To a stirred solution of (S)-5-azido-N-(2-(1-(3-ethoxy-4-methoxyphenyl)-2-(methylsulfonyl)ethyl)-1,3-dioxoisoindolin-4-yl)pentanamide (0.34 mmol, crude) in tetrahydrofuran (10 mL) and water (0.5 mL) was added triphenylphosphine (135 mg, 0.52 mmol). The mixture was stirred overnight and then concentrated. The residue was purified using prep-TLC eluting with dichloromethane/methanol (10:1) to give (S)-5-amino-N-(2-(1-(3-ethoxy-4-methoxyphenyl)-2-(methylsulfonyl)ethyl)-1,3-dioxoisoindolin-4-yl)pentanamide (70 mg) in 39% yield. MS (ESI) m/z: 518.2 $[M+H]^+$.

To a stirred solution of (S)-5-amino-N-(2-(1-(3-ethoxy-4-methoxyphenyl)-2-(methylsulfonyl)ethyl)-1,3-dioxoisoindolin-4-yl)pentanamide (70 mg, 0.135 mmol) and 4-((5-

(2,6-dioxopiperidin-3-yl)-4-oxo-5,6-dihydro-4H-thieno[3,4-c]pyrrol-1-yl)methoxy)benzaldehyde (52 mg, 0.135 mmol) in dichloromethane (4 mL) and methanol (1 mL) were added sodium cyanoborohydride (26 mg, 0.41 mmol) and acetic acid (1 drop). The mixture was stirred overnight and then concentrated. The residue was purified using prep-HPLC to give 5-((4-((5-(2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)pentanamide B78 (49.9 mg) in 42% yield. $^1$H NMR (400 MHz, DMSO-$d_6$) δ 9.67 (s, 1H), 8.46 (d, J=8.4 Hz, 1H), 8.00 (s, 1H), 7.79 (t, J=8.0 Hz, 1H), 7.56 (d, J=7.2 Hz, 1H), 7.25 (d, J=8.4 Hz, 2H), 7.07 (s, 1H), 6.98-6.91 (m, 4H), 5.77 (dd, J=4.0, 10.4 Hz, 1H), 5.27 (s, 2H), 5.01 (dd, J=4.8, 13.2 Hz, 1H), 4.36-4.31 (m, 2H), 4.24-4.11 (m, 2H), 4.01 (q, J=6.8 Hz, 2H), 3.72 (s, 3H), 3.64 (s, 2H), 3.18 (s, 3H), 2.89-2.83 (m, 1H), 2.60-2.53 (m, 3H), 2.46 (t, J=7.2 Hz, 2H), 2.35-2.31 (m, 1H), 2.01-1.96 (m, 1H), 1.66-1.61 (m, 2H), 1.52-1.47 (m, 2H), 1.31 (t, J=7.2 Hz, 3H); MS (ESI) m/z: 886.3 [M+H]$^+$.

Example 20

Synthesis of N-(6-(7-(1-(2-(2,6-Dioxopiperidin-3-yl)-1,3-dioxoisoindolin-4-yl)piperidin-4-yl)heptyl)-2-((S)-1-(3-ethoxy-4-methoxyphenyl)-2-(methylsulfonyl)ethyl)-1,3-dioxoisoindolin-4-yl)acetamide B88 and then quenched with sat. $NH_4Cl$ (aq.)(100 mL). The reaction mixture was extracted with ethyl acetate. The combined organic layers were dried over anhydrous sodium sulfate, filtered, and concentrated. The residue was purified using silica gel eluting with petroleum ether/ethyl acetate (20:1) to give 4-(6-((tetrahydro-2H-pyran-2-yl)oxy)hexyl)pyridine (9.5 g) in 82% yield. MS (ESI) m/z: 264.2 [M+H]$^+$.

To a stirred solution of 4-(6-((tetrahydro-2H-pyran-2-yl)oxy)hexyl)pyridine (9.5 g, 36.1 mmol) in ethyl acetate (100 mL) was added HCl/EtOAc (20 mL). The mixture was stirred overnight and then filtered. The filter cake was washed with ethyl acetate. The solid was dried under vacuum to give 6-(pyridin-4-yl)hexan-1-ol hydrochloride (6.0 g) in 78% yield. MS (ESI) m/z: 180.2 [M+H]$^+$.

To a stirred solution of 6-(pyridin-4-yl)hexan-1-ol hydrochloride (6.0 g, 27.78 mmol) in ethanol (180 mL) was added platinum dioxide (600 mg) under nitrogen. The mixture was degassed and backfilled with hydrogen. The mixture was stirred overnight under nitrogen and then filtered. The filtrate was concentrated to give 6-(piperidin-4-yl)hexan-1-ol hydrochloride (6.2 g) in a quantitative yield. MS (ESI) m/z: 186.2 [M+H]$^+$.

To a stirred solution of 6-(piperidin-4-yl)hexan-1-ol hydrochloride (6.2 g, 27.9 mmol) in tetrahydrofuran/water (1:1 80 mL) were added triethylamine (5.6 g, 55.9 mmol) and di-tert-butyl dicarbonate (9.1 g, 41.9 mmol). The mixture was stirred for 3 h and then extracted with ethyl acetate. The combined organic layers were dried over anhydrous $Na_2SO_4$, filtered, and concentrated. The residue was purified

B88

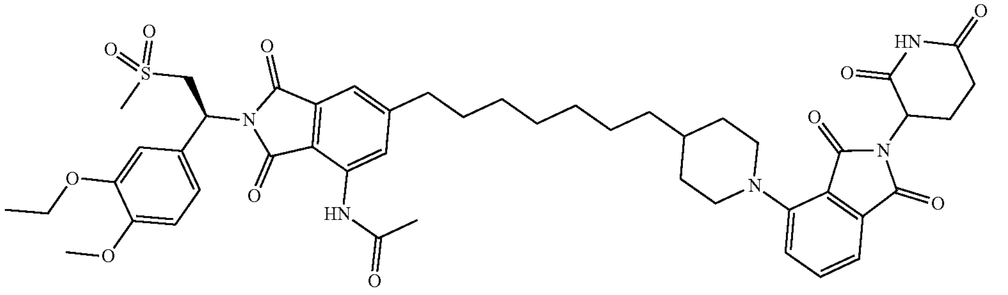

To a stirred solution of 5-bromopentan-1-ol (10.0 g, 59.88 mmol) in dichloromethane (100 mL) were added p-toluenesulfonic acid (1.5 g, 5.99 mmol) and a solution of 3,4-dihydro-2H-pyran (7.5 g, 89.82 mmol) in tetrahydrofuran (50 mL) at 0° C. After stirred at room temperature overnight, the mixture was diluted with water and extracted with dichloromethane. The combined organic layers were dried over anhydrous sodium sulfate, filtered, and concentrated. The residue was purified using silica gel eluting with petroleum ether/ethyl acetate (100:1) to give 2-((5-bromopentyl)oxy)tetrahydro-2H-pyran (11.0 g) in 73% yield. $^1$H NMR (400 MHz, $CDCl_3$) δ 5.30 (s, 1H), 4.96-4.94 (m, 2H), 3.90-3.85 (m, 2H), 3.55-3.49 (m, 2H), 1.89-1.73 (m, 5H), 1.64-1.48 (m, 8H).

To a stirred solution of 4-methylpyridine (6.2 g, 66.0 mmol) in tetrahydrofuran (100 mL) was added 2.5M n-BuLi in tetrahydrofuran (31.7 mL, 79.2 mmol) at −60° C. dropwise. The mixture was stirred at room temperature for 1.5 hours. 2-((5-Bromopentyl)oxy)tetrahydro-2H-pyran (11.0 g, 44.0 mmol) in tetrahydrofuran (50 mL) was added at −60° C. The reaction was stirred at room temperature overnight using silica gel eluting with petroleum ether/ethyl acetate (20:1) to give tert-butyl 4-(6-hydroxyhexyl)piperidine-1-carboxylate (7.2 g) in 90% yield. $^1$H NMR (400 MHz, $CDCl_3$) δ 4.02 (s, 2H), 3.60 (t, J=6.4 Hz, 2H), 2.63 (t, J=12.0 Hz, 2H), 1.77 (s, 1H), 1.62-1.49 (m, 4H), 1.42 (s, 9H), 1.36-1.16 (m, 8H), 1.07-0.98 (m, 2H).

To a stirred solution of tert-butyl 4-(6-hydroxyhexyl)piperidine-1-carboxylate (2 g, 7.02 mmol) in dichloromethane (40 mL) was added Dess-Matin reagent (3.57 g, 8.42 mmol). After stirred for 3 h, the mixture was filtered and washed with dichloromethane. The filtrate was concentrated and the residue was purified using silica gel eluting with methanol in dichloromethane from 0% to 10% to give tert-butyl 4-(6-oxohexyl)piperidine-1-carboxylate (1.6 g) in 81% yield. $^1$H NMR (400 MHz, $CDCl_3$) δ 9.80 (s, 1H), 4.10 (s, 2H), 2.70 (t, J=16.4 Hz, 2H), 2.46 (t, J=9.6 Hz, 2H), 1.69-1.64 (m, 4H), 1.49 (s, 9H), 1.36-1.25 (m, 7H), 1.16-1.07 (m, 2H).

To a stirred solution of tert-butyl 4-(6-oxohexyl)piperidine-1-carboxylate (1.6 g, 5.65 mmol) and potassium carbonate (1.56 g, 11.31 mmol) in methanol (30 mL) was added dimethyl (1-diazo-2-oxopropyl)phosphonate (1.14 g, 5.94 mmol). The mixture was stirred overnight and then diluted with water (50 mL). The organic solvent was removed under vacuum. The aqueous phase was extracted with petroleum ether. The combined organic layers were dried over anhydrous $Na_2SO_4$, filtered, and concentrated to give tert-butyl 4-(hept-6-yn-1-yl)piperidine-1-carboxylate (1.2 g) in 76% yield. $^1$H NMR (400 MHz, $CDCl_3$) δ 4.10 (s, 2H), 2.70-2.63 (m, 2H), 2.18 (m, 2H), 1.94 (t, J=2.4 Hz, 1H), 1.65-1.49 (m, 5H), 1.46 (s, 9H), 1.42-1.21 (m, 6H), 1.11-1.04 (m, 2H).

To a stirred solution of (S)—N-(2-(1-(3-ethoxy-4-methoxyphenyl)-2-(methylsulfonyl)ethyl)-6-iodo-1,3-dioxoisoindolin-4-yl)acetamide (1 g, crude), tert-butyl 4-(hept-6-yn-1-yl)piperidine-1-carboxylate (953 mg, 3.41 mmol), and triethylamine (517 mg, 5.12 mmol) in tetrahydrofuran (15 mL) were added cuprous iodide (65 mg, 0.341 mmol) and $Pd(PPh_3)Cl_2$ (240 mg, 0.34 mmol) under nitrogen. The mixture was degassed and backfilled with nitrogen. After stirred at 70° C. for 4 h, the mixture was diluted with water and extracted with ethyl acetate. The combined organic layers were dried over anhydrous $Na_2SO_4$, filtered, and concentrated. The residue was purified using silica gel eluting with PE/EtOAc (5:1) to give (S)-tert-butyl 4-(7-(7-acetamido-2-(1-(3-ethoxy-4-methoxyphenyl)-2-(methylsulfonyl)ethyl)-1,3-dioxoisoindolin-5-yl)hept-6-yn-1-yl)piperidine-1-carboxylate (520 mg). MS (ESI) m/z: 638.3 $[M+H]^+$.

To a stirred solution of (S)-tert-butyl 4-(7-(7-acetamido-2-(1-(3-ethoxy-4-methoxyphenyl)-2-(methylsulfonyl)ethyl)-1,3-dioxoisoindolin-5-yl)hept-6-yn-1-yl)piperidine-1-carboxylate (520 mg, 0.706 mmol) in MeOH (20 mL) was added Pd/C (100 mg) under nitrogen. The mixture was degassed and backfilled with hydrogen. The mixture was stirred overnight and then filtered. The filtrate was concentrated to give (S)-tert-butyl 4-(7-(7-acetamido-2-(1-(3-ethoxy-4-methoxyphenyl)-2-(methylsulfonyl)ethyl)-1,3-dioxoisoindolin-5-yl)heptyl)piperidine-1-carboxylate (470 mg) in 83% yield. MS (ESI) m/z: 642.4 $[M+H]^+$.

To a stirred solution of (S)-tert-butyl 4-(7-(7-acetamido-2-(1-(3-ethoxy-4-methoxyphenyl)-2-(methylsulfonyl)ethyl)-1,3-dioxoisoindolin-5-yl)heptyl)piperidine-1-carboxylate (50 mg, 0.068 mmol) in dichloromethane (1.5 mL) was added trifluoroacetic acid (0.5 mL). The mixture was stirred for 1 h and then concentrated. The residue was dissolved in tetrahydrofuran (2 mL) and then potassium carbonate (19 mg, 0.14 mmol) was added. The mixture was stirred for 10 min and then concentrated. The residue was purified using silica gel eluting with dichloromethane/methanol (20:1) and further purified using prep-HPLC to afford (S)—N-(2-(1-(3-ethoxy-4-methoxyphenyl)-2-(methylsulfonyl)ethyl)-1,3-dioxo-6-(7-(piperidin-4-yl)heptyl)isoindolin-4-yl)acetamide (43 mg) in a quantitative yield. MS (ESI) m/z: 642.4 $[M+H]^+$.

To a stirred solution of (S)—N-(2-(1-(3-ethoxy-4-methoxyphenyl)-2-(methylsulfonyl)ethyl)-1,3-dioxo-6-(7-(piperidin-4-yl)heptyl)isoindolin-4-yl)acetamide (43 mg, 0.067 mmol) and DIPEA (22 mg, 0.168 mmol) in N-methylpyrrolidone (2 mL) was added 2-(2,6-dioxopiperidin-3-yl)-4-fluoroisoindoline-1,3-dione (6) (22 mg, 0.081 mmol) under nitrogen. After heated at 150° C. under microwave for 2.5 h, the mixture was poured into ethyl acetate (25 mL) and then washed with 1M LiCl aqueous solution. The combined organic layers were dried over anhydrous $Na_2SO_4$, filtered, and concentrated. The residue was purified using silica gel eluting with methanol in dichloromethane from 0% to 10% and further purified using prep-HPLC to afford N-(6-(7-(1-(2-(2,6-dioxopiperidin-3-yl)-1,3-dioxoisoindolin-4-yl)piperidin-4-yl)heptyl)-2-((S)-1-(3-ethoxy-4-methoxyphenyl)-2-(methylsulfonyl)ethyl)-1,3-dioxoisoindolin-4-yl) acetamide (15.5 mg) B88 in 26% yield. $^1$H NMR (400 MHz, DMSO-$d_6$) δ 11.08 (s, 1H), 9.64 (s, 1H), 8.28 (s, 1H), 7.66 (t, J=7.6 Hz, 1H), 7.43 (s, 1H), 7.33-7.30 (m, 2H), 7.06 (s, 1H), 6.96-6.91 (m, 2H), 5.75 (dd, J=10.8 Hz, 4.4 Hz, 1H), 5.08 (dd, J=12.8 Hz, 5.2 Hz, 1H), 4.34-4.30 (m, 1H), 4.15-4.11 (m, 1H), 4.01 (q, J=6.8 Hz, 2H), 3.73 (s, 3H), 3.67 (d, J=12.4 Hz, 2H), 3.01 (s, 3H), 2.86-2.80 (m, 3H), 2.73-2.70 (m, 2H), 2.54-2.50 (m, 2H), 2.17 (s, 3H), 2.03-1.98 (m, 2H), 1.74 (d, J=12.0 Hz, 2H), 1.60-1.57 (m, 2H), 1.33-1.30 (m, 15H); MS (ESI) m/z: 898.4 $[M+H]^+$.

Example 21

Synthesis of 3-(2-(2-((2-(2,6-Dioxopiperidin-3-yl)-1,3-dioxoisoindolin-4-yl)amino)ethoxy)ethoxy)-N-(2-((S)-1-(3-ethoxy-4-methoxyphenyl)-2-(methylsulfonyl)ethyl)-1,3-dioxoisoindolin-4-yl) propanamide B89

B89

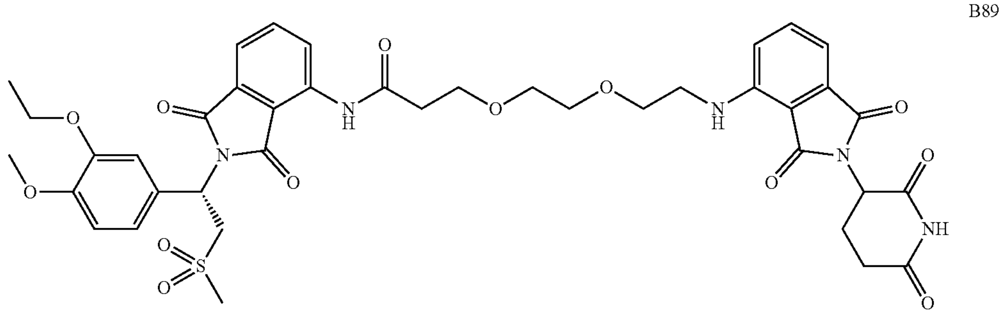 [SMILES: CCOc1cc([C@@H](CS(C)(=O)=O)N2C(=O)c3cccc(NC(=O)CCOCCOCCNc4cccc5c4C(=O)N(C4CCC(=O)NC4=O)C5=O)c3C2=O)ccc1OC]

To a stirred solution of tert-butyl (2-(2-hydroxyethoxy)ethyl)carbamate (2 g, 9.76 mmol) in toluene (20 mL) were added ethyl acrylate (2.928 g, 29.28 mmol) and cesium carbonate (6.344 g, 19.52 mmol). After stirred at 50° C. overnight, the mixture was concentrated, diluted with $H_2O$, and extracted with ethyl acetate. The combined organic layers were concentrated. The residue was purified using silica gel eluting with ethyl acetate in petroleum ether from 0 to 50% to give ethyl 2,2-dimethyl-4-oxo-3,8,11-trioxa-5-azatetradecan-14-oate (948 mg) in 32% yield.

To a stirred solution of ethyl 2,2-dimethyl-4-oxo-3,8,11-trioxa-5-azatetradecan-14-oate (948 mg, 3.11 mmol) in tetrahydrofuran (8 mL), methanol (2 mL), and $H_2O$ (2 mL) at 0° C. was added lithium hydroxide (266 mg, 6.22 mmol). After stirred at room temperature overnight, the mixture was concentrated, diluted with $H_2O$, and extracted with methyl tert-butyl ether. The aqueous phase was acidified to pH 5-6 with 1N hydrochloric acid and extracted with ethyl acetate. The combined organic layers were dried over anhydrous sodium sulfate, filtered, and concentrated to give 2,2-dimethyl-4-oxo-3,8,11-trioxa-5-azatetradecan-14-oic acid (644 mg) in 74% yield. MS (ESI) m/z: 275 $[M-H]^+$.

To a stirred solution of 2,2-dimethyl-4-oxo-3,8,11-trioxa-5-azatetradecan-14-oic acid (644 mg, 2.32 mmol) in dichloromethane (8 mL) at 0° C. were added oxalyl chloride (359 mg, 2.78 mmol) and 1 drop of N,N-dimethylformamide. The mixture was stirred at room temperature for 1 h and then concentrated to give tert-butyl (2-(2-(3-chloro-3-oxopropoxy)ethoxy)ethyl)carbamate (650 mg, crude).

To a stirred solution of tert-butyl (2-(2-(3-chloro-3-oxopropoxy)ethoxy)ethyl)-carbamate (2.32 mmol, crude) in tetrahydrofuran (3 mL) was added (S)-4-amino-2-(1-(3-ethoxy-4-methoxyphenyl)-2-(methylsulfonyl)ethyl) isoindoline-1,3-dione (388 mg, 0.93 mmol). The mixture was stirred overnight and then concentrated. The residue was purified using prep-TLC eluting with dichloromethane/methanol (10:1) to give (S)-14-amino-N-(2-(1-(3-ethoxy-4-methoxyphenyl)-2-(methylsulfonyl)ethyl)-1,3-dioxoisoindolin-4-yl)-3,6,9,12-tetraoxatetradecan-1-amide (35 mg) in 7% yield. MS (ESI) m/z: 578.2 $[M+H]^+$.

To a stirred solution of ((S)-14-amino-N-(2-(1-(3-ethoxy-4-methoxyphenyl)-2-(methylsulfonyl)ethyl)-1,3-dioxoisoindolin-4-yl)-3,6,9,12-tetraoxatetradecan-1-amide (35 mg, 0.06 mmol) and 2-(2,6-dioxopiperidin-3-yl)-4-fluoroisoindoline-1,3-dione (33 mg, 0.12 mmol) in N,N-dimethylformamide (3 mL) was added N,N-diisopropylethylamine (23 mg, 0.18 mmol). The mixture was stirred at 150° C. for 1 h under microwave. Water was added and the mixture was extracted with ethyl acetate. The combined organic layers were washed with brine, dried over anhydrous sodium sulfate, filtered, and concentrated. The residue was purified using prep-TLC eluting with ethyl acetate to give 3-(2-(2-((2-(2,6-dioxopiperidin-3-yl)-1,3-dioxoisoindolin-4-yl)amino)ethoxy)ethoxy)-N-(2-((S)-1-(3-ethoxy-4-methoxyphenyl)-2-(methylsulfonyl)ethyl)-1,3-dioxoisoindolin-4-yl) propanamide B89 (16.3 mg) in 33% yield. $^1H$ NMR (400 MHz, DMSO-$d_6$) δ 11.08 (s, 1H), 9.87 (s, 1H), 8.52 (d, J=8.4 Hz, 1H), 7.75 (t, J=7.6 Hz, 1H), 7.53-7.48 (m, 2H), 7.10-7.05 (m, 1H), 6.99-6.97 (m, 3H), 6.92 (d, J=8.0 Hz, 1H), 6.53 (t, J=5.6 Hz, 1H), 5.77 (dd, J=4.4, 10.8 Hz, 1H), 5.03 (dd, J=5.2, 12.4 Hz, 1H), 4.36-4.30 (m, 1H), 4.14 (dd, J=4.4, 14.8 Hz, 1H), 4.01 (q, J=6.4 Hz, 2H), 3.76-3.75 (m, 2H), 3.72 (s, 3H), 3.61-3.57 (m, 6H), 3.01 (s, 3H), 2.91-2.82 (m, 1H), 2.69-2.65 (m, 2H), 2.59-2.55 (m, 1H), 2.45-2.43 (m, 2H), 2.05-1.98 (m, 2H), 1.31 (t, J=6.8 Hz, 3H); MS (ESI) m/z: 834.3 $[M+H]^+$.

Example 22

Synthesis of N-(3,5-Dichloropyridin-4-yl)-4-(difluoromethoxy)-3-((7-((4-((5-(2,6-dioxopiperidin-3-yl)-4-oxo-5,6-dihydro-4H-thieno[3,4-c]pyrrol-1-yl)methoxy)benzyl)amino)heptyl)oxy)benzamide B92

B92

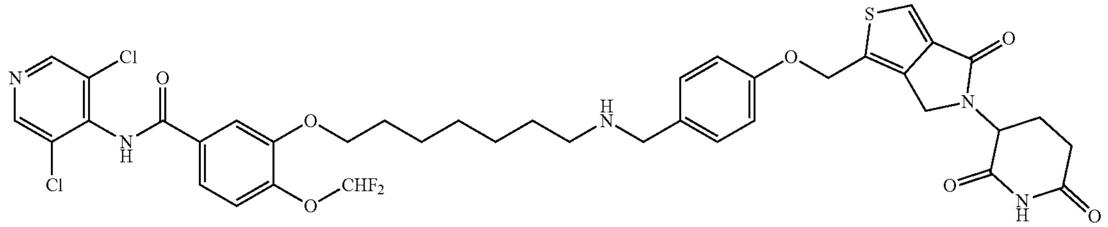

To a solution of tert-butyl 5-amino-4-(1-(hydroxymethyl)-4-oxo-4H-thieno[3,4-c]pyrrol-5(6H)-yl)-5-oxopentanoate (650 mg, 1.84 mmol) in dichloromethane (20 mL) at 0° C. was added triethylamine (371 mg, 3.68 mmol), followed by addition of methanesulfonyl chloride (420 mg, 3.68 mmol). The mixture was stirred overnight and then concentrated. The residue was purified using silica gel eluting with ethyl acetate in petroleum ether from 10% to 70% to give tert-butyl 5-amino-4-(1-(chloromethyl)-4-oxo-4H-thieno[3,4-c]pyrrol-5(6H)-yl)-5-oxopentanoateve (458 mg) in 67% yield. MS (ESI) m/z: 373.1 $[M+H]^+$.

To a solution of tert-butyl 5-amino-4-(1-(chloromethyl)-4-oxo-4H-thieno[3,4-c]pyrrol-5(6H)-yl)-5-oxopentanoateve (423 mg, 1.14 mmol) in N,N-dimethylformamide (20 mL) were added tert-butyl 4-hydroxybenzylcarbamate (304 mg, 1.36 mmol) and potassium carbonate (314 mg, 2.28 mmol). After heated at 80° C. for 2 h, the mixture was diluted with $H_2O$ and extracted with ethyl acetate. The combined organic layers were dried over anhydrous $Na_2SO_4$, filtered, and concentrated. The residue was purified using silica gel eluting with ethyl acetate in petroleum ether from 10% to 80% to give tert-butyl 5-amino-4-(1-((4-(((tert-butoxycarbonyl)amino)methyl)-phenoxy)methyl)-4-oxo-4H-thieno[3,4-c]pyrrol-5(6H)-yl)-5-oxopentanoate (576 mg) in 91% yield. MS (ESI) m/z: 560.2 $[M+H]^+$.

To a solution of tert-butyl 5-amino-4-(1-((4-(((tert-butoxycarbonyl)amino)methyl)-phenoxy)methyl)-4-oxo-4H-thieno[3,4-c]pyrrol-5(6H)-yl)-5-oxopentanoate (576 mg, 1.03 mmol) in tetrahydrofuran/$H_2O$ (15 mL/15 mL) was added $LiOH \cdot H_2O$ (46 mg, 1.03 mmol). The mixture was stirred overnight and then concentrated. The residue was acidified to pH 5 with 2N HCl and then extracted with dichloromethane/methanol (10:1). The combined organic layers were dried over anhydrous $Na_2SO_4$, filtered, and concentrated to give 5-amino-4-(1-((4-(((tert-butoxycarbonyl)-amino)methyl)phenoxy)methyl)-4-oxo-4H-thieno[3,4-c]pyrrol-5(6H)-yl)-5-oxopentanoic acid (359 mg) in 69% yield. MS (ESI) m/z: 504.2 $[M+H]^+$.

To a solution of 5-amino-4-(1-((4-(((tert-butoxycarbonyl)amino)methyl)phenoxy)-methyl)-4-oxo-4H-thieno[3,4-c]pyrrol-5(6H)-yl)-5-oxopentanoic acid (359 mg, 0.714 mmol) in acetonitrile (20 mL) was added 1,1'-carbonyldiimidazole (346 mg, 2.14 mmol). The mixture was stirred at 95° C. for 4 h. The resulting solid was filtered and dried under vacuum to give tert-butyl 4-((5-(2,6-dioxopiperidin-3-yl)-4-oxo-5,6-dihydro-4H-thieno[3,4-c]pyrrol-1-yl) methoxy)-benzylcarbamate (197 mg). The filtrate was concentrated and the residue was purified using silica gel eluting with ethyl acetate in petroleum ether from 10% to 70% to give additional tert-butyl 4-((5-(2,6-dioxopiperidin-3-yl)-4-oxo-5,6-dihydro-4H-thieno[3,4-c]pyrrol-1-yl)methoxy)benzylcarbamate (108 mg). The combined total of the desired product was 305 mg (88% yield). MS (ESI) m/z: 486.2 $[M+H]^+$.

To a solution of tert-butyl 4-((5-(2,6-dioxopiperidin-3-yl)-4-oxo-5,6-dihydro-4H-thieno[3,4-c]pyrrol-1-yl)methoxy) benzylcarbamate (44 mg, 0.091 mmol) in dichloromethane (4 mL) was added trifluoroacetic acid (1 mL). The mixture was stirred for 1 h and then concentrated to give 3-(1-((4-(aminomethyl)phenoxy)methyl)-4-oxo-4H-thieno[3,4-c] pyrrol-5(6H)-yl)piperidine-2,6-dione (35 mg, crude). MS (ESI) m/z: 386.1$[M+H]^+$.

To a solution of N-(3,5-dichloropyridin-4-yl)-4-(difluoromethoxy)-3-((7-(methoxy(methyl)amino)-7-oxoheptyl) oxy)benzamide (80 mg, 0.15 mmol) in tetrahydrofuran (5 mL) at −70° C. under $N_2$ was added $LiAlH_4$ (0.31 mL, 1 M in THF). After stirred at this temperature for 30 min, the reaction was quenched with sat. $NH_4Cl$ (5 mL) and the reaction mixture was extracted with ethyl acetate. The combined organic layers were dried over anhydrous $Na_2SO_4$, filtered, and concentrated to give N-(3,5-dichloropyridin-4-yl)-4-(difluoromethoxy)-3-((7-oxoheptyl)oxy) benzamide (75 mg, crude). MS (ESI) m/z: 461.1 $[M+H]^+$.

To a solution of N-(3,5-dichloropyridin-4-yl)-4-(difluoromethoxy)-3-((7-oxoheptyl)oxy)benzamide (54 mg, 0.12 mmol) in dichloromethane/methanol (4 mL/1 mL) were added 3-(1-((4-(aminomethyl)phenoxy)methyl)-4-oxo-4H-thieno[3,4-c]pyrrol-5(6H)-yl)piperidine-2,6-dione (35 mg, crude) and N,N-diisopropylethylamine (12 mg, 0.09 mmol), followed by addition of $NaBH_3CN$ (18 mg, 0.27 mmol). The mixture was stirred overnight and then concentrated. The residue was purified using silica gel eluting with methanol in dichloromethane from 0% to 10% and further purified using prep-HPLC to give N-(3,5-dichloropyridin-4-yl)-4-(difluoromethoxy)-3-((7-((4-((5-(2,6-dioxopiperidin-3-yl)-4-oxo-5,6-dihydro-4H-thieno[3,4-c]pyrrol-1-yl)methoxy)benzyl)amino)heptyl)oxy)benzamide B92 (21.7 mg) in 28.9% yield. $^1H$ NMR (400 MHz, DMSO-$d_6$) δ 8.70 (s, 2H), 8.01 (s, 1H), 7.72 (d, J=1.6 Hz, 1H), 7.65 (dd, J=2.0, 8.8 Hz, 1H), 7.35-7.32 (m, 1H), 7.26-7.24 (m, 2H), 7.17 (s, 1H), 6.98-6.95 (m, 2H), 5.28 (s, 2H), 5.01 (dd, J=5.3, 13.2 Hz, 1H), 4.37-4.20 (m, 2H), 4.10 (t, J=6.4 Hz, 2H), 3.64 (s, 2H), 3.52-3.48 (m, 2H), 2.93-2.84 (m, 1H), 2.60-2.55 (m, 2H), 2.39-2.29 (m, 1H), 2.00-1.95 (m, 1H), 1.79-1.73 (m, 2H), 1.45-1.41 (m, 4H), 1.32-1.31 (m, 4H); MS (ESI) m/z: 832.2 $[M+H]^+$.

The following compounds were prepared similarly according to the synthetic procedures or methodologies exemplified herein.

3-(Cyclopropylmethoxy)-N-(3,5-dichloropyridin-4-yl)-4-(difluoromethoxy)-N-(7-(4-(2-(2,6-dioxopiperidin-3-yl)-6-fluoro-1-oxoisoindolin-4-yl)piperidin-1-yl)heptyl)benzamide B3. $^1H$ NMR (400 MHz, DMSO-$d_6$) δ 11.06 (s, 1H), 10.57 (s, 1H), 9.12 (s, 1H), 8.72 (s, 2H), 7.43 (d, J=6.8 Hz, 1H), 7.29-7.28 (m, 1H), 7.11-6.86 (m, 4H), 5.17 (dd, J=5.2, 13.2 Hz, 1H), 4.58-4.35 (m, 2H), 3.74-3.72 (m, 2H), 3.59-3.54 (m, 2H), 3.12-3.11 (m, 2H), 2.99-2.92 (m, 4H), 2.65-2.57 (m, 1H), 2.37-2.31 (m, 1H), 2.20-2.13 (m, 1H), 2.06-1.98 (m, 2H), 1.72-1.71 (m, 2H), 1.60-1.59 (m, 2H), 1.31-1.26 (m, 10H), 1.14-1.11 (m, 1H), 0.56-0.54 (m, 2H), 0.30-0.29 (m, 2H); MS (ESI) m/z: 844.3 $[M+H]^+$.

B3

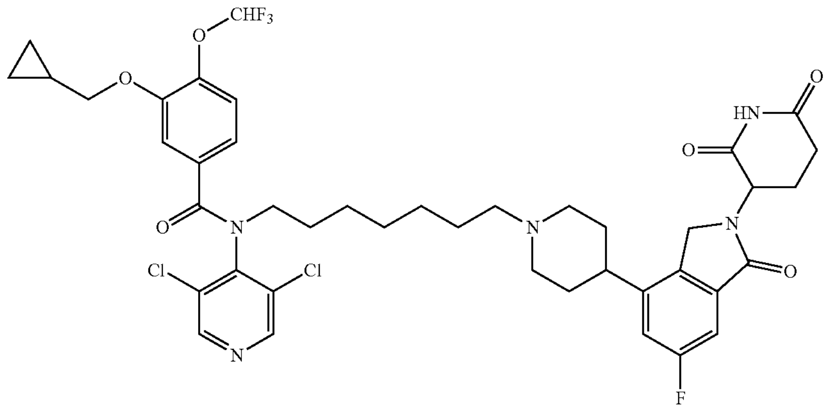

3-(2-(2-(2-((2-(2,6-Dioxopiperidin-3-yl)-1,3-dioxoisoindolin-4-yl)amino)ethoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B43. $^1H$ NMR (400 MHz, DMSO-$d_6$) δ 11.09 (s, 1H), 9.86 (s, 1H), 8.53 (d, J=8.4 Hz, 1H), 7.78 (t, J=8.0 Hz, 1H), 7.56-7.52 (m, 2H), 7.09-7.07 (m, 2H), 7.02-6.92 (m, 3H), 6.56 (t, J=6.0 Hz, 1H), 5.78 (dd, J=4.0, 10.4 Hz, 1H), 5.05 (dd, J=5.2, 12.8 Hz, 1H), 4.37-4.31 (m, 1H), 4.17-4.12 (m, 1H), 4.01 (q, J=7.2 Hz, 2H), 3.72-3.71 (m, 5H), 3.56-3.55 (m, 6H), 3.49 (s, 4H), 3.43-3.40 (m, 2H), 3.01 (s, 3H), 2.89-2.84 (m, 1H), 2.69 (t, J=6.0 Hz, 2H), 2.61-2.53 (m, 2H), 2.04-2.01 (m, 1H), 1.31 (t, J=6.8 Hz, 3H); MS (ESI) m/z: 878.3 $[M+H]^+$.

B43

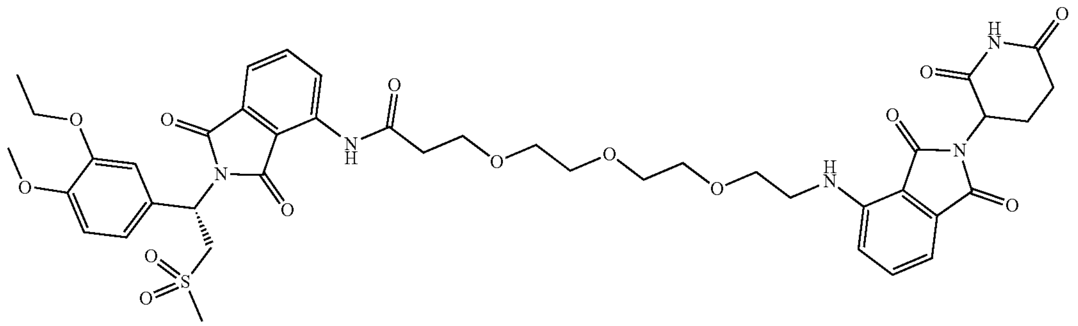

N-(3,5-Dichloropyridin-4-yl)-4-(difluoromethoxy)-3-((9-(4-(2-(2,6-dioxopiperidin-3-yl)-6-fluoro-1-oxoisoindolin-4-yl)piperidin-1-yl)nonyl)oxy)benzamide B45. $^1$H NMR (400 MHz, DMSO-$d_6$) δ 11.05 (s, 1H), 10.73 (s, 1H), 10.32 (s, 1H), 8.77 (s, 2H), 7.75 (d, J=1.6 Hz, 1H), 7.67 (dd, J=1.6, 8.0 Hz, 1H), 7.43 (dd, J=1.6, 7.6 Hz, 1H), 7.39-7.02 (m, 3H), 5.17 (dd, J=5.2, 13.2 Hz, 1H), 4.58-4.35 (m, 2H), 4.13 (t, J=6.4 Hz, 2H), 3.60-3.50 (m, 2H), 3.07-2.89 (m, 6H), 2.67-2.57 (m, 1H), 2.39-2.33 (m, 1H), 2.07-1.96 (m, 5H), 1.81-1.69 (m, 4H), 1.47-1.44 (m, 2H), 1.33-1.29 (m, 8H); MS (ESI) m/z: 819.7 $[M+H]^+$.

B45

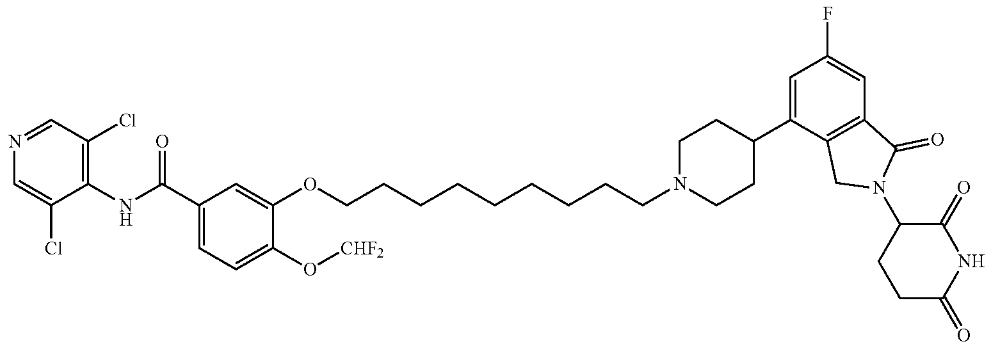

N-(3,5-Dichloropyridin-4-yl)-4-(difluoromethoxy)-3-((5-(4-(2-(2,6-dioxopiperidin-3-yl)-6-fluoro-1-oxoisoindolin-4-yl)piperidin-1-yl)pentyl)oxy)benzamide B46. $^1$H NMR (400 MHz, DMSO-$d_6$) δ 11.05 (s, 1H), 10.67 (s, 1H), 9.18 (s, 1H), 8.77 (s, 2H), 7.73-7.68 (m, 2H), 7.45-7.37 (m, 2H), 7.31-6.95 (m, 2H), 5.17 (dd, J=5.2, 13.2 Hz, 1H), 4.56-4.40 (m, 2H), 4.17 (t, J=6.4 Hz, 2H), 3.62 (d, J=10.4 Hz, 2H), 3.15-3.10 (m, 2H), 3.04-2.93 (m, 4H), 2.66-2.61 (m, 1H), 2.35-2.27 (m, 1H), 2.06-2.03 (m, 3H), 1.89-1.74 (m, 6H), 1.54-1.47 (m, 2H); MS (ESI) m/z: 764.2 $[M+H]^+$.

B46

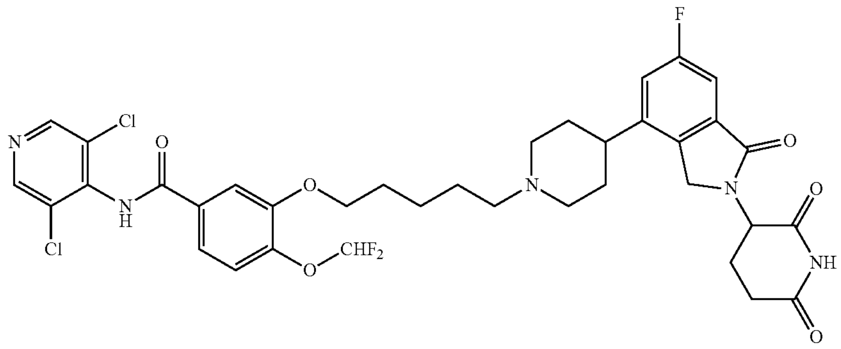

3-(6-Fluoro-4-(1-(7-(2-methoxy-5-(1-oxoisoindolin-2-yl)phenoxy)heptyl)piperidin-4-yl)-1-oxoisoindolin-2-yl)piperidine-2,6-dione B49. $^{1}H$ NMR (400 MHz, DMSO-$d_6$) δ 11.01 (s, 1H), 7.75 (d, J=7.6 Hz, 1H), 7.68-7.64 (m, 3H), 7.56-7.52 (m, 1H), 7.39 (dd, J=2.0, 12.0 Hz, 1H), 7.34 (dd, J=2.4, 7.6 Hz, 1H), 7.28 (dd, J=2.8, 8.8 Hz, 1H), 7.01 (d, J=8.4 Hz, 1H), 5.14 (dd, J=4.8, 12.8 Hz, 1H), 4.99 (s, 2H), 4.52-4.31 (m, 2H), 3.99 (t, J=6.8 Hz, 2H), 3.77 (s, 3H), 2.99-2.87 (m, 3H), 2.62-2.58 (m, 2H), 2.45-2.41 (m, 1H), 2.33-2.29 (m, 2H), 2.04-1.94 (m, 3H), 1.79-1.67 (m, 6H), 1.48-1.30 (m, 8H); MS (ESI) m/z: 697.4 $[M+H]^+$.

B49

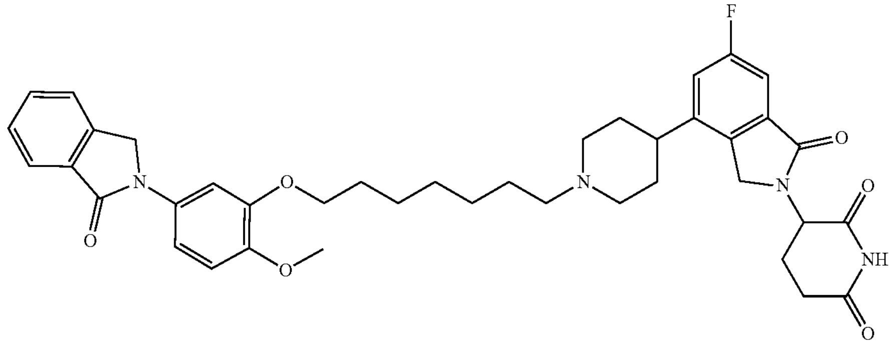

3-(4-(1-(7-(2-(Cyclopentyloxy)-4-(1-oxoisoindolin-2-yl)phenoxy)heptyl)piperidin-4-yl)-6-fluoro-1-oxoisoindolin-2-yl)piperidine-2,6-dione B50. $^{1}H$ NMR (400 MHz, DMSO-$d_6$) δ 11.01 (s, 1H), 7.75 (d, J=7.6 Hz, 1H), 7.68-7.65 (m, 3H), 7.55-7.53 (m, 1H), 7.39-7.33 (m, 2H), 7.27-7.24 (m, 1H), 7.00 (d, J=8.8 Hz, 1H), 5.13 (dd, J=5.2, 13.2 Hz, 1H), 4.97 (s, 2H), 4.82-4.80 (m, 1H), 4.52-4.31 (m, 2H), 3.95 (t, J=6.4 Hz, 2H), 2.96-2.92 (m, 3H), 2.62-2.58 (m, 2H), 2.47-2.41 (m, 1H), 2.28 (t, J=7.2 Hz, 2H), 2.03-1.85 (m, 5H), 1.78-1.64 (m, 10H), 1.60-1.56 (m, 2H), 1.44-1.38 (m, 4H), 1.35-1.29 (m, 4H); MS (ESI) m/z: 751.4 $[M+H]^+$.

B50

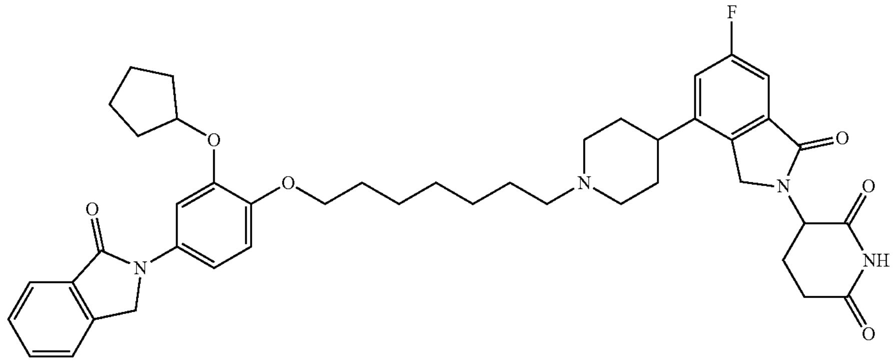

2-(3-((7-(4-(2-(2,6-Dioxopiperidin-3-yl)-6-fluoro-1-oxoisoindolin-4-yl)piperidin-1-yl)heptyl)oxy)-4-methoxyphenyl)isoindoline-1,3-dione B51. $^1$H NMR (400 MHz, DMSO-$d_6$) δ 11.05 (s, 1H), 9.41 (s, 1H), 7.96-7.91 (m, 4H), 7.43 (d, J=7.2 Hz, 1H), 7.31 (d, J=8.8 Hz, 1H), 7.10-7.08 (m, 2H), 6.97 (d, J=7.6 Hz, 1H), 5.17 (dd, J=5.2, 13.2 Hz, 1H), 4.56-4.36 (m, 2H), 3.95 (t, J=6.4 Hz, 2H), 3.83 (s, 3H), 3.61-3.59 (m, 2H), 3.09-2.92 (m, 6H), 2.66-2.62 (m, 1H), 2.37-2.33 (m, 1H), 2.08-1.93 (m, 5H), 1.77-1.69 (m, 4H), 1.45-1.24 (m, 6H); MS (ESI) m/z: 711.3 $[M+H]^+$.

B51

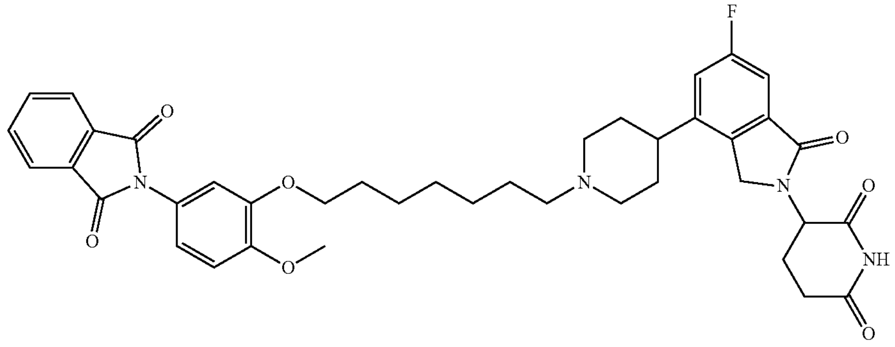

5-Amino-2-(3-((7-(4-(2-(2,6-dioxopiperidin-3-yl)-6-fluoro-1-oxoisoindolin-4-yl)piperidin-1-yl)heptyl)oxy)-4-methoxyphenyl)isoindoline-1,3-dione B52. $^1$H NMR (400 MHz, DMSO-$d_6$) δ 11.06 (s, 1H), 7.54 (s, 1H), 7.41 (s, 1H), 7.31 (s, 1H), 7.02 (s, 3H), 6.89 (s, 2H), 6.66 (s, 2H), 5.18-5.14 (m, 1H), 4.61-4.35 (m, 2H), 3.94 (s, 2H), 3.81 (s, 3H), 3.09-2.92 (m, 6H) 2.37-2.33 (m, 5H), 2.08-1.99 (m, 4H), 1.77-1.69 (m, 4H), 1.42-1.25 (m, 6H); MS (ESI) m/z: 726.3 $[M+H]^+$.

B52

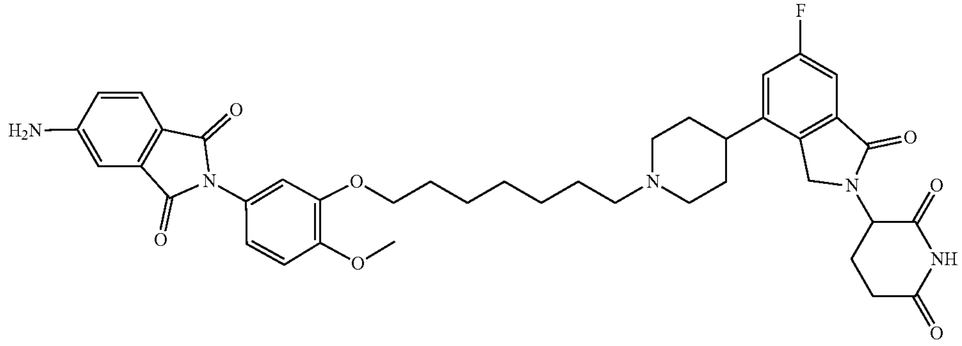

3-(6-Fluoro-4-(1-(7-(2-methoxy-5-(5-oxopyrrolidin-3-yl)phenoxy)heptyl)piperidin-4-yl)-1-oxoisoindolin-2-yl)piperidine-2,6-dione B53. $^1$H NMR (400 MHz, DMSO-$d_6$) δ 11.01 (s, 1H), 7.66 (s, 1H), 7.40 (dd, J=2.4, 10.8 Hz, 1H), 7.34 (dd, J=2.0, 7.2 Hz, 1H), 6.91-6.86 (m, 2H), 6.78 (dd, J=2.0, 8.0 Hz, 1H), 5.13 (dd, J=4.8, 13.2 Hz, 1H), 4.52-4.31 (m, 2H), 3.94 (t, J=6.8 Hz, 2H), 3.72 (s, 3H), 3.55-3.49 (m, 2H), 3.18-3.14 (m, 2H), 2.98-2.91 (m, 2H), 2.62-2.58 (m, 2H), 2.50-2.40 (m, 2H), 2.33-2.26 (m, 3H), 2.01-1.90 (m, 3H), 1.73-1.68 (m, 6H), 1.44-1.32 (m, 8H); MS (ESI) m/z: 649.3 $[M+H]^+$.

B53

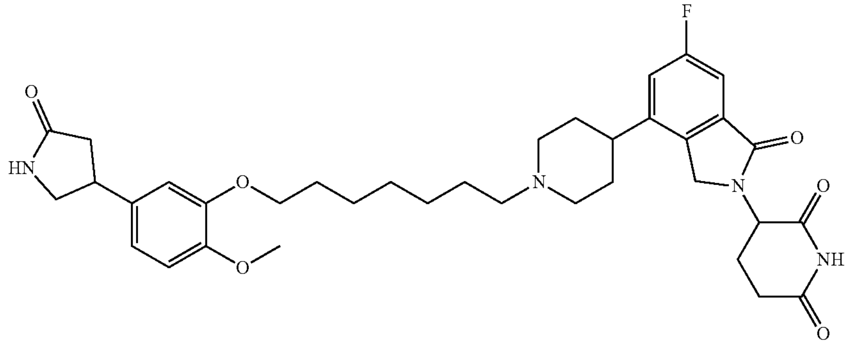

2-(3-(Cyclopentyloxy)-4-methoxyphenyl)-5-((7-(4-(2-(2,6-dioxopiperidin-3-yl)-6-fluoro-1-oxoisoindolin-4-yl)piperidin-1-yl)heptyl)amino)isoindoline-1,3-dione B54. $^1$H NMR (400 MHz, DMSO-$d_6$) δ 11.01 (s, 1H), 7.59 (d, J=8.4 Hz, 1H), 7.40-7.36 (m, 2H), 7.08 (t, J=5.2 Hz, 1H), 7.02-6.95 (m, 3H), 6.88-6.84 (m, 2H), 5.13 (dd, J=5.2, 13.2 Hz, 1H), 4.73-4.70 (m, 1H), 4.52-4.30 (m, 2H), 3.78 (s, 3H), 3.19-3.14 (m, 3H), 2.96-2.87 (m, 3H), 2.61-2.55 (m, 2H), 2.44-2.40 (m, 1H), 2.28 (t, J=7.2 Hz, 2H), 2.02-1.94 (m, 3H), 1.72-1.68 (m, 8H), 1.58-1.55 (m, 4H), 1.46-1.31 (m, 9H); MS (ESI) m/z: 794.4 $[M+H]^+$.

B54

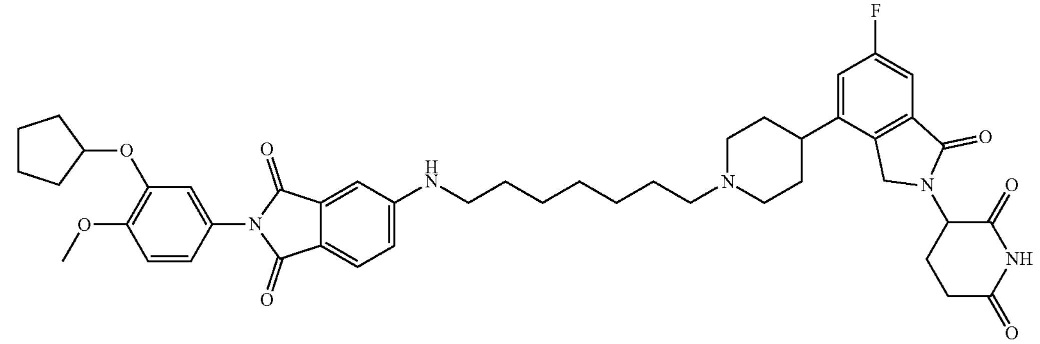

3-(6-Fluoro-5-(1-(7-(2-methoxy-5-(5-oxopyrrolidin-3-yl)phenoxy)heptyl)piperidin-4-yl)-1-oxoisoindolin-2-yl)piperidine-2,6-dione B55. $^1$H NMR (400 MHz, DMSO-$d_6$) δ 11.00 (s, 1H), 7.66 (s, 1H), 7.40 (dd, J=2.4, 10.8 Hz, 1H), 7.35 (dd, J=2.0, 7.2 Hz, 1H), 6.91 (d, J=2.0 Hz, 1H), 6.87 (d, J=8.4 Hz, 1H), 6.79 (dd, J=2.0, 8.0 Hz, 1H), 5.13 (dd, J=4.8, 13.2 Hz, 1H), 4.43-4.26 (m, 2H), 3.94 (t, J=6.8 Hz, 2H), 3.72 (s, 3H), 3.57-3.47 (m, 2H), 3.18-3.14 (m, 1H), 2.98-2.90 (m, 2H), 2.62-2.57 (m, 2H), 2.49-2.40 (m, 1H), 2.32-2.26 (m, 5H), 2.02-1.93 (m, 3H), 1.73-1.68 (m, 6H), 1.44-1.32 (m, 8H); MS (ESI) m/z: 649.3 [M+H]$^+$.

B55

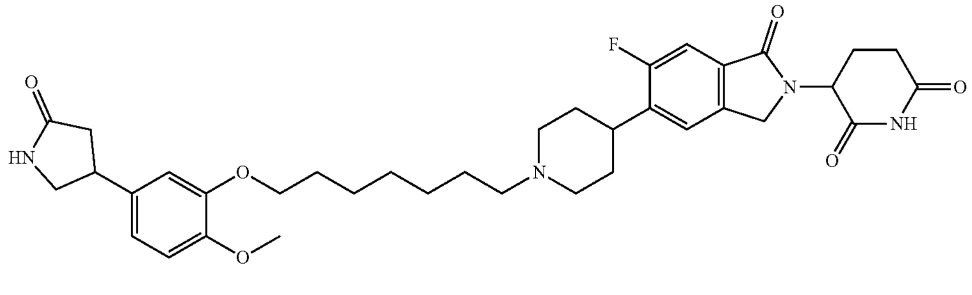

3-(4-(1-(7-((2-(3-(Cyclopentyloxy)-4-methoxyphenyl)-3-oxoisoindolin-5-yl)amino)heptyl)piperidin-4-yl)-6-fluoro-1-oxoisoindolin-2-yl)piperidine-2,6-dione B56. $^1$H NMR (400 MHz, DMSO-$d_6$) δ 11.01 (s, 1H), 7.67 (d, J=2.4 Hz, 1H), 7.40-7.30 (m, 3H), 7.20 (dd, J=2.0, 8.8 Hz, 1H), 6.96 (d, J=8.4 Hz, 1H), 6.88 (dd, J=1.6, 8.0 Hz, 1H), 6.81 (s, 1H), 5.91 (t, J=10.0 Hz, 1H), 5.12 (dd, J=4.8, 13.2 Hz, 1H), 4.77 (s, 3H), 4.52-4.35 (m, 2H), 3.74 (s, 3H), 3.07-3.02 (m, 2H), 2.97-2.91 (m, 3H), 2.62-2.58 (m, 2H), 2.45-2.42 (m, 1H), 2.28 (t, J=6.8 Hz, 2H), 2.03-1.91 (m, 5H), 1.73-1.68 (m, 8H), 1.57-1.54 (m, 4H), 1.38-1.31 (m, 8H); MS (ESI) m/z: 780.5 [M+H]$^+$.

B56

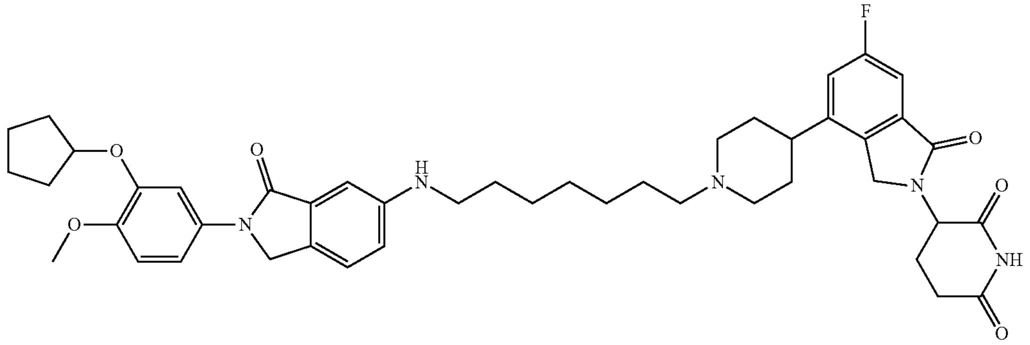

3-(4-(1-(7-(2-(Cyclopentyloxy)-4-(5-oxopyrrolidin-3-yl)phenoxy)heptyl)piperidin-4-yl)-6-fluoro-1-oxoisoindolin-2-yl)piperidine-2,6-dione B57. $^{1}$H NMR (400 MHz, DMSO-$d_6$) δ 11.01 (s, 1H), 7.67 (s, 1H), 7.40-7.35 (m, 2H), 6.87 (d, J=4.0 Hz, 2H), 6.78 (d, J=8.0 Hz, 1H), 5.12 (dd, J=4.8, 13.2 Hz, 1H), 4.78 (s, 1H), 4.54-4.32 (m, 2H), 3.91 (t, J=6.0 Hz, 2H), 3.16 (t, J=7.6 Hz, 2H), 2.99-2.89 (m, 6H), 2.64-2.59 (m, 2H), 2.48-2.44 (m, 1H), 2.33-2.24 (m, 3H), 2.04-1.98 (m, 4H), 1.81-1.71 (m, 10H), 1.60-1.54 (m, 2H), 1.46-1.31 (m, 8H); MS (ESI) m/z: 703.4 $[M+H]^+$.

B57

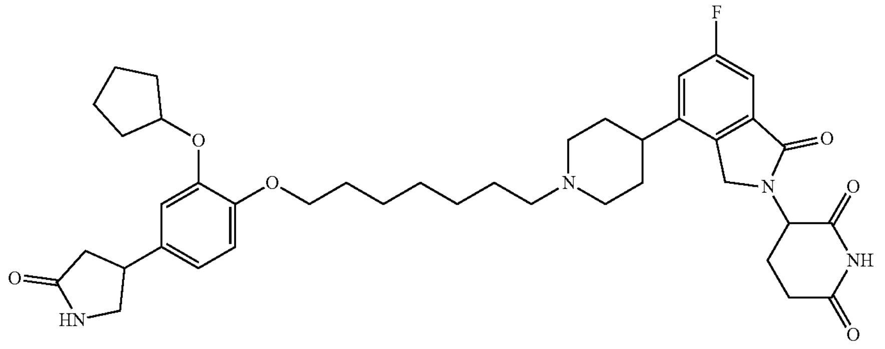

5-Amino-2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B58. $^{1}$H NMR (400 MHz, DMSO-$d_6$) δ 11.06 (s, 1H), 9.41 (s, 1H), 7.55 (d, J=8.4 Hz, 1H), 7.44 (d, J=7.2 Hz, 1H), 7.32 (d, J=10.4 Hz, 1H), 7.03 (d, J=8.8 Hz, 1H), 6.98 (s, 2H), 6.86 (d, J=8.4 Hz, 2H), 5.16 (dd, J=4.8, 13.6 Hz, 1H), 4.74 (s, 1H), 4.56-4.36 (m, 2H), 4.00 (t, J=6.0 Hz, 1H), 3.60-3.47 (m, 3H), 3.09-2.89 (m, 8H), 2.66-2.60 (m, 1H), 2.40-2.29 (m, 1H), 2.07-1.89 (m, 5H), 1.83-1.72 (m, 10H), 1.62-1.58 (m, 2H), 1.47-1.37 (m, 6H); MS (ESI) m/z: 780.4 $[M+H]^+$.

B58

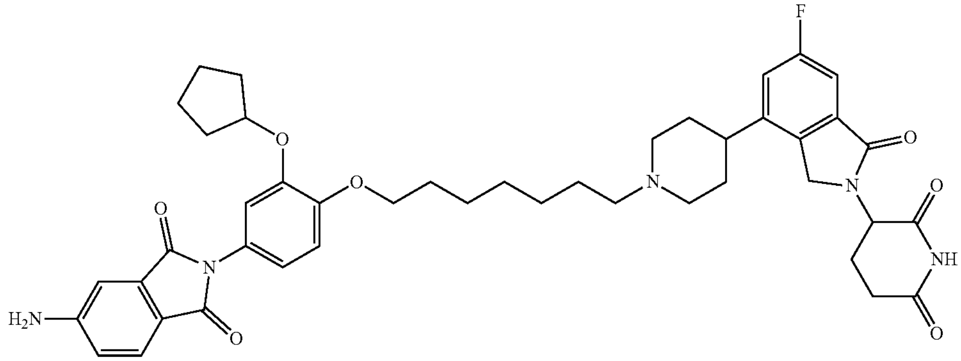

3-(4-(1-(7-(5-(6-Amino-1-oxoisoindolin-2-yl)-2-methoxyphenoxy)heptyl)piperidin-4-yl)-6-fluoro-1-oxoisoindolin-2-yl)piperidine-2,6-dione B60. $^{1}$H NMR (400 MHz, DMSO-$d_6$) δ 11.08 (s, 1H), 9.22 (s, 1H), 7.71 (s, 1H), 7.44 (dd, J=2.0, 7.2 Hz, 1H), 7.31-7.28 (m, 2H), 7.23-7.19 (m, 1H), 7.01-6.97 (m, 1H), 6.94-6.90 (m, 2H), 5.18 (dd, J=4.8 Hz, 13.2 Hz, 1H), 4.79 (s, 2H), 4.55-4.35 (m, 2H), 3.99 (t, J=6.0 Hz, 2H), 3.77 (s, 3H), 3.13-3.08 (m, 2H), 3.02-2.90 (m, 3H), 2.66-2.60 (m, 2H), 2.35-2.31 (m, 2H), 2.09-1.92 (m, 5H), 1.80-1.75 (m, 2H), 1.72-1.66 (m, 2H), 1.49-1.34 (m, 8H); MS (ESI) m/z: 712.4 $[M+H]^+$.

B60

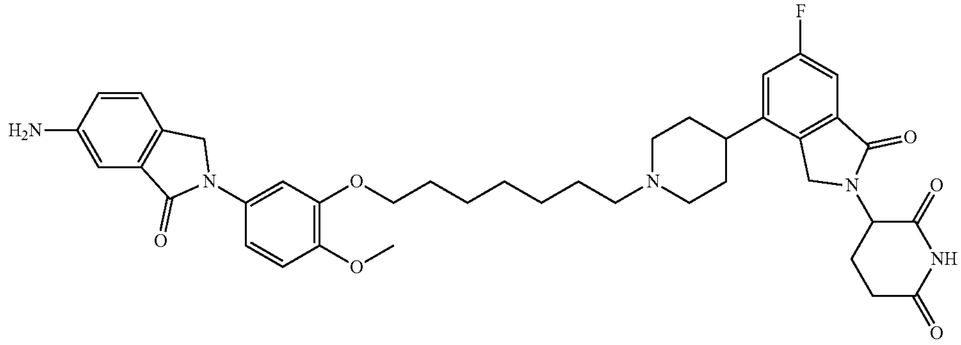

3-(4-(1-(7-(5-(6-Amino-1-oxoisoindolin-2-yl)-2-methoxyphenoxy)heptyl)piperidin-4-yl)-6-fluoro-1-oxoisoindolin-2-yl)piperidine-2,6-dione B62. $^{1}$H NMR (400 MHz, DMSO-$d_6$) δ 11.06 (s, 1H), 8.80 (s, 1H), 7.58 (s, 1H), 7.44-7.38 (m, 2H), 7.31 (d, J=8.0 Hz, 1H), 7.09 (d, J=8.8 Hz, 1H), 6.89 (dd, J=1.6, 8.0 Hz, 1H), 6.82-6.80 (m, 2H), 5.92 (s, 1H), 5.16 (dd, J=3.6, 13.2 Hz, 1H), 4.78-4.75 (m, 3H), 4.56-4.35 (m, 2H), 4.23-4.19 (m, 2H), 3.19-3.17 (m, 2H), 3.07-3.04 (m, 2H), 2.99-2.92 (m, 4H), 2.65-2.62 (m, 1H), 2.42-2.35 (m, 1H), 2.06-1.87 (m, 8H), 1.79-1.74 (m, 4H), 1.64-1.54 (m, 4H), 1.48-1.29 (m, 8H); MS (ESI) m/z: 766.5 $[M+H]^+$.

B62

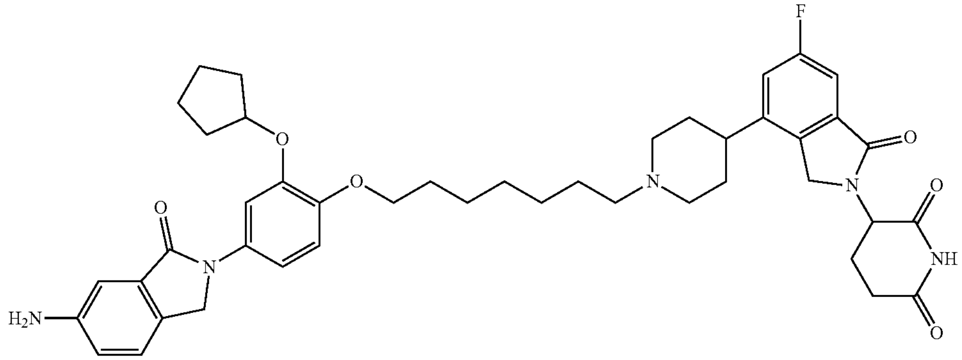

3-((4-((2-((2-(2,6-Dioxopiperidin-3-yl)-1,3-dioxoisoindolin-4-yl)amino)ethoxy)-methyl)benzyl)oxy)-N-(2-((S)-1-(3-ethoxy-4-methoxyphenyl)-2-(methylsulfonyl)ethyl)-1,3-dioxoisoindolin-4-yl)propanamide B64. $^{1}$H NMR (400 MHz, DMSO-$d_6$) δ 11.09 (s, 1H), 9.90 (s, 1H), 8.52 (d, J=8.0 Hz, 1H), 7.79 (t, J=8.0 Hz, 1H), 7.58-7.53 (m, 2H), 7.29-7.23 (m, 4H), 7.13-7.08 (m, 2H), 7.03 (d, J=7.2 Hz, 1H), 6.98-6.91 (m, 2H), 6.64 (t, J=6.0 Hz, 1H), 5.78 (dd, J=4.4, 10.4 Hz, 1H), 5.06 (dd, J=5.2, 12.8 Hz, 1H), 4.53 (s, 2H), 4.48 (s, 2H), 4.36-4.30 (m, 1H), 4.16-4.12 (m, 1H), 3.99 (q, J=6.4 Hz, 2H), 3.74-3.72 (m, 5H), 3.61-3.58 (m, 2H), 3.51-3.47 (m, 2H), 3.00 (s, 3H), 2.88-2.85 (m, 1H), 2.74 (t, J=6.0 Hz, 2H), 2.61-2.53 (m, 2H), 2.04-2.01 (m, 1H), 1.29 (t, J=7.2 Hz, 3H); MS (ESI) m/z: 910.3 $[M+H]^+$.

B64

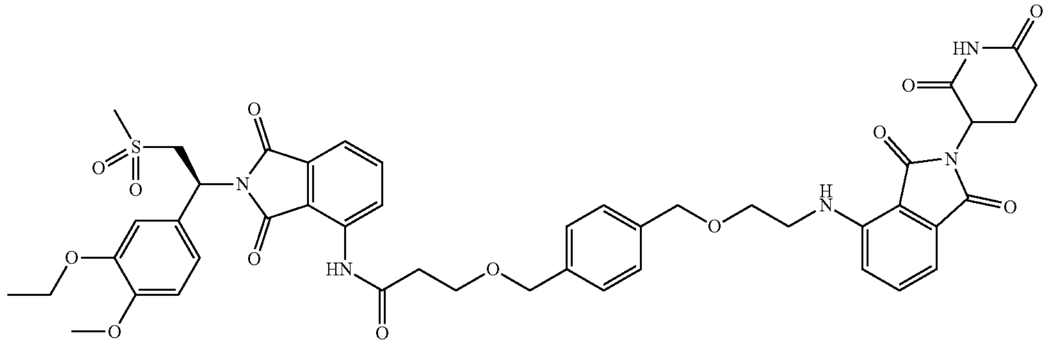

2-(2,6-Dioxopiperidin-3-yl)-4-((7-(2-methoxy-5-(5-oxopyrrolidin-3-yl)phenoxy)-heptyl)amino)isoindoline-1,3-dione B66. $^{1}$H NMR (400 MHz, DMSO-$d_6$) δ 11.09 (s, 1H), 7.66 (s, 1H), 7.58 (t, J=7.6 Hz, 1H), 7.09 (d, J=8.4 Hz, 1H), 7.02 (d, J=6.0 Hz, 1H), 6.91-6.86 (m, 2H), 6.79-6.77 (m, 1H), 6.54 (s, 1H), 5.05 (dd, J=5.2, 12.8 Hz, 1H), 3.94 (t, J=8.8 Hz, 1H), 3.71 (s, 3H), 3.58-3.47 (m, 3H), 3.31-3.29 (m, 2H), 3.18-3.14 (m, 1H), 2.92-2.83 (m, 1H), 2.60-2.56 (m, 1H), 2.47-2.42 (m, 1H), 2.33-2.26 (m, 1H), 2.05-1.97 (m, 1H), 1.71-1.69 (m, 2H), 1.60-1.57 (m, 2H), 1.45-1.35 (m, 6H); MS (ESI) m/z: 577.3 $[M+H]^+$.

B66

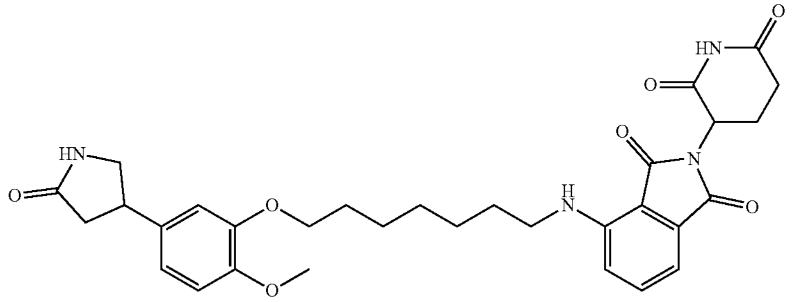

(2S,4R)-4-Hydroxy-1-((2S)-2-(9-(2-methoxy-5-(5-oxopyrrolidin-3-yl)phenoxy)-nonanamido)-3,3-dimethylbutanoyl)-N-(4-(4-methylthiazol-5-yl)benzyl)pyrrolidine-2-carboxamide B67. $^1$H NMR (400 MHz, DMSO-$d_6$) δ 8.99 (s, 1H), 8.58 (s, 1H), 7.86 (d, J=8.0 Hz, 1H), 7.68 (s, 1H), 7.44-7.38 (m, 4H), 6.91-6.86 (m, 2H), 6.89 (d, J=8.0 Hz, 1H), 5.17 (s, 1H), 4.55 (d, J=8.8 Hz, 1H), 4.46-4.21 (m, 1H), 4.25-4.20 (m, 1H), 3.93 (t, J=6.0 Hz, 2H), 3.72 (s, 3H), 3.67 (s, 2H), 3.59-3.52 (m, 3H), 3.17 (t, J=7.2 Hz, 1H), 2.51-2.50 (m, 2H), 2.45 (s, 3H), 2.33-2.26 (m, 2H), 2.14-2.02 (m, 2H), 1.98-1.89 (m, 1H), 1.69-1.67 (m, 2H), 1.51-1.28 (m, 10H), 0.94 (s, 9H); MS (ESI) m/z: 776.4 $[M+H]^+$.

B67

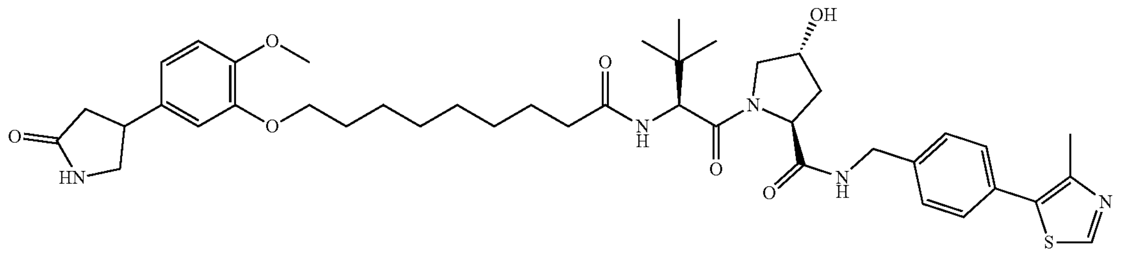

9-((4-((5-(2,6-Dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)nonanamide B70. $^1$H NMR (400 MHz, DMSO-$d_6$) δ 9.66 (s, 1H), 8.46 (d, J=8.4 Hz, 1H), 8.00 (s, 1H), 7.78 (t, J=8.0 Hz, 1H), 7.56 (d, J=7.6 Hz, 1H), 7.22 (d, J=8.0 Hz, 2H), 7.07 (s, 1H), 6.98-6.91 (m, 4H), 5.78-5.75 (m, 1H), 5.27 (s, 2H), 5.01 (dd, J=4.8, 13.2 Hz, 1H), 4.36-4.30 (m, 2H), 4.23-4.11 (m, 2H), 4.01 (q, J=7.2 Hz, 2H), 3.72 (s, 3H), 3.58 (s, 2H), 3.04 (s, 3H), 2.91-2.85 (m, 1H), 2.60-2.54 (m, 1H), 2.47-2.40 (m, 4H), 2.35-2.31 (m, 1H), 2.00-1.96 (m, 2H), 1.62-1.58 (m, 2H), 1.40-1.35 (m, 2H), 1.33-1.29 (m, 6H), 1.28-1.24 (m, 5H); MS (ESI) m/z: 942.4 $[M+H]^+$.

B70

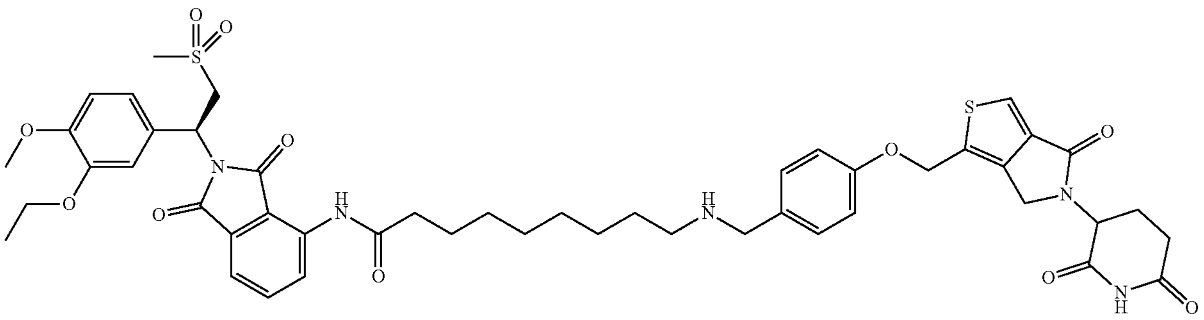

N-(3,5-Dichloropyridin-4-yl)-4-(difluoromethoxy)-3-((7-((2-(2,6-dioxopiperidin-3-yl)-1,3-dioxoisoindolin-4-yl)amino)heptyl)oxy)benzamide B72. $^1$H NMR (400 MHz, DMSO-$d_6$) δ 11.02 (s, 1H), 10.72 (brs, 1H), 8.77 (s, 2H), 7.74 (s, 1H), 7.67 (d, J=7.6 Hz, 1H), 7.41-7.00 (m, 4H), 5.15 (dd, J=3.6, 12 Hz, 1H), 4.54-4.33 (m, 2H), 4.17-4.07 (m, 2H), 3.03-2.90 (m, 3H), 2.64-2.60 (m, 2H), 2.47-2.43 (m, 1H), 2.36-2.24 (m, 2H), 2.09-1.92 (m, 4H), 1.85-1.63 (m, 6H), 1.54-1.45 (m, 4H), 1.44-1.27 (m, 14H); MS (ESI) m/z: 718.2 $[M+H]^+$.

B72

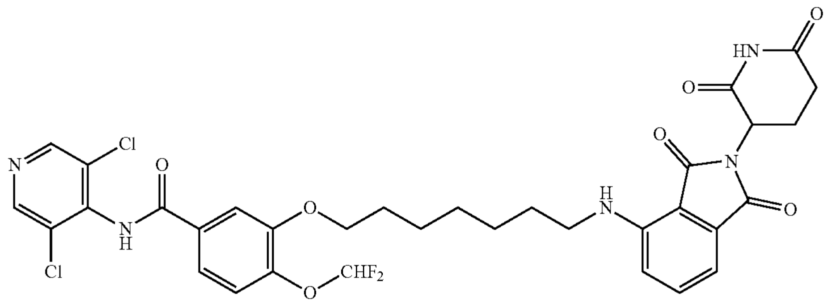

N-(3,5-Dichloropyridin-4-yl)-4-(difluoromethoxy)-3-((12-(4-(2-(2,6-dioxopiperidin-3-yl)-6-fluoro-1-oxoisoindolin-4-yl)piperidin-1-yl)dodecyl)oxy)benzamide B73. $^1$H NMR (400 MHz, DMSO-$d_6$) δ 11.02 (s, 1H), 10.72 (brs, 1H), 8.77 (s, 2H), 7.74 (s, 1H), 7.67 (d, J=7.6 Hz, 1H), 7.41-7.00 (m, 4H), 5.15 (dd, J=3.6, 12 Hz, 1H), 4.54-4.33 (m, 2H), 4.17-4.07 (m, 2H), 3.03-2.90 (m, 3H), 2.64-2.60 (m, 2H), 2.47-2.43 (m, 1H), 2.36-2.24 (m, 2H), 2.09-1.92 (m, 4H), 1.85-1.63 (m, 6H), 1.54-1.45 (m, 4H), 1.44-1.27 (m, 14H); MS (ESI) m/z: 860.3 $[M+H]^+$.

B73

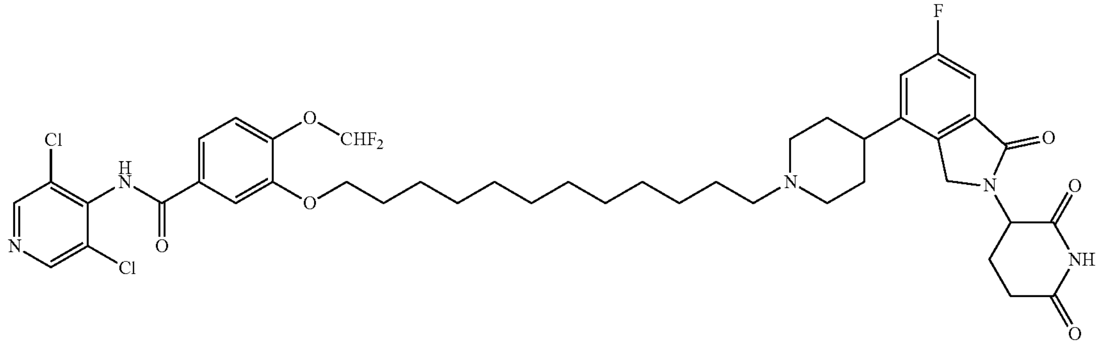

N-(3,5-Dichloropyridin-4-yl)-3-(difluoromethoxy)-4-(2-(2-(2-(2-((2-(2,6-dioxopiperidin-3-yl)-1,3-dioxoisoindolin-4-yl)amino)ethoxy)ethoxy)ethoxy)ethoxy)benzamide B74. $^{1}$H NMR (400 MHz, DMSO-$d_6$) δ 11.08 (s, 1H), 10.66 (s, 1H), 8.76 (s, 2H), 7.76 (s, 1H), 7.67 (d, J=8.4 Hz, 1H), 7.57 (t, J=8.0 Hz, 1H), 7.37 (t, J=10.4 Hz, 1H), 7.21 (s, 1H), 7.12 (d, J=8.4 Hz, 1H), 7.03 (d, J=6.8 Hz, 1H), 6.59 (t, J=5.6 Hz, 1H), 5.05 (dd, J=5.2, 12.8 Hz, 1H), 4.28-4.22 (m, 2H), 3.79-3.76 (m, 2H), 3.63-3.58 (m, 4H), 3.56-3.51 (m, 6H), 3.46-3.44 (m, 2H), 2.91-2.84 (m, 1H), 2.60-2.54 (m, 2H), 2.03-1.96 (m, 1H); MS (ESI) m/z: 780.1 $[M+H]^+$.

B74

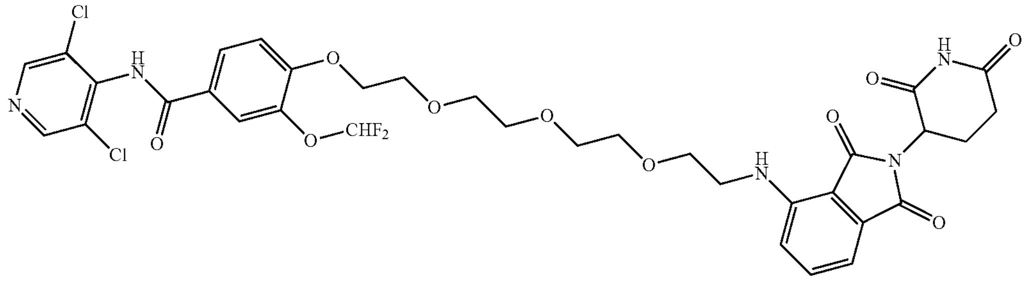

9-(4-(2-(2,6-Dioxopiperidin-3-yl)-6-fluoro-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B77. $^{1}$H NMR (400 MHz, DMSO-$d_6$) δ 11.00 (s, 1H), 9.68 (s, 1H), 8.46 (d, J=8.4 Hz, 1H), 7.79 (t, J=8.0 Hz, 1H), 7.56 (d, J=7.2 Hz, 1H), 7.39-7.34 (m, 2H), 7.08 (s, 1H), 6.99-6.92 (m, 2H), 5.78 (dd, J=4.0, 10.4 Hz, 1H), 5.13 (dd, J=5.2, 13.2 Hz, 1H), 4.52-4.31 (m, 3H), 4.14 (dd, J=4.0, 14.0 Hz, 1H), 4.02 (q, J=6.8 Hz, 2H), 3.73 (s, 3H), 3.01 (s, 3H), 2.95-2.87 (m, 3H), 2.63-2.58 (m, 2H), 2.47-2.45 (m, 2H), 2.26 (t, J=6.4 Hz, 2H), 2.03-1.91 (m, 3H), 1.71-1.61 (m, 6H), 1.47-1.41 (m, 2H), 1.34-1.30 (m, 12H); MS (ESI) m/z: 902.4 $[M+H]^+$.

B77

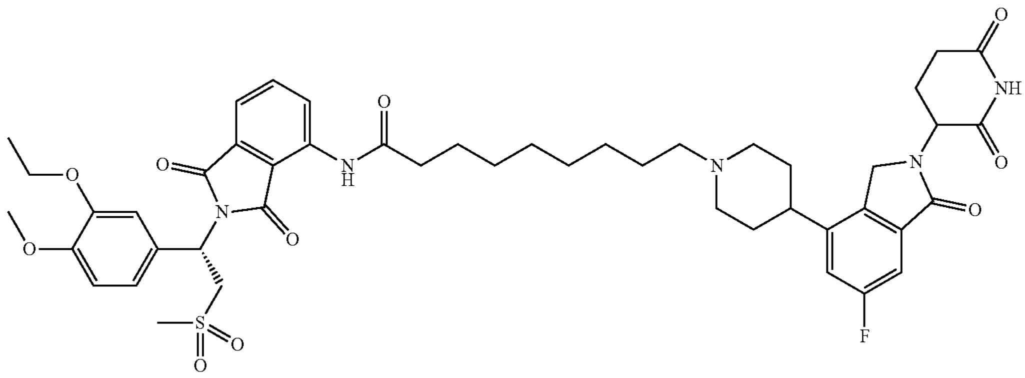

N-(6-(12-(4-(2-(2,6-Dioxopiperidin-3-yl)-6-fluoro-1-oxoisoindolin-4-yl)piperidin-1-yl)dodecyl)-2-((S)-1-(3-ethoxy-4-methoxyphenyl)-2-(methylsulfonyl)ethyl)-1,3-dioxoisoindolin-4-yl)acetamide B79. $^{1}H$ NMR (400 MHz, DMSO-$d_6$) δ 11.02 (s, 1H), 9.65 (s, 1H), 8.28 (s, 1H), 7.43-7.35 (m, 3H), 7.07 (s, 1H), 6.97-6.95 (m, 2H), 5.77 (d, J=10.4 Hz, 1H), 5.16-5.13 (m, 1H), 4.54-4.33 (m, 3H), 4.15-4.12 (m, 1H), 4.03-4.01 (m, 2H), 3.75-3.70 (m, 4H), 3.02-2.88 (m, 7H), 2.76-2.69 (m, 2H), 2.64-2.59 (m, 2H), 2.45-2.38 (m, 1H), 2.31-2.30 (m, 2H), 2.21-2.18 (m, 3H), 2.08-2.00 (m, 4H), 1.81-1.75 (m, 4H), 1.58 (s, 2H), 1.48-1.41 (m, 2H), 1.33-1.25 (m, 16H); MS (ESI) m/z: 972.5 $[M+H]^+$.

B79

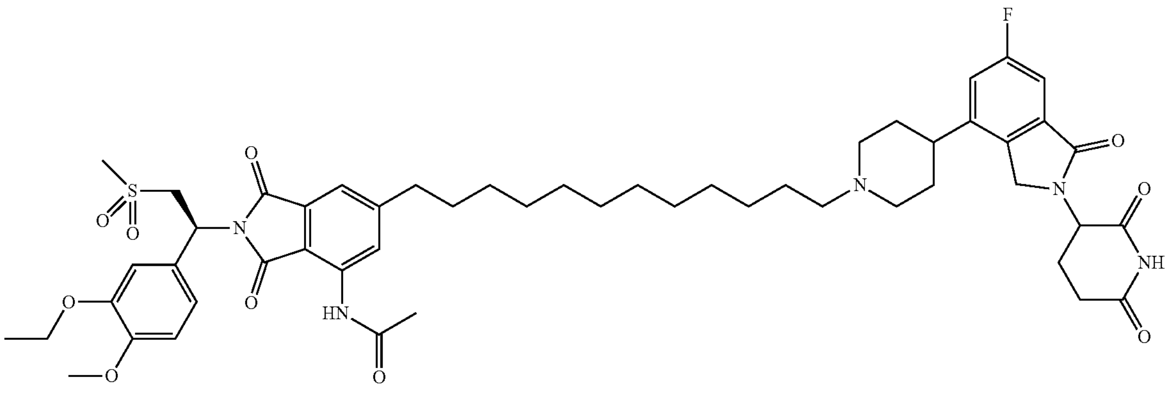

3-(6-Fluoro-4-(1-(7-(2-methoxy-5-(4-oxo-4,6-dihydro-5H-thieno[2,3-c]pyrrol-5-yl)phenoxy)heptyl)piperidin-4-yl)-1-oxoisoindolin-2-yl)piperidine-2,6-dione B80. $^{1}H$ NMR (400 MHz, DMSO-$d_6$) δ 11.00 (s, 1H), 7.70 (d, J=4.8 Hz, 1H), 7.50 (s, 1H), 7.39 (d, J=11.2 Hz, 1H), 7.35 (d, J=7.2 Hz, 1H), 7.33 (d, J=5.2 Hz, 1H), 7.15 (d, J=10.0 Hz, 1H), 6.98 (d, J=8.8 Hz, 1H), 5.13 (dd, J=4.8, 13.2 Hz, 1H), 5.04 (s, 2H), 4.53-4.32 (m, 2H), 3.97 (t, J=6.4 Hz, 2H), 3.76 (s, 3H), 2.98-2.88 (m, 3H), 2.62-2.58 (m, 2H), 2.46-2.42 (m, 1H), 2.29 (t, J=7.2 Hz, 2H), 2.03-1.93 (m, 3H), 1.80-1.72 (m, 6H), 1.45-1.31 (m, 8H); MS (ESI) m/z: 703.3 $[M+H]^+$.

B80

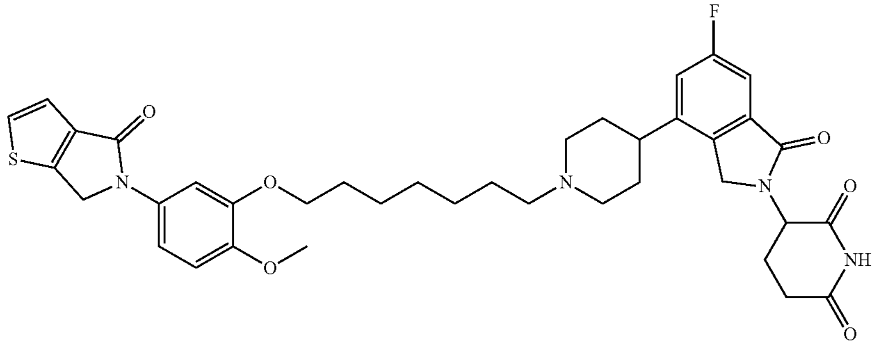

3-(Cyclopropylmethoxy)-N-(3,5-dichloropyridin-4-yl)-4-(2-(2-(2-(3-((2-(2,6-dioxopiperidin-3-yl)-1-oxoisoindolin-4-yl)amino)propoxy)ethoxy)ethoxy)ethoxy)benzamide B81. $^1$H NMR (400 MHz, DMSO-$d_6$) δ 11.09 (s, 1H), 10.41 (s, 1H), 8.74 (s, 2H), 7.64 (dd, J=2.0, 8.4 Hz, 1H), 7.57 (t, J=7.6 Hz, 1H), 7.41-7.39 (m, 1H), 7.13 (d, J=8.8 Hz, 2H), 7.03 (d, J=7.6 Hz, 1H), 6.60 (t, J=5.2 Hz, 1H), 5.23 (dd, J=4.8, 12.4 Hz, 1H), 4.74-4.71 (m, 1H), 4.17 (t, J=3.6 Hz, 2H), 3.77 (t, J=4.4 Hz, 2H), 3.64-3.62 (m, 4H), 3.57-3.55 (m, 5H), 3.48-3.43 (m, 4H), 2.92-2.84 (m, 1H), 2.60-2.56 (m, 1H), 2.45-2.39 (m, 2H), 2.10-1.99 (m, 3H), 1.78-1.75 (m, 1H), 1.66-1.59 (m, 1H); MS (ESI) m/z: 784.2 $[M+H]^+$.

B81

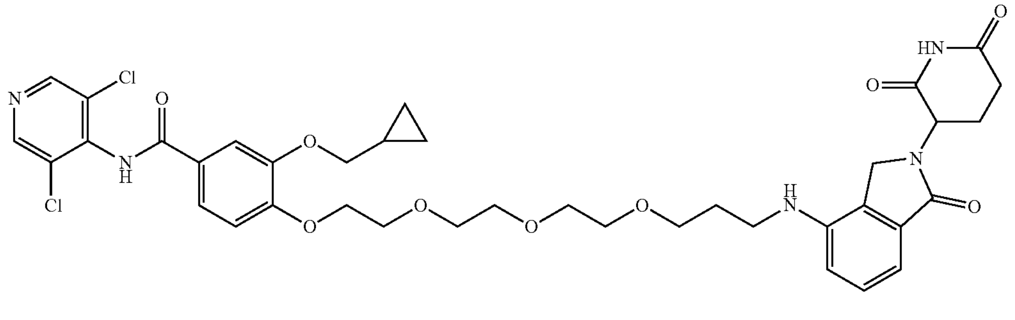

3-(Cyclopropylmethoxy)-N-(3,5-dichloropyridin-4-yl)-4-((7-(4-(2-(2,6-dioxopiperidin-3-yl)-6-fluoro-1-oxoisoindolin-4-yl)piperidin-1-yl)heptyl)oxy)benzamide B82. $^1$H NMR (400 MHz, DMSO-$d_6$) δ 11.00 (s, 1H), 11.14 (s, 1H), 8.74 (s, 2H), 7.65 (d, J=8.4 Hz, 1H), 7.41-7.34 (m, 3H), 7.12 (d, J=8.4 Hz, 1H), 5.13 (dd, J=4.8, 12.8 Hz, 1H), 4.73 (t, J=7.2 Hz, 1H), 4.52-4.32 (m, 2H), 4.07 (t, J=6.4 Hz, 2H), 2.99-2.87 (m, 2H), 2.60-2.52 (m, 2H), 2.43 (d, J=8.4 Hz, 2H), 2.30 (t, J=6.8 Hz, 2H), 2.10-1.91 (m, 4H), 1.80-1.63 (m, 6H), 1.47-1.24 (m, 13H); MS (ESI) m/z: 794.3 $[M+H]^+$.

B82

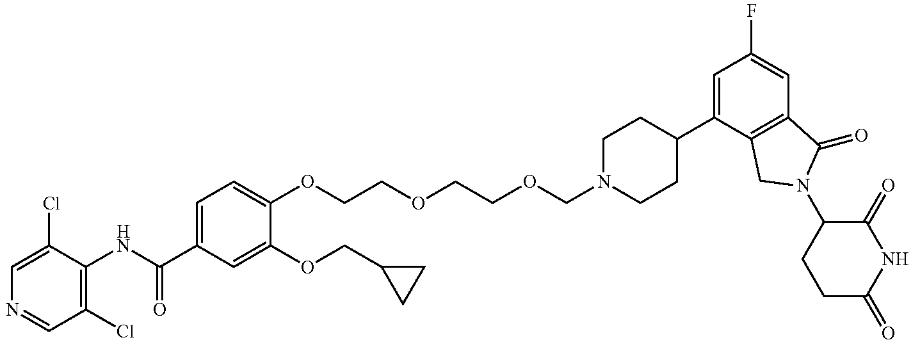

N-(3,5-Dichloropyridin-4-yl)-4-(difluoromethoxy)-3-(3-(4-(2-(2,6-dioxopiperidin-3-yl)-6-fluoro-1-oxoisoindolin-4-yl)piperidin-1-yl)propoxy)benzamide B83. $^1$H NMR (400 MHz, DMSO-$d_6$) δ 11.01 (s, 1H), 10.69 (s, 1H), 8.77 (s, 2H), 7.77 (s, 1H), 7.68 (d, J=8.4 Hz, 1H), 7.41-7.04 (m, 4H), 5.14 (dd, J=4.8, 13.2 Hz, 1H), 4.54-4.32 (m, 2H), 4.21 (s, 2H), 3.03-2.88 (m, 3H), 2.67-2.58 (m, 2H), 2.50-2.32 (m, 3H), 2.03-1.99 (m, 5H), 1.89-1.79 (m, 4H); MS (ESI) m/z: 734.2 [M+H]$^+$.

B83

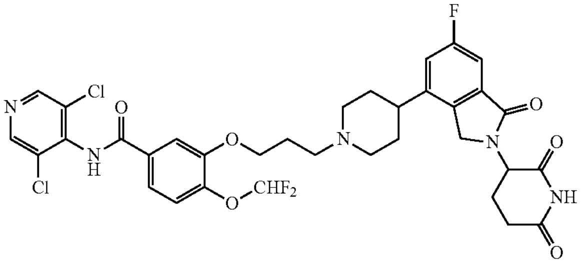

3-(Cyclopropylmethoxy)-N-(3,5-dichloropyridin-4-yl)-4-((9-(4-(2-(2,6-dioxopiperidin-3-yl)-6-fluoro-1-oxoisoindolin-4-yl)piperidin-1-yl)nonyl)oxy)benzamide B84. $^1$H NMR (400 MHz, DMSO-$d_6$) δ 11.05 (s, 1H), 10.41 (s, 1H), 9.32 (s, 1H), 8.75 (s, 2H), 7.65 (d, J=8.4 Hz, 1H), 7.44-7.41 (m, 2H), 7.31 (d, J=10.4 Hz, 1H), 7.12 (d, J=8.8 Hz, 1H), 5.17 (dd, J=4.8, 13.2 Hz, 1H), 4.75-4.71 (m, 1H), 4.55-4.35 (m, 2H), 4.06 (t, J=6.0 Hz, 2H), 3.60 (d, J=10.4 Hz, 2H), 3.08-2.90 (m, 6H), 2.65-2.61 (m, 1H), 2.46-2.32 (m, 3H), 2.09-1.93 (m, 7H), 1.83-1.76 (m, 3H), 1.67-1.61 (m, 3H), 1.47-1.45 (m, 2H), 1.36-1.33 (m, 8H); MS (ESI) m/z: 822.3 [M+H]$^+$.

B84

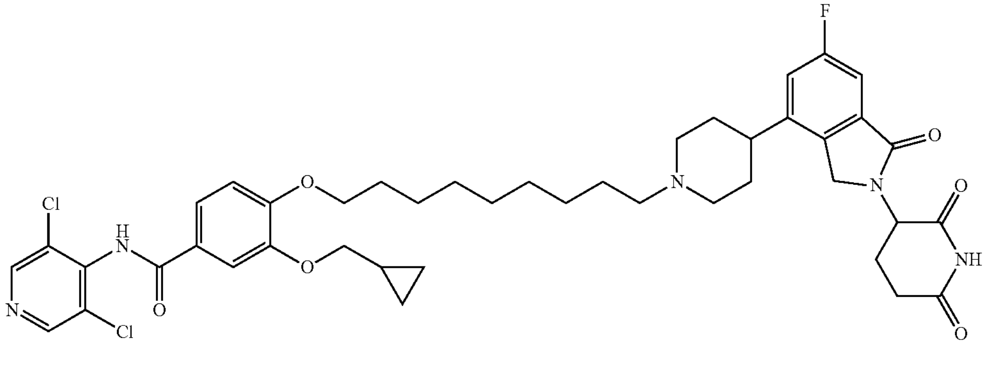

3-((9-(4-(2-(1-Acetamido-1-oxopropan-2-yl)-6-fluoro-1-oxoisoindolin-4-yl)piperidin-1-yl)nonyl)oxy)-N-(3,5-dichloropyridin-4-yl)-4-(difluoromethoxy)benzamide B85. $^1H$ NMR (400 MHz, DMSO-$d_6$) δ 11.88 (s, 1H), 10.60 (brs, 1H), 8.75 (s, 2H), 7.72 (s, 1H), 7.65 (d, J=7.6 Hz, 1H), 7.42-7.00 (m, 4H), 5.05 (d, J=7.2 Hz, 1H), 4.68-4.58 (m, 2H), 4.21-4.05 (m, 2H), 2.94 (d, J=8.8 Hz, 2H), 2.69-2.67 (m, 1H), 2.34-2.30 (m, 2H), 2.20 (s, 3H), 2.06-1.93 (m, 3H), 1.85-1.66 (m, 5H), 1.54-1.52 (m, 3H), 1.45-1.40 (m, 5H), 1.30-1.26 (m, 8H); MS (ESI) m/z: 820.3 $[M+H]^+$.

B85

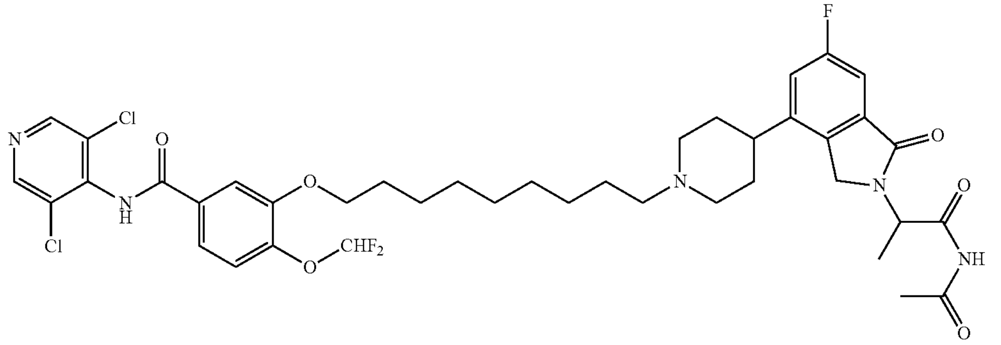

(2S,4R)-1-((S)-2-(9-(2-(Cyclopropylmethoxy)-5-((3,5-dichloropyridin-4-yl)carbamoyl)phenoxy)nonanamido)-3,3-dimethylbutanoyl)-4-hydroxy-N-(4-(4-methylthiazol-5-yl)benzyl)pyrrolidine-2-carboxamide B86. $^1H$ NMR (400 MHz, DMSO-$d_6$) δ 10.37 (s, 1H), 8.95 (s, 1H), 8.71 (s, 2H), 8.53 (s, 1H), 7.82 (d, J=8.4 Hz, 1H), 7.62 (d, J=7.6 Hz, 1H), 7.40-7.37 (m, 5H), 7.08 (d, J=8.8 Hz, 1H), 5.10 (s, 1H), 4.71-4.68 (m, 1H), 4.52 (d, J=9.2 Hz, 1H), 4.42-4.38 (m, 2H), 4.33 (s, 1H), 4.19 (dd, J=4.0 Hz, 15.6 Hz, 1H), 4.02-3.63 (m, 2H), 3.33 (s, 2H), 2.48-2.42 (m, 5H), 2.26-2.28 (m, 1H), 2.10-2.08 (m, 4H), 2.04-2.02 (m, 1H), 1.88-1.86 (m, 3H) 1.76-1.72 (m, 1H), 1.64-1.59 (m, 4H), 1.48-1.40 (m, 7H), 1.25 (s, 9H); MS (ESI) m/z: 924.2 $[M+H]^+$.

B86

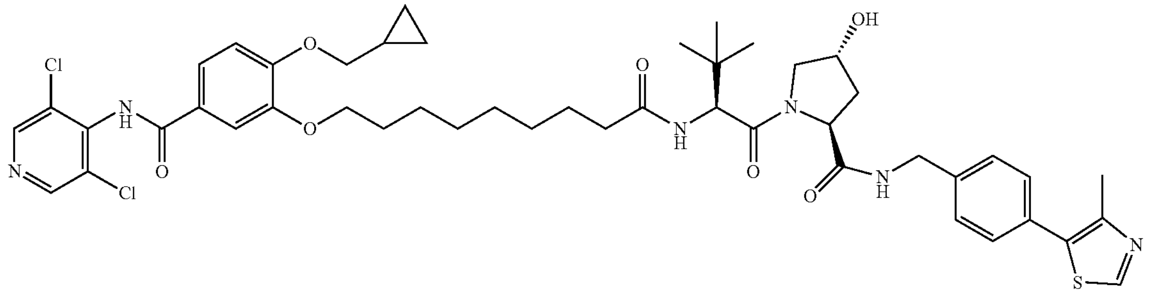

5-(3-(Cyclopentyloxy)-4-((7-(4-(2-(2,6-dioxopiperidin-3-yl)-6-fluoro-1-oxoisoindolin-4-yl)piperidin-1-yl)heptyl)oxy)phenyl)-4H-thieno[2,3-c]pyrrole-4,6(5H)-dione B87. $^1H$ NMR (400 MHz, DMSO-$d_6$) δ 10.99 (s, 1H), 8.28 (d, J=4.8 Hz, 1H), 7.55 (d, J=4.8 Hz, 1H), 7.40-7.33 (m, 2H), 7.05-7.01 (m, 2H), 6.90-6.87 (m, 1H), 5.13 (dd, J=5.2, 13.6 Hz, 1H), 4.73-4.71 (m, 1H), 4.52-4.31 (m, 2H), 3.99 (t, J=6.0 Hz, 2H), 2.99-2.91 (m, 3H), 2.62-2.58 (m, 2H), 2.45-2.42 (m, 1H), 2.31 (t, J=6.4 Hz, 2H), 2.02-1.99 (m, 3H), 1.86-1.83 (m, 2H), 1.74-1.72 (m, 10H), 1.60-1.57 (m, 2H), 1.45-1.40 (m, 4H), 1.36-1.31 (m, 4H); MS (ESI) m/z: 771.3 $[M+H]^+$.

B87

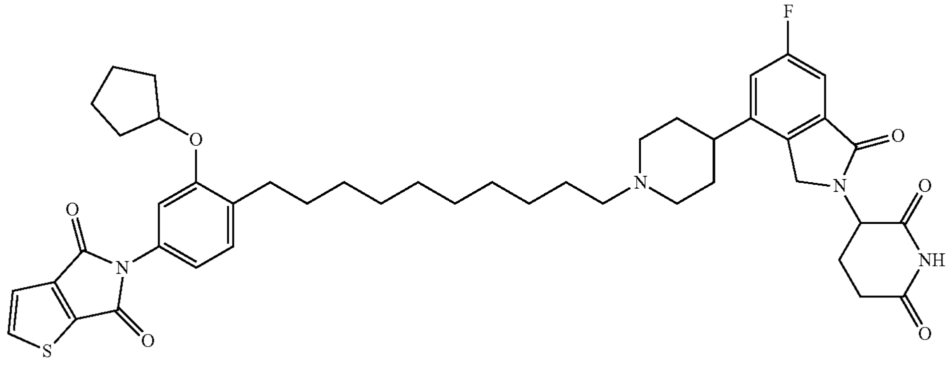

N-(3,5-Dichloropyridin-4-yl)-4-(difluoromethoxy)-3-((7-(1-(2-(2,6-dioxopiperidin-3-yl)-1,3-dioxoisoindolin-4-yl)piperidin-4-yl)heptyl)oxy)benzamide B90. $^1$H NMR (400 MHz, DMSO-$d_6$) δ 11.07 (s, 1H), 10.65 (s, 1H), 8.76 (s, 2H), 7.72 (s, 1H), 7.68-7.64 (m, 2H), 7.37-7.00 (m, 4H), 5.09 (dd, J=5.2, 12.8 Hz, 1H), 4.12 (t, J=6.4 Hz, 2H), 2.86-2.80 (m, 3H), 2.60-2.56 (m, 1H), 2.02-1.98 (m, 2H), 1.79-1.73 (m, 4H), 1.45-1.27 (m, 16H); MS (ESI) m/z: 786.2 $[M+H]^+$.

B90

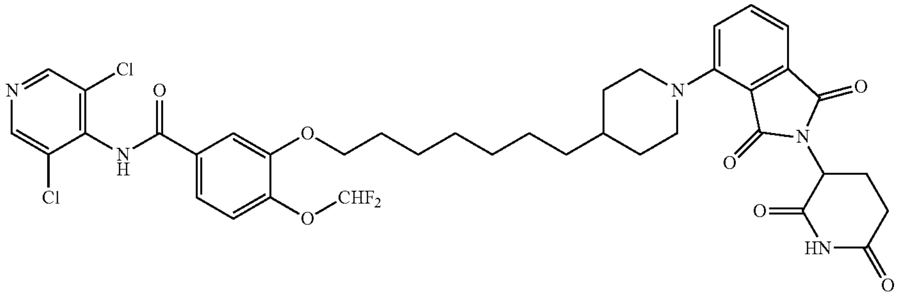

3-(4-(1-(7-(2-(Cyclopentyloxy)-4-(4-oxo-4,6-dihydro-5H-thieno[2,3-c]pyrrol-5-yl)phenoxy)heptyl)piperidin-4-yl)-6-fluoro-1-oxoisoindolin-2-yl)piperidine-2,6-dione B91. $^1$H NMR (400 MHz, DMSO-$d_6$) δ 11.00 (s, 1H), 7.70 (d, J=5.2 Hz, 1H), 7.49 (d, J=2.4 Hz, 1H), 7.39 (d, J=10.4 Hz, 1H), 7.35 (d, J=7.6 Hz, 1H), 7.23 (d, J=8.8 Hz, 1H), 7.13 (dd, J=2.4, 8.8 Hz, 1H), 6.98 (d, J=8.8 Hz, 1H), 5.13 (dd, J=5.2, 13.6 Hz, 1H), 5.04 (s, 2H), 4.79 (s, 1H), 4.43-4.31 (m, 2H), 3.94 (t, J=6.0 Hz, 2H), 3.30 (s, 3H), 2.97-2.95 (m, 2H), 2.92-2.87 (m, 1H), 2.67-2.57 (m, 2H), 2.45-2.39 (m, 1H), 2.33-2.31 (m, 2H), 2.02-1.98 (m, 2H), 1.87-1.82 (m, 2H), 1.77-1.69 (m, 8H), 1.61-1.57 (m, 2H), 1.47-1.42 (m, 4H), 1.37-1.30 (m, 4H); MS (ESI) m/z: 757.4 $[M+H]^+$.

B91

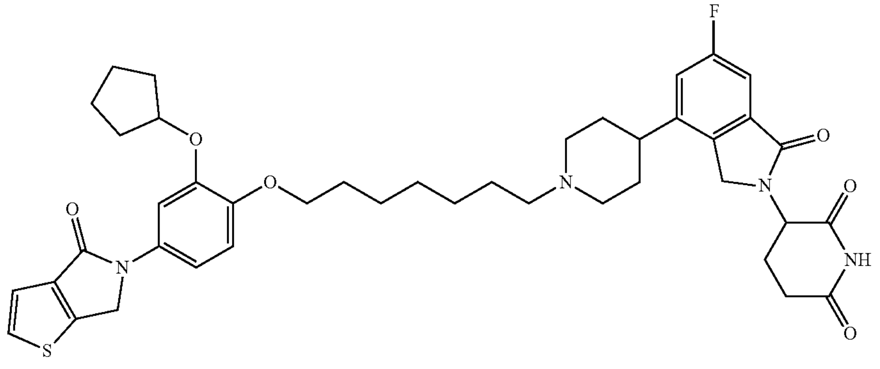

The following compounds are prepared similarly according to the synthetic procedures or methodologies exemplified herein.

8-(4-(2-(2,6-Dioxopiperidin-3-yl)-6-fluoro-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)octanamide B1.

B1

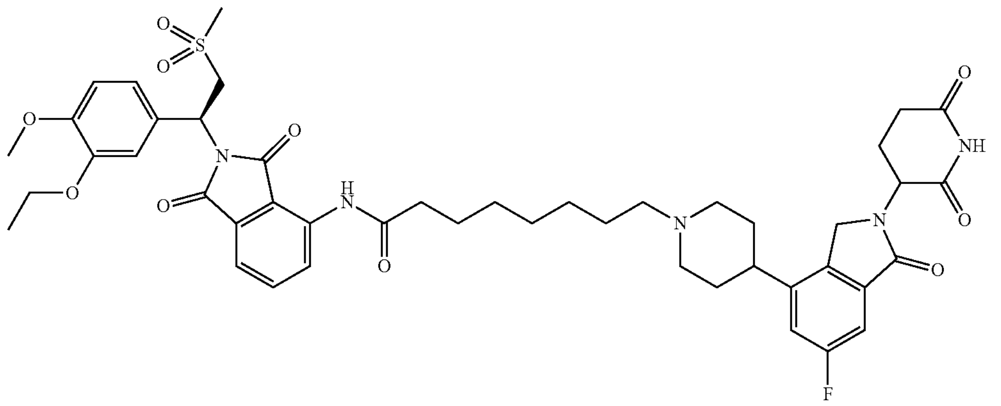

3-(7-(4-(2-(2,6-Dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B5.

B5

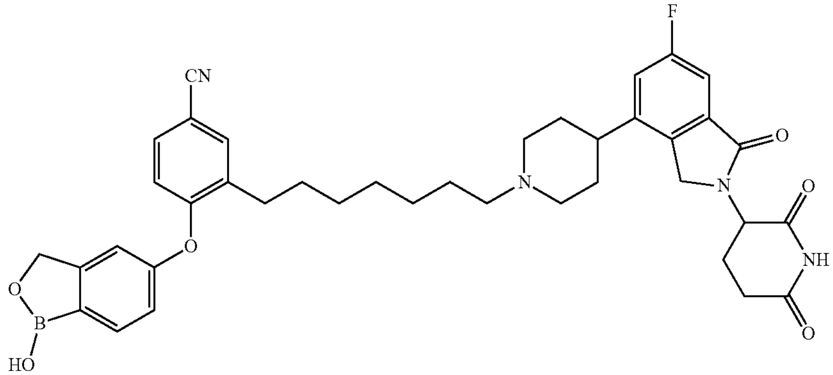

2-(7-(4-(2-(2,6-Dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B6.

B6

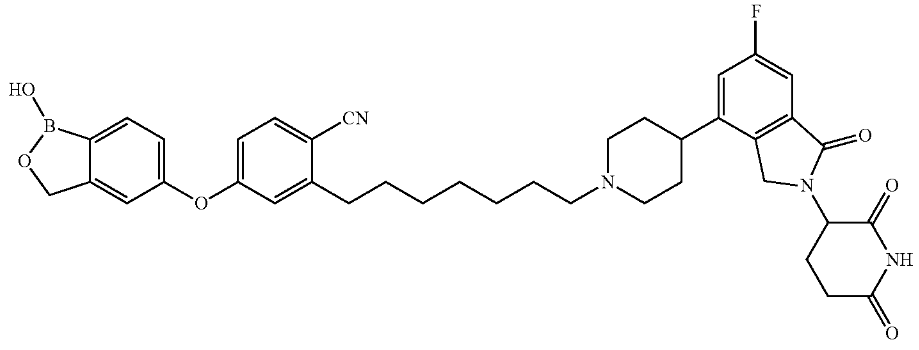

3-(4-(1-(7-((4-((3,5-Dichloropyridin-4-yl)amino)-7-methoxy-2-oxo-2H-chromen-8-yl)oxy)heptyl)piperidin-4-yl)-6-fluoro-1-oxoisoindolin-2-yl)piperidine-2,6-dione B7.

B7

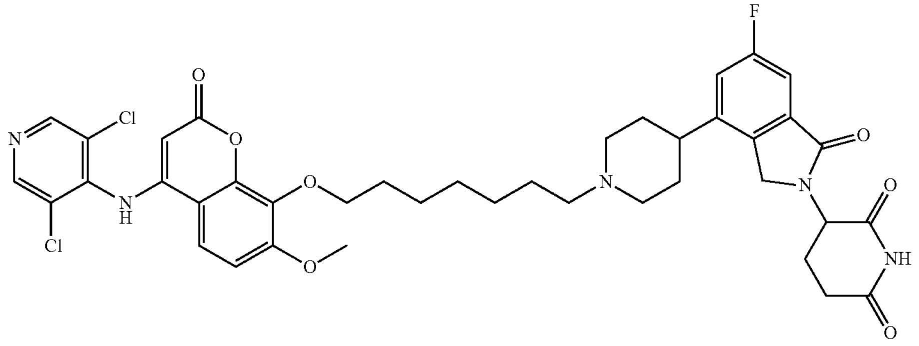

3-(2-(2-(3-((2-(2,6-Dioxopiperidin-3-yl)-1-oxoisoindolin-4-yl)amino)propoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B8.

B8

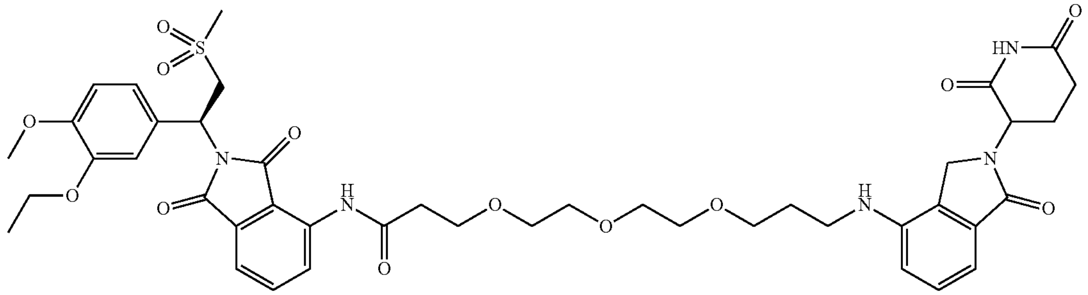

N-(6-(2-(2-(2-(3-((2-(2,6-Dioxopiperidin-3-yl)-1-oxoisoindolin-4-yl)amino)propoxy)-ethoxy)ethoxy)ethyl)-2-((S)-1-(3-ethoxy-4-methoxyphenyl)-2-(methylsulfonyl)ethyl)-1,3-dioxoisoindolin-4-yl)acetamide B9.

B9

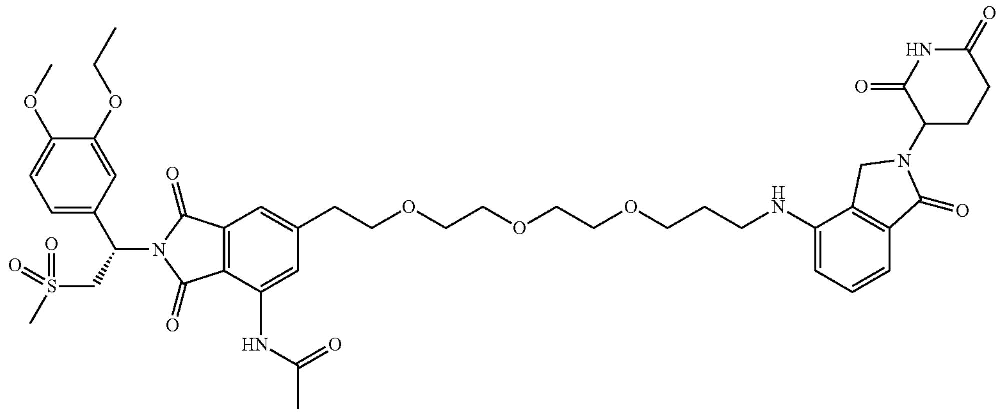

3-(Cyclopropylmethoxy)-N-(3,5-dichloropyridin-4-yl)-4-(difluoromethoxy)-N-(2-(2-(2-(3-((2-(2,6-dioxopiperidin-3-yl)-1-oxoisoindolin-4-yl)amino)propoxy)ethoxy)ethoxy)-ethyl)benzamide B10.

B10

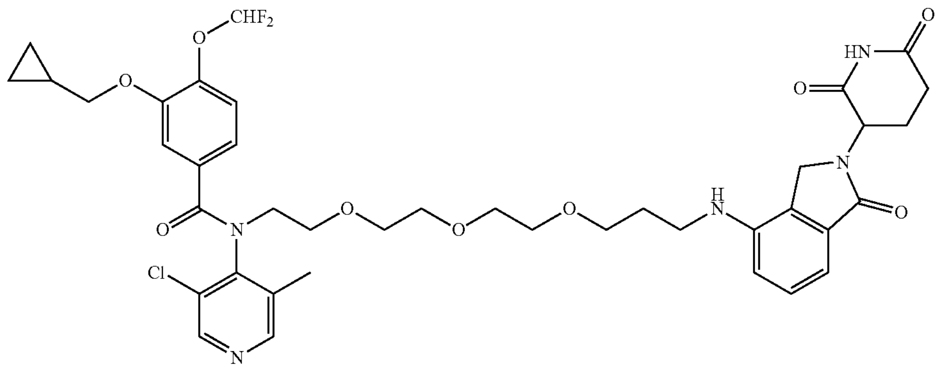

N-(3,5-Dichloropyridin-4-yl)-4-(difluoromethoxy)-3-(2-(2-(2-(3-((2-(2,6-dioxopiperidin-3-yl)-1-oxoisoindolin-4-yl)amino)propoxy)ethoxy)ethoxy)ethoxy)benzamide B11.

B11

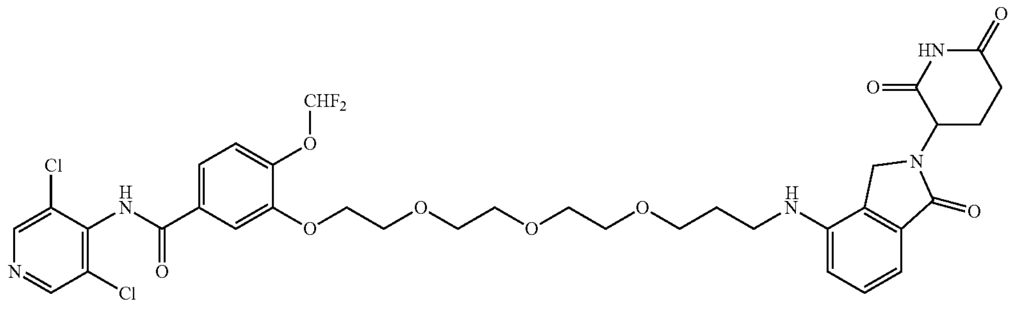

4-(2-(2-(2-(3-((2-(2,6-Dioxopiperidin-3-yl)-1-oxoisoindolin-4-yl)amino)propoxy)-ethoxy)ethoxy)ethyl)-3-((1-hydroxy-1,3-dihydrobenzo[c][1,2]oxaborol-5-yl)oxy)benzonitrile B12.

B12

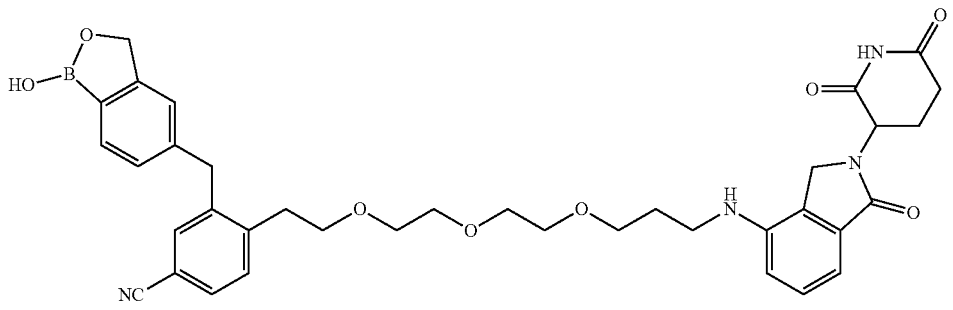

2-(2-(2-(2-(3-((2-(2,6-Dioxopiperidin-3-yl)-1-oxoisoindolin-4-yl)amino)propoxy)-ethoxy)ethoxy)ethyl)-4-((1-hydroxy-1,3-dihydrobenzo[c][1,2]oxaborol-5-yl)oxy)benzonitrile B13.

B13

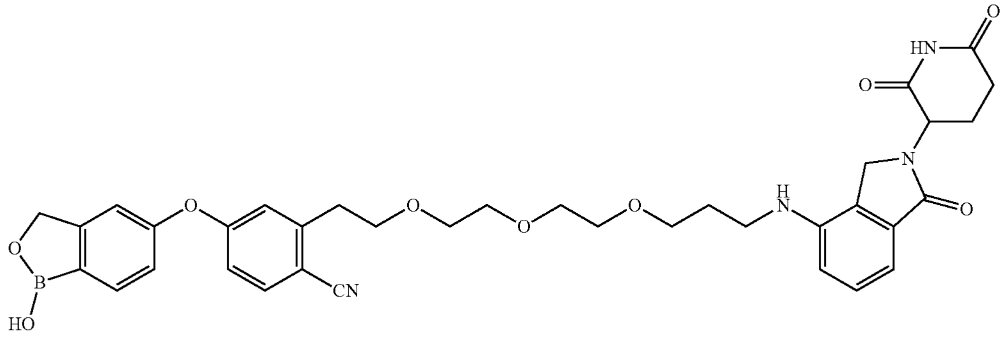

3-(4-((3-(2-(2-(2-((4-((3,5-Dichloropyridin-4-yl)amino)-7-methoxy-2-oxo-2H-chromen-8-yl)oxy)ethoxy)ethoxy)ethoxy)propyl)amino)-1-oxoisoindolin-2-yl)piperidine-2,6-dione B14.

B14

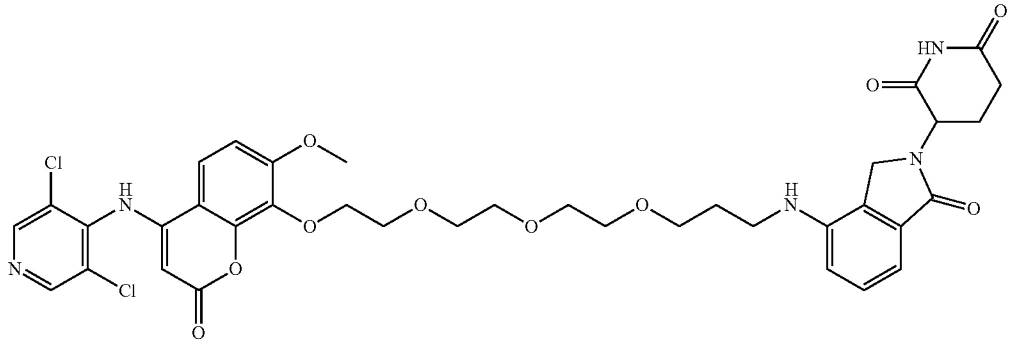

6-(4-((2-(2,6-Dioxopiperidin-3-yl)-1-oxoisoindolin-4-yl)ethynyl)piperidin-1-yl)-N-(2-((S)-1-(3-ethoxy-4-methoxyphenyl)-2-(methylsulfonyl)ethyl)-1,3-dioxoisoindolin-4-yl)-6-oxohexanamide B15.

B15

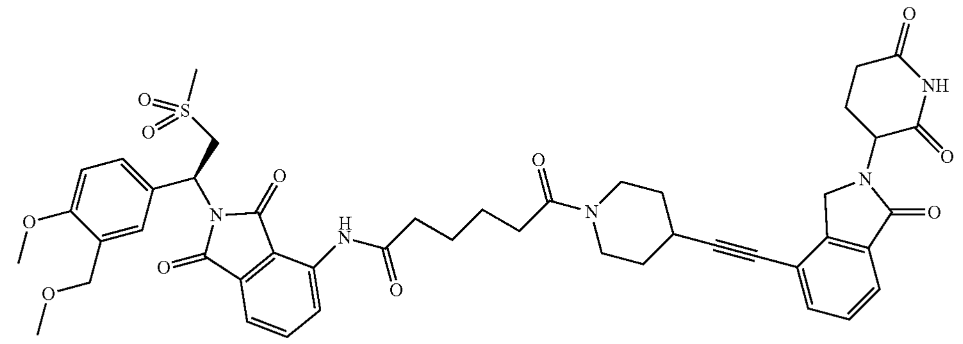

3-(Cyclopropylmethoxy)-N-(3,5-dichloropyridin-4-yl)-4-(difluoromethoxy)-N-(5-(4-((2-(2,6-dioxopiperidin-3-yl)-1-oxoisoindolin-4-yl)ethynyl)piperidin-1-yl)-5-oxopentyl)benzamide B17.

B17

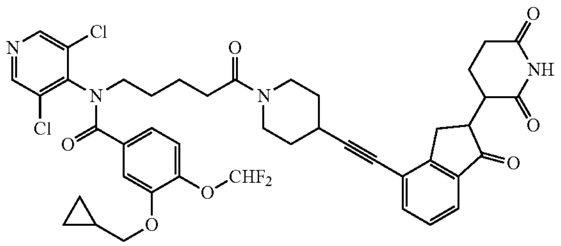

4-(5-(4-((2-(2,6-Dioxopiperidin-3-yl)-1-oxoisoindolin-4-yl)ethynyl)piperidin-1-yl)-5-oxopentyl)-3-((1-hydroxy-1,3-dihydrobenzo[c][1,2]oxaborol-5-yl)oxy)benzonitrile B19.

B19

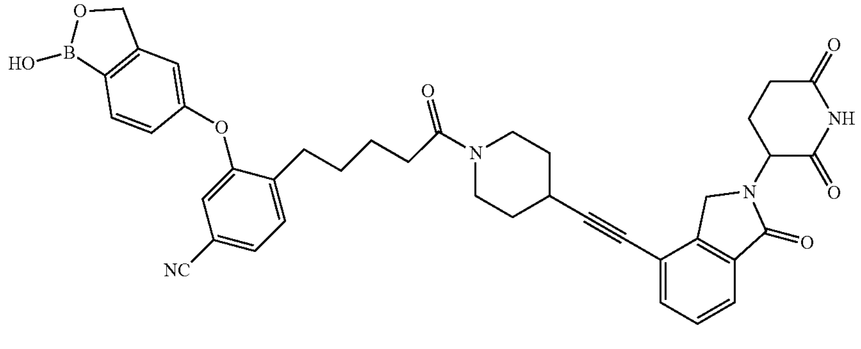

2-(5-(4-((2-(2,6-Dioxopiperidin-3-yl)-1-oxoisoindolin-4-yl)ethynyl)piperidin-1-yl)-5-oxopentyl)-4-((1-hydroxy-1,3-dihydrobenzo[c][1,2]oxaborol-5-yl)oxy)benzonitrile B20.

B20

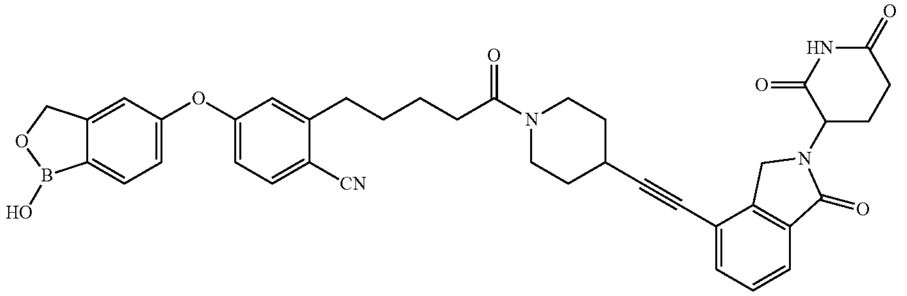

3-(4-((1-(5-((4-((3,5-Dichloropyridin-4-yl)amino)-7-methoxy-2-oxo-2H-chromen-8-yl)oxy)pentanoyl)piperidin-4-yl)ethynyl)-1-oxoisoindolin-2-yl)piperidine-2,6-dione B21.

B21

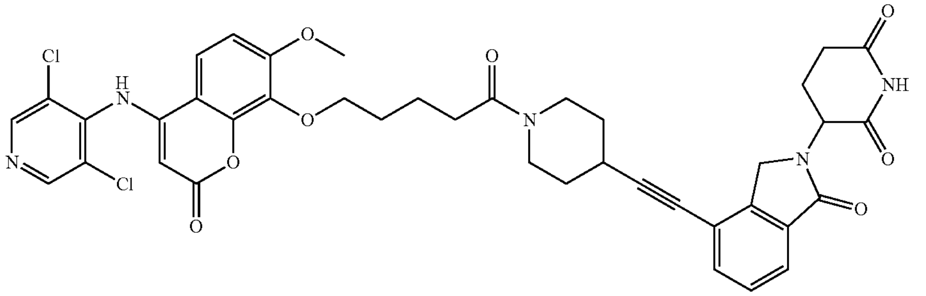

8-(4-(2-(2,6-Dioxopiperidin-3-yl)-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)octanamide B22.

B22

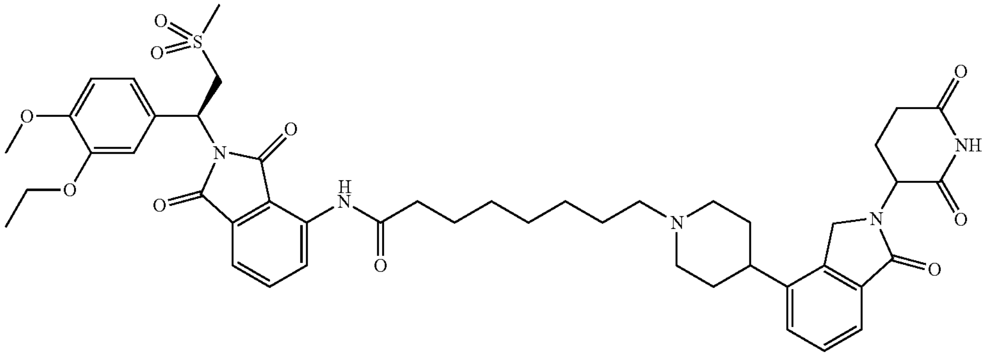

N-(6-(7-(4-(2-(2,6-Dioxopiperidin-3-yl)-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B23.

B23

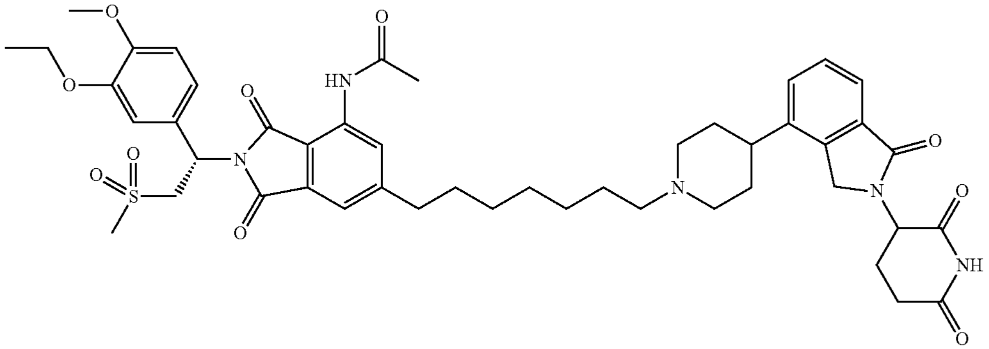

3-(Cyclopropylmethoxy)-N-(3,5-dichloropyridin-4-yl)-4-(difluoromethoxy)-N-(7-(4-(2-(2,6-dioxopiperidin-3-yl)-1-oxoisoindolin-4-yl)piperidin-1-yl)heptyl)benzamide B24.

B24

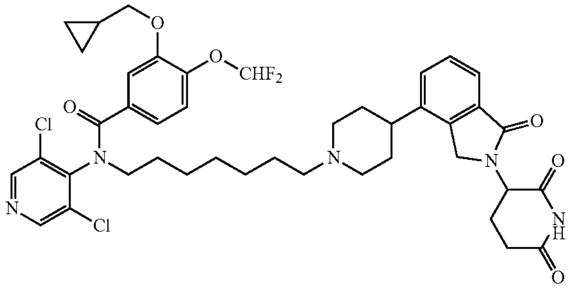

N-(3,5-Dichloropyridin-4-yl)-4-(difluoromethoxy)-3-((7-(4-(2-(2,6-dioxopiperidin-3-yl)-1-oxoisoindolin-4-yl)piperidin-1-yl)heptyl)oxy)benzamide B25.

B25

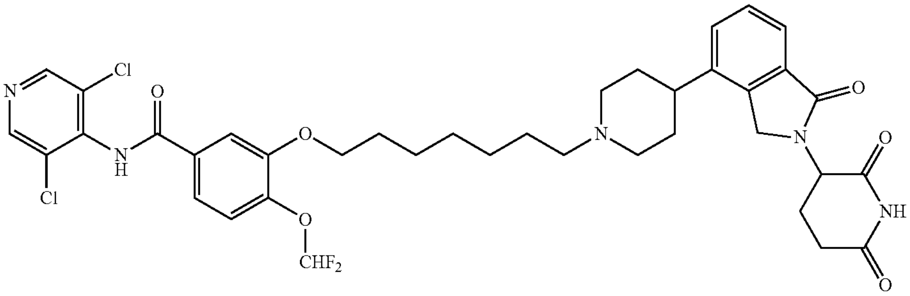

3-(7-(4-(2-(2,6-Dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B26.

B26

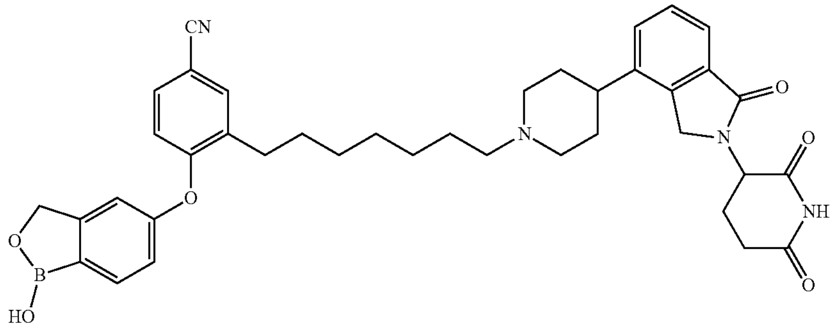

2-(7-(4-(2-(2,6-Dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B27.

B27

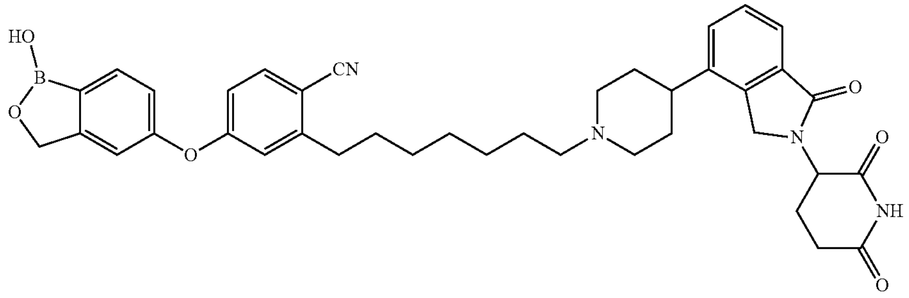

3-(4-(1-(7-((4-((3,5-Dichloropyridin-4-yl)amino)-7-methoxy-2-oxo-2H-chromen-8-yl)oxy)heptyl)piperidin-4-yl)-1-oxoisoindolin-2-yl)piperidine-2,6-dione B28.

B28

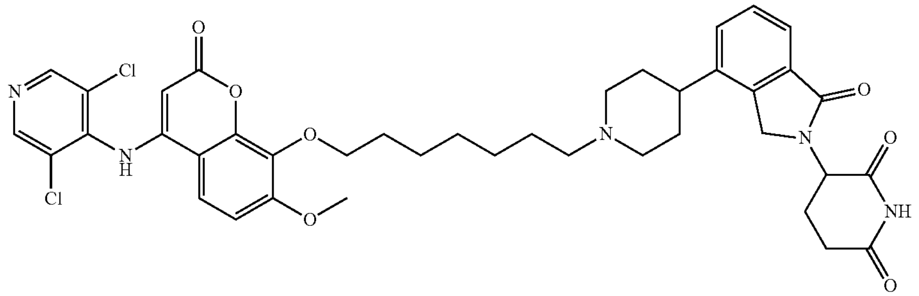

8-(4-((5-(2,6-Dioxopiperidin-3-yl)-4-oxo-5,6-dihydro-4H-thieno[3,4-c]pyrrol-1-yl)methoxy)phenyl)-N-(2-((S)-1-(3-ethoxy-4-methoxyphenyl)-2-(methylsulfonyl)ethyl)-1,3-dioxoisoindolin-4-yl)octanamide B29.

B29

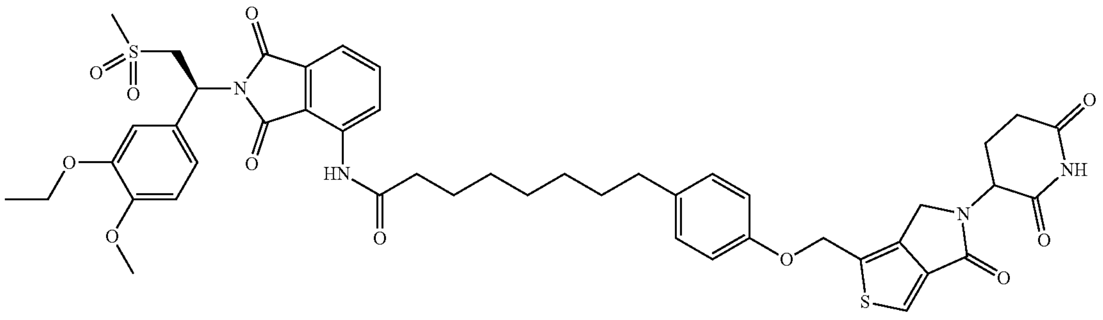

N-(6-(7-(4-((5-(2,6-Dioxopiperidin-3-yl)-4-oxo-5,6-dihydro-4H-thieno[3,4-c]pyrrol-1-yl)methoxy)phenyl)heptyl)-2-((S)-1-(3-ethoxy-4-methoxyphenyl)-2-(methylsulfonyl)ethyl)-1,3-dioxoisoindolin-4-yl)acetamide B30.

B30

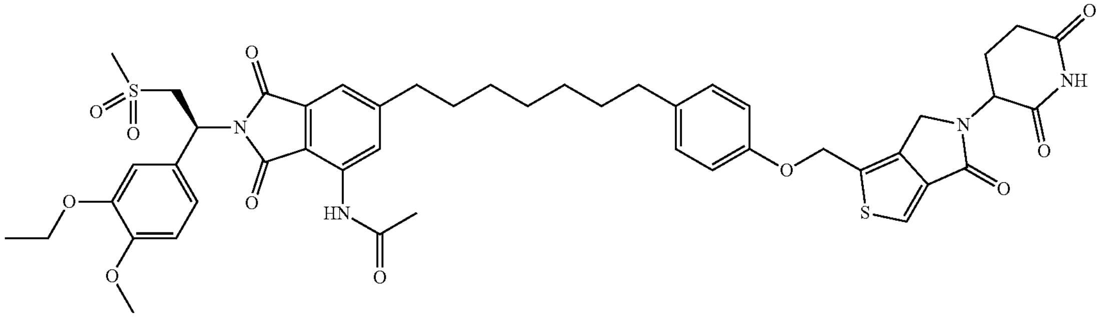

3-(Cyclopropylmethoxy)-N-(3,5-dichloropyridin-4-yl)-4-(difluoromethoxy)-N-(7-(4-((5-(2,6-dioxopiperidin-3-yl)-4-oxo-5,6-dihydro-4H-thieno[3,4-c]pyrrol-1-yl)methoxy)phenyl)-heptyl)benzamide B31.

B31

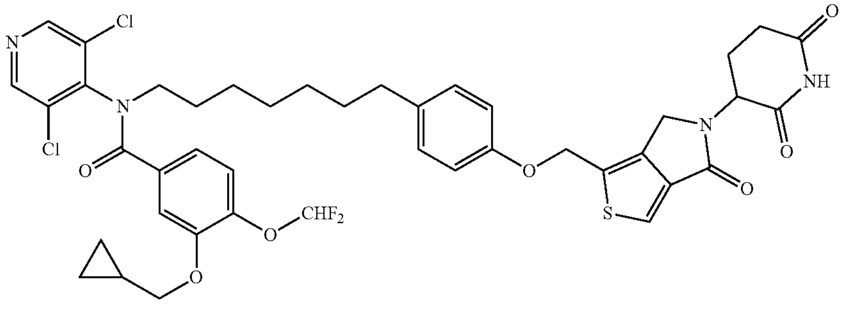

N-(3,5-Dichloropyridin-4-yl)-4-(difluoromethoxy)-3-((7-(4-((5-(2,6-dioxopiperidin-3-yl)-4-oxo-5,6-dihydro-4H-thieno[3,4-c]pyrrol-1-yl)methoxy)phenyl)heptyl)oxy)benzamide B32.

B32

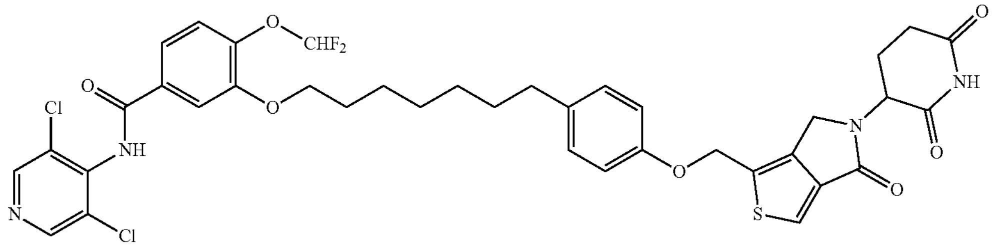

3-(7-(4-((5-(2,6-Dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B33.

B33

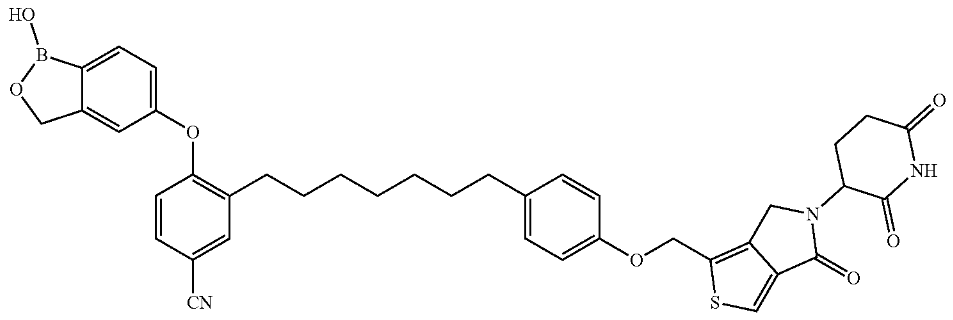

2-(7-(4-((5-(2,6-Dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B34.

B34

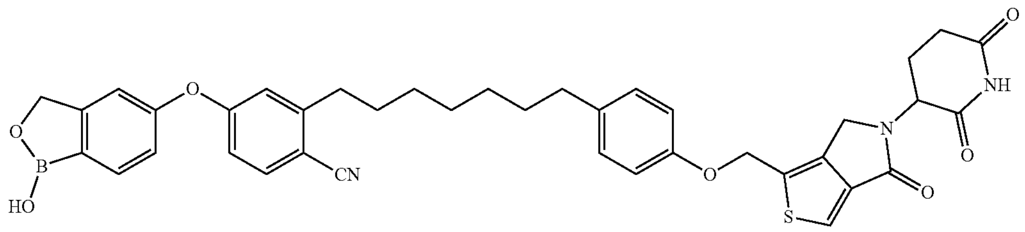

3-(1-((4-(7-((4-((3,5-Dichloropyridin-4-yl)amino)-7-methoxy-2-oxo-2H-chromen-8-yl)oxy)heptyl)phenoxy)methyl)-4-oxo-4H-thieno[3,4-c]pyrrol-5(6H)-yl)piperidine-2,6-dione B35.

B35

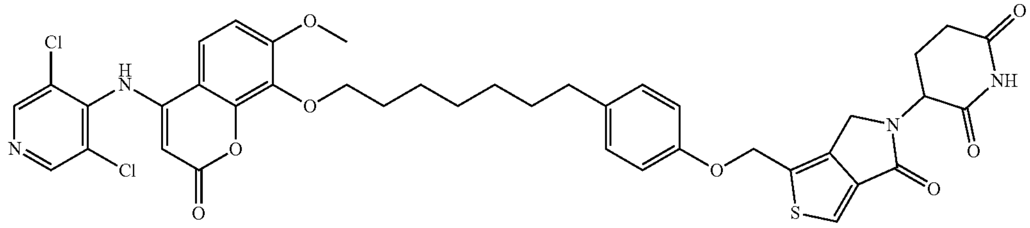

(2S,4R)-1-((S)-2-((8-((2-((S)-1-(3-Ethoxy-4-methoxyphenyl)-2-(methylsulfonyl)-ethyl)-1,3-dioxoisoindolin-4-yl) amino)-8-oxooctyl)amino)-3,3-dimethylbutanoyl)-4-hydroxy-N-(4-(4-methylthiazol-5-yl)benzyl)pyrrolidine-2-carboxamide B36.

B36

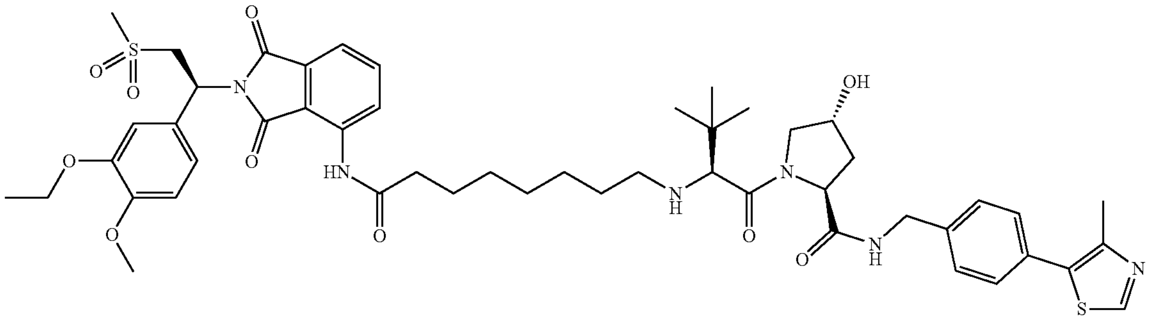

(2S,4R)-1-((S)-2-((7-(7-Acetamido-2-((S)-1-(3-ethoxy-4-methoxyphenyl)-2-(methylsulfonyl)ethyl)-1,3-dioxoisoindolin-5-yl)heptyl)amino)-3,3-dimethylbutanoyl)-4-hydroxy-N-(4-(4-methylthiazol-5-yl)benzyl)pyrrolidine-2-carboxamide B37.

B37

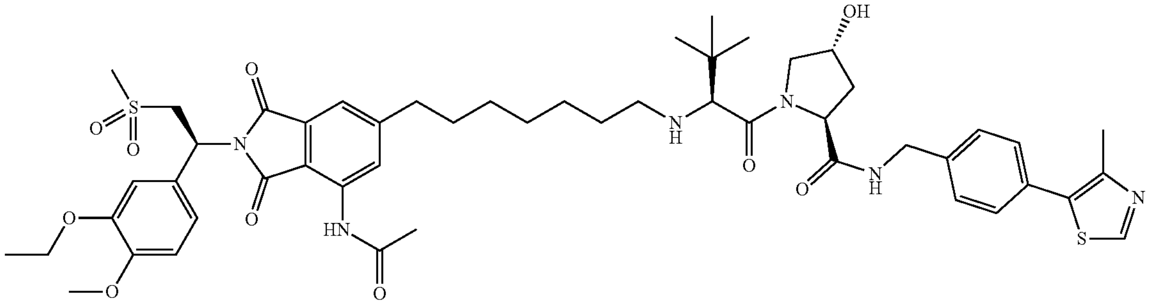

(2S,4R)-1-((S)-2-((7-(3-(Cyclopropylmethoxy)-N-(3,5-dichloropyridin-4-yl)-4-(difluoromethoxy)benzamido)heptyl)amino)-3,3-dimethylbutanoyl)-4-hydroxy-N-(4-(4-methylthiazol-5-yl)benzyl)pyrrolidine-2-carboxamide B38.

B38

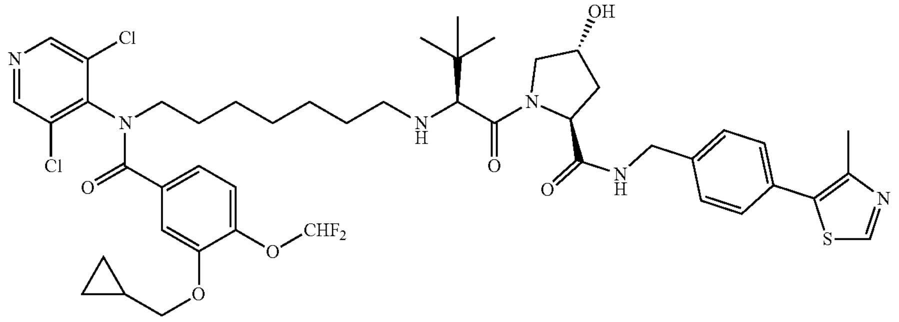

(2S,4R)-1-((S)-2-((7-(5-((3,5-Dichloropyridin-4-yl)carbamoyl)-2-(difluoromethoxy)-phenoxy)heptyl)amino)-3,3-dimethylbutanoyl)-4-hydroxy-N-(4-(4-methylthiazol-5-yl) benzyl)-pyrrolidine-2-carboxamide B39.

B39

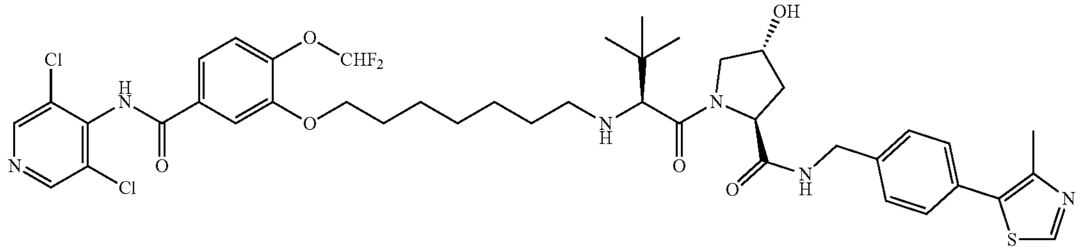

(2S,4R)-1-((S)-2-((7-(5-Cyano-2-((1-hydroxy-1,3-dihydrobenzo[c][1,2]oxaborol-5-yl)oxy)phenyl)heptyl)amino)-3,3-dimethylbutanoyl)-4-hydroxy-N-(4-(4-methylthiazol-5-yl)benzyl)pyrrolidine-2-carboxamide B40.

B40

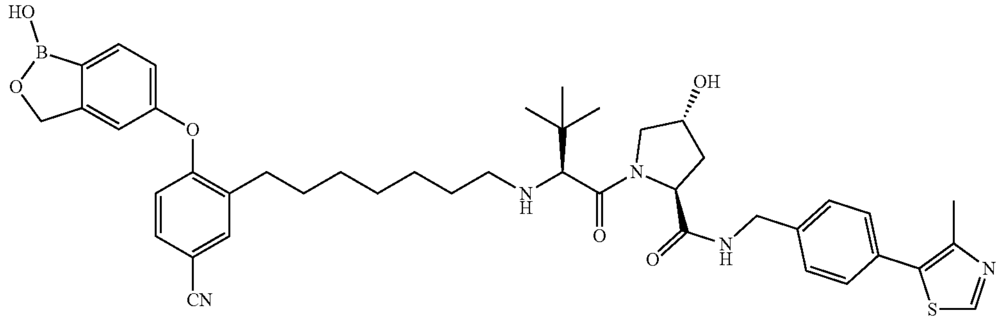

(2S,4R)-1-((S)-2-((7-(3-Cyano-5-((1-hydroxy-1,3-dihydrobenzo[c][1,2]oxaborol-5-yl)oxy)phenyl)heptyl)amino)-3,3-dimethylbutanoyl)-4-hydroxy-N-(4-(4-methylthiazol-5-yl)benzyl)pyrrolidine-2-carboxamide B41.

B41

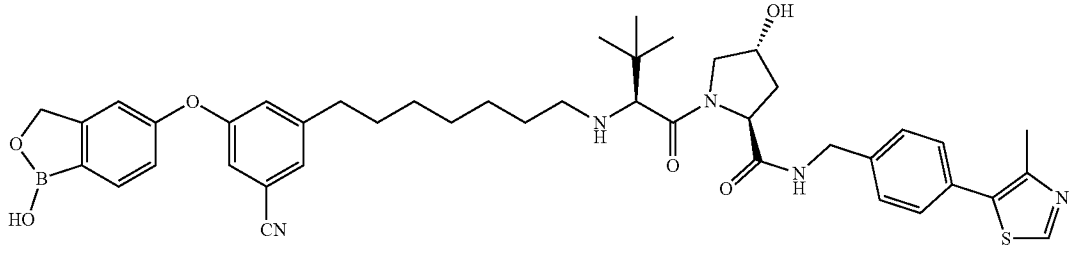

(2S,4R)-1-((S)-2-((7-((4-((3,5-Dichloropyridin-4-yl)amino)-7-methoxy-2-oxo-2H-chromen-8-yl)oxy)heptyl)amino)-3,3-dimethylbutanoyl)-4-hydroxy-N-(4-(4-methylthiazol-5-yl)benzyl)pyrrolidine-2-carboxamide B42.

B42

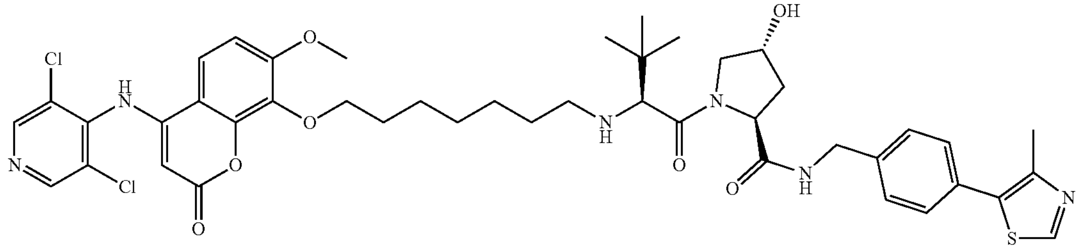

Example B1. Cell-based TNF-α Inhibition Assay

Frozen primary blood mononuclear cells (PBMCs) were quick thawed, washed once with RPMI 1640 media supplemented with 10% fetal bovine serum, 1% penicillin, and 1% streptomycin, and plated in a 96 well plate at 200,000 cells per well. The cells were pretreated with DMSO only as a control or a compound for 1 h, and then induced with LPS (lipopolysaccharide) (100 ng/mL) for 18-24 h. The supernatant was analyzed for TNF-α using the Meso Scale assay. Compound activity was determined as a percentage of the stimulated DMSO control. The results are summarized in Table 1, where A represents a percent inhibition value ≥60%; B represents a percent inhibition value <60% and ≥40%; C represents a percent inhibition value <40% and >20%; and D represents a single percent inhibition value <20%.

TABLE 1

| TNF-α Inhibition | | |
|---|---|---|
| | Compound Concentration | |
| Compound No. | 0.1 μM | 1 μM |
| A1 | D | B |
| A2 | C | C |
| A3 | C | C |
| A4 | B | A |
| A5 | D | C |
| A6 | D | C |
| A7 | D | D |
| A8 | D | D |
| A9 | B | A |
| A10 | D | A |
| A11 | C | A |
| B2 | | A |
| B3 | D | D |

TABLE 1-continued

| TNF-α Inhibition | | |
|---|---|---|
| | Compound Concentration | |
| Compound No. | 0.1 μM | 1 μM |
| B4 | A | A |
| B16 | A | A |
| B18 | A | A |
| B43 | A | A |
| B44 | | A |
| B45 | | A |
| B46 | | A |
| B47 | | A |
| B48 | | A |
| B49 | | D |
| B50 | | D |
| B51 | | C |
| B52 | | D |
| B53 | | D |
| B54 | | C |
| B55 | | C |
| B56 | | B |
| B57 | | D |
| B58 | | D |
| B59 | | D |
| B60 | | C |
| B61 | A | A |
| B62 | | D |
| B63 | A | A |
| B64 | A | A |
| B65 | | D |
| B66 | | A |
| B67 | | A |
| B68 | A | A |
| B69 | B | A |
| B70 | A | A |
| B71 | A | A |
| B72 | A | A |
| B73 | A | A |

TABLE 1-continued

TNF-α Inhibition

| | Compound Concentration | |
|---|---|---|
| Compound No. | 0.1 μM | 1 μM |
| B74 | A | A |
| B75 | A | A |
| B76 | A | A |
| B77 | B | A |
| B78 | | A |
| B79 | A | A |
| B80 | | A |
| B82 | A | A |
| B83 | | C |
| B84 | | A |
| B85 | | C |
| B86 | | A |
| B87 | | D |

Example B2. Protein Degradation Assay

A549 cells were grown in RPMI 1640 media supplemented with 10% fetal bovine serum, streptomycin, and penicillin. The cells were plated in 6-well plates in the growth media. The next day, fresh growth media were replaced on the cells. The cells were then treated with a compound for 24 h at predetermined concentrations. Whole cell extracts were prepared using an immunoprecipitation (IP) lysis buffer. Briefly, the cells were washed once in PBS, and the cell pellets were resuspended in the IP lysis buffer and incubated for 15 min on ice. Cells debris was removed by centrifugation and the cleared whole cell lysates were transferred to new tubes for further analysis.

For a western blot analysis, the whole cell protein extracts were separated on 4-12% SDS-polyacrylamide gels, transferred to nitrocellulose, and probed with primary antibodies. Membranes were subsequently washed and probed with IRDYE® secondary antibodies. The signals were detected using an ODYSSEY® Imaging System. The antibodies used in the assay included anti-PDE4B antibody; anti-PDE4D antibodies (top, bottom, and short isoform); β-actin mouse monoclonal antibody; IRDYE® 680RD goat anti-rabbit antibody; and IRDYE® 800CW goat anti-mouse antibody. Compounds B2 to B4, B18, B49 to B52, B76, B77, B79, B81 to B83, B88, B89, and B91 were determined to be able to degradate PDE4B as high as about 50% relative to DMSO. Compounds B2 to B4, B16, B18, B43, B44, B47, B51, B52, B54, B58, B70, B74 to B79, B88, and B89 were determined to be able to degradate PDE4D, in particular, PDE4D short isoform, as high as about 95% relative to DMSO; whereas apremilast did not degradate the PDE4D under the same conditions.

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (II):

$$R^{W}\text{-}L^{2}\text{-}X\text{-}L^{1}\text{-}R^{1} \quad (II)$$

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is

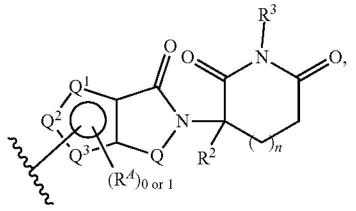

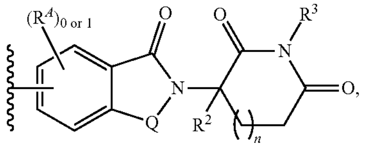

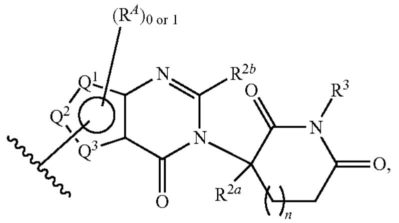

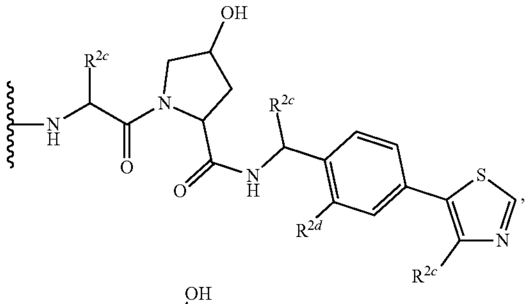

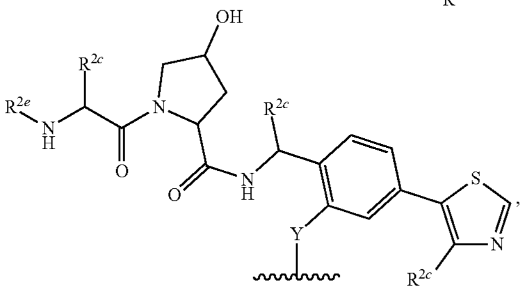

or

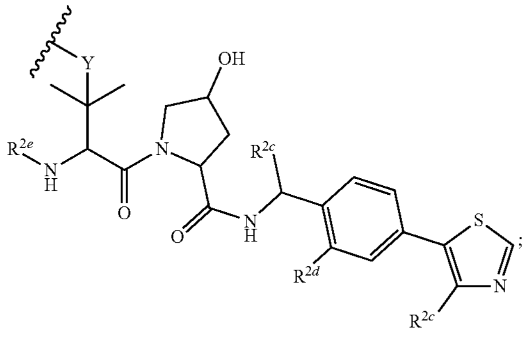

$R^W$ is
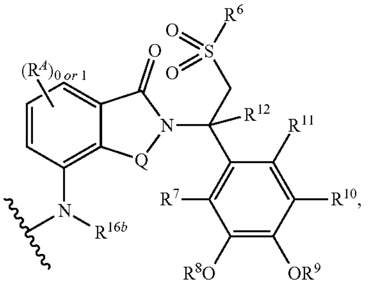
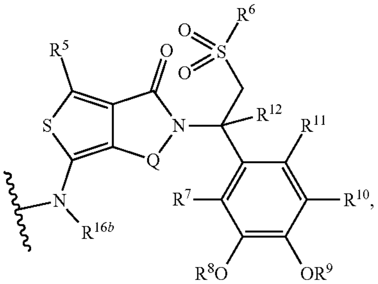
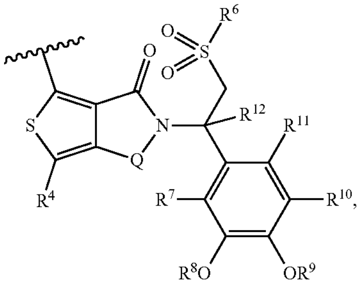
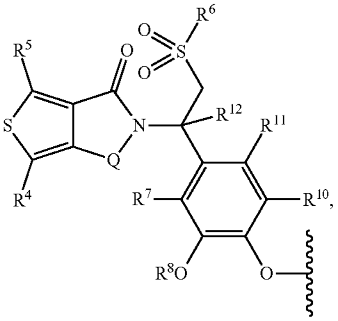
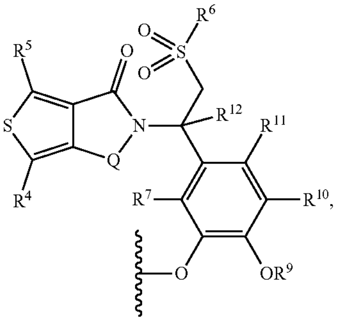
-continued
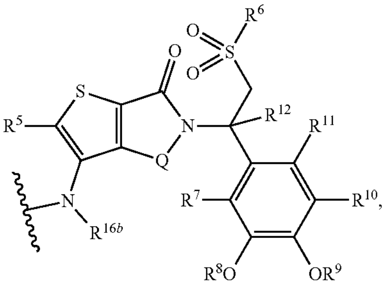
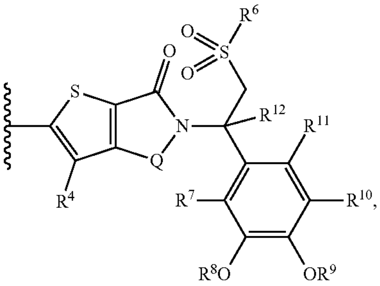
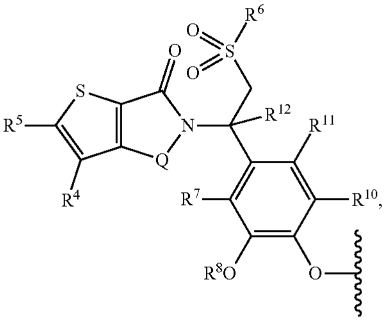
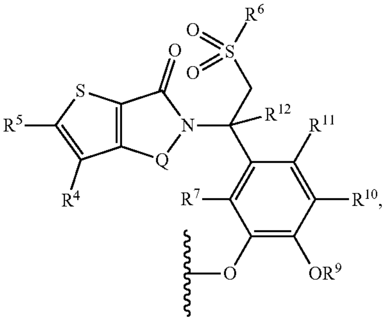
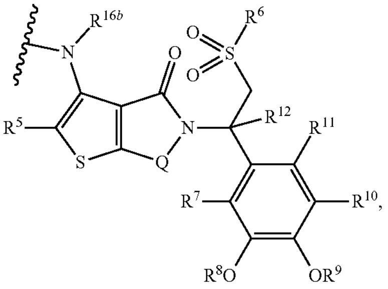

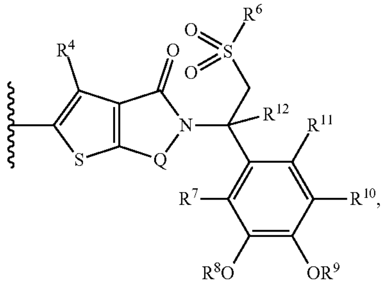
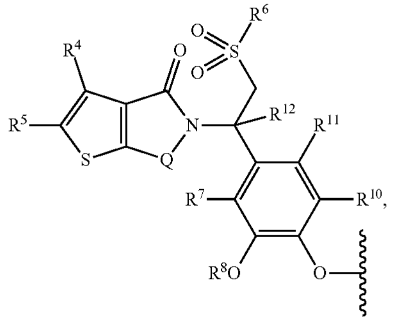
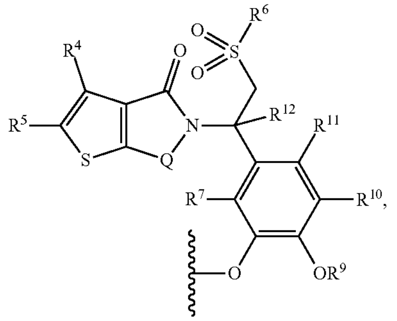
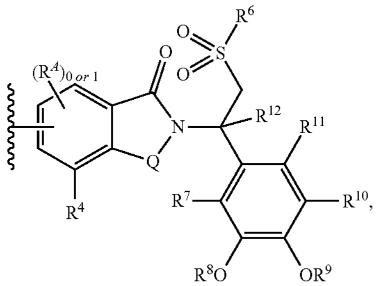
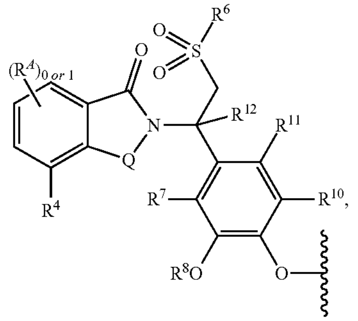
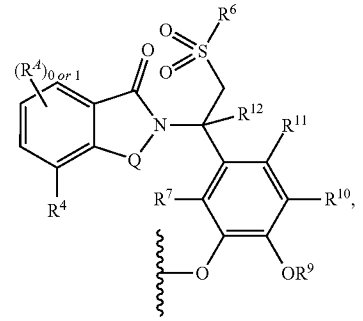
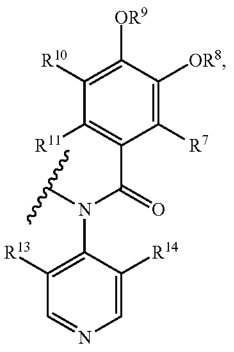
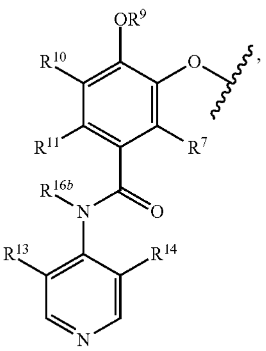
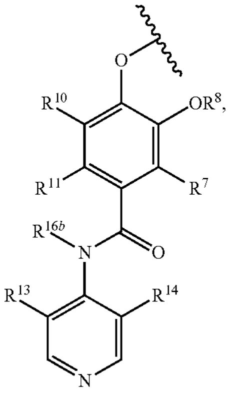
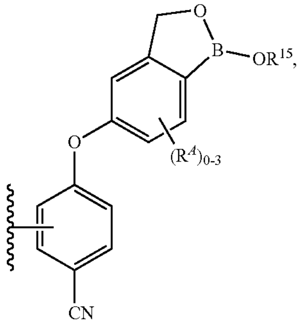
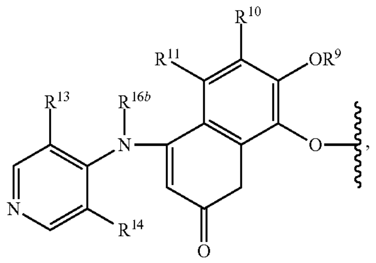

-continued

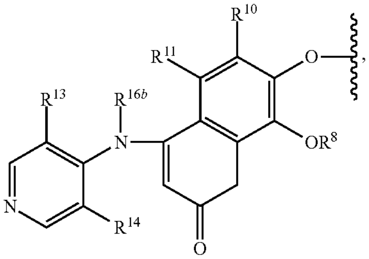

, or

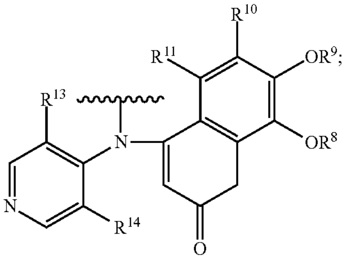

X is $C_1$-$C_{15}$ alkylene, heteroalkylene, $C_2$-$C_{10}$ alkenylene, $C_2$-$C_{10}$ alkynylene, phenylene, five to six membered heteroarylene, three to six membered heterocyclylene, or $C_3$-$C_8$ cycloalkylene, wherein each of phenylene, five to six membered heteroarylene, three to six membered heterocyclylene, or $C_3$-$C_8$ cycloalkylene is optionally substituted with one or more $R^{18}$; or X is $C_1$-$C_{15}$ alkylene, heteroalkylene, $C_2$-$C_{10}$ alkenylene, or $C_2$-$C_{10}$ alkynylene, wherein one or more methylene repeating units is replaced by a ring structure selected from the group consisting of phenylene, five to six membered heteroarylene, three to six membered heterocyclylene, or $C_3$-$C_8$ cycloalkylene, and wherein each ring structure is optionally substituted with one or more $R^{18}$;

each Y is independently $CH_2$, O, S, or NH;

$L^1$ is a bond,

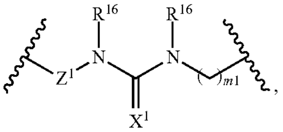

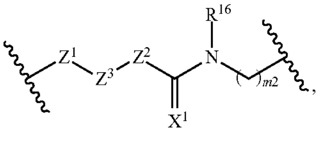

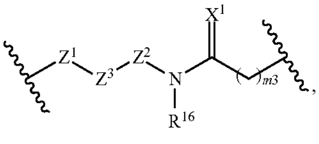

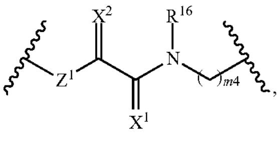

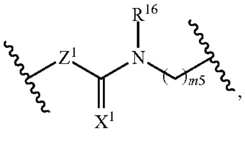

-continued

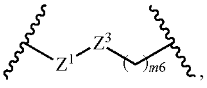

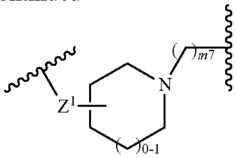

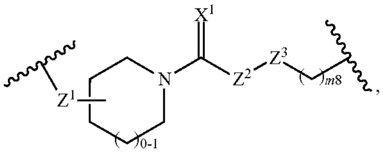

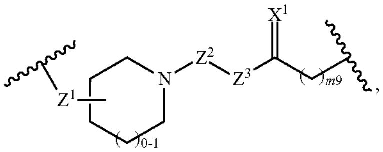

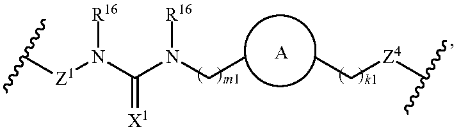

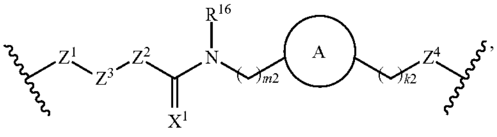

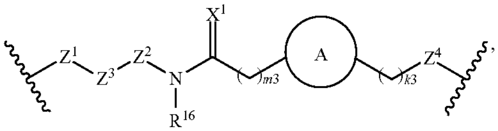

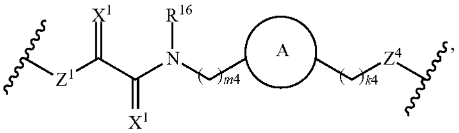

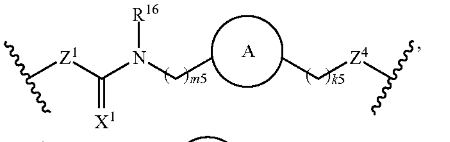

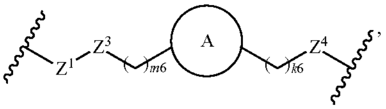

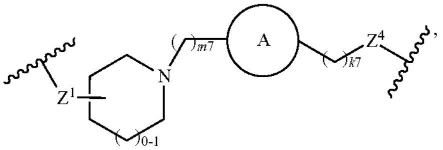

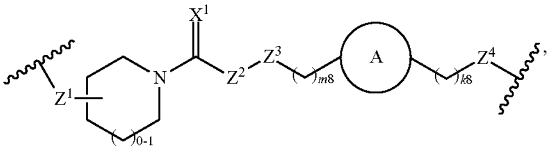

or

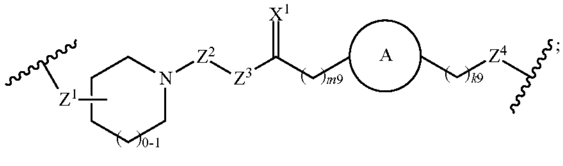

$L^2$ is a bond, —O—, —S—, —$NR^{16a}$—, —$(CH_2)_{1-3}$—, —C(═O)—, or —$(CH_2)_{0-3}C(=O)NR^{16a}$—;

each Q is independently $CH_2$ or C(═O);

each of $Q^1$, $Q^2$, and $Q^3$ is independently S or CH, provided that one of $Q^1$, $Q^2$, and $Q^3$ is S;

each $R^A$ is independently halogen, deuterium, hydroxyl, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C═O)$NR^{17a}R^{17b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl; and $R^B$ is H or $R^A$;

each of $R^2$, $R^{2a}$ and $R^{2b}$ is independently H, deuterium, halogen, or $C_1$-$C_6$ alkyl;

each $R^{2c}$ is independently H, $C_1$-$C_6$ alkyl, or $C_3$-$C_8$ cycloalkyl, wherein the $C_3$-$C_8$ cycloalkyl is optionally substituted with $C_1$-$C_6$ alkyl, halogen, or $C_1$-$C_6$haloalkyl;

each $R^{2d}$ is independently H, OH, halogen, —O—$C_1$-$C_6$ alkyl, —O—$C_1$-$C_6$ haloalkyl, or —O—$C_3$-$C_8$ cycloalkyl, wherein —O—$C_3$-$C_8$ cycloalkyl is optionally substituted with $C_1$-$C_6$ alkyl, halogen, or $C_1$-$C_6$ haloalkyl;

each $R^{2e}$ is independently —C(═O)—$C_1$-$C_6$ alkyl or —C(═O)—$C_3$-$C_8$ cycloalkyl, each optionally substituted with one or more substituents, each of which is independently selected from the group consisting of cyano, halogen, hydroxyl, amino, and $C_1$-$C_6$ haloalkyl;

each $R^3$ is independently H, deuterium, $C_1$-$C_6$ alkyl,

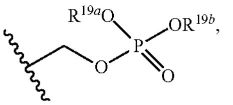

or

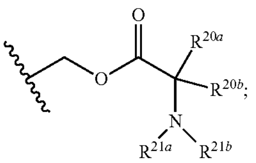

each $R^4$ is independently —$NR^{4A}R^{4B}$, —$NR^{4A}C(=O)R^{4C}$, —$NR^{4A}SO_2R^{4C}$, or —$N(C(=O)R^{4A})(C(=O)R^{4C})$;

each of $R^{4A}$ and $R^{4B}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl;

each $R^{4C}$ is independently $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^5$ is independently H, deuterium, halogen, or optionally substituted $C_1$-$C_6$ alkyl;

each $R^6$ is independently $C_1$-$C_6$ alkyl, hydroxyl, —$NR^{4A}R^{4B}$, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^7$, $R^{10}$, and $R^{11}$ is independently H, deuterium, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^8$ and $R^9$ is independently optionally substituted $C_1$-$C_6$ alkyl, $C_1$-$C_6$ haloalkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

each $R^{12}$ is independently H or deuterium;

each of $R^{13}$ and $R^{14}$ is independently halogen, hydroxyl, cyano, nitro, optionally substituted $C_1$-$C_6$ alkyl, $C_1$-$C_6$ haloalkyl, $C_1$-$C_6$ alkoxy, $C_1$-$C_6$ haloalkoxy, optionally substituted amino, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^{15}$, $R^{16}$, $R^{16a}$, and $R^{16b}$ is independently H or $C_1$-$C_6$ alkyl;

each $R^{17a}$ and $R^{17b}$ is independently H or $C_1$-$C_6$ alkyl, or $R^{17a}$ and $R^{17b}$ together with the nitrogen atom to which they are attached form 5 or 6 membered heterocyclyl, each optionally substituted with one or more $R^{18}$;

each $R^{18}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy) $C_1$-$C_6$ alkyl, —O—($C_1$-$C_6$ alkoxy)$C_1$-$C_6$ alkyl, optionally substituted amino, halogen, or cyano; or two geminal $R^{18}$ form oxo;

each of $R^{19a}$ and $R^{19b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{20a}$ and $R^{20b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{21a}$ and $R^{21b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each of $X^1$ and $X^2$ is independently O or S;

each $Z^1$ is independently a bond, —$(CR^aR^b)_{q1}$—, —C(═O)—, —CH═CH—, or —C≡C—;

each $Z^2$ is independently —$(CR^cR^d)_{q2}$—;

each of $Z^3$ and $Z^4$ is independently $NR^{16}$, O, S, or a bond;

each of $R^a$, $R^b$, $R^c$, and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each Ring A is independently phenylene, five to six membered heteroarylene, three to six membered heterocyclylene, or $C_3$-$C_8$ cycloalkylene, each optionally substituted with one or more $R^{18}$;

each of m1, m2, m3, m4, m5, m6, m7, m8, m9, k1, k2, k3, k4, k5, k6, k7, k8, and k9 is independently an integer of 0, 1, 2, 3, 4, or 5;

each n is independently an integer of 0, 1, or 2; and each q1 and q2 is independently an integer of 1, 2, or 3.

2. The compound of claim 1, wherein $R^1$ is

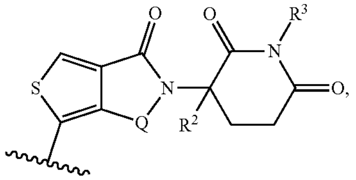

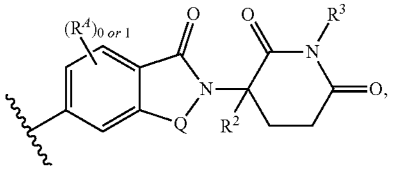

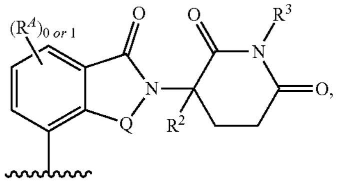

-continued

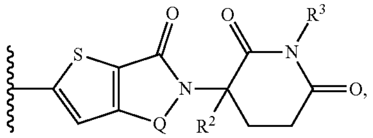

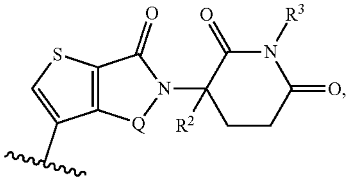

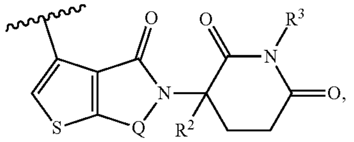

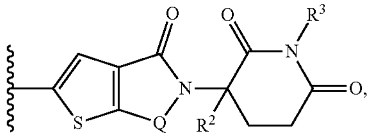

or

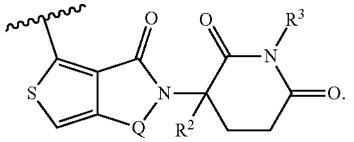

3. The compound of claim 1, having the structure of Formula (III):

(III)

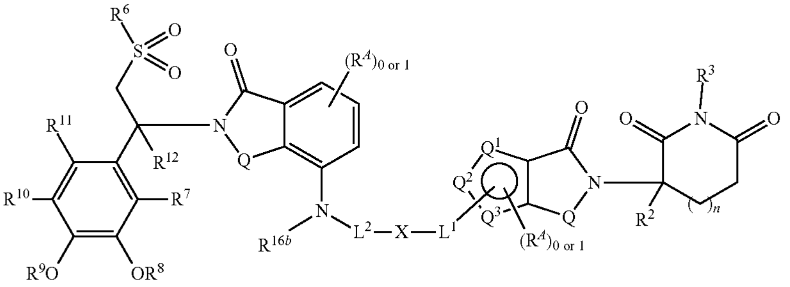

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

4. The compound of claim 1, having the structure of Formula (IV):

(IV)

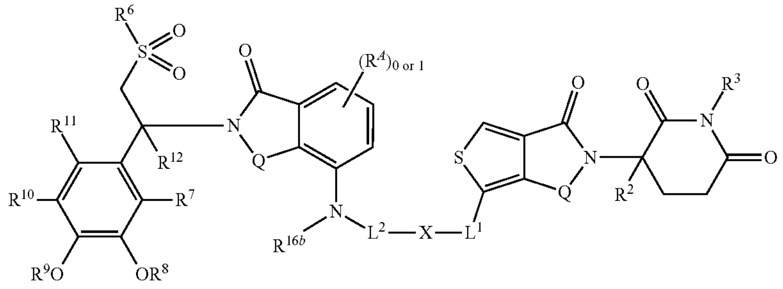

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

5. The compound of claim 1, having the structure of Formula (XV):

(XV)

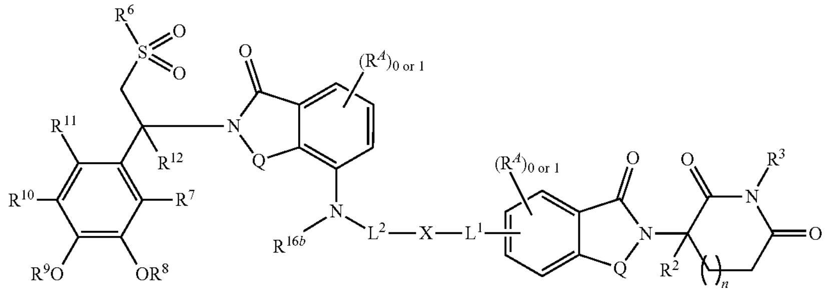

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

6. The compound of claim 1, having the structure of Formula (XVI):

(XVI)

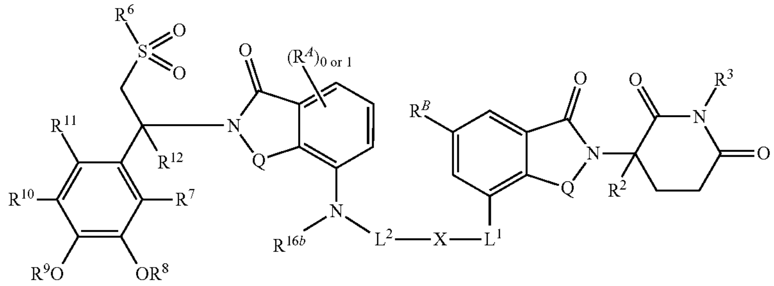

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

7. The compound of claim 1, having the structure of Formula (XXVII):

(XXVII)

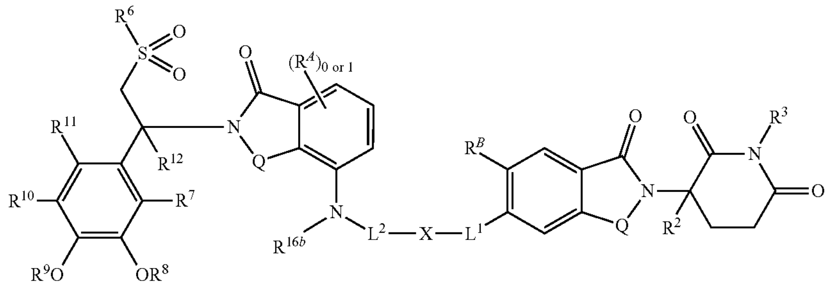

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

8. The compound of claim 1, having the structure of Formula (V):

(V)

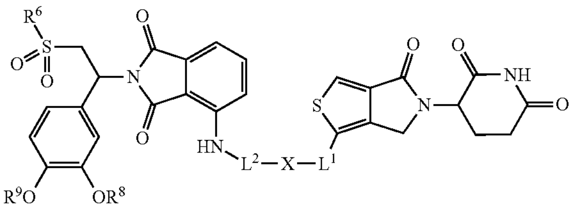

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

9. The compound of claim 6, having the structure of Formula (XVII):

(XVII)

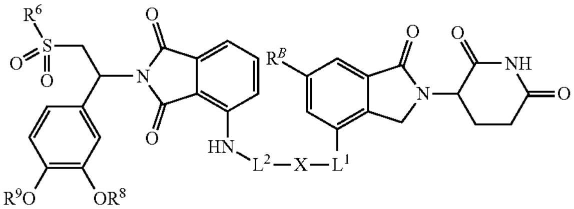

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

10. The compound of claim 7, having the structure of Formula (XXVIII):

(XXVIII)

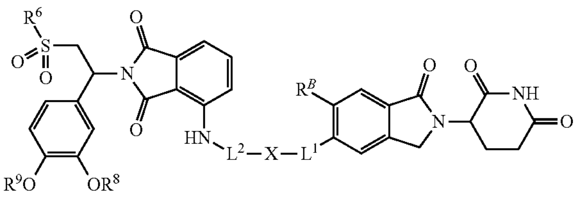

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

11. The compound of claim 1, having the structure of Formula (IX):

(IX)

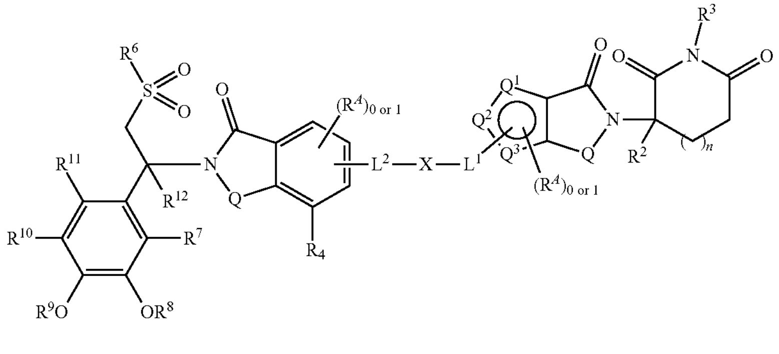

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

12. The compound of claim 1, having the structure of Formula (X):

(X)

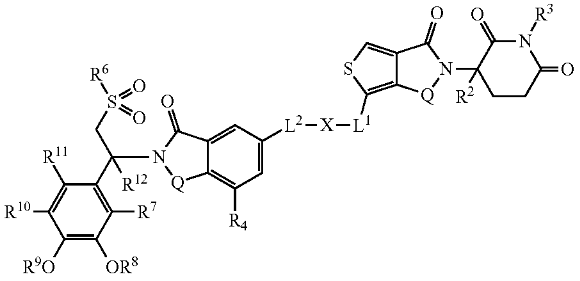

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

13. The compound of claim 1, having the structure of Formula (XXI):

(XXI)

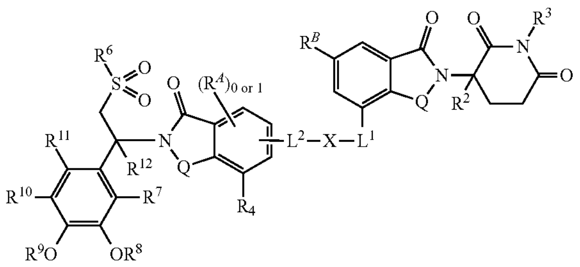

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

14. The compound of claim 13, having the structure of Formula (XXII):

(XXII)

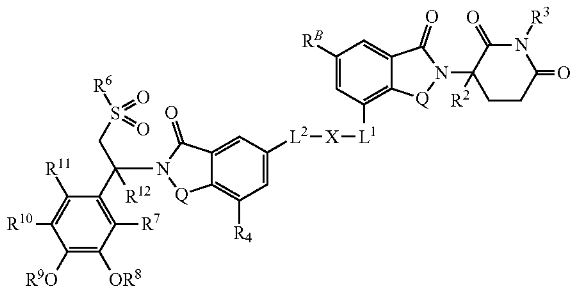

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

15. The compound of claim 1, having the structure of Formula (XXXII):

(XXXII)

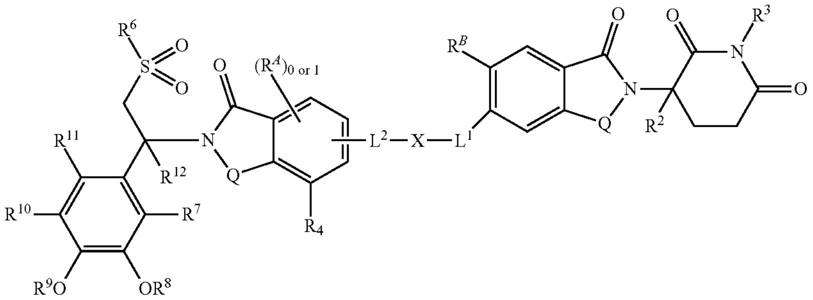

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

16. The compound of claim 15, having the structure of Formula (XXXIII):

(XXXIII)

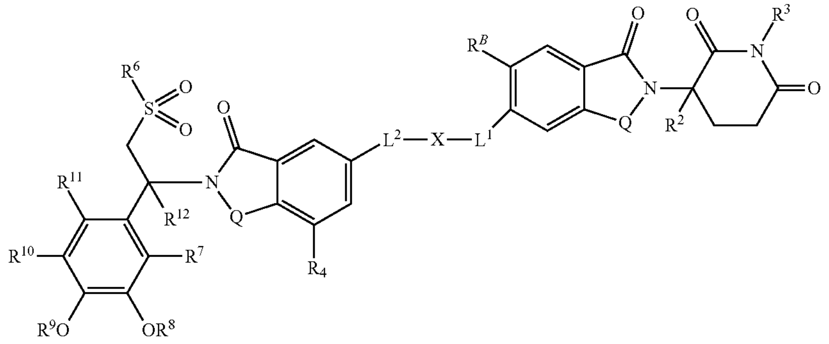

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

17. The compound of claim 12, having the structure of Formula (XI):

(XI)

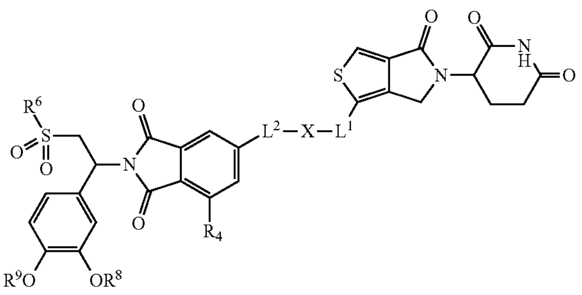

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

18. The compound of claim 14, having the structure of Formula (XXIII):

(XXIII)

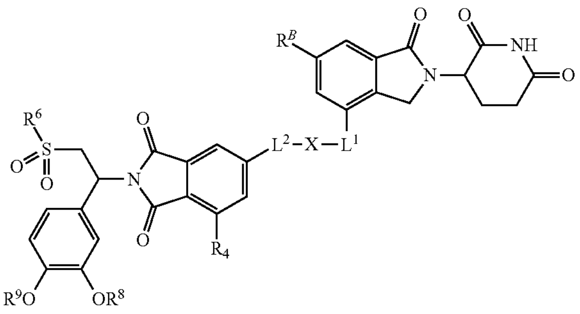

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

19. The compound of claim 16, having the structure of Formula (XXXIV):

(XXXIV)

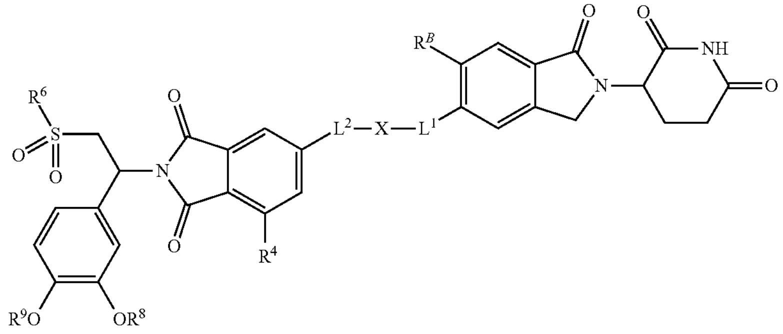

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

20. The compound of claim 1, having the structure of Formula (XXXVIII):

(XXXVIII)

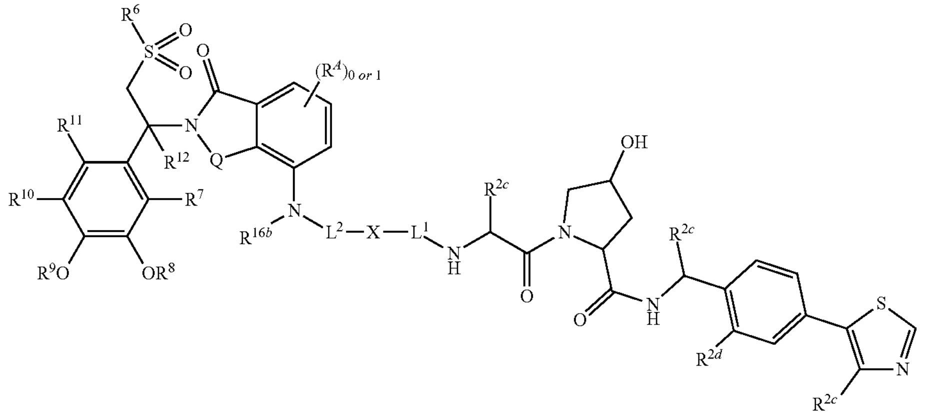

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

21. The compound of claim 1, wherein $R^6$ is optionally substituted $C_1$-$C_6$ alkyl or optionally substituted $C_3$-$C_7$ cycloalkyl.

22. The compound of claim 1, wherein $R^6$ is methyl.

23. The compound of claim 1, wherein $R^8$ is optionally substituted $C_1$-$C_6$ alkyl or optionally substituted $C_3$-$C_7$ cycloalkyl.

24. The compound of claim 1, wherein $R^8$ is ethyl.

25. The compound of claim 1, wherein $R^9$ is optionally substituted $C_1$-$C_6$ alkyl or optionally substituted $C_3$-$C_7$ cycloalkyl.

26. The compound of claim 1, wherein $R^9$ is methyl.

27. The compound of claim 1, wherein $L^1$ is a bond,

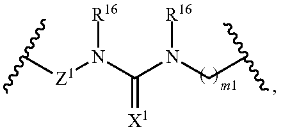

-continued

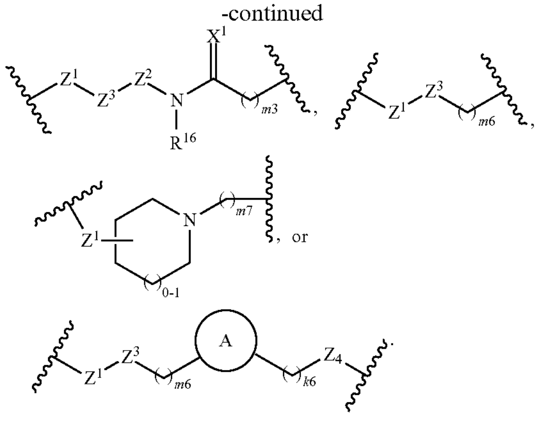

28. The compound of claim 1, wherein $L^1$ is a bond, —NH—, pyrrolidin-1,3-diyl, piperidin-1,3-diyl, piperidin-1,4-diyl,

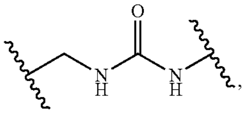, 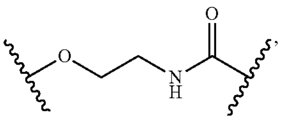,

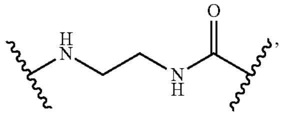,

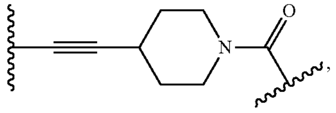, or

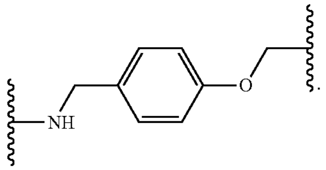.

29. The compound of claim 1, wherein $L^2$ is a bond, —O—, —$NR^{16a}$—, —$(CH_2)_{1-3}$—, —C(=O)—, or —$(CH_2)_{0-3}C(=O)NR^{16a}$—.

30. The compound of claim 1, wherein $L^2$ is a bond, —O—, —NH—, or —C(=O)NH—.

31. The compound of claim 1, wherein X is $C_1$-$C_{15}$ alkylene or heteroalkylene.

32. The compound of claim 1, wherein X is $C_1$-$C_{15}$ alkylene or heteroalkylene, where one or more methylene repeating units is replaced by a ring structure, each ring structure independently selected from the group consisting of phenylene, five to six membered heteroarylene, five to six membered heterocyclylene, and $C_3$-$C_8$ cycloalkylene.

33. The compound of claim 1, wherein X is propan-1,3-diyl, butan-1,4-diyl, pentan-1,5-diyl, hexan-1,6-diyl, heptan-1,7-diyl, octan-1,8-diyl, nonan-1,9-diyl, decan-1,10-diyl, undecan-1,11-diyl, dodecan-1,12-diyl, hept-1-yn-1,7-diyl,

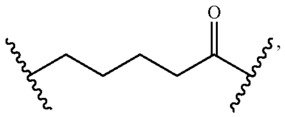,

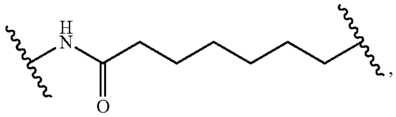,

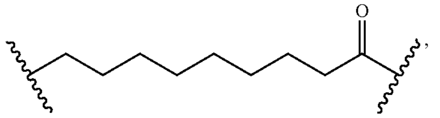,

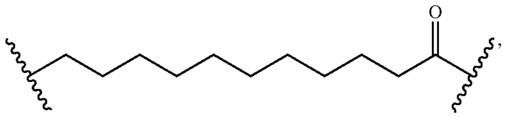,

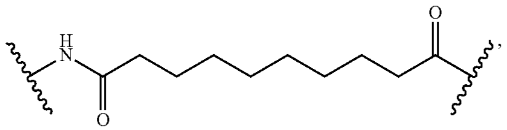,

-continued

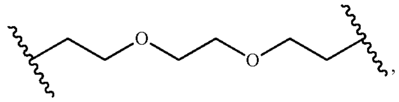,

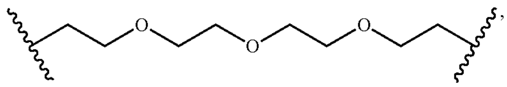,

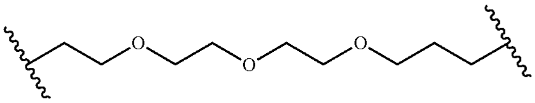,

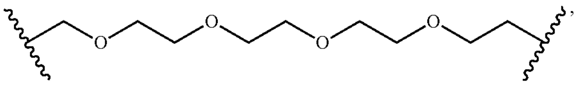,

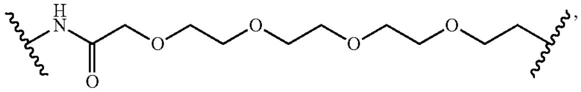,

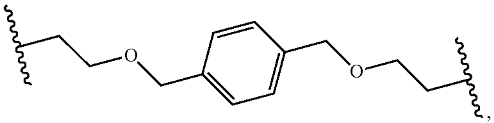, or

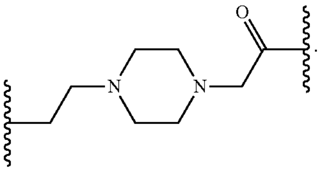.

34. The compound of claim 1, wherein the compound is 8-(4-(2-(2,6-dioxopiperidin-3-yl)-6-fluoro-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)octanamide B1;

N-(6-(7-(4-(2-(2,6-dioxopiperidin-3-yl)-6-fluoro-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B2;

3-(cyclopropylmethoxy)-N-(3,5-dichloropyridin-4-yl)-4-(difluoromethoxy)-N-(7-(4-(2-(2,6-dioxopiperidin-3-yl)-6-fluoro-1-oxoisoindolin-4-yl)piperidin-1-yl)heptyl)benzamide B3;

N-(3,5-dichloropyridin-4-yl)-4-(difluoromethoxy)-3-((7-(4-(2-(2,6-dioxopiperidin-3-yl)-6-fluoro-1-oxoisoindolin-4-yl)piperidin-1-yl)heptyl)oxy)benzamide B4;

3-(7-(4-(2-(2,6-dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B5;

2-(7-(4-(2-(2,6-dioxopiperidin-3-yl)-6-fluoro-1-oxoisoindolin-4-yl)piperidin-1-yl)heptyl)-4-((1-hydroxy-1,3-dihydrobenzo[c][1,2]oxaborol-5-yl)oxy)benzonitrile B6;

3-(4-(1-(7-((4-((3,5-dichloropyridin-4-yl)amino)-7-methoxy-2-oxo-2H-chromen-8-yl)oxy)heptyl)piperidin-4-yl)-6-fluoro-1-oxoisoindolin-2-yl)piperidine-2,6-dione B7;

3-(2-(2-(3-((2-(2,6-dioxopiperidin-3-yl)-1-oxoisoindolin-4-yl)amino)propoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B8;

N-(6-(2-(2-(2-(3-((2-(2,6-dioxopiperidin-3-yl)-1-oxoisoindolin-4-yl)amino)propoxy)-ethoxy)ethoxy)ethyl)-

2-((S)-1-(3-ethoxy-4-methoxyphenyl)-2-(methylsulfonyl)ethyl)-1,3-dioxoisoindolin-4-yl)acetamide B9;

3-(cyclopropylmethoxy)-N-(3,5-dichloropyridin-4-yl)-4-(difluoromethoxy)-N-(2-(2-(2-(3-((2-(2,6-dioxopiperidin-3-yl)-1-oxoisoindolin-4-yl)amino)propoxy)ethoxy)ethoxy)-ethyl)benzamide B10;

N-(3,5-dichloropyridin-4-yl)-4-(difluoromethoxy)-3-(2-(2-(2-(3-((2-(2,6-dioxopiperidin-3-yl)-1-oxoisoindolin-4-yl)amino)propoxy)ethoxy)ethoxy)ethoxy)benzamide B11;

4-(2-(2-(2-(3-((2-(2,6-dioxopiperidin-3-yl)-1-oxoisoindolin-4-yl)amino)propoxy)-ethoxy)ethoxy)ethyl)-3-((1-hydroxy-1,3-dihydrobenzo[c][1,2]oxaborol-5-yl)oxy)benzonitrile B12;

2-(2-(2-(2-(3-((2-(2,6-dioxopiperidin-3-yl)-1-oxoisoindolin-4-yl)amino)propoxy)-ethoxy)ethoxy)ethyl)-4-((1-hydroxy-1,3-dihydrobenzo[c][1,2]oxaborol-5-yl)oxy)benzonitrile B13;

3-(4-((3-(2-(2-(2-((4-((3,5-dichloropyridin-4-yl)amino)-7-methoxy-2-oxo-2H-chromen-8-yl)oxy)ethoxy)ethoxy)ethoxy)propyl)amino)-1-oxoisoindolin-2-yl)piperidine-2,6-dione B14;

6-(4-((2-(2,6-dioxopiperidin-3-yl)-1-oxoisoindolin-4-yl)ethynyl)piperidin-1-yl)-N-(2—((S)-1-(3-ethoxy-4-methoxyphenyl)-2-(methylsulfonyl)ethyl)-1,3-dioxoisoindolin-4-yl)-6-oxohexanamide B15;

N-(6-(5-(4-((2-(2,6-dioxopiperidin-3-yl)-1-oxoisoindolin-4-yl)ethynyl)piperidin-1-yl)-5-oxopentyl)-2-((S)-1-(3-ethoxy-4-methoxyphenyl)-2-(methylsulfonyl)ethyl)-1,3-dioxoisoindolin-4-yl)acetamide B16;

3-(cyclopropylmethoxy)-N-(3,5-dichloropyridin-4-yl)-4-(difluoromethoxy)-N-(5-(4-((2-(2,6-dioxopiperidin-3-yl)-1-oxoisoindolin-4-yl)ethynyl)piperidin-1-yl)-5-oxopentyl)benzamide B17;

N-(3,5-dichloropyridin-4-yl)-4-(difluoromethoxy)-3-((5-(4-((2-(2,6-dioxopiperidin-3-yl)-1-oxoisoindolin-4-yl)ethynyl)piperidin-1-yl)-5-oxopentyl)oxy)benzamide B18;

4-(5-(4-((2-(2,6-dioxopiperidin-3-yl)-1-oxoisoindolin-4-yl)ethynyl)piperidin-1-yl)-5-oxopentyl)-3-((1-hydroxy-1,3-dihydrobenzo[c][1,2]oxaborol-5-yl)oxy)benzonitrile B19;

2-(5-(4-((2-(2,6-dioxopiperidin-3-yl)-1-oxoisoindolin-4-yl)ethynyl)piperidin-1-yl)-5-oxopentyl)-4-((1-hydroxy-1,3-dihydrobenzo[c][1,2]oxaborol-5-yl)oxy)benzonitrile B20;

3-(4-((1-(5-((4-((3,5-dichloropyridin-4-yl)amino)-7-methoxy-2-oxo-2H-chromen-8-yl)oxy)pentanoyl)piperidin-4-yl)ethynyl)-1-oxoisoindolin-2-yl)piperidine-2,6-dione B21;

8-(4-(2-(2,6-dioxopiperidin-3-yl)-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)octanamide B22;

N-(6-(7-(4-(2-(2,6-dioxopiperidin-3-yl)-1-oxoisoindolin-4-yl)piperidin-1-yl)heptyl)-2-((S)-1-(3-ethoxy-4-methoxyphenyl)-2-(methylsulfonyl)ethyl)-1,3-dioxoisoindolin-4-yl)acetamide B23;

3-(cyclopropylmethoxy)-N-(3,5-dichloropyridin-4-yl)-4-(difluoromethoxy)-N-(7-(4-(2-(2,6-dioxopiperidin-3-yl)-1-oxoisoindolin-4-yl)piperidin-1-yl)heptyl)benzamide B24;

N-(3,5-dichloropyridin-4-yl)-4-(difluoromethoxy)-3-((7-(4-(2-(2,6-dioxopiperidin-3-yl)-1-oxoisoindolin-4-yl)piperidin-1-yl)heptyl)oxy)benzamide B25;

3-(7-(4-(2-(2,6-dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B26;

2-(7-(4-(2-(2,6-dioxopiperidin-3-yl)-1-oxoisoindolin-4-yl)piperidin-1-yl)heptyl)-4-((1-hydroxy-1,3-dihydrobenzo[c][1,2]oxaborol-5-yl)oxy)benzonitrile B27;

3-(4-(1-(7-((4-((3,5-dichloropyridin-4-yl)amino)-7-methoxy-2-oxo-2H-chromen-8-yl)oxy)heptyl)piperidin-4-yl)-1-oxoisoindolin-2-yl)piperidine-2,6-dione B28;

8-(4-((5-(2,6-dioxopiperidin-3-yl)-4-oxo-5,6-dihydro-4H-thieno[3,4-c]pyrrol-1-yl)methoxy)phenyl)-N-(2-((S)-1-(3-ethoxy-4-methoxyphenyl)-2-(methylsulfonyl)ethyl)-1,3-dioxoisoindolin-4-yl)octanamide B29;

N-(6-(7-(4-((5-(2,6-dioxopiperidin-3-yl)-4-oxo-5,6-dihydro-4H-thieno[3,4-c]pyrrol-1-yl)methoxy)phenyl)heptyl)-2-((S)-1-(3-ethoxy-4-methoxyphenyl)-2-(methylsulfonyl)ethyl)-1,3-dioxoisoindolin-4-yl)acetamide B30;

3-(cyclopropylmethoxy)-N-(3,5-dichloropyridin-4-yl)-4-(difluoromethoxy)-N-(7-(4-((5-(2,6-dioxopiperidin-3-yl)-4-oxo-5,6-dihydro-4H-thieno[3,4-c]pyrrol-1-yl)methoxy)phenyl)-heptyl)benzamide B31;

N-(3,5-dichloropyridin-4-yl)-4-(difluoromethoxy)-3-((7-(4-((5-(2,6-dioxopiperidin-3-yl)-4-oxo-5,6-dihydro-4H-thieno[3,4-c]pyrrol-1-yl)methoxy)phenyl)heptyl)oxy)benzamide B32;

3-(7-(4-((5-(2,6-dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B33;

2-(7-(4-((5-(2,6-dioxopiperidin-3-yl)-4-oxo-5,6-dihydro-4H-thieno[3,4-c]pyrrol-1-yl)methoxy)phenyl)heptyl)-4-((1-hydroxy-1,3-dihydrobenzo[c][1,2]oxaborol-5-yl)oxy)benzonitrile B34;

3-(1-((4-(7-((4-((3,5-dichloropyridin-4-yl)amino)-7-methoxy-2-oxo-2H-chromen-8-yl)oxy)heptyl)phenoxy)methyl)-4-oxo-4H-thieno[3,4-c]pyrrol-5(6H)-yl)piperidine-2,6-dione B35;

(2S,4R)-1-((S)-2-((8-((2-((S)-1-(3-ethoxy-4-methoxyphenyl)-2-(methylsulfonyl)-ethyl)-1,3-dioxoisoindolin-4-yl)amino)-8-oxooctyl)amino)-3,3-dimethylbutanoyl)-4-hydroxy-N-(4-(4-methylthiazol-5-yl)benzyl)pyrrolidine-2-carboxamide B36;

(2S,4R)-1-((S)-2-((7-(7-acetamido-2-((S)-1-(3-ethoxy-4-methoxyphenyl)-2-(methylsulfonyl)ethyl)-1,3-dioxoisoindolin-5-yl)heptyl)amino)-3,3-dimethylbutanoyl)-4-hydroxy-N-(4-(4-methylthiazol-5-yl)benzyl)pyrrolidine-2-carboxamide B37;

(2S,4R)-1-((S)-2-((7-(3-(cyclopropylmethoxy)-N-(3,5-dichloropyridin-4-yl)-4-(difluoromethoxy)benzamido)heptyl)amino)-3,3-dimethylbutanoyl)-4-hydroxy-N-(4-(4-methylthiazol-5-yl)benzyl)pyrrolidine-2-carboxamide B38;

(2S,4R)-1-((S)-2-((7-(5-((3,5-dichloropyridin-4-yl)carbamoyl)-2-(difluoromethoxy)-phenoxy)heptyl)amino)-3,3-dimethylbutanoyl)-4-hydroxy-N-(4-(4-methylthiazol-5-yl)benzyl)-pyrrolidine-2-carboxamide B39;

(2S,4R)-1-((S)-2-((7-(5-cyano-2-((1-hydroxy-1,3-dihydrobenzo[c][1,2]oxaborol-5-yl)oxy)phenyl)heptyl)amino)-3,3-dimethylbutanoyl)-4-hydroxy-N-(4-(4-methylthiazol-5-yl)benzyl)pyrrolidine-2-carboxamide B40;

(2S,4R)-1-((S)-2-((7-(3-cyano-5-((1-hydroxy-1,3-dihydrobenzo[c][1,2]oxaborol-5-yl)oxy)phenyl)heptyl)

amino)-3,3-dimethylbutanoyl)-4-hydroxy-N-(4-(4-methylthiazol-5-yl)benzyl)pyrrolidine-2-carboxamide B41;

(2S,4R)-1-((S)-2-((7-((4-((3,5-dichloropyridin-4-yl)amino)-7-methoxy-2-oxo-2H-chromen-8-yl)oxy)heptyl)amino)-3,3-dimethylbutanoyl)-4-hydroxy-N-(4-(4-methylthiazol-5-yl)benzyl)pyrrolidine-2-carboxamide B42;

3-(2-(2-(2-((2-(2,6-dioxopiperidin-3-yl)-1,3-dioxoisoindolin-4-yl)amino)ethoxy)-ethoxy)ethoxy)-N-(2-((S)-1-(3-ethoxy-4-methoxyphenyl)-2-(methylsulfonyl)ethyl)-1,3-dioxoisoindolin-4-yl)propanamide B43;

7-((4-((5-((S)-2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)heptanamide B44;

N-(3,5-dichloropyridin-4-yl)-4-(difluoromethoxy)-3-((9-(4-(2-(2,6-dioxopiperidin-3-yl)-6-fluoro-1-oxoisoindolin-4-yl)piperidin-1-yl)nonyl)oxy)benzamide B45;

N-(3,5-dichloropyridin-4-yl)-4-(difluoromethoxy)-3-((5-(4-(2-(2,6-dioxopiperidin-3-yl)-6-fluoro-1-oxoisoindolin-4-yl)piperidin-1-yl)pentyl)oxy)benzamide B46;

N-(6-(7-(4-(2-(2,6-dioxopiperidin-3-yl)-6-fluoro-1-oxoisoindolin-4-yl)piperidin-1-yl)hept-1-yn-1-yl)-2-((S)-1-(3-ethoxy-4-methoxyphenyl)-2-(methylsulfonyl)ethyl)-1,3-dioxoisoindolin-4-yl)acetamide B47;

14-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)-3,6,9,12-tetraoxatetradecan-1-amide B48;

3-(6-fluoro-4-(1-(7-(2-methoxy-5-(1-oxoisoindolin-2-yl)phenoxy)heptyl)piperidin-4-yl)-1-oxoisoindolin-2-yl)piperidine-2,6-dione B49;

3-(4-(1-(7-(2-(cyclopentyloxy)-4-(1-oxoisoindolin-2-yl)phenoxy)heptyl)piperidin-4-yl)-6-fluoro-1-oxoisoindolin-2-yl)piperidine-2,6-dione B50;

2-(3-((7-(4-(2-(2,6-dioxopiperidin-3-yl)-6-fluoro-1-oxoisoindolin-4-yl)piperidin-1-yl)heptyl)oxy)-4-methoxyphenyl)isoindoline-1,3-dione B51;

5-amino-2-(3-((7-(4-(2-(2,6-dioxopiperidin-3-yl)-6-fluoro-1-oxoisoindolin-4-yl)piperidin-1-yl)heptyl)oxy)-4-methoxyphenyl)isoindoline-1,3-dione B52;

3-(6-fluoro-4-(1-(7-(2-methoxy-5-(5-oxopyrrolidin-3-yl)phenoxy)heptyl)piperidin-4-yl)-1-oxoisoindolin-2-yl)piperidine-2,6-dione B53;

2-(3-(cyclopentyloxy)-4-methoxyphenyl)-5-((7-(4-(2-(2,6-dioxopiperidin-3-yl)-6-fluoro-1-oxoisoindolin-4-yl)piperidin-1-yl)heptyl)amino)isoindoline-1,3-dione B54;

3-(6-fluoro-5-(1-(7-(2-methoxy-5-(5-oxopyrrolidin-3-yl)phenoxy)heptyl)piperidin-4-yl)-1-oxoisoindolin-2-yl)piperidine-2,6-dione B55;

3-(4-(1-(7-((2-(3-(cyclopentyloxy)-4-methoxyphenyl)-3-oxoisoindolin-5-yl)amino)heptyl)piperidin-4-yl)-6-fluoro-1-oxoisoindolin-2-yl)piperidine-2,6-dione B56;

3-(4-(1-(7-(2-(cyclopentyloxy)-4-(5-oxopyrrolidin-3-yl)phenoxy)heptyl)piperidin-4-yl)-6-fluoro-1-oxoisoindolin-2-yl)piperidine-2,6-dione B57;

5-amino-2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B58;

2-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)isoindoline-1,3-dione B59;

3-(4-(1-(7-(5-(6-amino-1-oxoisoindolin-2-yl)-2-methoxyphenoxy)heptyl)piperidin-4-yl)-6-fluoro-1-oxoisoindolin-2-yl)piperidine-2,6-dione B60;

N-(3,5-dichloropyridin-4-yl)-4-(difluoromethoxy)-3-((7-(4-(2-(2,6-dioxopiperidin-3-yl)-6-fluoro-1-oxoisoindolin-5-yl)piperidin-1-yl)heptyl)oxy)benzamide B61;

3-(4-(1-(7-(5-(6-amino-1-oxoisoindolin-2-yl)-2-methoxyphenoxy)heptyl)piperidin-4-yl)-6-fluoro-1-oxoisoindolin-2-yl)piperidine-2,6-dione B62;

$N^1$-(2-((S)-1-(3-ethoxy-4-methoxyphenyl)-2-(methylsulfonyl)ethyl)-1,3-dioxoisoindolin-4-yl)-$N^{10}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide B63;

3-((4-((2-((2-(2,6-dioxopiperidin-3-yl)-1,3-dioxoisoindolin-4-yl)amino)ethoxy)-methyl)benzyl)oxy)-N-(2-((S)-1-(3-ethoxy-4-methoxyphenyl)-2-(methylsulfonyl)ethyl)-1,3-dioxoisoindolin-4-yl)propanamide B64;

5-(3-((7-(4-(2-(2,6-dioxopiperidin-3-yl)-6-fluoro-1-oxoisoindolin-4-yl)piperidin-1-yl)heptyl)oxy)-4-methoxyphenyl)-4H-thieno[2,3-c]pyrrole-4,6(5H)-dione B65;

2-(2,6-dioxopiperidin-3-yl)-4-((7-(2-methoxy-5-(5-oxopyrrolidin-3-yl)phenoxy)-heptyl)amino)isoindoline-1,3-dione B66;

(2S,4R)-4-hydroxy-1-((2S)-2-(9-(2-methoxy-5-(5-oxopyrrolidin-3-yl)phenoxy)-nonanamido)-3,3-dimethylbutanoyl)-N-(4-(4-methylthiazol-5-yl)benzyl)pyrrolidine-2-carboxamide B67;

(2S,4R)-1-((S)-2-(9-(5-((3,5-dichloropyridin-4-yl)carbamoyl)-2-(difluoromethoxy)phenoxy)nonanamido)-3,3-dimethylbutanoyl)-4-hydroxy-N-(4-(4-methylthiazol-5-yl)benzyl)pyrrolidine-2-carboxamide B68;

N-(6-(3-(4-(2-(2,6-dioxopiperidin-3-yl)-6-fluoro-1-oxoisoindolin-4-yl)piperidin-1-yl)propyl)-2-((S)-1-(3-ethoxy-4-methoxyphenyl)-2-(methylsulfonyl)ethyl)-1,3-dioxoisoindolin-4-yl)acetamide B69;

9-((4-((5-(2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)nonanamide B70;

12-((2-(2,6-dioxopiperidin-3-yl)-1,3-dioxoisoindolin-4-yl)amino)-N-(2-((S)-1-(3-ethoxy-4-methoxyphenyl)-2-(methylsulfonyl)ethyl)-1,3-dioxoisoindolin-4-yl)dodecanamide B71;

N-(3,5-dichloropyridin-4-yl)-4-(difluoromethoxy)-3-((7-((2-(2,6-dioxopiperidin-3-yl)-1,3-dioxoisoindolin-4-yl)amino)heptyl)oxy)benzamide B72;

N-(3,5-dichloropyridin-4-yl)-4-(difluoromethoxy)-3-((12-(4-(2-(2,6-dioxopiperidin-3-yl)-6-fluoro-1-oxoisoindolin-4-yl)piperidin-1-yl)dodecyl)oxy)benzamide B73;

N-(3,5-dichloropyridin-4-yl)-3-(difluoromethoxy)-4-(2-(2-(2-(2-((2-(2,6-dioxopiperidin-3-yl)-1,3-dioxoisoindolin-4-yl)amino)ethoxy)ethoxy)ethoxy)ethoxy)benzamide B74;

9-(4-(2-(2,6-dioxopiperidin-3-yl)-6-fluoro-1-oxoisoindolin-5-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B75;

(2S,4R)-1-((S)-2-(11-(5-((3,5-dichloropyridin-4-yl)carbamoyl)-2-(difluoromethoxy)-phenoxy)undecanamido)-3,3-dimethylbutanoyl)-4-hydroxy-N-(4-(4-methylthiazol-5-yl)benzyl)pyrrolidine-2-carboxamide B76;

9-(4-(2-(2,6-dioxopiperidin-3-yl)-6-fluoro-1-oxoisoindolin-4-yl)piperidin-1-yl)-N-(2-((S)-1-(3-ethoxy-4-methoxyphenyl)-2-(methylsulfonyl)ethyl)-1,3-dioxoisoindolin-4-yl)nonanamide B77;

5-((4-((5-(2,6-dioxopiperidin-3-yl)-4-oxo-5,6-dihydro-4H-thieno[3,4-c]pyrrol-1-yl)methoxy)benzyl)amino)-N-(2-((S)-1-(3-ethoxy-4-methoxyphenyl)-2-(methylsulfonyl)ethyl)-1,3-dioxoisoindolin-4-yl)pentanamide B78;

N-(6-(12-(4-(2-(2,6-dioxopiperidin-3-yl)-6-fluoro-1-oxoisoindolin-4-yl)piperidin-1-yl)dodecyl)-2-((S)-1-(3-ethoxy-4-methoxyphenyl)-2-(methylsulfonyl)ethyl)-1,3-dioxoisoindolin-4-yl)acetamide B79;

3-(6-fluoro-4-(1-(7-(2-methoxy-5-(4-oxo-4,6-dihydro-5H-thieno[2,3-c]pyrrol-5-yl)phenoxy)heptyl)piperidin-4-yl)-1-oxoisoindolin-2-yl)piperidine-2,6-dione B80;

3-(cyclopropylmethoxy)-N-(3,5-dichloropyridin-4-yl)-4-(2-(2-(2-(3-((2-(2,6-dioxopiperidin-3-yl)-1-oxoisoindolin-4-yl)amino)propoxy)ethoxy)ethoxy)ethoxy)benzamide B81;

3-(cyclopropylmethoxy)-N-(3,5-dichloropyridin-4-yl)-4-((7-(4-(2-(2,6-dioxopiperidin-3-yl)-6-fluoro-1-oxoisoindolin-4-yl)piperidin-1-yl)heptyl)oxy)benzamide B82;

N-(3,5-dichloropyridin-4-yl)-4-(difluoromethoxy)-3-(3-(4-(2-(2,6-dioxopiperidin-3-yl)-6-fluoro-1-oxoisoindolin-4-yl)piperidin-1-yl)propoxy)benzamide B83;

3-(cyclopropylmethoxy)-N-(3,5-dichloropyridin-4-yl)-4-((9-(4-(2-(2,6-dioxopiperidin-3-yl)-6-fluoro-1-oxoisoindolin-4-yl)piperidin-1-yl)nonyl)oxy)benzamide B84;

3-((9-(4-(2-(1-acetamido-1-oxopropan-2-yl)-6-fluoro-1-oxoisoindolin-4-yl)piperidin-1-yl)nonyl)oxy)-N-(3,5-dichloropyridin-4-yl)-4-(difluoromethoxy)benzamide B85;

(2S,4R)-1-((S)-2-(9-(2-(cyclopropylmethoxy)-5-((3,5-dichloropyridin-4-yl)carbamoyl)phenoxy)nonanamido)-3,3-dimethylbutanoyl)-4-hydroxy-N-(4-(4-methylthiazol-5-yl)benzyl)pyrrolidine-2-carboxamide B86;

5-(3-(cyclopentyloxy)-4-((7-(4-(2-(2,6-dioxopiperidin-3-yl)-6-fluoro-1-oxoisoindolin-4-yl)piperidin-1-yl)heptyl)oxy)phenyl)-4H-thieno[2,3-c]pyrrole-4,6(5H)-dione B87;

N-(6-(7-(1-(2-(2,6-dioxopiperidin-3-yl)-1,3-dioxoisoindolin-4-yl)piperidin-4-yl)heptyl)-2—((S)-1-(3-ethoxy-4-methoxyphenyl)-2-(methylsulfonyl)ethyl)-1,3-dioxoisoindolin-4-yl)acetamide B88;

3-(2-(2-((2-(2,6-dioxopiperidin-3-yl)-1,3-dioxoisoindolin-4-yl)amino)ethoxy)ethoxy)-N-(2-((S)-1-(3-ethoxy-4-methoxyphenyl)-2-(methylsulfonyl)ethyl)-1,3-dioxoisoindolin-4-yl)propanamide B89;

N-(3,5-dichloropyridin-4-yl)-4-(difluoromethoxy)-3-((7-(1-(2-(2,6-dioxopiperidin-3-yl)-1,3-dioxoisoindolin-4-yl)piperidin-4-yl)heptyl)oxy)benzamide B90;

3-(4-(1-(7-(2-(cyclopentyloxy)-4-(4-oxo-4,6-dihydro-5H-thieno[2,3-c]pyrrol-5-yl)phenoxy)heptyl)piperidin-4-yl)-6-fluoro-1-oxoisoindolin-2-yl)piperidine-2,6-dione B91; or N-(3,5-dichloropyridin-4-yl)-4-(difluoromethoxy)-3-((7-((4-((5-(2,6-dioxopiperidin-3-yl)-4-oxo-5,6-dihydro-4H-thieno[3,4-c]pyrrol-1-yl)methoxy)benzyl)amino)heptyl)oxy)benzamide B92;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

35. A compound of Formula (I):

(I)

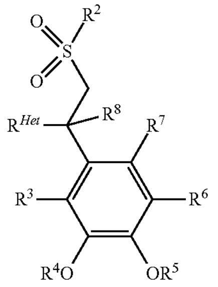

or a pharmaceutically acceptable salt thereof, wherein:

$R^{Het}$ is

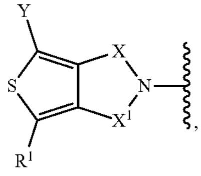
,
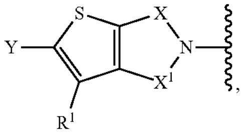
, or
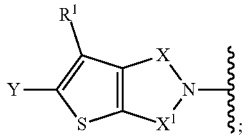
;

each of X and $X^1$ is independently $CH_2$, C═O, SO, $SO_2$, or $CH_2C(═O)$;

each Y is independently H, deuterium, halogen, or optionally substituted $C_1$-$C_6$ alkyl;

each $R^1$ is independently deuterium, hydroxyl, halogen, nitro, cyano, —$NR^9R^{10}$, —$NR^9C(═O)R^{11}$, —$NR^9SO_2R^{11}$, —$N(C(═O)R^9)(C(═O)R^{11})$, optionally substituted $C_1$-$C_6$ alkyl, optionally substituted $C_1$-$C_6$ alkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

$R^2$ is hydroxyl, —$NR^9R^{10}$, optionally substituted $C_1$-$C_6$ alkyl, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^3$, $R^6$, and $R^7$ is independently H, deuterium, halogen, optionally substituted $C_1$-$C_6$ alkyl, $C_1$-$C_6$ haloalkyl, optionally substituted $C_1$-$C_6$ alkoxy, $C_1$-$C_6$ haloalkoxy, optionally substituted $C_3$-$C_7$ cycloalkyl, optionally substituted 3 to 10 membered heterocyclyl, optionally substituted $C_6$-$C_{10}$ aryl, or optionally substituted 5 to 10 membered heteroaryl;

each of $R^4$ and $R^5$ is independently optionally substituted $C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

$R^8$ is H or deuterium;

each of $R^9$ and $R^{10}$ is independently H, optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted 3 to 10 membered heterocyclyl, optionally substituted $C_6$-$C_{10}$ aryl, optionally substituted $C_7$-$C_{14}$ aralkyl, or optionally substituted 5 to 10 membered heteroaryl; and $R^{11}$ is optionally substituted $C_1$-$C_6$ alkyl, $C_1$-$C_6$ haloalkyl, ($C_1$-$C_6$ alkoxy)$C_1$-$C_6$ alkyl, optionally substituted $C_3$-$C_7$ cycloalkyl, optionally substituted ($C_3$-$C_7$ cycloalkyl)$C_1$-$C_6$ alkyl, optionally substituted 3 to 10 membered heterocyclyl, optionally substituted (3 to 10 membered heterocyclyl)$C_1$-$C_6$ alkyl, optionally substituted $C_6$-$C_{10}$ aryl, optionally substituted $C_7$-$C_{14}$ aralkyl, optionally substituted 5 to 10 membered heteroaryl, or (optionally substituted 5 to 10 membered heteroaryl)$C_1$-$C_6$ alkyl;

provided that at least one of $R^2$, $R^4$, and $R^5$ is optionally substituted $C_3$-$C_7$ cycloalkyl.

36. A pharmaceutical composition comprising a compound of claim 1, or a pharmaceutically acceptable salt thereof, and a pharmaceutically acceptable excipient.

37. A method of treating, preventing, or ameliorating one or more symptoms of a disease, disorder, or condition associated with a PDE4, an inflammatory disease, psoriasis, psoriatic arthritis, or atopic dermatitis in a subject, comprising administering to the subject in need thereof a therapeutically effective amount of a compound of claim 1.

* * * * *